(12) United States Patent
Tong et al.

(10) Patent No.: US 8,710,065 B2
(45) Date of Patent: Apr. 29, 2014

(54) TRICYCLIC INHIBITORS OF KINASES

(75) Inventors: Yunsong Tong, Libertyville, IL (US); Thomas D. Penning, Elmhurst, IL (US); Alan S. Florjancic, Kenosha, WI (US); Julie Miyashiro, Morton Grove, IL (US); Keith W. Woods, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/406,937

(22) Filed: Feb. 28, 2012

(65) Prior Publication Data

US 2012/0220572 A1    Aug. 30, 2012

Related U.S. Application Data

(60) Provisional application No. 61/447,405, filed on Feb. 28, 2011.

(51) Int. Cl.
*A61K 31/505* (2006.01)
*C07D 491/00* (2006.01)

(52) U.S. Cl.
USPC .......................................... 514/267; 544/251

(58) Field of Classification Search
USPC ............ 514/267, 215, 252.16, 233.2, 252.02, 514/228.5; 544/251; 540/577
See application file for complete search history.

(56) References Cited

U.S. PATENT DOCUMENTS

| 2005/0020590 A1 | 1/2005 | Lang et al. | |
| 2005/0070554 A1* | 3/2005 | Nunes et al. | 514/257 |
| 2005/0250836 A1 | 11/2005 | Booth et al. | |

FOREIGN PATENT DOCUMENTS

| EP | 2213673 A1 | 8/2010 |
| WO | WO2005021551 A1 | 3/2005 |
| WO | WO2010067886 A1 | 6/2010 |

OTHER PUBLICATIONS

International Search Report and Written Opinion for Application No. PCT/US2012/026685, mailed on May 31, 2012, 10 pages.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Glotzer M., et al., "Cyclin is Degraded by the Ubiquitin Pathway," Nature, 1991, vol. 349 (6305), pp. 132-138.
Hashimoto O., et al., "Cell cycle Regulation by the Wee1 Inhibitor PD0166285, Pyrido [2,3-d] Pyimidine, in the B16 Mouse Melanoma Cell Line," Bio Medical Center Cancer, 2006, vol. 6, pp. 292.
Hirai H., et al., "Small-molecule Inhibition of Wee1 Kinase by MK-1775 Selectively Sensitizes p53-deficient Tumor Cells to DNA-damaging Agents," Molecular Cancer Therapeutics, 2009, vol. 8 (11), pp. 2992-3000.
Leijen S., et al., "Abrogation of the G2 Checkpoint by Inhibition of Wee-1 Kinase Results in Sensitization of p53-deficient Tumor Cells to DNA-damaging Agents," Current Clinical Pharmacology, 2010, vol. 5 (3), pp. 186-191.
Lindqvist A., et al., "The Decision to Enter Mitosis: Feedback and Redundancy in the Mitotic Entry Network," Journal of Cell Biology, 2009, vol. 185 (2), pp. 193-202.
McGowan C.H., et al., "Human Wee1 Kinase Inhibits Cell Division by Phosphorylating p34cdc2 Exclusively on Tyr15," The EMBO Journal, 1993, vol. 12 (1), pp. 75-85.
Nurse P., "Universal Control Mechanism Regulating Onset of M-Phase," Nature, 1990, vol. 344 (6266), pp. 503-508.
O'Connell M.J., et al., "Chk1 is a Wee1 Kinase in the G2 DNA Damage Checkpoint Inhibiting Cdc2 by Y15 Phosphorylation," The EMBO Journal, 1997, vol. 16 (3), pp. 545-554.
Parker L.L., et al., "Inactivation of the p34cdc2-Cyclin B Complex by the Human WEE1 Tyrosine Kinase," Science, 1992, vol. 257 (5078), pp. 1955-1957.
Sabin E.A., et al., "High-Level Expression and in Vivo Processing of Chimeric Ubiquitin Fusion Proteins in Saccharomyces Cerevisiae," Nature Biotechnology, 1989, vol. 7 (7), pp. 705-709.
Sancar A., et al., "Molecular Mechanisms of Mammalian DNA Repair and the DNA Damage Checkpoints," Annual Review of Biochemistry, 2004, vol. 73, pp. 39-85.
Stumpff J., et al., "*Drosophila* Wee1 Kinase Regulates Cdk1 and Mitotic Entry during Embryogenesis," Current Biology, 2004, vol. 14 (23), pp. 2143-2148.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.
Wang, Y., et al., "Knockdown of Chk1, Wee1 and Myt1 by RNA Interference Abrogates G2 Checkpoint and Induces Apoptosis," Cancer Biology & Therapy, 2004, vol. 3 (3), pp. 305-313.

* cited by examiner

*Primary Examiner* — Andrew D Kosar
*Assistant Examiner* — John S Kenyon
(74) *Attorney, Agent, or Firm* — Lisa V. Mueller; Michael Best & Friedrich LLP

(57) ABSTRACT

The present invention relates to compounds of formula (I) or pharmaceutical acceptable salts,

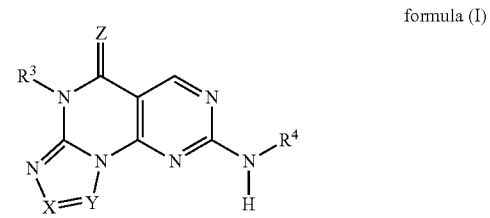

formula (I)

wherein X, Y, Z, $R^3$ and $R^4$ are defined in the description. The present invention relates also to compositions containing said compounds which are useful for inhibiting kinases such as wee-1 and methods of treating diseases such as cancer.

5 Claims, No Drawings

TRICYCLIC INHIBITORS OF KINASES

CROSS-REFERENCE TO RELATED APPLICATIONS

This claims priority to U.S. Patent Application No. 61/447,405, filed on Feb. 28, 2011, the contents of which are fully incorporated herein by reference.

FIELD OF THE INVENTION

This invention pertains to compounds which inhibit the activity of Wee-1 kinase, methods of making the compounds, compositions containing the compounds, and methods of treatment using the compounds.

BACKGROUND OF THE INVENTION

In order to undergo proper cell division, eukaryotic cells must faithfully replicate their genome and then correctly segregate their chromosomes into two daughter cells. This process of cell division, also called the cell cycle, is a step-wise process that is governed by checkpoints to ensure genomic integrity. Upon completion of DNA replication (S-phase), cells enter a growth phase (G2-phase) prior to proceeding into mitosis for chromosome segregation (M-phase). A key regulator of mitosis is the kinase Cdk1 (as called Cdc2) (Nurse, P. (1990) Universal control mechanism regulating onset of M-phase. Nature 344, 503-508). Activation of Cdk1 results in the onset of mitosis, and its subsequent inactivation initiates the exit from mitosis. Cdk1 is activated by the binding of Cyclin A or Cyclin B. Both Cyclin A-Cdk1 and Cyclin B-Cdk1 complexes function to initiate mitosis (Lindqvist, A., et. Al. (2009) The decision to enter mitosis: feedback and redundancy in the mitotic entry network. The Journal of cell biology 185, 193-202). The degradation of Cyclin B triggers the inactivation of Cdk1, resulting in the mitotic exit and entry into a growth (G1) phase prior to beginning a new round of the cell cycle (Glotzer, M., et al. (1991) Cyclin is degraded by the ubiquitin pathway. Nature 349, 132-138). In addition to Cyclins, Cdk1 is also regulated by Wee1, an atypical tyrosine kinase that phosphorylates Cdk1 on tyrosine 15 (Y15) and inactivates Cdk1 (McGowan, C. H., et al. (1993) Human Wee1 kinase inhibits cell division by phosphorylating p34cdc2 exclusively on Tyr15. The EMBO journal 12, 75-85; Parker, L. L., et al. (1992) Inactivation of the p34cdc2-cyclin B complex by the human WEE1 tyrosine kinase. Science 257, 1955-1957). Wee1 is a critical negative regulator of Cdk1 and functions at the G2-M phase checkpoint to ensure that DNA replication has been completed and the genome is not damaged prior to entering mitosis (O'Connell, et al. (1997) Chk1 is a wee1 kinase in the G2 DNA damage checkpoint inhibiting cdc2 by Y15 phosphorylation. The EMBO journal 16, 545-554). Loss of Wee1 can result in premature entry into mitosis, resulting in mitotic catastrophe and cell death (Stumpff, J., et al. (2004) Drosophila Wee1 kinase regulates Cdk1 and mitotic entry during embryogenesis. Curr Biol 14, 2143-2148). Furthermore, many cancers are defective in their G1-phase checkpoints and are reliant on G2-M phase checkpoints (Sancar, A., et al. (2004) Molecular mechanisms of mammalian DNA repair and the DNA damage checkpoints Annual review of biochemistry 73, 39-85). Indeed, loss of expression of Wee1 has been shown to lead to the abrogation of the G2-M phase checkpoint and sensitize tumor cells to DNA damage, especially tumors that have lost their G1-phase checkpoint due to a deficiency in the p53 protein (Wang, Y., et al. (2004) Knockdown of Chk1, Wee1 and Myt1 by RNA interference abrogates G2 checkpoint and induces apoptosis. Cancer biology & therapy 3, 305-313).

Inhibitors of Wee1 have the potential to selectively cause lethality in cancerous cells that are defective in other cell cycle checkpoints, while sparing normal tissues that can activate other cell cycle checkpoints. Thus, small molecule inhibitors of Wee1 would be beneficial for therapeutic intervention in cancer and other cell proliferative disorders.

SUMMARY OF THE INVENTION

The present invention has numerous embodiments. One embodiment of this invention, therefore, pertains to compounds that have formula (I)

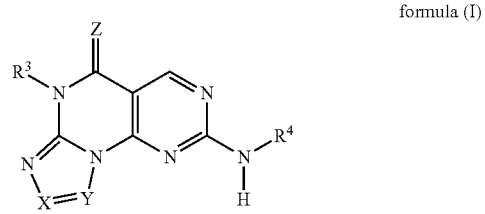

formula (I)

wherein X, Y, Z, $R^3$, $R^4$ are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)) oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of formula (I)

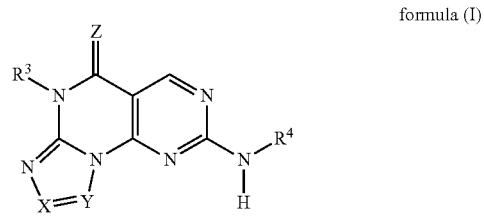

formula (I)

wherein
  X is N or $CR^1$;
  Y is N or $CR^2$;
  Z is O, S, or NH;
  $R^1$ is H or $C_{1-6}$-alkyl;
  $R^2$ is H or $C_{1-6}$-alkyl;
  $R^3$ is $C_{1-8}$-alkyl, $C_{2-8}$-alkenyl, $C_{3-8}$-cycloalkyl, aryl, or heteroaryl, wherein (a) the $C_{1-8}$-alkyl or $C_{2-8}$-alkenyl is optionally substituted with one or more substituents selected from the group consisting of halogen, cyano, nitro, —$OR^a$, —$C(O)R^a$, —$C(O)OR^a$, —$OC(O)R^a$, —$NR^bR^c$, —$NR^bC(O)R^a$, —$NHC(O)NHR^b$, —$C(O)NR^bR^c$, —$NHSO_2R^a$, and —$SO_2NR^bNR^c$; and (b) the $C_{3-8}$-cycloalkyl, aryl, and heteroaryl are optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —NHC(O)$R^e$, —NHC(O)NHR$^e$, —NHC(O)OR$^e$, —$NHSO_2R^d$, —C(O)NHR$^e$, and —$SO_2NHNR^e$;

$R^4$ is (a) phenyl, naphthyl, tetrahydronaphthyl, indenyl, or indanyl, wherein the phenyl, naphthyl, tetrahydronaphthyl, indenyl, or indanyl are optionally substituted with one or more $R^5$; or (b) 5-16 membered monocyclic, bicyclic, or tricyclic heterocyclyl, wherein the heterocyclyl is optionally substituted with one or more $R^6$;

$R^5$, at each occurrence, is independently CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, $-NH_2$, $-NHC_{1-6}$-alkyl, and $-N(C_{1-6}$-alkyl)$_2$; wherein the aryl, cycloalkyl, heteroaryl, or heterocycloalkyl, alone or as part of another moiety, is optionally substituted with one or more $R^7$;

$R^6$, at each occurrence, is independently CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, $-NH_2$, $-NHC_{1-6}$-alkyl, and $-N(C_{1-6}$-alkyl)$_2$; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl;

$R^7$, at each occurrence, is independently CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $-NH_2$, $-NHC_{1-6}$-alkyl, and $-N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl;

$R^a$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^d$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^g$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-C(O)$ $C_{1-6}$-alkyl, $-S(O)_2C_{1-6}$-alkyl, $-NH_2$, $-NH(C_{1-6}$-alkyl), $-N(C_{1-6}$-alkyl)$_2$, and $-N(C_{1-6}$-alkyl)($C_{3-8}$-cycloalkyl);

$R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-C(O)C_{1-6}$-alkyl, $-S(O)_2C_{1-6}$-alkyl, $-NH_2$, $-NH(C_{1-6}$-alkyl), $N(C_{1-6}$-alkyl)$_2$, and $-N(C_{1-6}$-alkyl)($C_{3-8}$-cycloalkyl);

$R^j$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-NH_2$, $-NH(C_{1-6}$-alkyl), and $N(C_{1-6}$-alkyl)$_2$;

$R^k$ and $R^l$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-NH_2$, $-NH(C_{1-6}$-alkyl), and $N(C_{1-6}$-alkyl)$_2$;

$R^m$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-NH_2$, $-NH(C_{1-6}$-alkyl), and $N(C_{1-6}$-alkyl)$_2$;

$R''$ and $R^o$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, $-NH_2$, $-NHC_{1-6}$-alkyl, and $-N(C_{1-6}$-alkyl)$_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $-NH_2$, $-NH(C_{1-6}$-alkyl), and $N(C_{1-6}$-alkyl)$_2$;

or a pharmaceutically acceptable salt or solvate thereof; with the proviso that said compound is not 6-(2,6-dimethylphenyl)-2-((4-(4-methyl-1-piperazinyl)phenyl)amino)imidazo[1,2-a]pyrimido[5,4-e]pyrimidin-5(6H)-one.

In one embodiment of formula (I), X is CR¹ and Y is CR². In another embodiment of formula (I), X is CR¹, Y is CR², R¹ is H, and R² is H. In another embodiment of formula (I), X is CR¹, Y is CR², R¹ is $C_{1-6}$ alkyl, and R² is H. In another embodiment of formula (I), X is CR¹, Y is CR², R¹ is H, and R² is $C_{1-6}$ alkyl. In another embodiment of formula (I), X is CR¹, Y is CR², R¹ is $C_{1-6}$ alkyl, and R² is $C_{1-6}$ alkyl.

In another embodiment of formula (I), X is N and Y is CR². In another embodiment of formula (I), X is N, Y is CR², and R² is H. In another embodiment of formula (I), X is N, Y is CR², and R² is $C_{1-6}$ alkyl.

In another embodiment of formula (I), X is N and Y is N.

In one embodiment of formula (I), Z is O.

In one embodiment of formula (I), R³ is $C_{1-8}$-alkyl or $C_{2-8}$-alkenyl, wherein the $C_{1-8}$-alkyl or $C_{2-8}$-alkenyl is optionally substituted with one or more substituents selected from the group consisting of halogen, cyano, nitro, —OR$^a$, —C(O)R$^a$, —C(O)OR$^a$, —OC(O)R$^a$, —NR$^b$R$^c$, —NR$^b$C(O)R$^a$, —NHC(O)NHR$^b$, —C(O)NR$^b$R$^c$, —NHSO₂R$^a$, and —SO₂NR$^b$NR$^c$. In another embodiment of formula (I), R³ is $C_{1-8}$-alkyl or $C_{2-8}$-alkenyl, wherein the $C_{1-8}$-alkyl or $C_{2-8}$-alkenyl is unsubstituted. In yet another embodiment of formula (I), R³ is —CH₃, —CH₂CH₃, —CH₂CH₂CH₃, —CH₂CH₂CH₂CH₃, —CH(CH₃)₂, —CH₂CH(CH₃)₂, —CH₂CH=CH₂, or —CH₂CH₂CH=CH₂.

In one embodiment of formula (I), R³ is $C_{3-8}$ cycloalkyl, wherein the $C_{3-8}$ cylcoalkyl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —OR$^d$, —C(O)R$^d$, —C(O)OR$^d$, —OC(O)R$^d$, —SR$^d$, —S(O)R$^d$, —SO₂R$^d$, —NR$^e$R$^f$, —NHC(O)R$^e$, —NHC(O)NHR$^e$, —NHC(O)OR$^e$, —NHSO₂R$^d$, —C(O)NHR$^e$, and —SO₂NHNR$^e$. In one another embodiment of formula (I), R³ is optionally substituted with one or more substituents selected from the group consisting of $C_{1-6}$-alkyl, $C_{1-6}$-haloalkyl, heterocycloalkyl, aryl, halogen, cyano, and —OR$^d$. In another embodiment, R³ is $C_{3-8}$ cycloalkyl which is unsubstituted.

In one embodiment of formula (I), R³ is heteroaryl, wherein the heteroaryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —OR$^d$, —C(O)R$^d$, —C(O)OR$^d$, —OC(O)R$^d$, —SR$^d$, —S(O)R$^d$, —SO₂R$^d$, —NR$^e$R$^f$, —NHC(O)R$^e$, —NHC(O)NHR$^e$, —NHC(O)OR$^e$, —NHSO₂R$^d$, —C(O)NHR$^e$, and —SO₂NHNR$^e$. In another embodiment, R³ is heteroaryl, wherein the heteroaryl is pyridinyl, furanyl, thienyl, pyrrolyl, pyrazolyl, pyrazinyl, imidazolyl, indolyl, tetrazolyl, isoxazolyl, oxazolyl, oxadiazolyl, thiadiazolyl, thiazolyl, or triazolyl.

In one embodiment of formula (I), R³ is aryl, wherein the aryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —OR$^d$, —C(O)R$^d$, —C(O)OR$^d$, —OC(O)R$^d$, —SR$^d$, —S(O)R$^d$, —SO₂R$^d$, —NR$^e$R$^f$, —NHC(O)R$^e$, —NHC(O)NHR$^e$, —NHC(O)OR$^e$, —NHSO₂R$^d$, —C(O)NHR$^e$, and —SO₂NHNR$^e$. In another embodiment of formula (I), R³ is aryl, wherein the aryl is selected from the group consisting of phenyl, naphthyl, indenyl, indanyl, and tetrahydronaphthyl. In yet another embodiment of formula (I), R³ is phenyl. In yet another embodiment of formula (I), R³ is phenyl, which is optionally substituted with one or more substituents selected from the group consisting of halogen, $C_{1-6}$ alkyl, $C_{1-6}$ haloalkyl, —OC$_{1-6}$ alkyl, or —OC$_{1-6}$ haloalkyl. In another embodiment of formula (I), R³ is substituted with one substituent selected from the group consisting of halogen, $C_{1-6}$ alkyl, $C_{1-6}$ haloalkyl, —OC$_{1-6}$ alkyl, or —OC$_{1-6}$ haloalkyl. In yet another embodiment of formula (I), R³ is

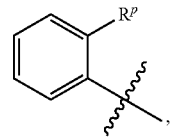

wherein R$^p$ is selected from the group consisting of halogen, $C_{1-6}$ alkyl, $C_{1-6}$ haloalkyl, —OC$_{1-6}$ alkyl, or —OC$_{1-6}$ haloalkyl. In yet another embodiment of formula (I), R$^p$ is halogen. In yet another embodiment of formula (I), R³ is

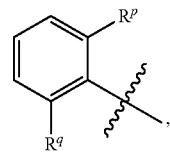

wherein R$^p$ and R$^q$ are independently selected from the group consisting of halogen, $C_{1-6}$ alkyl, $C_{1-6}$ haloalkyl, —OC$_{1-6}$ alkyl, or —OC$_{1-6}$ haloalkyl. In yet another embodiment of formula (I), both R$^p$ and R$^q$ are halogen.

In one embodiment of formula (I), R⁴ is phenyl, naphthyl, tetrahydronaphthyl, indenyl, or indanyl, wherein the phenyl, naphthyl, tetrahydronaphthyl, indenyl, or indanyl is optionally substituted with one or more R⁵; and CN, NO₂, halo, $C_{1-6}$-alkyl, OR$^g$, SR$^g$, C(O)R$^g$, C(O)NR$^h$R$^i$, C(O)OR$^g$, NR$^h$R$^i$, NR$^h$C(O)R$^g$, S(O)₂R$^g$, NR$^h$S(O)₂R$^g$, S(O)₂NR$^h$R$^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, S(O)₂NH(C$_{1-6}$-alkyl), $C_{1-6}$-alkoxy, heterocycloalkyl, cycloalkyl, heteroaryl, aryl, —NH₂, —NHC$_{1-6}$-alkyl, and —N(C$_{1-6}$-alkyl)₂; wherein the aryl, cycloalkyl, heteroaryl, or heterocycloalkyl, alone or as part of another moiety, is optionally substituted with one, two, or three R⁷; wherein R⁷ is CN, NO₂, halo, oxo, $C_{1-6}$ alkyl, aryl, $C_{3-8}$ cycloalkyl, heteroaryl, heterocycloalkyl, OR$^m$, SR$^m$, C(O)R$^m$, C(O)NR″R$^o$, C(O)OR$^m$, OC(O)R$^m$, OC(O)NR″R$^o$, NR″R$^o$, NR″C(O)R$^m$, S(O)R$^m$, S(O)NR″R$^o$, S(O)₂R$^m$, NR″S(O)₂R$^m$, or S(O)₂NR″R$^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —NH₂, —NHC$_{1-6}$-alkyl, and —N(C$_{1-6}$-alkyl)₂, wherein the aryl, $C_{3-8}$ cycloalkyl, heteroaryl, and heterocycloalkyl, alone or as part of another moiety, are optionally substituted with one, two or three substituents independently selected from CN, halo, and C$_{1-6}$ alkyl. In another embodiment of formula (I), R⁴ is naphthyl, tetrahydronaphthyl, indenyl, or indanyl, wherein the naphthyl, tetrahydronaphthyl, indenyl, or indanyl is unsubstituted. In yet another embodiment of formula (I), R⁴ is naphthyl, tetrahydronaphthyl, indenyl, or indanyl, wherein the naphthyl, tetrahydronaphthyl, indenyl, or indanyl are substituted with one, two, or three substituents selected from the group consisting of CN, NO₂, halo, $C_{1-6}$-alkyl, $C_{1-6}$-haloalkyl, OR$^g$, SR$^g$, C(O)R$^g$, C(O)NR$^h$R$^i$, C(O)OR$^g$, NR$^h$R$^i$, NR$^h$C(O)R$^g$, S(O)₂R$^g$, NR$^h$S(O)₂R$^g$, and S(O)₂NR$^h$R$^i$.

In one embodiment of formula (I), R⁴ is phenyl. In another embodiment of formula (I), R⁴ is phenyl, wherein the phenyl is unsubstituted. In another embodiment of formula (I), $R^4$ is phenyl, wherein the phenyl is substituted with one, two, or three $R^5$, and $R^5$ is CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, $—NH_2$, $—NHC_{1-6}$-alkyl, and $—N(C_{1-6}$-alkyl$)_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR^nR^o$, $C(O)OR^m$, $OC(O)R^m$, $OC(O)NR^nR^o$, $NR^nR^o$, $NR^nC(O)R^m$, $S(O)R^m$, $S(O)NR^nR^o$, $S(O)_2R^m$, $NR^nS(O)_2R^m$, or $S(O)_2NR^nR^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $—NH_2$, $—NHC_{1-6}$-alkyl, and $—N(C_{1-6}$-alkyl$)_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In yet another embodiment of formula (I), $R^7$ is $C_{1-6}$-alkyl, $C_{1-6}$ haloalkyl, or $C(O)R^m$; and $R^m$ is $C_{1-6}$ alkyl, $C_{1-6}$ haloalkyl, or $C_{3-8}$ cycloalkyl.

In one embodiment of formula (I), $R^4$ is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^g$, wherein the heterocycloalkyl is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR^nR^o$, $C(O)OR^m$, $OC(O)R^m$, $OC(O)NR^nR^o$, $NR^nR^o$, $NR^nC(O)R^m$, $S(O)R^m$, $S(O)NR^nR^o$, $S(O)_2R^m$, $NR^nS(O)_2R^m$, or $S(O)_2NR^nR^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $—NH_2$, $—NHC_{1-6}$-alkyl, and $—N(C_{1-6}$-alkyl$)_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (I), the $R^5$ heterocycloalkyl is piperazinyl, diazepanyl, piperidinyl, pyrrolidinyl, morpholinyl, hexahydropyrrolo[1,2-a]pyrazinyl, oxopiperazinyl, (1S,4S)-2,5-diazabicyclo[2.2.1]hept-2-yl, (1R,4R)-2,5-diazabicyclo[2.2.1]hept-2-yl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, octahydro-2H-pyrido[1,2-a]pyrazin-2-yl, thiazolidin-2-yl, 4-oxo-1,3-thiazolidin-2-yl, (3R)-1-azabicyclo[2.2.2]oct-3yl, or thiomorpholinyl.

In another embodiment of formula (I), $R^4$ is

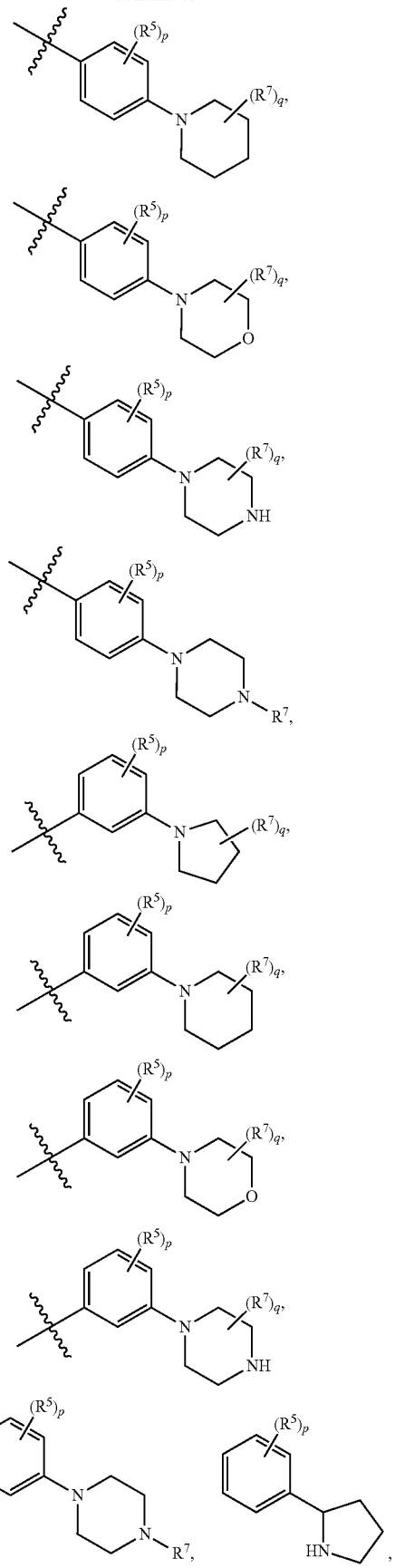

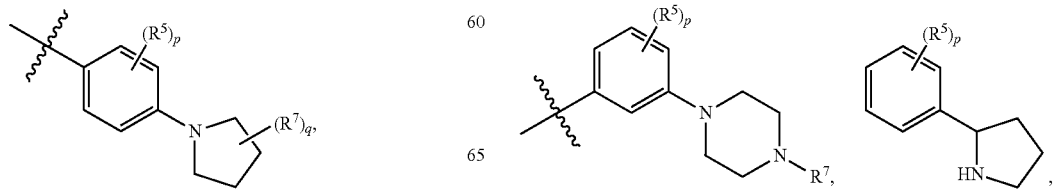

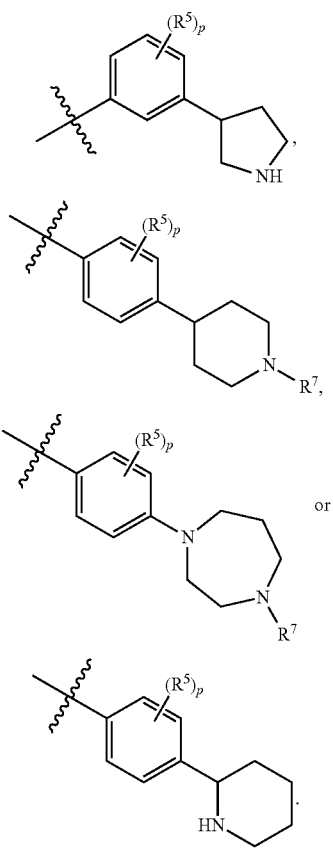

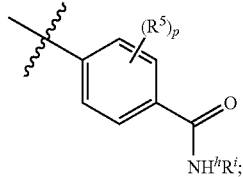

wherein R⁵ is halo, $C_{1-6}$-alkyl, $C_{1-6}$ haloalkyl, or OR$^g$; p is 0 or 1; R⁷ is CN, NO₂, halo, $C_{1-6}$-alkyl, $C_{1-6}$-haloalkyl, OR$^m$, SR$^m$, C(O)R$^m$, C(O)NR″R°, C(O)OR$^m$, NR″R°, NR″C(O)R$^m$, S(O)₂R$^m$, NR″S(O)₂R$^m$, or S(O)₂NR″R°; and q is 0 or 1.

In one embodiment of formula (I), R³ is phenyl, wherein the phenyl is substituted with one substituent selected from the group consisting of $C_{1-6}$-alkyl, $C_{1-6}$-haloalkyl, halogen, and —OR$^d$;

R⁴ is

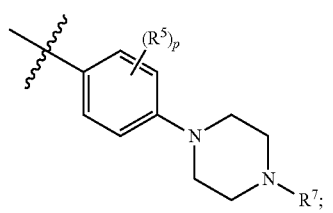

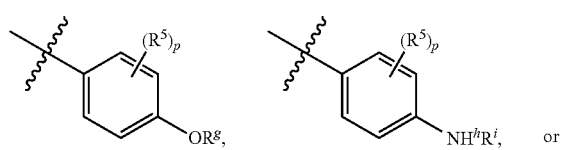

R⁵ is halo, $C_{1-6}$-alkyl, $C_{1-6}$ haloalkyl, or OR$^g$; and p is 0 or 1.

In one embodiment of formula (I), R⁴ is wherein R⁵ is halo, $C_{1-6}$-alkyl, $C_{1-6}$ haloalkyl, or OR$^g$; R$^g$ is selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —NH₂, —NHC$_{1-6}$-alkyl, and —N($C_{1-6}$-alkyl)₂, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)₂$C_{1-6}$-alkyl, —NH₂, —NH($C_{1-6}$-alkyl), —N($C_{1-6}$-alkyl)₂, and —N($C_{1-6}$-alkyl)($C_{3-8}$-cycloalkyl); and R$^h$ and R$^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —NH₂, —NHC$_{1-6}$-alkyl, and —N($C_{1-6}$-alkyl)₂, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)₂$C_{1-6}$-alkyl, —NH₂, —NH($C_{1-6}$-alkyl), N($C_{1-6}$-alkyl)₂, and —N($C_{1-6}$-alkyl)($C_{3-8}$-cycloalkyl); p is 0, 1, or 2.

In one embodiment of formula (I), R⁴ is a 5-16 membered monocyclic, bicyclic, or tricyclic heterocyclyl, wherein the heterocyclyl is optionally substituted with one or more R⁶, and R⁶ is CN, NO₂, halo, $C_{3-8}$ cycloalkyl, OR$^j$, SR$^j$, C(O)R$^j$, C(O)NR$^k$R$^l$, C(O)OR$^j$, NR$^k$R$^l$, NR$^k$C(O)R$^j$, S(O)₂R$^j$, NR$^k$S(O)₂R$^j$, or S(O)₂NR$^k$R$^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, —NH₂, —NHC$_{1-6}$-alkyl, and —N($C_{1-6}$-alkyl)₂; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl.

In one embodiment of formula (I), R⁴ is a 4-8 membered monocyclic heterocyclyl. In another embodiment, R⁴ is a 4-8 membered heterocycloalkyl or heterocycloalkenyl. In another embodiment, R⁴ is a 5-7 membered heteroaryl. In yet another embodiment of formula (I), R⁴ is pyrrolidinyl, tetrahydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxopyrrolidinyl, 2-oxopiperidinyl, 4-oxopiperidinyl, or 2,6-dioxopiperidinyl. In yet another embodiment of formula (I), R⁴ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, R⁴ is unsubstituted. In another embodiment, R⁴ is substituted with one, two, or three $R^6$, and $R^6$ is halo, $C_{1-6}$-alkyl, $C_{1-6}$-haloalkyl, $OR^j$, $C(O)R^j$, $NR^kR^l$, or $S(O)_2R^j$.

In one embodiment of formula (I), $R^4$ is a 7-11 membered bicyclic heterocyclyl. In another embodiment, $R^4$ is a 7-11 membered bicyclic heterocycloalkyl or bicyclic heterocycloalkenyl. In another embodiment, $R^4$ is a 7-11 membered bicyclic heteroaryl. In yet another embodiment, $R^4$ is 2,3-dihydro-2-oxo-1H-indolyl, hexahydropyrrolo[1,2-a]pyrazinyl, (1R,4R)-2,5-diazabicyclo[2.2.1]hept-2-yl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, benzisothiazolyl, benzisoxazolyl, benzodiazinyl, benzofurazanyl, benzothiopyranyl, octahydro-2H-pyrido[1,2-a]pyrazin-2-yl, benzotriazolyl, benzpyrazolyl, 1,3-benzodioxolyl, (3R)-1-azabicyclo[2.2.2]oct-3yl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, 4-oxo-1,4-dihydrocinnolin-6-yl, isochromanyl, isoindolinyl, naphthyridinyl, phthalazinyl, piperonyl, purinyl, pyridopyridyl, pyrrolotriazinyl, quinazolinyl, 1,2,3-benzothiadiazoly-5-yl, 1,3-benzothiazol-6-yl, tetrahydroquinolinyl, thienofuryl, thienopyridyl, [1,2-a]pyridine-2-yl, 2,3-dihydroimidazol[2,1-b][1,3]thiazol-6-yl, imidazo[2,1-b][1,3]thiazol-6-yl, 3-oxo-2,3-dihydro-1H-indazol-7-yl, 5,6,7,8-tetrahydro-1,6-naphthyridin-3-yl, 2,7-diazaspiro[3.5]non-7-yl, 2,6-diazaspiro[3.3]hept-2-yl, 2,6-diazaspiro[3.4]oct-2-yl, 2,7-diazaspiro[3.5]non-2-yl, 3,0-diazaspiro[5.5]undec-3-yl, (3aR,6aR)-hexahydropyrrolo[3,4-b]pyrrol-1(2H)-yl, 2,3,4,5-tetrahydro-1H-2-benzazepinyl, 2,3,4,5-tetrahydro-1H-3-benzazepinyl, 1,2,3,4-tetrahydroisoquinolin-7-yl, 1,2,3,4-tetrahydroquinolinyl, 4,4-dimethyl-1,2,3,4-tetrahydroisoquinolin-7-yl, 2,3-dihydro-1H-indol-5-yl, indolinyl, 2,3-dihydro-1H-indazolyl, isoindolinyl, 1,2,3,4-tetrahydroisoquinolin-6-yl, or thienothienyl. In one embodiment of formula (I), $R^4$ is unsubstituted. In another embodiment of formula (I), $R^4$ is substituted with one, two, or three $R^6$, and $R^6$ is CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, $-NH_2$, $-NHC_{1-6}$-alkyl, and $-N(C_{1-6}$-alkyl$)_2$; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl.

In one embodiment of formula (I), $R^4$ is

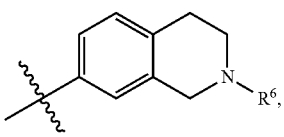

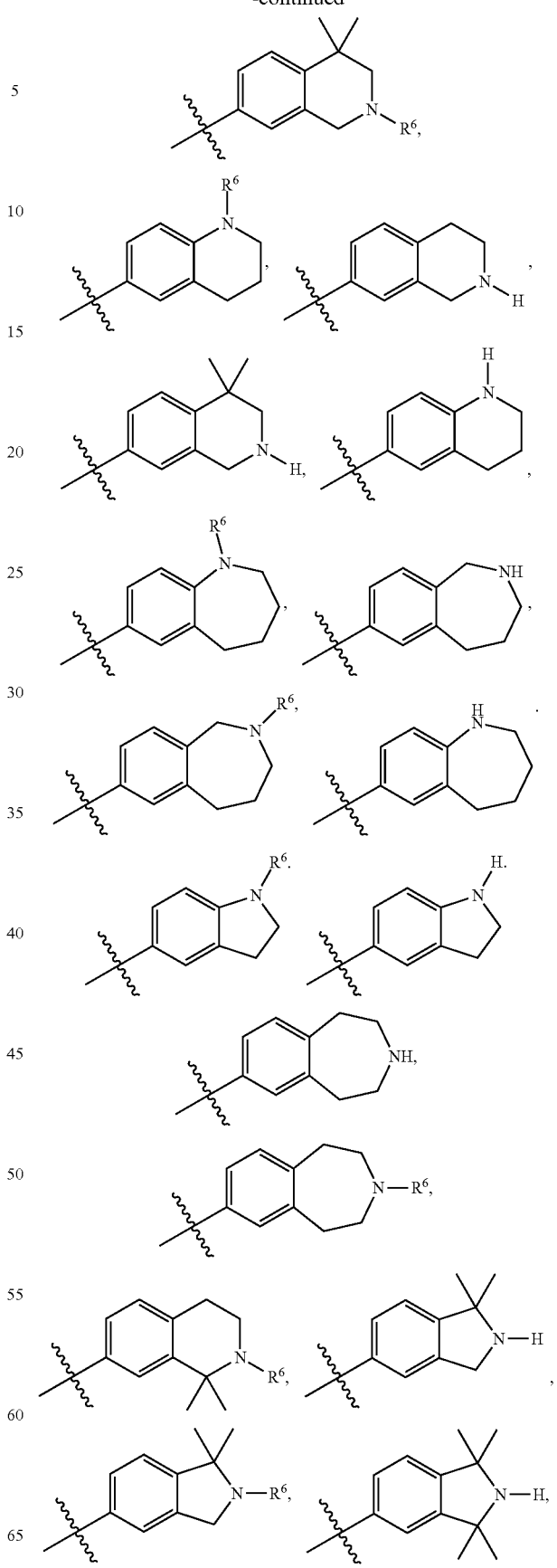

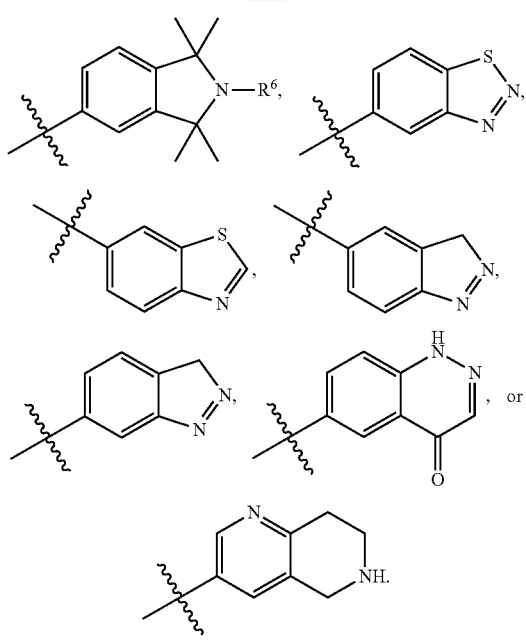

In one embodiment of formula (I), $R^4$ is 10-15 membered tricyclic heterocyclyl. In another embodiment, $R^4$ is a 10-15 membered tricyclic heterocycloalkyl or tricyclic heterocycloalkenyl. In another embodiment, $R^4$ is a 10-15 membered tricyclic heteroaryl. In one embodiment of formula (I), $R^4$ is 5-oxo-5,6-dihydroimidazo[1,2-a]pyrimido[5,4-e]pyrimidiny-2-yl or 2',3'-dihydro-1'H-spiro[cyclopropane-1,4'-isoquinolin]-7'-yl. In one embodiment of formula (I), $R^4$ is unsubstituted. In another embodiment of formula (I), $R^4$ is substituted with one, two, or three $R^6$, and $R^6$ is halo, $C_{1-6}$-alkyl, $C_{1-6}$-haloalkyl, $OR^j$, $C(O)R^j$, $NR^kR^l$, or $S(O)_2R^j$.

In on embodiment of formula (I), $R^4$ is

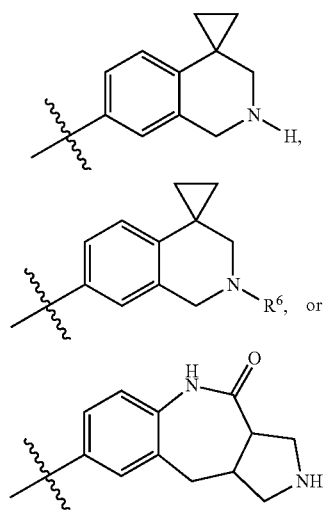

Embodiments of Formula (II)

In one embodiment, the present invention is directed, in part, to a class of compounds having a structure of formula (II),

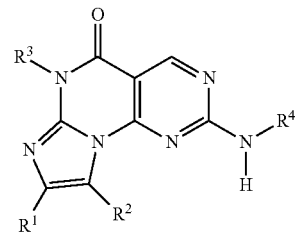

formula (II)

wherein $R^1$, $R^2$, $R^3$, and $R^4$ are as described in formula (I), with the proviso that said compound is not 6-(2,6-dimethylphenyl)-2-((4-(4-methyl-1-piperazinyl)phenyl)amino)imidazo[1,2-a]pyrimido[5,4-e]pyrimidin-5(6H)-one.

In one embodiment of formula (II), $R^1$ is H, and $R^2$ is H. In another embodiment of formula (II), $R^1$ is $C_{1-6}$ alkyl and $R^2$ is H. In another embodiment of formula (II), $R^1$ is H and $R^2$ is $C_{1-6}$ alkyl. In another embodiment of formula (II), $R^1$ is $C_{1-6}$ alkyl, and $R^2$ is $C_{1-6}$ alkyl.

In one embodiment of formula (II), $R^3$ is aryl, wherein the aryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, $-OR^d$, $-C(O)R^d$, $-C(O)OR^d$, $-OC(O)R^d$, $-SR^d$, $-S(O)R^d$, $-SO_2R^d$, $-NR^eR^f$, $-NHC(O)R^e$, $-NHC(O)NHR^e$, $-NHC(O)OR^e$, $-NHSO_2R^d$, $-C(O)NHR^e$, and $-SO_2NHNR^e$. In another embodiment of formula (II), $R^3$ is aryl, wherein the aryl is selected from the group consisting of phenyl, naphthyl, indenyl, indanyl, and tetrahydronaphthyl. In yet another embodiment of formula (II), $R^3$ is phenyl. In yet another embodiment of formula (II), $R^3$ is phenyl, which is optionally substituted with one or more substituents selected from the group consisting of halogen, $C_{1-6}$ alkyl, $C_{1-6}$ haloalkyl, $-OC_{1-6}$ alkyl, and $-OC_{1-6}$ haloalkyl. In another embodiment of formula (II), $R^3$ is phenyl which is substituted with one substituent selected from the group consisting of halogen, $C_{1-6}$ alkyl, $C_{1-6}$ haloalkyl, $-OC_{1-6}$ alkyl, and $-OC_{1-6}$ haloalkyl. In yet another embodiment of formula (II), $R^3$ is

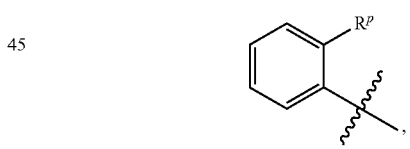

wherein $R^p$ is selected from the group consisting of halogen, $C_{1-6}$ alkyl, $C_{1-6}$ haloalkyl, $-OC_{1-6}$ alkyl, and $-OC_{1-6}$ haloalkyl. In yet another embodiment of formula (II), $R^p$ is halogen. In yet another embodiment of formula (I), $R^3$ is

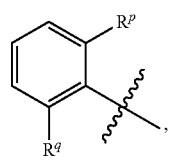

wherein $R^p$ and $R^q$ are independently selected from the group consisting of halogen, $C_{1-6}$ alkyl, $C_{1-6}$ haloalkyl, $-OC_{1-6}$ alkyl, or $-OC_{1-6}$ haloalkyl. In yet another embodiment of formula (I), both $R^p$ and $R^q$ are halogen.

In one embodiment of formula (II), $R^4$ is phenyl, naphthyl, tetrahydronaphthyl, indenyl, or indanyl, wherein the phenyl, naphthyl, tetrahydronaphthyl, indenyl, or indanyl is optionally substituted with one or more $R^5$; and CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, —$NH_2$, —$NHC_{1-6}$-alkyl, and —$N(C_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR'''$, $SR'''$, $C(O)R'''$, $C(O)NR''R^o$, $C(O)OR'''$, $OC(O)R'''$, $OC(O)NR''R^o$, $NR''R^o$, $NR''C(O)R'''$, $S(O)R'''$, $S(O)NR''R^o$, $S(O)_2R'''$, $NR''S(O)_2R'''$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (II), $R^4$ is naphthyl, tetrahydronaphthyl, indenyl, or indanyl, wherein the naphthyl, tetrahydronaphthyl, indenyl, or indanyl is unsubstituted. In yet another embodiment of formula (II), $R^4$ is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In one embodiment of formula (II), $R^4$ is phenyl. In another embodiment of formula (II), $R^4$ is phenyl, wherein the phenyl is unsubstituted. In another embodiment of formula (II), $R^4$ is phenyl, wherein the phenyl is substituted with one, two, or three $R^5$, and $R^5$ is CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, —$NH_2$, —$NHC_{1-6}$-alkyl, and —$N(C_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR'''$, $SR'''$, $C(O)R'''$, $C(O)NR''R^o$, $C(O)OR'''$, $OC(O)R'''$, $OC(O)NR''R^o$, $NR''R^o$, $NR''C(O)R'''$, $S(O)R'''$, $S(O)NR''R^o$, $S(O)_2R'''$, $NR''S(O)_2R'''$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In yet another embodiment of formula (II), $R^7$ is $C_{1-6}$-alkyl, $C_{1-6}$ haloalkyl, or $C(O)R'''$; and $R'''$ is $C_{1-6}$ alkyl, $C_{1-6}$ haloalkyl, or $C_{3-8}$ cycloalkyl.

In one embodiment of formula (II), $R^4$ is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^g$, wherein the heterocycloalkyl is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR'''$, $SR'''$, $C(O)R'''$, $C(O)NR''R^o$, $C(O)OR'''$, $OC(O)R'''$, $OC(O)NR''R^o$, $NR''R^o$, $NR''C(O)R'''$, $S(O)R'''$, $S(O)NR''R^o$, $S(O)_2R'''$, $NR''S(O)_2R'''$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (II), the $R^5$ heterocycloalkyl is piperazinyl, diazepanyl, piperidinyl, pyrrolidinyl, morpholinyl, hexahydropyrrolo[1,2-a]pyrazinyl, oxopiperazinyl, (1S,4S)-2,5-diazabicyclo[2.2.1]hept-2-yl, (1R,4R)-2,5-diazabicyclo[2.2.1]hept-2-yl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, octahydro-2H-pyrido[1,2-a]pyrazin-2-yl, thiazolidin-2-yl, 4-oxo-1,3-thiazolidin-2-yl, (3R)-1-azabicyclo[2.2.2]oct-3yl, or thiomorpholinyl.

In another embodiment of formula (II), $R^4$ is

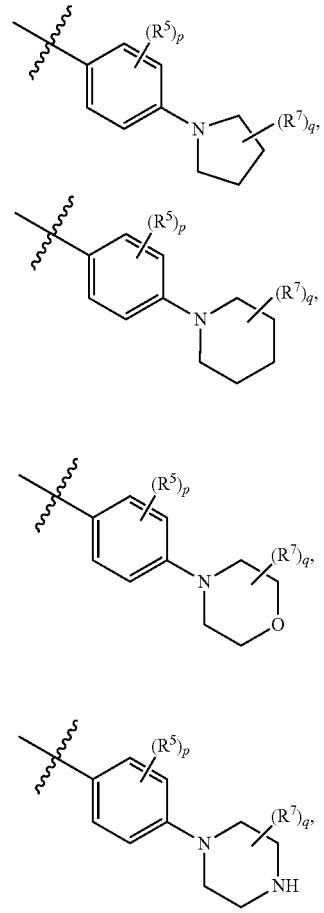

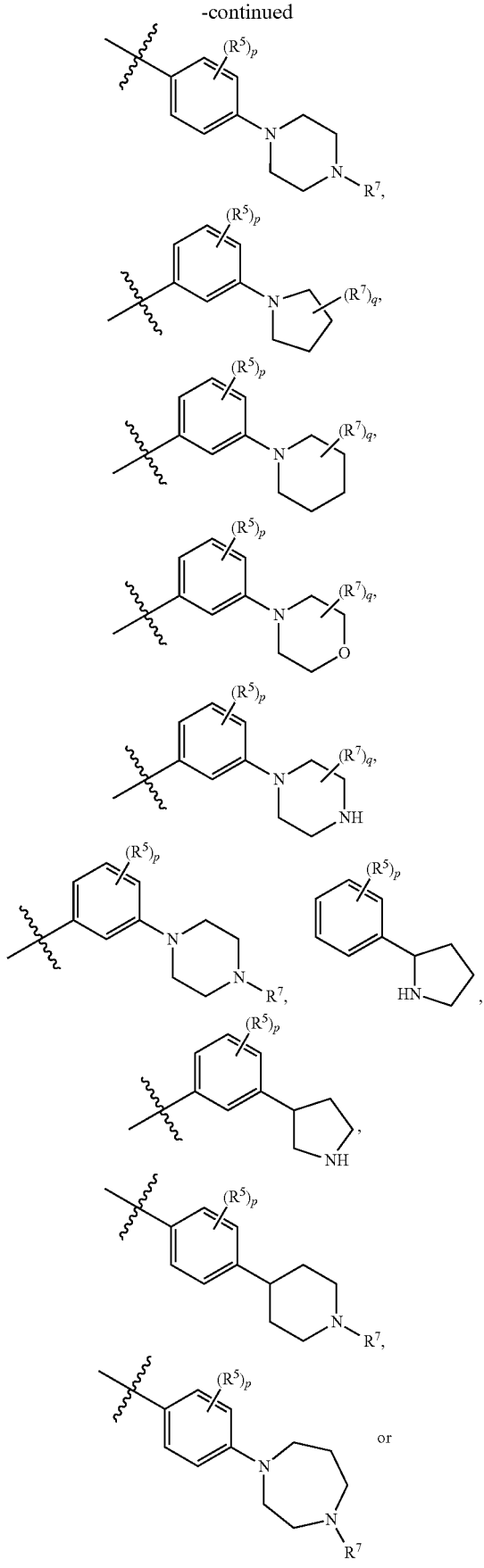

wherein $R^5$ is halo, $C_{1-6}$-alkyl, $C_{1-6}$ haloalkyl, or $OR^g$; p is 0 or 1; $R^7$ is CN, $NO_2$, halo, $C_{1-6}$-alkyl, $C_{1-6}$-haloalkyl, $OR^m$, $SR^m$, $C(O)R^m$, $C(O)NR''R^o$, $C(O)OR^m$, $NR''R^o$, $NR''C(O)R^m$, $S(O)_2R^m$, $NR''S(O)_2R^m$, or $S(O)_2NR'''R^o$; and q is 0 or 1.

In one embodiment of formula (II), $R^3$ is phenyl, wherein the phenyl is substituted with one substituent selected from the group consisting of $C_{1-6}$-alkyl, $C_{1-6}$-haloalkyl, halogen, and —$OR^d$;

$R^4$ is $R^5$ is halo, $C_{1-6}$-alkyl, $C_{1-6}$ haloalkyl, or $OR^g$; and p is 0 or 1.

In one embodiment of formula (II), $R^4$ is wherein $R^5$ is halo, $C_{1-6}$-alkyl, $C_{1-6}$ haloalkyl, or $OR^g$; $R^g$ is selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$C(O)C_{1-6}$-alkyl, —$S(O)_2C_{1-6}$-alkyl, —$NH_2$, —$NH(C_{1-6}$-alkyl), —$N(C_{1-6}$-alkyl$)_2$, and —$N(C_{1-6}$-alkyl)($C_{3-8}$-cycloalkyl); and $R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —NHC$_{1-6}$-alkyl, and —N(C$_{1-6}$-alkyl)$_2$, and wherein the aryl, C$_{3-8}$ cycloalkyl, heteroaryl, or heterocycloalkyl, alone or as part of another moiety, is optionally substituted with one or more substituents selected from the group consisting of halo, C$_{1-6}$-alkyl, C$_{1-6}$-haloalkyl, C$_{1-6}$-hydroxyalkyl, hydroxy, oxo, C$_{1-6}$-alkoxy, C$_{1-6}$-haloalkoxy, —C(O)C$_{1-6}$-alkyl, —S(O)$_2$C$_{1-6}$-alkyl, —NH$_2$, —NH(C$_{1-6}$-alkyl), N(C$_{1-6}$-alkyl)$_2$, and —N(C$_{1-6}$-alkyl)(C$_{3-8}$-cycloalkyl); p is 0, 1, or 2.

In one embodiment of formula (II), R$^4$ is a 5-16 membered monocyclic, bicyclic, or tricyclic heterocyclyl, wherein the heterocyclyl is optionally substituted with one or more R$^6$, and R$^6$ is CN, NO$_2$, halo, C$_{3-8}$ cycloalkyl, OR$^j$, SR$^j$, C(O)R$^j$, C(O)NR$^k$R$^l$, C(O)OR$^j$, NR$^k$R$^l$, NR$^k$C(O)R$^j$, S(O)$_2$R$^j$, NR$^k$S(O)$_2$R$^j$, or S(O)$_2$NR$^k$R$^l$, wherein the C$_{1-6}$-alkyl is optionally substituted with one or more substituents selected from the group consisting of CN, halo, hydroxy, C$_{1-6}$-alkoxy, heterocycloalkyl, cycloalkyl, heteroaryl, aryl, —NH$_2$, —NHC$_{1-6}$-alkyl, and —N(C$_{1-6}$-alkyl)$_2$; wherein the heterocycloalkyl, cycloalkyl, heteroaryl, aryl, alone or as part of another moiety, are optionally substituted with one, two or three substituents independently selected from CN, halo, heteroaryl, benzyl, and C$_{1-6}$ alkyl.

In one embodiment of formula (II), R$^4$ is a 4-8 membered monocyclic heterocyclyl. In another embodiment, R$^4$ is a 4-8 membered heterocycloalkyl or heterocycloalkenyl. In another embodiment, R$^4$ is a 5-7 membered heteroaryl. In yet another embodiment of formula (II), R$^4$ is pyrrolidinyl, tetrhydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxopyrrolidinyl, 2-oxopiperidinyl, 4-oxopiperidinyl, or 2,6-dioxopiperidinyl. In yet another embodiment of formula (I), R$^4$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, R$^4$ is unsubstituted. In another embodiment, R$^4$ is substituted with one, two, or three R$^6$, and R$^6$ is halo, C$_{1-6}$-alkyl, C$_{1-6}$-haloalkyl, OR$^j$, C(O)R$^j$, NR$^k$R$^l$, or S(O)$_2$R$^j$.

In one embodiment of formula (II), R$^4$ is a 7-11 membered bicyclic heterocyclyl. In another embodiment, R$^4$ is a 7-11 membered bicyclic heterocycloalkyl or bicyclic heterocycloalkenyl. In another embodiment, R$^4$ is a 7-11 membered bicyclic heteroaryl. In yet another embodiment, R$^4$ is 2,3-dihydro-2-oxo-1H-indolyl, hexahydropyrrolo[1,2-a]pyrazinyl, (1R,4R)-2,5-diazabicyclo[2.2.1]hept-2-yl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, benzisothiazolyl, benzisoxazolyl, benzodiazinyl, benzofurazanyl, benzothiopyranyl, octahydro-2H-pyrido[1,2-a]pyrazin-2-yl, benzotriazolyl, benzpyrazolyl, 1,3-benzodioxolyl, (3R)-1-azabicyclo[2.2.2]oct-3yl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, 4-oxo-1,4-dihydrocinnolin-6-yl, isochromanyl, isoindolinyl, naphthyridinyl, phthalazinyl, piperonyl, purinyl, pyridopyridyl, pyrrolotriazinyl, quinazolinyl, 1,2,3-benzothiadiazoly-5-yl, 1,3-benzothiazol-6-yl, tetrahydroquinolinyl, thienofuryl, thienopyridyl, [1,2-a]pyridine-2-yl, 2,3-dihydroimidazol[2,1-b][1,3]thiazol-6-yl, imidazo[2,1-b][1,3]thiazol-6-yl, 3-oxo-2,3-dihydro-1H-indazol-7-yl, 5,6,7,8-tetrahydro-1,6-naphthyridin-3-yl, 2,7-diazaspiro[3.5]non-7-yl, 2,6-diazaspiro[3.3]hept-2-yl, 2,6-diazaspiro[3.4]oct-2-yl, 2,7-diazaspiro[3.5]non-2-yl, 3,0-diazaspiro[5.5]undec-3-yl, (3aR,6aR)-hexahydropyrrolo[3,4-b]pyrrol-1(2H)-yl, 2,3,4,5-tetrahydro-1H-2-benzazepinyl, 2,3,4,5-tetrahydro-1H-3-benzazepinyl, 1,2,3,4-tetrahydroisoquinolin-7-yl, 1,2,3,4-tetrahydroquinolinyl, 4,4-dimethyl-1,2,3,4-tetrahydroisoquinolin-7-yl, 2,3-dihydro-1H-indol-5-yl, indolinyl, 2,3-dihydro-1H-indazolyl, isoindolinyl, 1,2,3,4-tetrahydroisoquinolin-6-yl, or thienothienyl. In one embodiment of formula (I), R$^4$ is unsubstituted. In another embodiment of formula (II), R$^4$ is substituted with one, two, or three R$^6$, and R$^6$ is CN, NO$_2$, halo, C$_{3-8}$ cycloalkyl, OR$^j$, SR$^j$, C(O)R$^j$, C(O)NR$^k$R$^l$, C(O)OR$^j$, NR$^k$R$^l$, NR$^k$C(O)R$^j$, S(O)$_2$R$^j$, NR$^k$S(O)$_2$R$^j$, or S(O)$_2$NR$^k$R$^l$, wherein the C$_{1-6}$-alkyl is optionally substituted with one or more substituents selected from the group consisting of CN, halo, hydroxy, C$_{1-6}$-alkoxy, heterocycloalkyl, cycloalkyl, heteroaryl, aryl, —NH$_2$, —NHC$_{1-6}$-alkyl, and —N(C$_{1-6}$-alkyl)$_2$; wherein the heterocycloalkyl, cycloalkyl, heteroaryl, aryl, alone or as part of another moiety, are optionally substituted with one, two or three substituents independently selected from CN, halo, heteroaryl, benzyl, and C$_{1-6}$ alkyl.

In one embodiment of formula (II), R$^4$ is

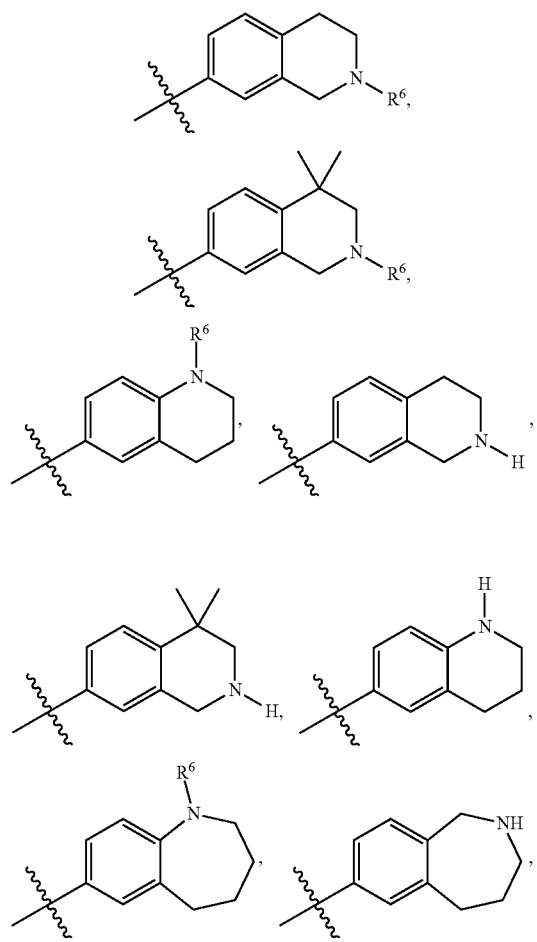

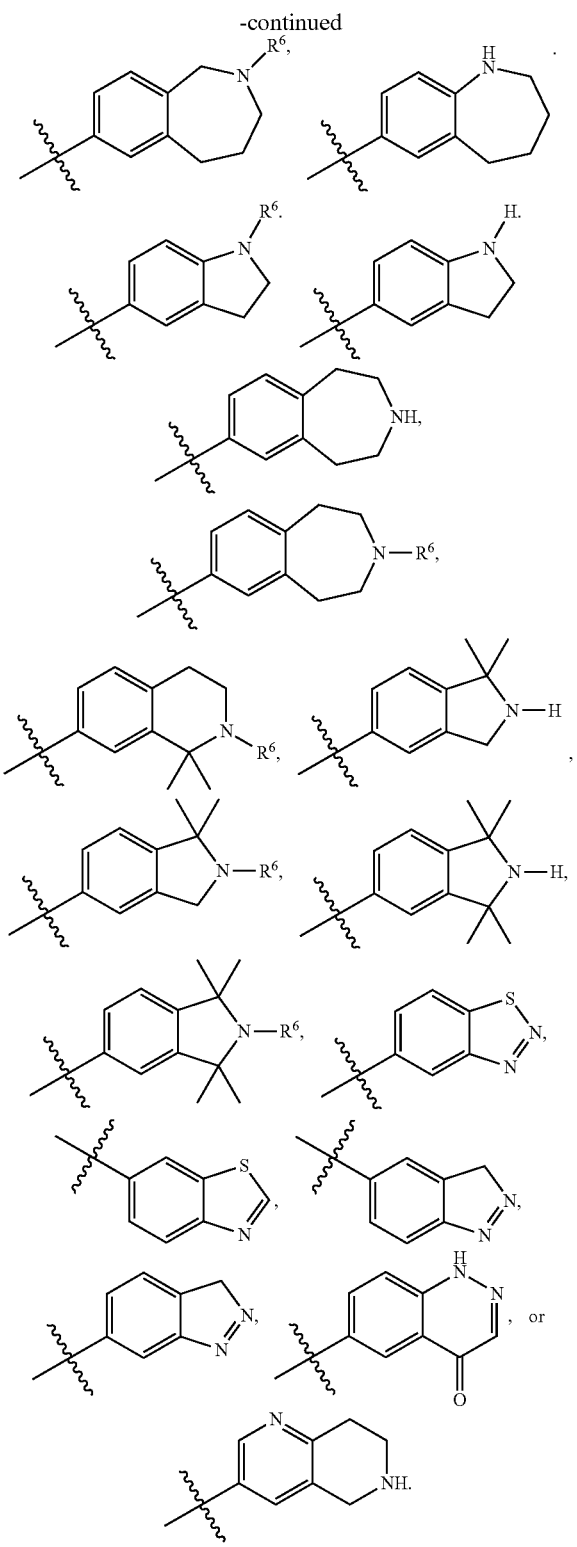

quinolin]-7'-yl. In one embodiment of formula (II), R⁴ is unsubstituted. In another embodiment of formula (II), R⁴ is substituted with one, two, or three R⁶, and R⁶ is halo, $C_{1-6}$-alkyl, $C_{1-6}$-haloalkyl, OR$^j$, C(O)R$^j$, NR$^k$R$^l$, or S(O)₂R$^j$.

In on embodiment of formula (II), R⁴ is

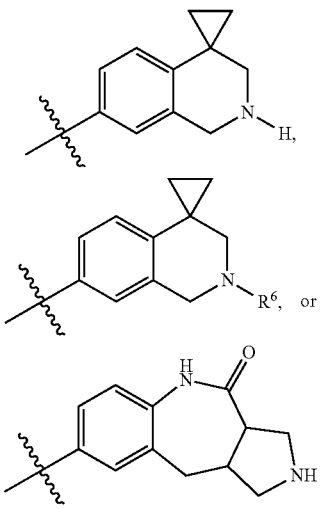

In one embodiment, the present invention is directed, in part, to a class of compounds having a structure of formula (IIa),

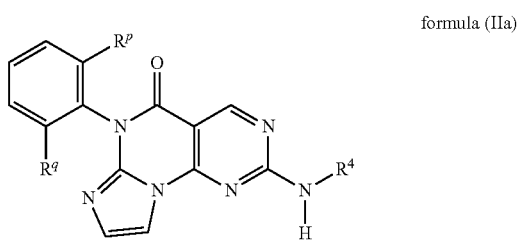

formula (IIa)

wherein R⁴ is as described in formula (II) and R$^q$ and R$^p$ are independently halo or hydrogen.

Embodiments of Formula (III)

In one embodiment, the present invention is directed, in part, to a class of compounds having a structure of formula (III),

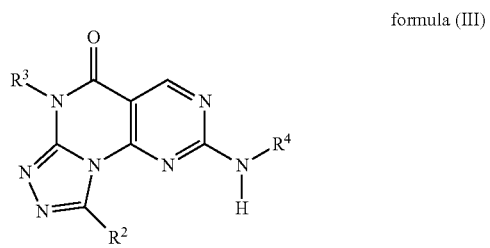

formula (III)

wherein R¹, R², R³, and R⁴ are as described in formula (I).

In one embodiment of formula (III), R² is H. In another embodiment of formula (III), R² is $C_{1-6}$ alkyl.

In one embodiment of formula (III), R³ is aryl, wherein the aryl is optionally substituted with one or more substituents In one embodiment of formula (II), R⁴ is 10-15 membered tricyclic heterocyclyl. In another embodiment, R⁴ is a 10-15 membered tricyclic heterocycloalkyl or tricyclic heterocycloalkenyl. In another embodiment, R⁴ is a 10-15 membered tricyclic heteroaryl. In one embodiment of formula (II), R⁴ is 5-oxo-5,6-dihydroimidazo[1,2-a]pyrimido[5,4-e]pyrimidiny-2-yl or 2',3'-dihydro-1'H-spiro[cyclopropane-1,4'-isoselected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, $-OR^d$, $-C(O)R^d$, $-C(O)OR^d$, $-OC(O)R^d$, $-SR^d$, $-S(O)R^d$, $-SO_2R^d$, $-NR^eR^f$, $-NHC(O)R^e$, $-NHC(O)NHR^e$, $-NHC(O)OR^e$, $-NHSO_2R^d$, $-C(O)NHR^e$, and $-SO_2NHNR^e$. In another embodiment of formula (III), $R^3$ is aryl, wherein the aryl is selected from the group consisting of phenyl, naphthyl, indenyl, indanyl, and tetrahydronaphthyl. In yet another embodiment of formula (III), $R^3$ is phenyl. In yet another embodiment of formula (III), $R^3$ is phenyl, which is optionally substituted with one or more substituents selected from the group consisting of halogen, $C_{1-6}$ alkyl, $C_{1-6}$ haloalkyl, $-OC_{1-6}$ alkyl, or $-OC_{1-6}$ haloalkyl. In another embodiment of formula (III), $R^3$ is phenyl which is substituted with one substituent selected from the group consisting of halogen, $C_{1-6}$ alkyl, $C_{1-6}$ haloalkyl, $-OC_{1-6}$ alkyl, and $-OC_{1-6}$ haloalkyl. In yet another embodiment of formula (III), $R^3$ is

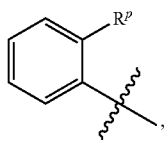

wherein $R^p$ is selected from the group consisting of halogen, $C_{1-6}$ alkyl, $C_{1-6}$ haloalkyl, $-OC_{1-6}$ alkyl, and $-OC_{1-6}$ haloalkyl. In yet another embodiment of formula (III), $R^p$ is halogen. In yet another embodiment of formula (III), $R^p$ is halogen. In yet another embodiment of formula (I), $R^3$ is

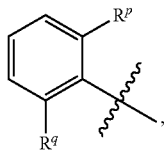

wherein $R^p$ and $R^q$ are independently selected from the group consisting of halogen, $C_{1-6}$ alkyl, $C_{1-6}$ haloalkyl, $-OC_{1-6}$ alkyl, or $-OC_{1-6}$ haloalkyl. In yet another embodiment of formula (III), both $R^p$ and $R^q$ are halogen.

In one embodiment of formula (III), $R^4$ is phenyl, naphthyl, tetrahydronaphthyl, indenyl, or indanyl, wherein the phenyl, naphthyl, tetrahydronaphthyl, indenyl, or indanyl is optionally substituted with one or more $R^5$; and CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, $-NH_2$, $-NHC_{1-6}$-alkyl, and $-N(C_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $-NH_2$, $-NHC_{1-6}$-alkyl, and $-N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (III), $R^4$ is naphthyl, tetrahydronaphthyl, indenyl, or indanyl, wherein the naphthyl, tetrahydronaphthyl, indenyl, or indanyl is unsubstituted. In yet another embodiment of formula (III), $R^4$ is naphthyl, tetrahydronaphthyl, indenyl, or indanyl, wherein the naphthyl, tetrahydronaphthyl, indenyl, or indanyl are substituted with one, two, or three substituents selected from the group consisting of CN, $NO_2$, halo, $C_{1-6}$-alkyl, $C_{1-6}$-haloalkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, and $S(O)_2NR^hR^i$.

In one embodiment of formula (III), $R^4$ is phenyl. In another embodiment of formula (III), $R^4$ is phenyl, wherein the phenyl is unsubstituted. In another embodiment of formula (III), $R^4$ is phenyl, wherein the phenyl is substituted with one, two, or three $R^5$, and $R^5$ is CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, $-NH_2$, $-NHC_{1-6}$-alkyl, and $-N(C_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $-NH_2$, $-NHC_{1-6}$-alkyl, and $-N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In yet another embodiment of formula (II), $R^7$ is $C_{1-6}$-alkyl, $C_{1-6}$ haloalkyl, or $C(O)R^m$; and $R^m$ is $C_{1-6}$ alkyl, $C_{1-6}$ haloalkyl, or $C_{3-8}$ cycloalkyl.

In one embodiment of formula (III), $R^4$ is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^g$, wherein the heterocycloalkyl is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, $-NH_2$, $-NHC_{1-6}$-alkyl, and $-N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (III), the $R^5$ heterocycloalkyl is piperazinyl, diazepanyl, piperidinyl, pyrrolidinyl, morpholinyl, hexahydropyrrolo[1,2-a]pyrazinyl, oxopiperazinyl, (1S,4S)-2,5-diazabicyclo[2.2.1]hept-2-yl, (1R,4R)-2,5-diazabicyclo[2.2.1]hept-2-yl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, octahydro-2H-pyrido[1,2-a]pyrazin-2-yl, thiazolidin-2-yl, 4-oxo-1,3-thiazolidin-2-yl, (3R)-1-azabicyclo[2.2.2]oct-3yl, or thiomorpholinyl.

In another embodiment of formula (III), R⁴ is

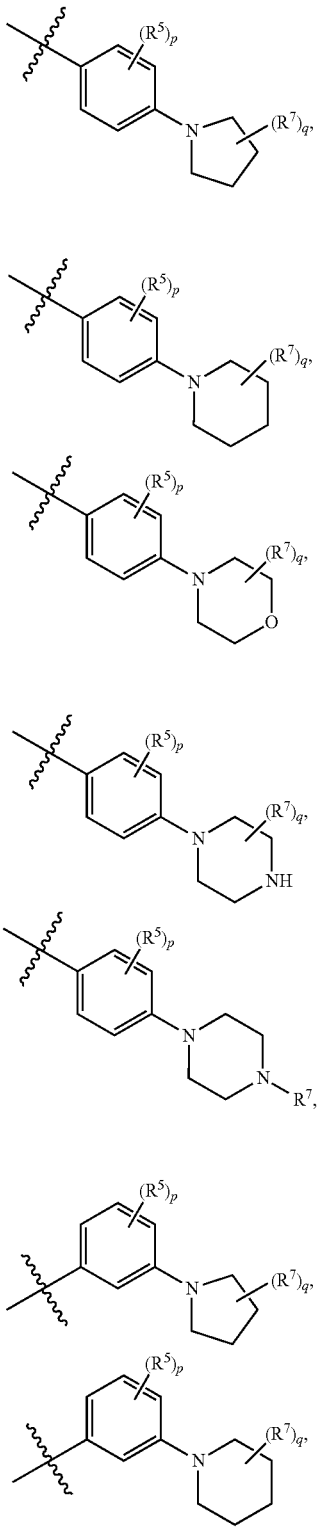
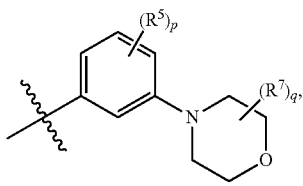
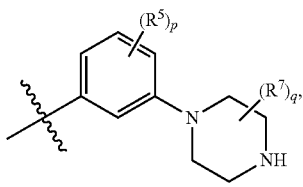
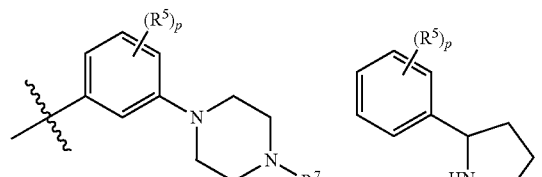
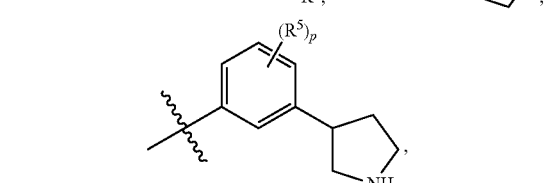
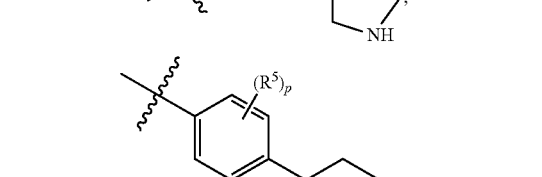
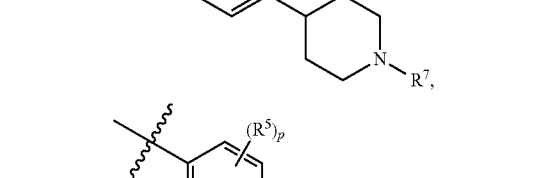
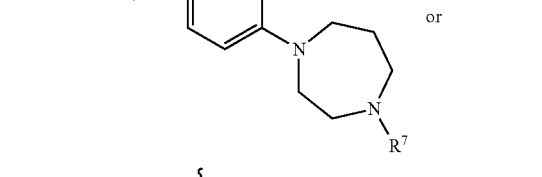
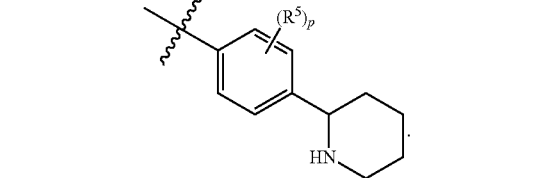

wherein R⁵ is halo, $C_{1-6}$-alkyl, $C_{1-6}$ haloalkyl, or OR$^g$; p is 0 or 1; R⁷ is CN, NO₂, halo, $C_{1-6}$-alkyl, $C_{1-6}$-haloalkyl, OR$^m$, SR$^m$, C(O)R$^m$, C(O)NR$^n$R$^o$, C(O)OR$^m$, NR$^n$R$^o$, NR$^n$C(O)R$^m$, S(O)₂R$^m$, NR$^n$S(O)₂R$^m$, or S(O)₂NR$^m$R$^o$; and q is 0 or 1.

In one embodiment of formula (III), R³ is phenyl, wherein the phenyl is substituted with one substituent selected from the group consisting of $C_{1-6}$-alkyl, $C_{1-6}$-haloalkyl, halogen, and —OR$^d$;

$R^4$ is

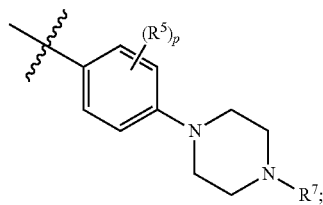

$R^5$ is halo, $C_{1-6}$-alkyl, $C_{1-6}$ haloalkyl, or $OR^g$; and p is 0 or 1.

In one embodiment of formula (III), $R^4$ is

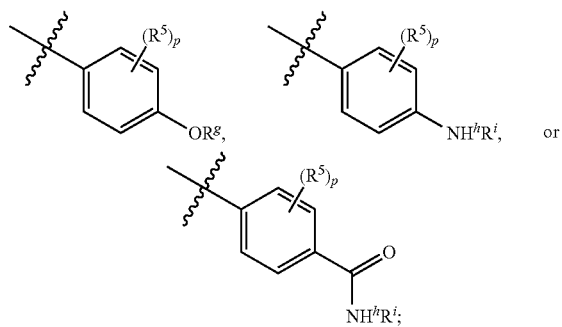

wherein $R^5$ is halo, $C_{1-6}$-alkyl, $C_{1-6}$ haloalkyl, or $OR^g$; $R^g$ is selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)$_2C_{1-6}$-alkyl, —$NH_2$, —NH($C_{1-6}$-alkyl), —N($C_{1-6}$-alkyl)$_2$, and —N($C_{1-6}$-alkyl)($C_{3-8}$-cycloalkyl); and $R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —$NHC_{1-6}$-alkyl, and —$N(C_{1-6}$-alkyl)$_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)$_2$$C_{1-6}$-alkyl, —$NH_2$, —NH($C_{1-6}$-alkyl), N($C_{1-6}$-alkyl)$_2$, and —N($C_{1-6}$-alkyl)($C_{3-8}$-cycloalkyl); p is 0, 1, or 2.

In one embodiment of formula (III), $R^4$ is a 5-16 membered monocyclic, bicyclic, or tricyclic heterocyclyl, wherein the heterocyclyl is optionally substituted with one or more $R^6$, and $R^6$ is CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, —$NH_2$, —$NHC_{1-6}$-alkyl, and —$N(C_{1-6}$-alkyl)$_2$; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl.

In one embodiment of formula (III), $R^4$ is a 4-8 membered monocyclic heterocyclyl. In another embodiment, $R^4$ is a 4-8 membered heterocycloalkyl or heterocycloalkenyl. In another embodiment, $R^4$ is a 5-7 membered heteroaryl. In yet another embodiment of formula (III), $R^4$ is pyrrolidinyl, tetrhydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxopyrrolidinyl, 2-oxopiperidinyl, 4-oxopiperidinyl, or 2,6-dioxopiperidinyl. In yet another embodiment of formula (I), $R^4$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, $R^4$ is unsubstituted. In another embodiment, $R^4$ is substituted with one, two, or three $R^6$, and $R^6$ is halo, $C_{1-6}$-alkyl, $C_{1-6}$-haloalkyl, $OR^j$, $C(O)R^j$, $NR^kR^l$, or $S(O)_2R^j$.

In one embodiment of formula (III), $R^4$ is a 7-11 membered bicyclic heterocyclyl. In another embodiment, $R^4$ is a 7-11 membered bicyclic heterocycloalkyl or bicyclic heterocycloalkenyl. In another embodiment, $R^4$ is a 7-11 membered bicyclic heteroaryl. In yet another embodiment, $R^4$ is 2,3-dihydro-2-oxo-1H-indolyl, hexahydropyrrolo[1,2-a]pyrazinyl, (1R,4R)-2,5-diazabicyclo[2.2.1]hept-2-yl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, benzisothiazolyl, benzisoxazolyl, benzodiazinyl, benzofurazanyl, benzothiopyranyl, octahydro-2H-pyrido[1,2-a]pyrazin-2-yl, benzotriazolyl, benzpyrazolyl, 1,3-benzodioxolyl, (3R)-1-azabicyclo[2.2.2]oct-3yl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, 4-oxo-1,4-dihydrocinnolin-6-yl, isochromanyl, isoindolinyl, naphthyridinyl, phthalazinyl, piperonyl, purinyl, pyridopyridyl, pyrrolotriazinyl, quinazolinyl, 1,2,3-benzothiadiazolyl-5-yl, 1,3-benzothiazol-6-yl, tetrahydroquinolinyl, thienofuryl, thienopyridyl, [1,2-a]pyridine-2-yl, 2,3-dihydroimidazol[2,1-b][1,3]thiazol-6-yl, imidazo[2,1-b][1,3]thiazol-6-yl, 3-oxo-2,3-dihydro-1H-indazol-7-yl, 5,6,7,8-tetrahydro-1,6-naphthyridin-3-yl, 2,7-diazaspiro[3.5]non-7-yl, 2,6-diazaspiro[3.3]hept-2-yl, 2,6-diazaspiro[3.4]oct-2-yl, 2,7-diazaspiro[3.5]non-2-yl, 3,0-diazaspiro[5.5]undec-3-yl, (3aR, 6aR)-hexahydropyrrolo[3,4-b]pyrrol-1(2H)-yl, 2,3,4,5-tetrahydro-1H-2-benzazepinyl, 2,3,4,5-tetrahydro-1H-3-benzazepinyl, 1,2,3,4-tetrahydroisoquinolin-7-yl, 1,2,3,4-tetrahydroquinolinyl, 4,4-dimethyl-1,2,3,4-tetrahydroisoquinolin-7-yl, 2,3-dihydro-1H-indol-5-yl, indolinyl, 2,3-dihydro-1H-indazolyl, isoindolinyl, 1,2,3,4-tetrahydroisoquinolin-6-yl, or thienothenyl. In one embodiment of formula (I), $R^4$ is unsubstituted. In another embodiment of formula (II), $R^4$ is substituted with one, two, or three $R^6$, and $R^6$ is CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, —NH$_2$, —NHC$_{1-6}$-alkyl, and —N(C$_{1-6}$-alkyl)$_2$; wherein the heterocycloalkyl, cycloalkyl, heteroaryl, aryl, alone or as part of another moiety, are optionally substituted with one, two or three substituents independently selected from CN, halo, heteroaryl, benzyl, and C$_{1-6}$ alkyl.

In one embodiment of formula (III), $R^4$ is

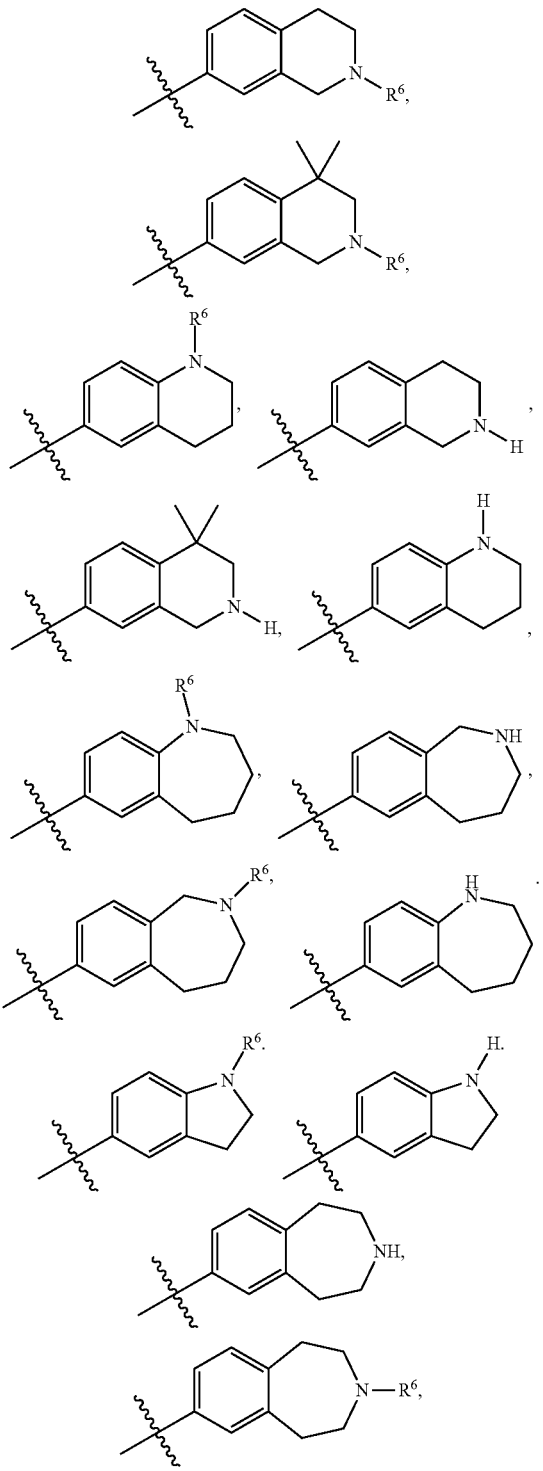

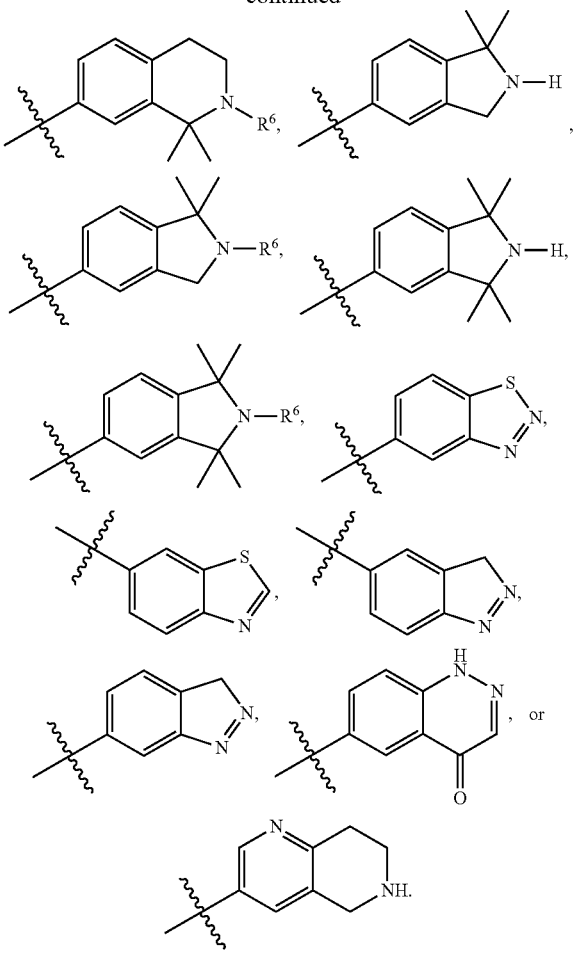

In one embodiment of formula (III), $R^4$ is 10-15 membered tricyclic heterocyclyl. In another embodiment, $R^4$ is a 10-15 membered tricyclic heterocycloalkyl or tricyclic heterocycloalkenyl. In another embodiment, $R^4$ is a 10-15 membered tricyclic heteroaryl. In one embodiment of formula (III), $R^4$ is 5-oxo-5,6-dihydroimidazo[1,2-a]pyrimido[5,4-e]pyrimidiny-2-yl or 2',3'-dihydro-1'H-spiro[cyclopropane-1,4'-isoquinolin]-7'-yl. In one embodiment of formula (III), $R^4$ is unsubstituted. In another embodiment of formula (III), $R^4$ is substituted with one, two, or three $R^6$, and $R^6$ is halo, C$_{1-6}$-alkyl, C$_{1-6}$-haloalkyl, OR$^j$, C(O)R$^j$, NR$^k$R$^l$, or S(O)$_2$R$^j$.

In on embodiment of formula (III), $R^4$ is

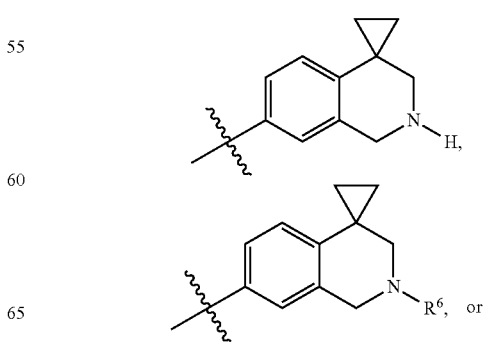

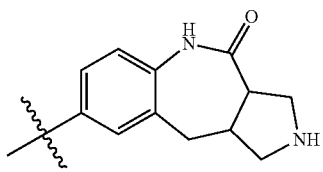

In one embodiment, the present invention is directed, in part, to a class of compounds having a structure of formula (IIIa), formula (IIIa)

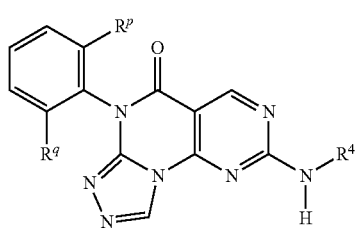

wherein $R^4$ are as described in formula (III) and $R^p$ and $R^q$ are independently halo or hydrogen.

Embodiments of Formula (IV)

In one embodiment, the present invention is directed, in part, to a class of compounds having a structure of formula (IV), formula (IV)

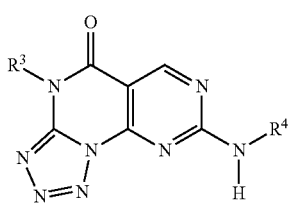

wherein $R^1$, $R^2$, $R^3$, and $R^4$ are as described in formula (I).

In one embodiment of formula (IV), $R^3$ is aryl, wherein the aryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —NHC(O)$R^e$, —NHC(O)NHR$^e$, —NHC(O)OR$^e$, —NHSO$_2$R$^d$, —C(O)NHR$^e$, and —SO$_2$NHNR$^e$. In another embodiment of formula (IV), $R^3$ is aryl, wherein the aryl is selected from the group consisting of phenyl, naphthyl, indenyl, indanyl, and tetrahydronaphthyl. In yet another embodiment of formula (IV), $R^3$ is phenyl. In yet another embodiment of formula (IV), $R^3$ is phenyl, which is optionally substituted with one or more substituents selected from the group consisting of halogen, $C_{1-6}$ alkyl, $C_{1-6}$ haloalkyl, —$OC_{1-6}$ alkyl, and —$OC_{1-6}$ haloalkyl. In another embodiment of formula (IV), $R^3$ is phenyl which is substituted with one substituent selected from the group consisting of halogen, $C_{1-6}$ alkyl, $C_{1-6}$ haloalkyl, —$OC_{1-6}$ alkyl, and —$OC_{1-6}$ haloalkyl. In yet another embodiment of formula (IV), $R^3$ is

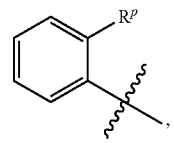

wherein $R^p$ is selected from the group consisting of halogen, $C_{1-6}$ alkyl, $C_{1-6}$ haloalkyl, —$OC_{1-6}$ alkyl, and —$OC_{1-6}$ haloalkyl. In yet another embodiment of formula (IV), $R^p$ is halogen. In yet another embodiment of formula ((IV), $R^p$ is halogen. In yet another embodiment of formula ((IV), $R^p$ is halogen. In yet another embodiment of formula (IV), $R^3$ is

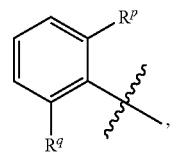

wherein $R^p$ and $R^q$ are independently selected from the group consisting of halogen, $C_{1-6}$ alkyl, $C_{1-6}$ haloalkyl, —$OC_{1-6}$ alkyl, or —$OC_{1-6}$ haloalkyl. In yet another embodiment of formula ((IV), both $R^p$ and $R^q$ are halogen.

In one embodiment of formula ((IV), $R^4$ is phenyl, naphthyl, tetrahydronaphthyl, indenyl, or indanyl, wherein the phenyl, naphthyl, tetrahydronaphthyl, indenyl, or indanyl is optionally substituted with one or more $R^5$; and CN, NO$_2$, halo, $C_{1-6}$-alkyl, OR$^g$, SR$^g$, C(O)R$^g$, C(O)NR$^h$R$^i$, C(O)OR$^g$, NR$^h$R$^i$, NR$^h$C(O)R$^g$, S(O)$_2$R$^g$, NR$^h$S(O)$_2$R$^g$, S(O)$_2$NR$^h$R$^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, S(O)$_2$NH(C$_{1-6}$-alkyl), $C_{1-6}$-alkoxy, heterocycloalkyl, cycloalkyl, heteroaryl, aryl, —NH$_2$, —NHC$_{1-6}$-alkyl, and —N(C$_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, NO$_2$, halo, oxo, $C_{1-6}$ alkyl, aryl, $C_{3-8}$ cycloalkyl, heteroaryl, heterocycloalkyl, OR$^m$, SR$^m$, C(O)R$^m$, C(O)NR″R$^o$, C(O)OR$^m$, OC(O)R$^m$, OC(O)NR″R$^o$, NR″R$^o$, NR″C(O)R$^m$, S(O)R$^m$, S(O)NR″R$^o$, S(O)$_2$R$^m$, NR″S(O)$_2$R$^m$, or S(O)$_2$NR″R$^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —NH$_2$, —NHC$_{1-6}$-alkyl, and —N(C$_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (IV), $R^4$ is naphthyl, tetrahydronaphthyl, indenyl, or indanyl, wherein the naphthyl, tetrahydronaphthyl, indenyl, or indanyl is unsubstituted. In yet another embodiment of formula (IV), $R^4$ is naphthyl, tetrahydronaphthyl, indenyl, or indanyl, wherein the naphthyl, tetrahydronaphthyl, indenyl, or indanyl are substituted with one, two, or three substituents selected from the group consisting of CN, NO$_2$, halo, $C_{1-6}$-alkyl, $C_{1-6}$-haloalkyl, OR$^g$, SR$^g$, C(O)R$^g$, C(O)NR$^h$R$^i$, C(O)OR$^g$, NR$^h$R$^i$, NR$^h$C(O)R$^g$, S(O)$_2$R$^g$, NR$^h$S(O)$_2$R$^g$, and S(O)$_2$NR$^h$R$^i$.

In one embodiment of formula (IV), $R^4$ is phenyl. In another embodiment of formula (IV), $R^4$ is phenyl, wherein the phenyl is unsubstituted. In another embodiment of formula (IV), $R^4$ is phenyl, wherein the phenyl is substituted with one, two, or three $R^5$, and $R^5$ is CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, —$NH_2$, —$NHC_{1-6}$-alkyl, and —$N(C_{1-6}$-alkyl)$_2$; wherein the aryl, cycloalkyl, heteroaryl, or heterocycloalkyl, alone or as part of another moiety, is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In yet another embodiment of formula (IV), $R^7$ is $C_{1-6}$-alkyl, $C_{1-6}$ haloalkyl, or $C(O)R^m$; and $R^m$ is $C_{1-6}$ alkyl, $C_{1-6}$ haloalkyl, or $C_{3-8}$ cycloalkyl.

In one embodiment of formula (IV), $R^4$ is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^g$, wherein the heterocycloalkyl is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl)$_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl. In another embodiment of formula (IV), the $R^5$ heterocycloalkyl is piperazinyl, diazepanyl, piperidinyl, pyrrolidinyl, morpholinyl, hexahydropyrrolo[1,2-a]pyrazinyl, oxopiperazinyl, (1S,4S)-2,5-diazabicyclo[2.2.1]hept-2-yl, (1R,4R)-2,5-diazabicyclo[2.2.1]hept-2-yl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, octahydro-2H-pyrido[1,2-a]pyrazin-2-yl, thiazolidin-2-yl, 4-oxo-1,3-thiazolidin-2-yl, (3R)-1-azabicyclo[2.2.2]oct-3yl, or thiomorpholinyl.

In another embodiment of formula (IV), $R^4$ is

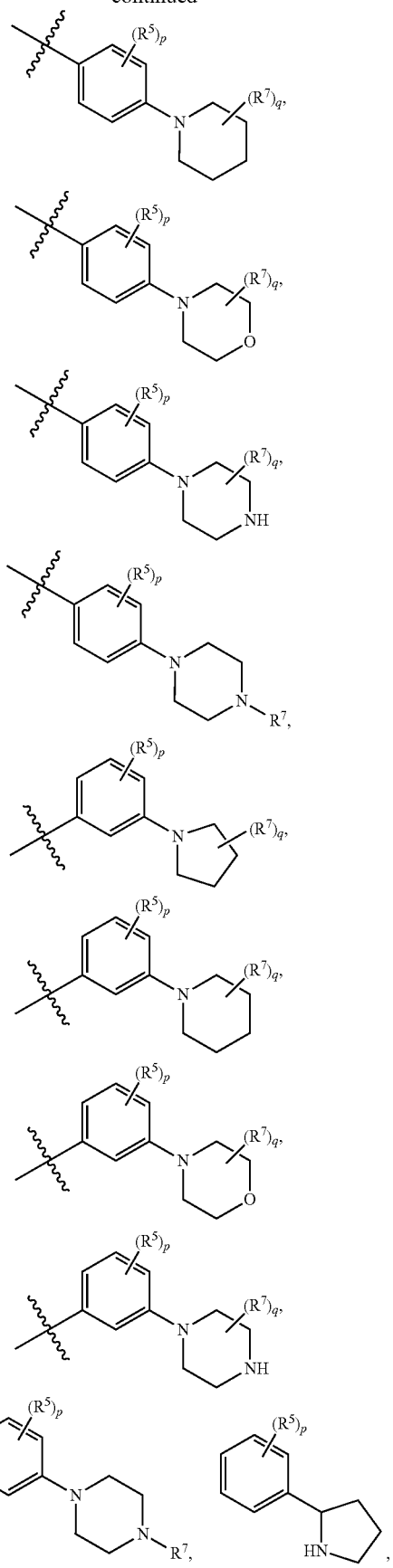

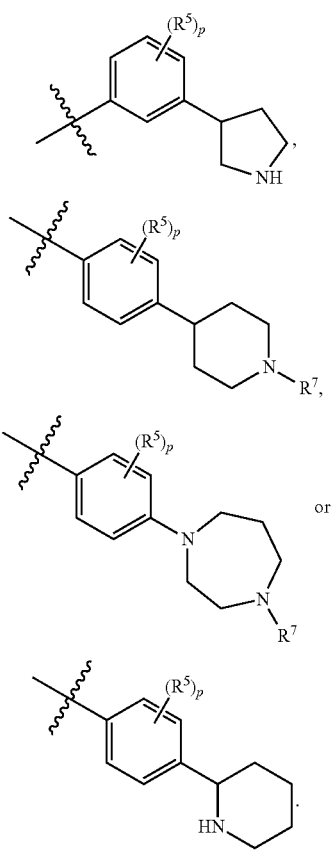

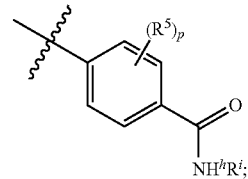

wherein $R^5$ is halo, $C_{1-6}$-alkyl, $C_{1-6}$ haloalkyl, or $OR^g$; p is 0 or 1; $R^7$ is CN, $NO_2$, halo, $C_{1-6}$-alkyl, $C_{1-6}$-haloalkyl, $OR^m$, $SR^m$, $C(O)R^m$, $C(O)NR''R^o$, $C(O)OR^m$, $NR''R^o$, $NR''C(O)R^m$, $S(O)_2R^m$, $NR''S(O)_2R^m$, or $S(O)_2NR'''R^o$; and q is 0 or 1.

In one embodiment of formula (IV), $R^3$ is phenyl, wherein the phenyl is substituted with one substituent selected from the group consisting of $C_{1-6}$-alkyl, $C_{1-6}$-haloalkyl, halogen, and $—OR^d$;

$R^4$ is

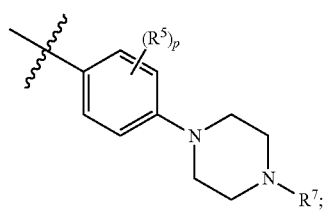

$R^5$ is halo, $C_{1-6}$-alkyl, $C_{1-6}$ haloalkyl or $OR^g$; and p is 0 or 1.

In one embodiment of formula (IV), $R^4$ is

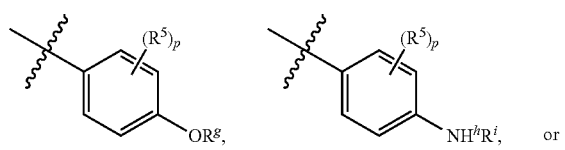

wherein $R^5$ is halo, $C_{1-6}$-alkyl, $C_{1-6}$ haloalkyl, or $OR^g$; $R^g$ is selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, $—NH_2$, $—NHC_{1-6}$-alkyl, and $—N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $—C(O)C_{1-6}$-alkyl, $—S(O)_2C_{1-6}$-alkyl, $—NH_2$, $—NH(C_{1-6}$-alkyl), $—N(C_{1-6}$-alkyl$)_2$, and $—N(C_{1-6}$-alkyl)($C_{3-8}$-cycloalkyl); and $R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, $—NH_2$, $—NHC_{1-6}$-alkyl, and $—N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, $—C(O)C_{1-6}$-alkyl, $—S(O)_2C_{1-6}$-alkyl, $—NH_2$, $—NH(C_{1-6}$-alkyl), $N(C_{1-6}$-alkyl$)_2$, and $—N(C_{1-6}$-alkyl)($C_{3-8}$-cycloalkyl); p is 0, 1, or 2.

In one embodiment of formula (IV), $R^4$ is a 5-16 membered monocyclic, bicyclic, or tricyclic heterocyclyl, wherein the heterocyclyl is optionally substituted with one or more $R^6$, and $R^6$ is CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, $—NH_2$, $—NHC_{1-6}$-alkyl, and $—N(C_{1-6}$-alkyl$)_2$; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl.

In one embodiment of formula (IV), $R^4$ is a 4-8 membered monocyclic heterocyclyl. In another embodiment, $R^4$ is a 4-8 membered heterocycloalkyl or heterocycloalkenyl. In another embodiment, $R^4$ is a 5-7 membered heteroaryl. In yet another embodiment of formula (IV), $R^4$ is pyrrolidinyl, tetrhydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxypyrrolidinyl, 2-oxopiperidinyl, 4-oxopiperidinyl, or 2,6-dioxopiperidinyl. In yet another embodiment of formula (I), $R^4$ is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, $R^4$ is unsubstituted. In another embodiment, $R^4$ is substituted with one, two, or three $R^6$, and $R^6$ is halo, $C_{1-6}$-alkyl, $C_{1-6}$-haloalkyl, $OR^j$, $C(O)R^j$, $NR^kR^l$, or $S(O)_2R^j$.

In one embodiment of formula (IV), $R^4$ is a 7-11 membered bicyclic heterocyclyl. In another embodiment, $R^4$ is a 7-11 membered bicyclic heterocycloalkyl or bicyclic heterocycloalkenyl. In another embodiment, $R^4$ is a 7-11 membered bicyclic heteroaryl. In yet another embodiment, $R^4$ is 2,3-dihydro-2-oxo-1H-indolyl, hexahydropyrrolo[1,2-a]pyrazinyl, (1R,4R)-2,5-diazabicyclo[2.2.1]hept-2-yl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl, dihydroisoindolyl, dihydroquinazolinyl, 3,4-dihydro-4-oxo-quinazolinyl, 6-oxo-1,4,5,6-tetrahydropyridazin-3-yl, octahydro-2H-quinolizinyl, 3,7-diazabicyclo[3.3.1]non-3-yl, (8aR)-hexahydropyrrolo[1,2-a]pyrazin-2(1H)-yl, benzisothiazolyl, benzisoxazolyl, benzodiazinyl, benzofurazanyl, benzothiopyranyl, octahydro-2H-pyrido[1,2-a]pyrazin-2-yl, benzotriazolyl, benzpyrazolyl, 1,3-benzodioxolyl, (3R)-1-azabicyclo[2.2.2]oct-3yl, dihydrobenzofuryl, dihydrobenzothienyl, dihydrobenzothiopyranyl, dihydrobenzothiopyranyl sulfone, dihydrobenzopyranyl, dihydrobenzoxazinyl, 3-oxo-3,4-dihydro-1,4-benzoxazinyl, indolinyl, indazolyl, 4-oxo-1,4-dihydrocinnolin-6-yl, isochromanyl, isoindolinyl, naphthyridinyl, phthalazinyl, piperonyl, purinyl, pyridopyridyl, pyrrolotriazinyl, quinazolinyl, 1,2,3-benzothiadiazoly-5-yl, 1,3-benzothiazol-6-yl, tetrahydroquinolinyl, thienofuryl, thienopyridyl, [1,2-a]pyridine-2-yl, 2,3-dihydroimidazol[2,1-b][1,3]thiazol-6-yl, imidazo[2,1-b][1,3]thiazol-6-yl, 3-oxo-2,3-dihydro-1H-indazol-7-yl, 5,6,7,8-tetrahydro-1,6-naphthyridin-3-yl, 2,7-diazaspiro[3.5]non-7-yl, 2,6-diazaspiro[3.3]hept-2-yl, 2,6-diazaspiro[3.4]oct-2-yl, 2,7-diazaspiro[3.5]non-2-yl, 3,0-diazaspiro[5.5]undec-3-yl, (3aR, 6aR)-hexahydropyrrolo[3,4-b]pyrrol-1(2H)-yl, 2,3,4,5-tetrahydro-1H-2-benzazepinyl, 2,3,4,5-tetrahydro-1H-3-benzazepinyl, 1,2,3,4-tetrahydroisoquinolin-7-yl, 1,2,3,4-tetrahydroquinolinyl, 4,4-dimethyl-1,2,3,4-tetrahydroisoquinolin-7-yl, 2,3-dihydro-1H-indol-5-yl, indolinyl, 2,3-dihydro-1H-indazolyl, isoindolinyl, 1,2,3,4-tetrahydroisoquinolin-6-yl, or thienothienyl. In one embodiment of formula (I), $R^4$ is unsubstituted. In another embodiment of formula (II), $R^4$ is substituted with one, two, or three $R^6$, and $R^6$ is CN, $NO_2$, halo, $C_{3-8}$ cycloalkyl, $OR^j$, $SR^j$, $C(O)R^j$, $C(O)NR^kR^l$, $C(O)OR^j$, $NR^kR^l$, $NR^kC(O)R^j$, $S(O)_2R^j$, $NR^kS(O)_2R^j$, or $S(O)_2NR^kR^l$, wherein the $C_{1-6}$-alkyl is optionally substituted with one or more substituents selected from the group consisting of CN, halo, hydroxy, $C_{1-6}$-alkoxy, heterocycloalkyl, cycloalkyl, heteroaryl, aryl, —$NH_2$, —$NHC_{1-6}$-alkyl, and —$N(C_{1-6}$-alkyl$)_2$; wherein the heterocycloalkyl, cycloalkyl, heteroaryl, aryl, alone or as part of another moiety, are optionally substituted with one, two or three substituents independently selected from CN, halo, heteroaryl, benzyl, and $C_{1-6}$ alkyl.

In one embodiment of formula (IV), $R^4$ is

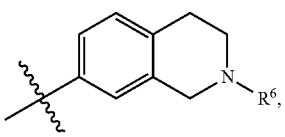

-continued

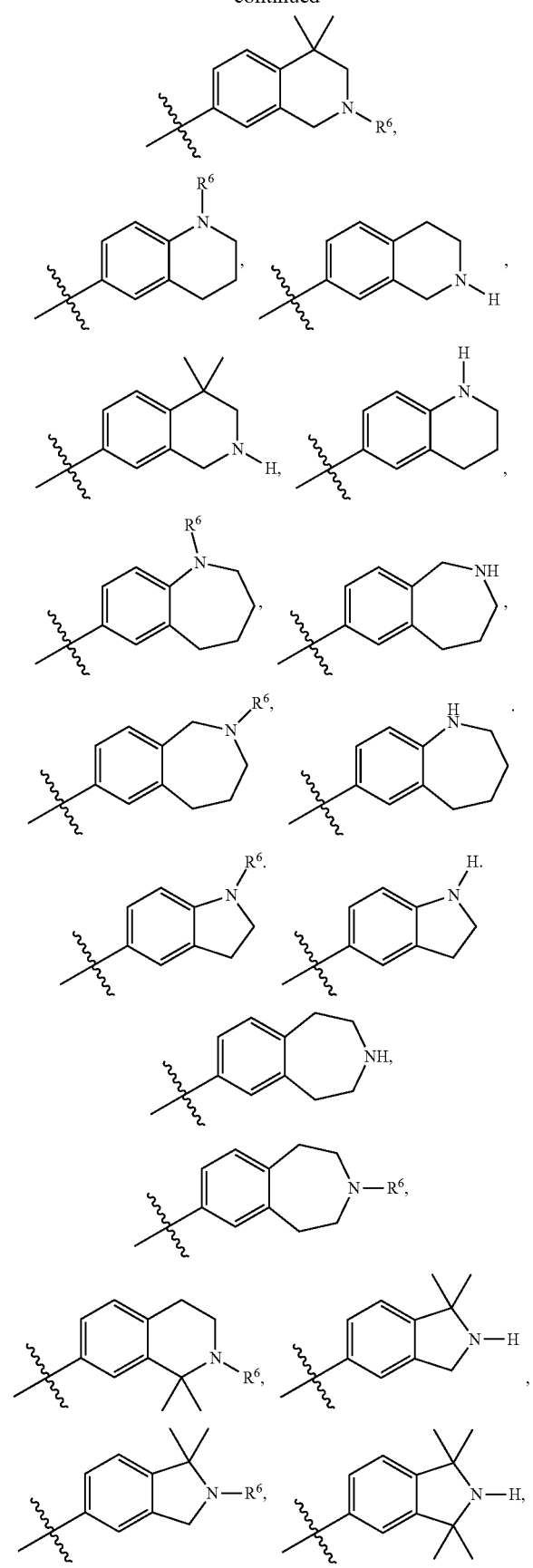

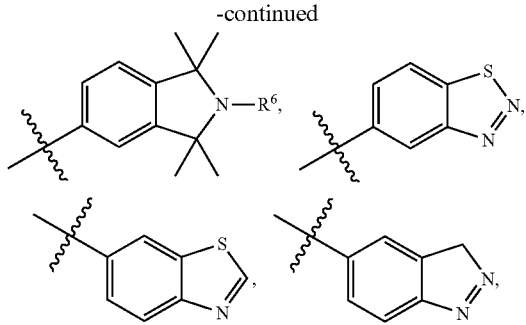
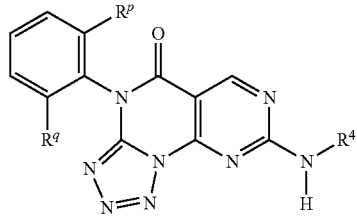
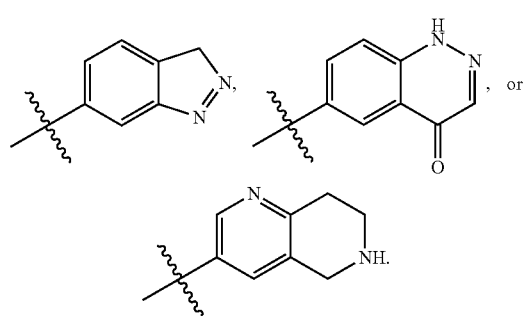

In one embodiment of formula (IV), $R^4$ is 10-15 membered tricyclic heterocyclyl. In another embodiment, $R^4$ is a 10-15 membered tricyclic heterocycloalkyl or tricyclic heterocycloalkenyl. In another embodiment, $R^4$ is a 10-15 membered tricyclic heteroaryl. In one embodiment of formula (IV), $R^4$ is 5-oxo-5,6-dihydroimidazo[1,2-a]pyrimido[5,4-e]pyrimidiny-2-yl or 2',3'-dihydro-1'H-spiro[cyclopropane-1,4'-isoquinolin]-7'-yl. In one embodiment of formula (IV), $R^4$ is unsubstituted. In another embodiment of formula (IV), $R^4$ is substituted with one, two, or three $R^6$, and $R^6$ is halo, $C_{1-6}$-alkyl, $C_{1-6}$-haloalkyl, $OR^j$, $C(O)R^j$, $NR^kR^l$, or $S(O)_2R^j$.

In on embodiment of formula (IV), $R^4$ is

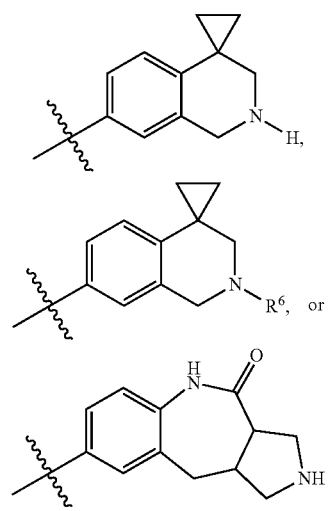

In one embodiment, the present invention is directed, in part, to a class of compounds having a structure of formula (IVa), formula (IVa)

wherein $R^4$ is as described in formula (IV) and $R^p$ and $R^q$ are independently halo or hydrogen.

Specific embodiments contemplated as part of the invention include, but are not limited to, compounds of formula (I), for example:

6-(2-chlorophenyl)-2-{[4-(4-methylpiperazin-1-yl)phenyl]amino}imidazo[1,2-a]pyrimido[5,4-e]pyrimidin-5(6H)-one;

2-anilino-6-(2-chlorophenyl)imidazo[1,2-a]pyrimido[5,4-e]pyrimidin-5(6H)-one;

6-(2-chlorophenyl)-2-(pyridin-4-ylamino)imidazo[1,2-a]pyrimido[5,4-e]pyrimidin-5(6H)-one;

6-(2-chlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one;

6-(2-chlorophenyl)-2-(5,6,7,8-tetrahydronaphthalen-2-ylamino)imidazo[1,2-a]pyrimido[5,4-e]pyrimidin-5(6H)-one;

6-(2-chlorophenyl)-2-{[3-(4-methylpiperazin-1-yl)phenyl]amino}imidazo[1,2-a]pyrimido[5,4-e]pyrimidin-5(6H)-one;

6-(2-chlorophenyl)-2-[(4-cyclohexylphenyl)amino]imidazo[1,2-a]pyrimido[5,4-e]pyrimidin-5(6H)-one;

6-(2-chlorophenyl)-2-{[4-(piperidin-1-yl)phenyl]amino}imidazo[1,2-a]pyrimido[5,4-e]pyrimidin-5(6H)-one;

6-(2-chlorophenyl)-2-{[4-(pyrrolidin-1-ylmethyl)phenyl]amino}imidazo[1,2-a]pyrimido[5,4-e]pyrimidin-5(6H)-one;

6-(2-chlorophenyl)-2-{[4-(morpholin-4-yl)phenyl]amino}imidazo[1,2-a]pyrimido[5,4-e]pyrimidin-5(6H)-one;

6-(2-chlorophenyl)-2-{[3-(pyrrolidin-1-ylmethyl)phenyl]amino}imidazo[1,2-a]pyrimido[5,4-e]pyrimidin-5(6H)-one;

2-[(1-acetyl-2,3-dihydro-1H-indol-6-yl)amino]-6-(2-chlorophenyl)imidazo[1,2-a]pyrimido[5,4-e]pyrimidin-5(6H)-one;

2-{[4-(4-acetylpiperazin-1-yl)phenyl]amino}-6-(2-chlorophenyl)imidazo[1,2-a]pyrimido[5,4-e]pyrimidin-5(6H)-one;

6-(2-methylphenyl)-2-{[4-(4-methylpiperazin-1-yl)phenyl]amino}imidazo[1,2-a]pyrimido[5,4-e]pyrimidin-5(6H)-one;

2-{[4-(4-methylpiperazin-1-yl)phenyl]amino}-6-[2-(trifluoromethyl)phenyl]imidazo[1,2-a]pyrimido[5,4-e]pyrimidin-5(6H)-one;

6-(2-methoxyphenyl)-2-{[4-(4-methylpiperazin-1-yl)phenyl]amino}imidazo[1,2-a]pyrimido[5,4-e]pyrimidin-5(6H)-one;

6-(2-chlorophenyl)-2-{[2-methoxy-4-(4-methylpiperazin-1-yl)phenyl]amino}imidazo[1,2-a]pyrimido[5,4-e]pyrimidin-5(6H)-one;

6-(2-chlorophenyl)-2-[(1-methyl-1,2,3,4-tetrahydroquinolin-7-yl)amino]imidazo[1,2-a]pyrimido[5,4-e]pyrimidin-5(6H)-one;

6-(2-chlorophenyl)-2-[(3-oxo-3,4-dihydro-2H-1,4-benzoxazin-6-yl)amino]imidazo[1,2-a]pyrimido[5,4-e]pyrimidin-5(6H)-one;

tert-butyl 7-{[6-(2-chlorophenyl)-5-oxo-5,6-dihydroimidazo[1,2-a]pyrimido[5,4-e]pyrimidin-2-yl]amino}-3,4-dihydroisoquinoline-2(1H)-carboxylate;

6-(2-chlorophenyl)-2-(1,2,3,4-tetrahydroisoquinolin-7-ylamino)imidazo[1,2-a]pyrimido[5,4-e]pyrimidin-5(6H)-one;

6-(2-chlorophenyl)-2-{[3-methyl-4-(4-methylpiperazin-1-yl)phenyl]amino}imidazo[1,2-a]pyrimido[5,4-e]pyrimidin-5(6H)-one;

6-allyl-2-{[4-(4-methylpiperazin-1-yl)phenyl]amino}imidazo[1,2-a]pyrimido[5,4-e]pyrimidin-5(6H)-one;

6-cyclohexyl-2-{[4-(4-methylpiperazin-1-yl)phenyl]amino}imidazo[1,2-a]pyrimido[5,4-e]pyrimidin-5(6H)-one;

6-(2-chlorophenyl)-9-methyl-2-{[4-(4-methylpiperazin-1-yl)phenyl]amino}imidazo[1,2-a]pyrimido[5,4-e]pyrimidin-5(6H)-one;

6-(2-chlorophenyl)-2-{[4-(4-methylpiperazin-1-yl)phenyl]amino}pyrimido[5,4-e][1,2,4]triazolo[4,3-a]pyrimidin-5(6H)-one;

6-(2-chlorophenyl)-9-methyl-2-{[4-(4-methylpiperazin-1-yl)phenyl]amino}pyrimido[5,4-e][1,2,4]triazolo[4,3-a]pyrimidin-5(6H)-one;

4-(2-chlorophenyl)-8-{[4-(4-methylpiperazin-1-yl)phenyl]amino}pyrimido[5,4-e]tetrazolo[1,5-a]pyrimidin-5(4H)-one;

6-(2-chlorophenyl)-2-({4-[4-(propan-2-yl)piperazin-1-yl]phenyl}amino)imidazo[1,2-a]pyrimido[5,4-e]pyrimidin-5(6H)-one;

6-(2-chlorophenyl)-2-({4-[4-(cyclohexylmethyl)piperazin-1-yl]phenyl}amino)imidazo[1,2-a]pyrimido[5,4-e]pyrimidin-5(6H)-one;

3-{[4-(4-{[6-(2-chlorophenyl)-5-oxo-5,6-dihydroimidazo[1,2-a]pyrimido[5,4-e]pyrimidin-2-yl]amino}phenyl)piperazin-1-yl]methyl}benzonitrile;

2-{[3-chloro-4-(4-methylpiperazin-1-yl)phenyl]amino}-6-(2-chlorophenyl)imidazo[1,2-a]pyrimido[5,4-e]pyrimidin-5(6H)-one;

6-(2-chlorophenyl)-2-({3-fluoro-4-[4-(propan-2-yl)piperazin-1-yl]phenyl}amino)imidazo[1,2-a]pyrimido[5,4-e]pyrimidin-5(6H)-one;

6-(2-chlorophenyl)-2-[(2-methyl-1,2,3,4-tetrahydroisoquinolin-7-yl)amino]imidazo[1,2-a]pyrimido[5,4-e]pyrimidin-5(6H)-one;

6-(2-chlorophenyl)-2-({4-[2-(dimethylamino)ethoxy]phenyl}amino)imidazo[1,2-a]pyrimido[5,4-e]pyrimidin-5(6H)-one;

6-(2-chlorophenyl)-2-({4-[2-(morpholin-4-yl)ethoxy]phenyl}amino)imidazo[1,2-a]pyrimido[5,4-e]pyrimidin-5(6H)-one;

6-(2-chlorophenyl)-2-{[3-methyl-4-(4-methyl-1,4-diazepan-1-yl)phenyl]amino}imidazo[1,2-a]pyrimido[5,4-e]pyrimidin-5(6H)-one;

6-(2-chlorophenyl)-2-{[4-(1-methylpiperidin-4-yl)phenyl]amino}imidazo[1,2-a]pyrimido[5,4-e]pyrimidin-5(6H)-one;

2-{[4-(4-methylpiperazin-1-yl)phenyl]amino}-6-phenylimidazo[1,2-a]pyrimido[5,4-e]pyrimidin-5(6H)-one;

6-(2-chloro-4-methylphenyl)-2-{4-(4-methylpiperazin-1-yl)phenyl]amino}imidazo[1,2-a]pyrimido[5,4-e]pyrimidin-5(6H)-one;

4-{[6-(2-chlorophenyl)-5-oxo-5,6-dihydroimidazo[1,2-a]pyrimido[5,4-e]pyrimidin-2-yl]amino}-N-cyclohexylbenzamide;

6-(2-chlorophenyl)-2-({4-[(4-methylpiperazin-1-yl)carbonyl]phenyl}amino)imidazo[1,2-a]pyrimido[5,4-e]pyrimidin-5(6H)-one;

6-(2-chlorophenyl)-2-{[4-(1H-pyrazol-4-yl)phenyl]amino}imidazo[1,2-a]pyrimido[5,4-e]pyrimidin-5(6H)-one;

6-(2-chlorophenyl)-2-({4-[2-(diethylamino)ethoxy]phenyl}amino)imidazo[1,2-a]pyrimido[5,4-e]pyrimidin-5(6H)-one;

6-(2-chlorophenyl)-2-{[4-(pyridin-3-yl)phenyl]amino}imidazo[1,2-a]pyrimido[5,4-e]pyrimidin-5(6H)-one;

4-{[6-(2-chlorophenyl)-5-oxo-5,6-dihydroimidazo[1,2-a]pyrimido[5,4-e]pyrimidin-2-yl]amino}-N-(trans-4-hydroxycyclohexyl)benzamide;

4-{[6-(2-chlorophenyl)-5-oxo-5,6-dihydroimidazo[1,2-a]pyrimido[5,4-e]pyrimidin-2-yl]amino}-N-ethylbenzamide;

6-(2-chlorophenyl)-2-({4-[(4-hydroxypiperidin-1-yl)carbonyl]phenyl}amino)imidazo[1,2-a]pyrimido[5,4-e]pyrimidin-5(6H)-one;

4-{[6-(2-chlorophenyl)-5-oxo-5,6-dihydroimidazo[1,2-a]pyrimido[5,4-e]pyrimidin-2-yl]amino}-N-(pyridin-4-yl)benzamide;

6-(2-chlorophenyl)-2-({4-[3-(diethylamino)propoxy]-3-fluorophenyl}amino)imidazo[1,2-a]pyrimido[5,4-e]pyrimidin-5(6H)-one;

6-(2-chlorophenyl)-2-({3-fluoro-4-[2-(4-methylpiperazin-1-yl)ethoxy]phenyl}amino)imidazo[1,2-a]pyrimido[5,4-e]pyrimidin-5(6H)-one;

6-(2-chlorophenyl)-2-{[2-(2-methoxyethyl)-1,2,3,4-tetrahydroisoquinolin-7-yl]amino}imidazo[1,2-a]pyrimido[5,4-e]pyrimidin-5(6H)-one;

6-(2-chlorophenyl)-2-[(2,4,4-trimethyl-1,2,3,4-tetrahydroisoquinolin-7-yl)amino]imidazo[1,2-a]pyrimido[5,4-e]pyrimidin-5(6H)-one;

6-(3-hydroxy-2-methylphenyl)-2-(phenylamino)imidazo[1,2-a]pyrimido[5,4-e]pyrimidin-5(6H)-one;

6-(2,6-dichlorophenyl)-2-{[4-(4-methylpiperazin-1-yl)phenyl]amino}imidazo[1,2-a]pyrimido[5,4-e]pyrimidin-5(6H)-one;

2-[(4-aminophenyl)amino]-6-(2-chlorophenyl)imidazo[1,2-a]pyrimido[5,4-e]pyrimidin-5(6H)-one;

N-(4-{[6-(2-chlorophenyl)-5-oxo-5,6-dihydroimidazo[1,2-a]pyrimido[5,4-e]pyrimidin-2-yl]amino}phenyl)acetamide;

N-(4-{[6-(2-chlorophenyl)-5-oxo-5,6-dihydroimidazo[1,2-a]pyrimido[5,4-e]pyrimidin-2-yl]amino}phenyl)cyclopentanecarboxamide;

N-(4-{[6-(2-chlorophenyl)-5-oxo-5,6-dihydroimidazo[1,2-a]pyrimido[5,4-e]pyrimidin-2-yl]amino}phenyl)-4-hydroxycyclohexanecarboxamide;

N-(4-{[6-(2-chlorophenyl)-5-oxo-5,6-dihydroimidazo[1,2-a]pyrimido[5,4-e]pyrimidin-2-yl]amino}phenyl)-1-methylpiperidine-4-carboxamide;

N-(4-{[6-(2-chlorophenyl)-5-oxo-5,6-dihydroimidazo[1,2-a]pyrimido[5,4-e]pyrimidin-2-yl]amino}phenyl)pyridine-4-carboxamide;

6-(2,6-dimethylphenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one;

2-({4-[4-(3-chlorobenzyl)piperazin-1-yl]phenyl}amino)-6-(2-chlorophenyl)imidazo[1,2-a]pyrimido[5,4-e]pyrimidin-5(6H)-one;

6-(2-chlorophenyl)-2-({4-[4-(2-methoxyethyl)piperazin-1-yl]phenyl}amino)imidazo[1,2-a]pyrimido[5,4-e]pyrimidin-5(6H)-one;

6-(2-chlorophenyl)-2-{[3-methoxy-4-(4-methylpiperazin-1-yl)phenyl]amino}imidazo[1,2-a]pyrimido[5,4-e]pyrimidin-5(6H)-one;

6-(2-chlorophenyl)-2-({3-methoxy-4-[4-(propan-2-yl)piperazin-1-yl]phenyl}amino)imidazo[1,2-a]pyrimido[5,4-e]pyrimidin-5(6H)-one;

6-(2-chlorophenyl)-2-({3-methoxy-4-[2-(4-methylpiperazin-1-yl)ethoxy]phenyl}amino)imidazo[1,2-a]pyrimido[5,4-e]pyrimidin-5(6H)-one;

6-(3-hydroxyphenyl)-2-(phenylamino)imidazo[1,2-a]pyrimido[5,4-e]pyrimidin-5(6H)-one;

6-(2-chlorophenyl)-2-[(4-methylphenyl)amino]imidazo[1,2-a]pyrimido[5,4-e]pyrimidin-5(6H)-one;

6-(2-chlorophenyl)-2-{[4-(piperidin-2-yl)phenyl]amino}imidazo[1,2-a]pyrimido[5,4-e]pyrimidin-5(6H)-one;

6-(2-chlorophenyl)-2-{[4-(pyrrolidin-2-yl)phenyl]amino}imidazo[1,2-a]pyrimido[5,4-e]pyrimidin-5(6H)-one;

6-(2-chlorophenyl)-2-{[4-(pyrrolidin-3-yl)phenyl]amino}imidazo[1,2-a]pyrimido[5,4-e]pyrimidin-5(6H)-one;

6-(2,6-dichlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one;

6-(2,6-dichlorophenyl)-2-{[3-methyl-4-(4-methyl-1,4-diazepan-1-yl)phenyl]amino}imidazo[1,2-a]pyrimido[5,4-e]pyrimidin-5(6H)-one;

6-(2-chlorophenyl)-2-{[4-(piperazin-1-yl)-3-(trifluoromethyl)phenyl]amino}imidazo[1,2-a]pyrimido[5,4-e]pyrimidin-5(6H)-one;

6-(2-chlorophenyl)-2-({4-[(2S)-pyrrolidin-2-ylmethoxy]phenyl}amino)imidazo[1,2-a]pyrimido[5,4-e]pyrimidin-5(6H)-one;

6-(2-chlorophenyl)-2-({2-methyl-4-[3-(4-methylpiperazin-1-yl)propoxy]phenyl}amino)imidazo[1,2-a]pyrimido[5,4-e]pyrimidin-5(6H)-one;

6-(2-chlorophenyl)-2-{[4-(morpholin-4-ylmethyl)phenyl]amino}imidazo[1,2-a]pyrimido[5,4-e]pyrimidin-5(6H)-one;

6-(2-chlorophenyl)-2-{[4-(1H-imidazol-1-ylmethyl)phenyl]amino}imidazo[1,2-a]pyrimido[5,4-e]pyrimidin-5(6H)-one;

6-(2-chlorophenyl)-2-{[4-(1H-imidazol-1-yl)phenyl]amino}imidazo[1,2-a]pyrimido[5,4-e]pyrimidin-5(6H)-one;

6-(2-chlorophenyl)-2-{[6-(piperazin-1-yl)pyridin-3-yl]amino}imidazo[1,2-a]pyrimido[5,4-e]pyrimidin-5(6H)-one;

6-(2-chlorophenyl)-2-({3-[3-(4-methylpiperazin-1-yl)propoxy]phenyl}amino)imidazo[1,2-a]pyrimido[5,4-e]pyrimidin-5(6H)-one;

6-(2-chlorophenyl)-2-({3-[3-(piperidin-1-yl)propoxy]phenyl}amino)imidazo[1,2-a]pyrimido[5,4-e]pyrimidin-5(6H)-one;

6-(2,6-dichlorophenyl)-2-(phenylamino)imidazo[1,2-a]pyrimido[5,4-e]pyrimidin-5(6H)-one;

6-(2-chlorophenyl)-2-({3-methoxy-4-[2-(propan-2-ylamino)ethoxy]phenyl}amino)imidazo[1,2-a]pyrimido[5,4-e]pyrimidin-5(6H)-one;

6-(2-chlorophenyl)-2-({3-chloro-4-[2-(propan-2-ylamino)ethoxy]phenyl}amino)imidazo[1,2-a]pyrimido[5,4-e]pyrimidin-5(6H)-one;

6-(2-chlorophenyl)-2-{[4-(hydroxymethyl)phenyl]amino}imidazo[1,2-a]pyrimido[5,4-e]pyrimidin-5(6H)-one;

6-(2-chlorophenyl)-2-{[4-(1H-pyrazol-1-ylmethyl)phenyl]amino}imidazo[1,2-a]pyrimido[5,4-e]pyrimidin-5(6H)-one;

6-(2-chlorophenyl)-2-{[4-(1H-pyrazol-1-yl)phenyl]amino}imidazo[1,2-a]pyrimido[5,4-e]pyrimidin-5(6H)-one;

6-(2-chlorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one;

2-[(2'-acetyl-2',3'-dihydro-1'H-spiro[cyclopropane-1,4'-isoquinolin]-7'-yl)amino]-6-(2-chlorophenyl)imidazo[1,2-a]pyrimido[5,4-e]pyrimidin-5(6H)-one;

6-(2-chlorophenyl)-2-[(1-methyl-1,2,3,4-tetrahydroquinolin-6-yl)amino]imidazo[1,2-a]pyrimido[5,4-e]pyrimidin-5(6H)-one;

6-(2-chlorophenyl)-2-({1-[2-(dimethylamino)ethyl]-2,3-dihydro-1H-indol-5-yl}amino)imidazo[1,2-a]pyrimido[5,4-e]pyrimidin-5(6H)-one;

6-(2-chlorophenyl)-2-{[2-(dimethylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[4-(4-methylpiperazin-1-yl)phenyl]amino}imidazo[1,2-a]pyrimido[5,4-e]pyrimidin-5(6H)-one;

6-(2-chloro-6-fluorophenyl)-2-{[3-methyl-4-(4-methyl-1,4-diazepan-1-yl)phenyl]amino}imidazo[1,2-a]pyrimido[5,4-e]pyrimidin-5(6H)-one;

6-(2-chloro-6-fluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one;

6-(2,6-difluorophenyl)-2-{[4-(4-methylpiperazin-1-yl)phenyl]amino}imidazo[1,2-a]pyrimido[5,4-e]pyrimidin-5(6H)-one;

6-(2-chlorophenyl)-2-{[2-(2-hydroxyethyl)-1,2,3,4-tetrahydroisoquinolin-7-yl]amino}imidazo[1,2-a]pyrimido[5,4-e]pyrimidin-5(6H)-one;

6-(2-chlorophenyl)-2-{[3-(hydroxymethyl)-4-(4-methyl-1,4-diazepan-1-yl)phenyl]amino}imidazo[1,2-a]pyrimido[5,4-e]pyrimidin-5(6H)-one;

6-(2-chlorophenyl)-2-{[4-(hexahydropyrrolo[1,2-a]pyrazin-2(1H)-yl)phenyl]amino}imidazo[1,2-a]pyrimido[5,4-e]pyrimidin-5(6H)-one;

6-(2-chlorophenyl)-2-[(4-hydroxy-3-methylphenyl)amino]imidazo[1,2-a]pyrimido[5,4-e]pyrimidin-5(6H)-one;

6-(2-chlorophenyl)-2-({4-[3-(diethylamino)propoxy]-3-methylphenyl}amino)imidazo[1,2-a]pyrimido[5,4-e]pyrimidin-5(6H)-one;

6-(2-chlorophenyl)-2-{[3-methyl-4-(piperazin-1-yl)phenyl]amino}imidazo[1,2-a]pyrimido[5,4-e]pyrimidin-5(6H)-one;

6-(2-chlorophenyl)-2-{[4-(1,4-diazepan-1-yl)-3-methylphenyl]amino}imidazo[1,2-a]pyrimido[5,4-e]pyrimidin-5(6H)-one;

6-(2-chlorophenyl)-2-(2,3,4,5-tetrahydro-1H-2-benzazepin-7-ylamino)imidazo[1,2-a]pyrimido[5,4-e]pyrimidin-5(6H)-one;

6-(2-chlorophenyl)-2-[(3-methyl-2,3,4,5-tetrahydro-1H-3-benzazepin-7-yl)amino]imidazo[1,2-a]pyrimido[5,4-e]pyrimidin-5(6H)-one;

6-(2-chlorophenyl)-2-[(1,1,2-trimethyl-1,2,3,4-tetrahydroisoquinolin-7-yl)amino]imidazo[1,2-a]pyrimido[5,4-e]pyrimidin-5(6H)-one;

6-(2,6-dichlorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one;

6-(2,6-dichlorophenyl)-2-{[3-methyl-4-(piperazin-1-yl)phenyl]amino}imidazo[1,2-a]pyrimido[5,4-e]pyrimidin-5(6H)-one;

6-(2,6-dichlorophenyl)-2-(1,2,3,4-tetrahydroisoquinolin-7-ylamino)imidazo[1,2-a]pyrimido[5,4-e]pyrimidin-5(6H)-one;

6-(2-chlorophenyl)-2-{[3-ethyl-4-(4-methylpiperazin-1-yl)phenyl]amino}imidazo[1,2-a]pyrimido[5,4-e]pyrimidin-5(6H)-one;

6-(2-chlorophenyl)-2-{[2-(cyclohexylmethyl)-4,4-dimethyl-1,2,3,4-tetrahydroisoquinolin-7-yl]amino}imidazo[1,2-a]pyrimido[5,4-e]pyrimidin-5(6H)-one;

6-(2,6-dichlorophenyl)-2-{[2-(dimethylamino)-2,3-dihydro-1H-inden-5-yl]amino}imidazo[1,2-a]pyrimido[5,4-e]pyrimidin-5(6H)-one;

6-(2,6-dichlorophenyl)-2-({4-[4-(propan-2-yl)piperazin-1-yl]phenyl}amino)imidazo[1,2-a]pyrimido[5,4-e]pyrimidin-5(6H)-one;

6-(2,6-dichlorophenyl)-2-{[4-(hexahydropyrrolo[1,2-a]pyrazin-2(1H)-yl)phenyl]amino}imidazo[1,2-a]pyrimido[5,4-e]pyrimidin-5(6H)-one;

6-(2-chlorophenyl)-2-{[2-(2-ethylbutyl)-4,4-dimethyl-1,2,3,4-tetrahydroisoquinolin-7-yl]amino}imidazo[1,2-a]pyrimido[5,4-e]pyrimidin-5(6H)-one;

6-(2,6-dichlorophenyl)-2-({4-[2-(4-methylpiperazin-1-yl)ethyl]phenyl}amino)imidazo[1,2-a]pyrimido[5,4-e]pyrimidin-5(6H)-one;

6-(2,6-dichlorophenyl)-2-({1-[2-(dimethylamino)ethyl]-2,3-dihydro-1H-indol-5-yl}amino)imidazo[1,2-a]pyrimido[5,4-e]pyrimidin-5(6H)-one;

6-(2,6-dichlorophenyl)-2-{[3-ethyl-4-(4-methylpiperazin-1-yl)phenyl]amino}imidazo[1,2-a]pyrimido[5,4-e]pyrimidin-5(6H)-one;

6-(2,6-dichlorophenyl)-2-{[3-(hydroxymethyl)-4-(4-methyl-1,4-diazepan-1-yl)phenyl]amino}imidazo[1,2-a]pyrimido[5,4-e]pyrimidin-5(6H)-one;

6-(2,6-dichlorophenyl)-2-(1,2,3,4-tetrahydroisoquinolin-6-ylamino)imidazo[1,2-a]pyrimido[5,4-e]pyrimidin-5(6H)-one;

6-(2,6-dichloro-4-fluorophenyl)-2-{[4-(4-methylpiperazin-1-yl)phenyl]amino}imidazo[1,2-a]pyrimido[5,4-e]pyrimidin-5(6H)-one;

6-(2,6-dichloro-4-fluorophenyl)-2-{[3-methyl-4-(4-methyl-1,4-diazepan-1-yl)phenyl]amino}imidazo[1,2-a]pyrimido[5,4-e]pyrimidin-5(6H)-one;

6-(2,6-dichloro-4-fluorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one;

6-(2,6-dichloro-4-fluorophenyl)-2-{[2-(dimethylamino)-2,3-dihydro-1H-inden-5-yl]amino}imidazo[1,2-a]pyrimido[5,4-e]pyrimidin-5(6H)-one;

6-(2,6-dichlorophenyl)-2-({4-[(4-methylpiperazin-1-yl)methyl]phenyl}amino)imidazo[1,2-a]pyrimido[5,4-e]pyrimidin-5(6H)-one;

6-(2,6-dichlorophenyl)-2-({4-[(3R,5S)-3,5-dimethylpiperazin-1-yl]-3-fluorophenyl}amino)imidazo[1,2-a]pyrimido[5,4-e]pyrimidin-5(6H)-one;

6-(2,6-dichlorophenyl)-2-{[3,5-difluoro-4-(piperazin-1-yl)phenyl]amino}imidazo[1,2-a]pyrimido[5,4-e]pyrimidin-5(6H)-one;

6-(2-chlorophenyl)-2-{[2-(cyclopropylmethyl)-4,4-dimethyl-1,2,3,4-tetrahydroisoquinolin-7-yl]amino}imidazo[1,2-a]pyrimido[5,4-e]pyrimidin-5(6H)-one;

6-(2-chlorophenyl)-2-{[4,4-dimethyl-2-(pyridin-3-ylmethyl)-1,2,3,4-tetrahydroisoquinolin-7-yl]amino}imidazo[1,2-a]pyrimido[5,4-e]pyrimidin-5(6H)-one;

6-(2-chlorophenyl)-2-{[4,4-dimethyl-2-(thiophen-3-ylmethyl)-1,2,3,4-tetrahydroisoquinolin-7-yl]amino}imidazo[1,2-a]pyrimido[5,4-e]pyrimidin-5(6H)-one;

6-(2-chlorophenyl)-2-[(1,1,2-trimethyl-1,2,3,4-tetrahydroisoquinolin-6-yl)amino]imidazo[1,2-a]pyrimido[5,4-e]pyrimidin-5(6H)-one;

6-(2,6-dichlorophenyl)-2-{[4-(pyrrolidin-2-yl)phenyl]amino}imidazo[1,2-a]pyrimido[5,4-e]pyrimidin-5(6H)-one;

6-(2,6-dichlorophenyl)-2-{[4-(piperidin-2-yl)phenyl]amino}imidazo[1,2-a]pyrimido[5,4-e]pyrimidin-5(6H)-one;

2-{[3-chloro-4-(4-methylpiperazin-1-yl)phenyl]amino}-6-(2,6-dichlorophenyl)imidazo[1,2-a]pyrimido[5,4-e]pyrimidin-5(6H)-one;

6-(2,6-dichlorophenyl)-2-({3-methoxy-4-[4-(propan-2-yl)piperazin-1-yl]phenyl}amino)imidazo[1,2-a]pyrimido[5,4-e]pyrimidin-5(6H)-one;

6-(2-chlorophenyl)-2-{[4-(4-hydroxypiperidin-1-yl)phenyl]amino}imidazo[1,2-a]pyrimido[5,4-e]pyrimidin-5(6H)-one;

6-(2-chloro-6-fluorophenyl)-2-{[2-(dimethylamino)-2,3-dihydro-1H-inden-5-yl]amino}imidazo[1,2-a]pyrimido[5,4-e]pyrimidin-5(6H)-one;

6-(2-chloro-6-fluorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one;

6-(2-chloro-6-fluorophenyl)-2-{[4-(1,4-diazepan-1-yl)-3-methylphenyl]amino}imidazo[1,2-a]pyrimido[5,4-e]pyrimidin-5(6H)-one;

2-[(2'-methyl-2',3'-dihydro-1'H-spiro[cyclopropane-1,4'-isoquinolin]-7'-yl)amino]-6-(propan-2-yl)imidazo[1,2-a]pyrimido[5,4-e]pyrimidin-5(6H)-one;

6-(2,6-dichlorophenyl)-2-{[4-(3-oxopiperazin-1-yl)phenyl]amino}imidazo[1,2-a]pyrimido[5,4-e]pyrimidin-5(6H)-one;

6-(2-chlorophenyl)-2-{[4,4-dimethyl-2-(propan-2-yl)-1,2,3,4-tetrahydroisoquinolin-7-yl]amino}imidazo[1,2-a]pyrimido[5,4-e]pyrimidin-5(6H)-one;

6-(2-chlorophenyl)-2-{[4,4-dimethyl-2-(4,4,4-trifluorobutyl)-1,2,3,4-tetrahydroisoquinolin-7-yl]amino}imidazo[1,2-a]pyrimido[5,4-e]pyrimidin-5(6H)-one;

6-(2-chlorophenyl)-2-[(1,1,2-trimethyl-2,3-dihydro-1H-isoindol-5-yl)amino]imidazo[1,2-a]pyrimido[5,4-e]pyrimidin-5(6H)-one;

6-(2-chlorophenyl)-2-[(1,1,2,3,3-pentamethyl-2,3-dihydro-1H-isoindol-5-yl)amino]imidazo[1,2-a]pyrimido[5,4-e]pyrimidin-5(6H)-one;

6-(2,6-dichlorophenyl)-2-{[3-methoxy-4-(4-methylpiperazin-1-yl)phenyl]amino}imidazo[1,2-a]pyrimido[5,4-e]pyrimidin-5(6H)-one;

6-(2,6-dichlorophenyl)-2-({4-[3-(diethylamino)propoxy]-3-fluorophenyl}amino)imidazo[1,2-a]pyrimido[5,4-e]pyrimidin-5(6H)-one;

6-(2,6-dichlorophenyl)-2-[(1,1,2-trimethyl-1,2,3,4-tetrahydroisoquinolin-6-yl)amino]imidazo[1,2-a]pyrimido[5,4-e]pyrimidin-5(6H)-one;

2-({4-[(1S,4S)-2,5-diazabicyclo[2.2.1]hept-2-yl]phenyl}amino)-6-(2,6-dichlorophenyl)imidazo[1,2-a]pyrimido[5,4-e]pyrimidin-5(6H)-one;

6-(2,6-dichlorophenyl)-2-[(2,4,4-trimethyl-1,2,3,4-tetrahydroisoquinolin-7-yl)amino]imidazo[1,2-a]pyrimido[5,4-e]pyrimidin-5(6H)-one;

6-(2,6-dichlorophenyl)-2-{[4-(4,4-difluoropiperidin-1-yl)phenyl]amino}imidazo[1,2-a]pyrimido[5,4-e]pyrimidin-5(6H)-one;

6-(2,6-dichlorophenyl)-2-{[4-(3,3-difluoropiperidin-1-yl)phenyl]amino}imidazo[1,2-a]pyrimido[5,4-e]pyrimidin-5(6H)-one;

6-(2,6-dichlorophenyl)-2-({3-fluoro-4-[4-(propan-2-yl)piperazin-1-yl]phenyl}amino)imidazo[1,2-a]pyrimido[5,4-e]pyrimidin-5(6H)-one;

6-(2,6-dichlorophenyl)-2-{[4-(piperazin-1-yl)-3-(trifluoromethyl)phenyl]amino}imidazo[1,2-a]pyrimido[5,4-e]pyrimidin-5(6H)-one;

6-(2-chlorophenyl)-2-{[4-(4-methylpiperazin-1-yl)-3-(propan-2-yl)phenyl]amino}imidazo[1,2-a]pyrimido[5,4-e]pyrimidin-5(6H)-one;

2-{[4-(4-acetylpiperazin-1-yl)phenyl]amino}-6-(2-chloro-6-fluorophenyl)imidazo[1,2-a]pyrimido[5,4-e]pyrimidin-5(6H)-one;

6-(2-chloro-6-fluorophenyl)-2-[(4,4-dimethyl-1,2,3,4-tetrahydroisoquinolin-7-yl)amino]imidazo[1,2-a]pyrimido[5,4-e]pyrimidin-5(6H)-one;

6-(2,6-dichloro-4-fluorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one;

6-(2-chlorophenyl)-2-[(2-ethyl-4,4-dimethyl-1,2,3,4-tetrahydroisoquinolin-7-yl)amino]imidazo[1,2-a]pyrimido[5,4-e]pyrimidin-5(6H)-one;

6-(2-chlorophenyl)-2-{[4,4-dimethyl-2-(2,2,2-trifluoroethyl)-1,2,3,4-tetrahydroisoquinolin-7-yl]amino}imidazo[1,2-a]pyrimido[5,4-e]pyrimidin-5(6H)-one;

6-(2-chlorophenyl)-2-({2-[4-(1H-imidazol-1-yl)benzyl]-4,4-dimethyl-1,2,3,4-tetrahydroisoquinolin-7-yl}amino)imidazo[1,2-a]pyrimido[5,4-e]pyrimidin-5(6H)-one;

2-({2-[(1-benzylpiperidin-4-yl)methyl]-4,4-dimethyl-1,2,3,4-tetrahydroisoquinolin-7-yl}amino)-6-(2-chlorophenyl)imidazo[1,2-a]pyrimido[5,4-e]pyrimidin-5(6H)-one;

2-[(2'-acetyl-2',3'-dihydro-1'H-spiro[cyclopropane-1,4'-isoquinolin]-7'-yl)amino]-6-(2,6-dichloro-4-fluorophenyl)imidazo[1,2-a]pyrimido[5,4-e]pyrimidin-5(6H)-one;

6-(2,6-dichlorophenyl)-2-{[4-(4-hydroxypiperidin-1-yl)phenyl]amino}imidazo[1,2-a]pyrimido[5,4-e]pyrimidin-5(6H)-one;

2-[(4-cyclohexylphenyl)amino]-6-(2,6-dichlorophenyl)imidazo[1,2-a]pyrimido[5,4-e]pyrimidin-5(6H)-one;

6-(2,6-dichlorophenyl)-2-{[4-(pyrrolidin-3-yl)phenyl]amino}imidazo[1,2-a]pyrimido[5,4-e]pyrimidin-5(6H)-one;

6-(2,6-dichlorophenyl)-2-{[4-(morpholin-4-yl)phenyl]amino}imidazo[1,2-a]pyrimido[5,4-e]pyrimidin-5(6H)-one;

6-(2,6-dichlorophenyl)-2-{[4,4-dimethyl-2-(2,2,2-trifluoroethyl)-1,2,3,4-tetrahydroisoquinolin-7-yl]amino}imidazo[1,2-a]pyrimido[5,4-e]pyrimidin-5(6H)-one;

2-{[2'-(cyclopropylcarbonyl)-2',3'-dihydro-1'H-spiro[cyclopropane-1,4'-isoquinolin]-7'-yl]amino}-6-(2,6-dichloro-4-fluorophenyl)imidazo[1,2-a]pyrimido[5,4-e]pyrimidin-5(6H)-one;

6-(2,6-dichloro-4-fluorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2,6-dichloro-4-fluorophenyl)-2-{[6-(piperazin-1-yl)pyridin-3-yl]amino}imidazo[1,2-a]pyrimido[5,4-e]pyrimidin-5(6H)-one;

6-(2,6-dichlorophenyl)-2-{[4-(2-oxopiperazin-1-yl)phenyl]amino}imidazo[1,2-a]pyrimido[5,4-e]pyrimidin-5(6H)-one;

2-({4-[(1R,4R)-2,5-diazabicyclo[2.2.1]hept-2-yl]phenyl}amino)-6-(2,6-dichlorophenyl)imidazo[1,2-a]pyrimido[5,4-e]pyrimidin-5(6H)-one;

6-(2,6-dichlorophenyl)-2-{[4-(4-methylpiperazin-1-yl)-3-(propan-2-yl)phenyl]amino}imidazo[1,2-a]pyrimido[5,4-e]pyrimidin-5(6H)-one;

6-(2,6-dichlorophenyl)-2-[(1,1,2,3,3-pentamethyl-2,3-dihydro-1H-isoindol-5-yl)amino]imidazo[1,2-a]pyrimido[5,4-e]pyrimidin-5(6H)-one;

6-(2,6-dichlorophenyl)-2-[(1,1,2-trimethyl-2,3-dihydro-1H-isoindol-5-yl)amino]imidazo[1,2-a]pyrimido[5,4-e]pyrimidin-5(6H)-one;

(3aS,10aS)-8-{[6-(2,6-dichlorophenyl)-5-oxo-5,6-dihydroimidazo[1,2-a]pyrimido[5,4-e]pyrimidin-2-yl]amino}-2,3,3a,5,10,10a-hexahydropyrrolo[3,4-c][1]benzazepin-4(1H)-one;

6-(2,6-dichlorophenyl)-2-{[4-(6-oxo-1,4,5,6-tetrahydropyridazin-3-yl)phenyl]amino}imidazo[1,2-a]pyrimido[5,4-e]pyrimidin-5(6H)-one;

2-(1,2,3-benzothiadiazol-5-ylamino)-6-(2,6-dichlorophenyl)imidazo[1,2-a]pyrimido[5,4-e]pyrimidin-5(6H)-one;

2-(1,3-benzothiazol-6-ylamino)-6-(2,6-dichlorophenyl)imidazo[1,2-a]pyrimido[5,4-e]pyrimidin-5(6H)-one;

2-({4-[bis(2-methoxyethyl)amino]phenyl}amino)-6-(2-chlorophenyl)imidazo[1,2-a]pyrimido[5,4-e]pyrimidin-5(6H)-one;

6-(2-chlorophenyl)-2-[(3-cyclopropyl-2,3,4,5-tetrahydro-1H-3-benzazepin-7-yl)amino]imidazo[1,2-a]pyrimido[5,4-e]pyrimidin-5(6H)-one;

6-(2-chlorophenyl)-2-{[3-(2,2-difluoroethyl)-2,3,4,5-tetrahydro-1H-3-benzazepin-7-yl]amino}imidazo[1,2-a]pyrimido[5,4-e]pyrimidin-5(6H)-one;

6-(2-chloro-4,6-difluorophenyl)-2-{[4-(4-methylpiperazin-1-yl)phenyl]amino}imidazo[1,2-a]pyrimido[5,4-e]pyrimidin-5(6H)-one;

6-(2-chloro-4,6-difluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one;

6-(2-chloro-4,6-difluorophenyl)-2-{[2-(dimethylamino)-2,3-dihydro-1H-inden-5-yl]amino}imidazo[1,2-a]pyrimido[5,4-e]pyrimidin-5(6H)-one;

6-(2-chlorophenyl)-2-[(4-{[3-(morpholin-4-yl)propyl]amino}phenyl)amino]imidazo[1,2-a]pyrimido[5,4-e]pyrimidin-5(6H)-one;

6-(2-chlorophenyl)-2-({4-[4-(pyrrolidin-1-yl)piperidin-1-yl]phenyl}amino)imidazo[1,2-a]pyrimido[5,4-e]pyrimidin-5(6H)-one;

6-(2-chlorophenyl)-2-({4-[4-(dimethylamino)piperidin-1-yl]phenyl}amino)imidazo[1,2-a]pyrimido[5,4-e]pyrimidin-5(6H)-one;

6-(2-chlorophenyl)-2-[(4-{[2-(1-methylpyrrolidin-2-yl)ethyl]amino}phenyl)amino]imidazo[1,2-a]pyrimido[5,4-e]pyrimidin-5(6H)-one;

4-(dimethylamino)cyclohexyl 4-{[6-(2,6-dichlorophenyl)-5-oxo-5,6-dihydroimidazo[1,2-a]pyrimido[5,4-e]pyrimidin-2-yl]amino}benzoate;

6-(2,6-dichlorophenyl)-2-(1H-indazol-5-ylamino)imidazo[1,2-a]pyrimido[5,4-e]pyrimidin-5(6H)-one;

6-(2,6-dichlorophenyl)-2-({4-[(3S)-3-(propan-2-yl)piperazin-1-yl]phenyl}amino)imidazo[1,2-a]pyrimido[5,4-e]pyrimidin-5(6H)-one;

6-(2,6-dichlorophenyl)-2-[(4-{1-[1-(dimethylamino)-3-methylbutyl]cyclobutyl}phenyl)amino]imidazo[1,2-a]pyrimido[5,4-e]pyrimidin-5(6H)-one;

6-(2,6-dichlorophenyl)-2-({4-[4-methyl-2-(methylamino)-1,3-thiazol-5-yl]phenyl}amino)imidazo[1,2-a]pyrimido[5,4-e]pyrimidin-5(6H)-one;

6-(2,6-dichlorophenyl)-2-{[6-(piperazin-1-yl)pyridin-3-yl]amino}imidazo[1,2-a]pyrimido[5,4-e]pyrimidin-5(6H)-one;

6-(2,6-dichlorophenyl)-2-(1H-indazol-6-ylamino)imidazo[1,2-a]pyrimido[5,4-e]pyrimidin-5(6H)-one;

(1R)-octahydro-2H-quinolizin-1-yl 4-{[6-(2,6-dichlorophenyl)-5-oxo-5,6-dihydroimidazo[1,2-a]pyrimido[5,4-e]pyrimidin-2-yl]amino}benzoate;

2-[cyclopropyl(methyl)amino]ethyl 4-{[6-(2,6-dichlorophenyl)-5-oxo-5,6-dihydroimidazo[1,2-a]pyrimido[5,4-e]pyrimidin-2-yl]amino}benzoate;

6-(2,6-dichlorophenyl)-2-[(4-{[(1R,5S)-7-ethyl-3,7-diazabicyclo[3.3.1]non-3-yl]carbonyl}phenyl)amino]imidazo[1,2-a]pyrimido[5,4-e]pyrimidin-5(6H)-one;

6-(2-chlorophenyl)-2-{[3,5-difluoro-4-(piperazin-1-yl)phenyl]amino}imidazo[1,2-a]pyrimido[5,4-e]pyrimidin-5(6H)-one;

6-(2-chlorophenyl)-2-({4-[(8aR)-hexahydropyrrolo[1,2-a]pyrazin-2(1H)-yl]phenyl}amino)imidazo[1,2-a]pyrimido[5,4-e]pyrimidin-5(6H)-one;

2-(2',3'-dihydro-1'H-spiro[cyclopropane-1,4'-isoquinolin]-7'-ylamino)-6-(4-hydroxyphenyl)imidazo[1,2-a]pyrimido[5,4-e]pyrimidin-5(6H)-one;

6-(2,6-dichlorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

2-[(2'-acetyl-2',3'-dihydro-1'H-spiro[cyclopropane-1,4'-isoquinolin]-7'-yl)amino]-6-(2,6-dichlorophenyl)imidazo[1,2-a]pyrimido[5,4-e]pyrimidin-5(6H)-one;

6-(2-chlorophenyl)-2-{[4-(octahydro-2H-pyrido[1,2-a]pyrazin-2-yl)phenyl]amino}imidazo[1,2-a]pyrimido[5,4-e]pyrimidin-5(6H)-one;

6-(2-chloro-6-fluorophenyl)-2-[(1,1,2-trimethyl-2,3-dihydro-1H-isoindol-5-yl)amino]imidazo[1,2-a]pyrimido[5,4-e]pyrimidin-5(6H)-one;

6-(2-chloro-6-fluorophenyl)-2-[(1,1,2,3,3-pentamethyl-2,3-dihydro-1H-isoindol-5-yl)amino]imidazo[1,2-a]pyrimido[5,4-e]pyrimidin-5(6H)-one;

6-(2-chlorophenyl)-2-({4-[4-(oxetan-3-yl)piperazin-1-yl]phenyl}amino)imidazo[1,2-a]pyrimido[5,4-e]pyrimidin-5(6H)-one;

6-(2,6-dichloro-4-fluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one;

6-(2,6-dichlorophenyl)-2-[(4-oxo-1,4-dihydrocinnolin-6-yl)amino]imidazo[1,2-a]pyrimido[5,4-e]pyrimidin-5(6H)-one;

2-{[4-(4-acetylpiperazin-1-yl)phenyl]amino}-6-(2,6-dichlorophenyl)imidazo[1,2-a]pyrimido[5,4-e]pyrimidin-5(6H)-one;

6-(2,6-dichlorophenyl)-2-({4-[4-(dimethylamino)piperidin-1-yl]phenyl}amino)imidazo[1,2-a]pyrimido[5,4-e]pyrimidin-5(6H)-one;

methyl 4-{[6-(2,6-dichlorophenyl)-5-oxo-5,6-dihydroimidazo[1,2-a]pyrimido[5,4-e]pyrimidin-2-yl]amino}benzoate;

6-(2-chlorophenyl)-2-{[3,5-dichloro-4-(piperazin-1-yl)phenyl]amino}imidazo[1,2-a]pyrimido[5,4-e]pyrimidin-5(6H)-one;

6-(2-chlorophenyl)-2-{[4-(imidazo[1,2-a]pyridin-2-yl)phenyl]amino}imidazo[1,2-a]pyrimido[5,4-e]pyrimidin-5(6H)-one;

6-(2-chlorophenyl)-2-({4-[4-oxo-3-(propan-2-yl)-1,3-thiazolidin-2-yl]phenyl}amino)imidazo[1,2-a]pyrimido[5,4-e]pyrimidin-5(6H)-one;

6-(2-chlorophenyl)-2-{[4-(2,3-dihydroimidazo[2,1-b][1,3]thiazol-6-yl)phenyl]amino}imidazo[1,2-a]pyrimido[5,4-e]pyrimidin-5(6H)-one;

6-(2-chlorophenyl)-2-{[4-(5-methyl-4-oxo-1,3-thiazolidin-2-yl)phenyl]amino}imidazo[1,2-a]pyrimido[5,4-e]pyrimidin-5(6H)-one;

6-(2-chlorophenyl)-2-{[4-(imidazo[2,1-b][1,3]thiazol-6-yl)phenyl]amino}imidazo[1,2-a]pyrimido[5,4-e]pyrimidin-5(6H)-one;

6-(2-chlorophenyl)-2-{[4-(3-oxo-2,3-dihydro-1H-indazol-7-yl)phenyl]amino}imidazo[1,2-a]pyrimido[5,4-e]pyrimidin-5(6H)-one;

6-(2-chloro-6-fluorophenyl)-2-{[2'-(2,2-difluoro ethyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2'-(2-fluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2'-(2-fluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2-(diethylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[2-(diethylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[2-(cyclopropylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[2-(cyclopropylamino)-2,3-dihydro-1H-inden-5-yl]amino}imidazo[1,2-a]pyrimido[5,4-e]pyrimidin-5(6H)-one;

6-(2-chloro-6-fluorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one;

2-{[4-(1,4'-bipiperidin-1'-yl)phenyl]amino}-6-(2-chlorophenyl)imidazo[1,2-a]pyrimido[5,4-e]pyrimidin-5(6H)-one;

6-(2-chlorophenyl)-2-({4-[(3R)-3-(dimethylamino)pyrrolidin-1-yl]phenyl}amino)imidazo[1,2-a]pyrimido[5,4-e]pyrimidin-5(6H)-one;

6-(2-chlorophenyl)-2-({4-[3-(trifluoromethyl)piperidin-1-yl]phenyl}amino)imidazo[1,2-a]pyrimido[5,4-e]pyrimidin-5(6H)-one;

3-[4-(4-{[6-(2-chlorophenyl)-5-oxo-5,6-dihydroimidazo[1,2-a]pyrimido[5,4-e]pyrimidin-2-yl]amino}phenyl)piperazin-1-yl]propanenitrile;

3-[(4-{[6-(2-chlorophenyl)-5-oxo-5,6-dihydroimidazo[1,2-a]pyrimido[5,4-e]pyrimidin-2-yl]amino}phenyl)(cyclopropyl)amino]propanenitrile;

6-(2-chlorophenyl)-2-[(4-{[2-(dimethylamino)ethyl]amino}phenyl)amino]imidazo[1,2-a]pyrimido[5,4-e]pyrimidin-5(6H)-one;

1-(4-{[6-(2-chlorophenyl)-5-oxo-5,6-dihydroimidazo[1,2-a]pyrimido[5,4-e]pyrimidin-2-yl]amino}phenyl)piperidine-4-carboxamide;

6-(2-chlorophenyl)-2-({4-[4-(morpholin-4-yl)piperidin-1-yl]phenyl}amino)imidazo[1,2-a]pyrimido[5,4-e]pyrimidin-5(6H)-one;

6-(2,6-dichlorophenyl)-2-[(4-{[4-(dimethylamino)piperidin-1-yl]carbonyl}phenyl)amino]imidazo[1,2-a]pyrimido[5,4-e]pyrimidin-5(6H)-one;

4-{[6-(2,6-dichlorophenyl)-5-oxo-5,6-dihydroimidazo[1,2-a]pyrimido[5,4-e]pyrimidin-2-yl]amino}-N-[4-(dimethylamino)cyclohexyl]benzamide;

4-{[6-(2,6-dichlorophenyl)-5-oxo-5,6-dihydroimidazo[1,2-a]pyrimido[5,4-e]pyrimidin-2-yl]amino}-N-(1-methylpiperidin-4-yl)benzamide;

6-(2,6-dichlorophenyl)-2-({4-[4-(pyrrolidin-1-yl)piperidin-1-yl]phenyl}amino)imidazo[1,2-a]pyrimido[5,4-e]pyrimidin-5(6H)-one;

2-[(2'-acetyl-2',3'-dihydro-1'H-spiro[cyclopropane-1,4'-isoquinolin]-7'-yl)amino]-6-(2-chloro-6-fluorophenyl)imidazo[1,2-a]pyrimido[5,4-e]pyrimidin-5(6H)-one;

6-(2-chloro-6-fluorophenyl)-2-{[2'-(cyclopropylcarbonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-({4-[(8aR)-hexahydropyrrolo[1,2-a]pyrazin-2(1H)-yl]phenyl}amino)imidazo[1,2-a]pyrimido[5,4-e]pyrimidin-5(6H)-one;

2-({4-[(3R)-1-azabicyclo[2.2.2]oct-3-ylamino]phenyl}amino)-6-(2-chlorophenyl)imidazo[1,2-a]pyrimido[5,4-e]pyrimidin-5(6H)-one;

6-(2-chlorophenyl)-2-[(4-{[2-(pyrrolidin-1-yl)ethyl]amino}phenyl)amino]imidazo[1,2-a]pyrimido[5,4-e]pyrimidin-5(6H)-one;

6-(2-chlorophenyl)-2-({4-[4-(pyridin-2-yl)piperazin-1-yl]phenyl}amino)imidazo[1,2-a]pyrimido[5,4-e]pyrimidin-5(6H)-one;

6-(2-chlorophenyl)-2-[(4-{[2-(morpholin-4-yl)ethyl]amino}phenyl)amino]imidazo[1,2-a]pyrimido[5,4-e]pyrimidin-5(6H)-one;

6-(2-chlorophenyl)-2-({4-[(2S)-2-(pyrrolidin-1-ylmethyl)pyrrolidin-1-yl]phenyl}amino)imidazo[1,2-a]pyrimido[5,4-e]pyrimidin-5(6H)-one;

6-(2-chlorophenyl)-2-[(4-{4-[3-(dimethylamino)propyl]piperazin-1-yl}phenyl)amino]imidazo[1,2-a]pyrimido[5,4-e]pyrimidin-5(6H)-one;

6-(2-chlorophenyl)-2-({4-[(2R)-2-(methoxymethyl)pyrrolidin-1-yl]phenyl}amino)imidazo[1,2-a]pyrimido[5,4-e]pyrimidin-5(6H)-one;

1-(4-{[6-(2-chlorophenyl)-5-oxo-5,6-dihydroimidazo[1,2-a]pyrimido[5,4-e]pyrimidin-2-yl]amino}phenyl)-N,N-diethylpiperidine-3-carboxamide;

6-(2-chlorophenyl)-2-[(4-{[3-(2-oxopyrrolidin-1-yl)propyl]amino}phenyl)amino]imidazo[1,2-a]pyrimido[5,4-e]pyrimidin-5(6H)-one;

6-(2-chlorophenyl)-2-({4-[4-(4-fluorophenyl)piperazin-1-yl]phenyl}amino)imidazo[1,2-a]pyrimido[5,4-e]pyrimidin-5(6H)-one;

6-(2-chloro-6-fluorophenyl)-2-({4-[4-(dimethylamino)piperidin-1-yl]phenyl}amino)imidazo[1,2-a]pyrimido[5,4-e]pyrimidin-5(6H)-one;

6-(2-chloro-6-fluorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one;

6-(2-chloro-6-fluorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one;

6-(2-chloro-6-fluorophenyl)-2-({2-[(2-fluoroethyl)amino]-2,3-dihydro-1H-inden-5-yl}amino)imidazo[1,2-a]pyrimido[5,4-e]pyrimidin-5(6H)-one;

6-(2-chloro-6-fluorophenyl)-2-({2-[(2-fluoroethyl)amino]-2,3-dihydro-1H-inden-5-yl}amino)imidazo[1,2-a]pyrimido[5,4-e]pyrimidin-5(6H)-one;

6-(2-chloro-6-fluorophenyl)-2-{[2-(propylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[2-(propylamino)-2,3-dihydro-1H-inden-5-yl]amino}imidazo[1,2-a]pyrimido[5,4-e]pyrimidin-5(6H)-one;

6-(2-chloro-6-fluorophenyl)-2-{[2-(pyrrolidin-1-yl)-2,3-dihydro-1H-inden-5-yl]amino}imidazo[1,2-a]pyrimido[5,4-e]pyrimidin-5(6H)-one;

6-(2-chlorophenyl)-2-[(4-{4-[2-(dimethylamino)ethyl]piperazin-1-yl}phenyl)amino]imidazo[1,2-a]pyrimido[5,4-e]pyrimidin-5(6H)-one;

6-(2-chlorophenyl)-2-[(4-{[3-(dimethylamino)propyl](methyl)amino}phenyl)amino]imidazo[1,2-a]pyrimido[5,4-e]pyrimidin-5(6H)-one;

6-(2-chlorophenyl)-2-[(4-{[2-(dimethylamino)ethyl](ethyl)amino}phenyl)amino]imidazo[1,2-a]pyrimido[5,4-e]pyrimidin-5(6H)-one;

6-(2-chlorophenyl)-2-[(4-{[2-(dimethylamino)ethyl](methyl)amino}phenyl)amino]imidazo[1,2-a]pyrimido[5,4-e]pyrimidin-5(6H)-one;

6-(2-chlorophenyl)-2-({4-[(2S)-2-(methoxymethyl)pyrrolidin-1-yl]phenyl}amino)imidazo[1,2-a]pyrimido[5,4-e]pyrimidin-5(6H)-one;

6-(2-chloro-6-fluorophenyl)-2-{[2'-(2-methylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2'-(2,2-dimethylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-{[2'-(cyclopentylcarbonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chlorophenyl)-2-[(4-{[2-(1H-imidazol-4-yl)ethyl]amino}phenyl)amino]imidazo[1,2-a]pyrimido[5,4-e]pyrimidin-5(6H)-one;

6-(2-chlorophenyl)-2-[(4-{[3-(1H-imidazol-1-yl)propyl]amino}phenyl)amino]imidazo[1,2-a]pyrimido[5,4-e]pyrimidin-5(6H)-one;

6-(2-chlorophenyl)-2-{[4-(thiomorpholin-4-yl)phenyl]amino}imidazo[1,2-a]pyrimido[5,4-e]pyrimidin-5(6H)-one;

6-(2-chlorophenyl)-2-[(4-{propan-2-yl[2-(propan-2-ylamino)ethyl]amino}phenyl)amino]imidazo[1,2-a]pyrimido[5,4-e]pyrimidin-5(6H)-one;

1-(4-{[6-(2-chlorophenyl)-5-oxo-5,6-dihydroimidazo[1,2-a]pyrimido[5,4-e]pyrimidin-2-yl]amino}phenyl)piperidine-3-carboxamide;

6-(2,6-dichlorophenyl)-2-[(4-{[2-(1-methylpyrrolidin-2-yl)ethyl]amino}phenyl)amino]imidazo[1,2-a]pyrimido[5,4-e]pyrimidin-5(6H)-one;

6-(2,6-dichlorophenyl)-2-{[2'-(2-methylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

2-{[2'-(cyclopropylcarbonyl)-2',3'-dihydro-1'H-spiro[cyclopropane-1,4'-isoquinolin]-7'-yl]amino}-6-(2,6-dichlorophenyl)imidazo[1,2-a]pyrimido[5,4-e]pyrimidin-5(6H)-one;

6-(2,6-dichlorophenyl)-2-{[2'-(2,2-dimethylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2-chloro-6-fluorophenyl)-2-(5,6,7,8-tetrahydro-1,6-naphthyridin-3-ylamino)imidazo[1,2-a]pyrimido[5,4-e]pyrimidin-5(6H)-one;

6-(2-chloro-3-hydroxyphenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one;

2-(2',3'-dihydro-1'H-spiro[cyclopropane-1,4'-isoquinolin]-7'-ylamino)-6-(4-hydroxy-2-methylphenyl)imidazo[1,2-a]pyrimido[5,4-e]pyrimidin-5(6H)-one;

6-(2-chloro-6-fluorophenyl)-2-{[2-(2,2-difluoro ethyl)-4,4-dimethyl-1,2,3,4-tetrahydroisoquinolin-7-yl]amino}imidazo[1,2-a]pyrimido[5,4-e]pyrimidin-5(6H)-one;

6-(2-chloro-6-fluorophenyl)-2-{[2-(2-fluoro ethyl)-4,4-dimethyl-1,2,3,4-tetrahydroisoquinolin-7-yl]amino}imidazo[1,2-a]pyrimido[5,4-e]pyrimidin-5(6H)-one;

2-{[4-(1,4'-bipiperidin-1'-yl)phenyl]amino}-6-(2,6-dichlorophenyl)imidazo[1,2-a]pyrimido[5,4-e]pyrimidin-5(6H)-one;

6-(2,6-dichlorophenyl)-2-({4-[(3R)-3-(dimethylamino)pyrrolidin-1-yl]phenyl}amino)imidazo[1,2-a]pyrimido[5,4-e]pyrimidin-5(6H)-one;

6-(2,6-dichlorophenyl)-2-[(4-{[2-(dimethylamino)ethyl]amino}phenyl)amino]imidazo[1,2-a]pyrimido[5,4-e]pyrimidin-5(6H)-one;

2-{[2'-(cyclopropylsulfonyl)-2',3'-dihydro-1'H-spiro[cyclopropane-1,4'-isoquinolin]-7'-yl]amino}-6-(2,6-dichlorophenyl)imidazo[1,2-a]pyrimido[5,4-e]pyrimidin-5(6H)-one;

6-(2,6-dichlorophenyl)-2-{[2'-(propan-2-ylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one;

6-(2,6-dichlorophenyl)-2-{[4-(1-methylpiperidin-4-yl)phenyl]amino}imidazo[1,2-a]pyrimido[5,4-e]pyrimidin-5(6H)-one;

2-{[4-(2,7-diazaspiro[3.5]non-7-yl)phenyl]amino}-6-(2,6-dichlorophenyl)imidazo[1,2-a]pyrimido[5,4-e]pyrimidin-5(6H)-one;

6-(2-chlorophenyl)-2-({4-[2-(trifluoromethyl)pyrrolidin-1-yl]phenyl}amino)imidazo[1,2-a]pyrimido[5,4-e]pyrimidin-5(6H)-one;

6-(2-chlorophenyl)-2-{[4-(piperidin-4-yloxy)phenyl]amino}imidazo[1,2-a]pyrimido[5,4-e]pyrimidin-5(6H)-one;

6-(2-chlorophenyl)-2-{[4-(piperidin-4-ylmethyl)phenyl]amino}imidazo[1,2-a]pyrimido[5,4-e]pyrimidin-5(6H)-one;

6-(2-chlorophenyl)-2-{[4-(hexahydropyrrolo[3,4-c]pyrrol-2(1H)-yl)phenyl]amino}imidazo[1,2-a]pyrimido[5,4-e]pyrimidin-5(6H)-one;

1-(4-{[6-(2-chlorophenyl)-5-oxo-5,6-dihydroimidazo[1,2-a]pyrimido[5,4-e]pyrimidin-2-yl]amino}phenyl)-N-methylmethanesulfonamide;

4-{[6-(2-chlorophenyl)-5-oxo-5,6-dihydroimidazo[1,2-a]pyrimido[5,4-e]pyrimidin-2-yl]amino}-N,N-diethylbenzenesulfonamide;

2-{[2-(cyclopropylamino)-2,3-dihydro-1H-inden-5-yl]amino}-6-(2,6-dichlorophenyl)imidazo[1,2-a]pyrimido[5,4-e]pyrimidin-5(6H)-one;

6-(2,6-dichlorophenyl)-2-({2-[(2-fluoro ethyl)amino]-2,3-dihydro-1H-inden-5-yl}amino)imidazo[1,2-a]pyrimido[5,4-e]pyrimidin-5(6H)-one;

6-(2,6-dichlorophenyl)-2-{[2-(propylamino)-2,3-dihydro-1H-inden-5-yl]amino}imidazo[1,2-a]pyrimido[5,4-e]pyrimidin-5(6H)-one;

2-{[4-(2-acetyl-2,7-diazaspiro[3.5]non-7-yl)phenyl]amino}-6-(2,6-dichlorophenyl)imidazo[1,2-a]pyrimido[5,4-e]pyrimidin-5(6H)-one;

6-(2,6-dichlorophenyl)-2-({4-[2-(methylsulfonyl)-2,7-diazaspiro[3.5]non-7-yl]phenyl}amino)imidazo[1,2-a]pyrimido[5,4-e]pyrimidin-5(6H)-one;

7'-{[6-(2-chloro-6-fluorophenyl)-5-oxo-5,6-dihydroimidazo[1,2-a]pyrimido[5,4-e]pyrimidin-2-yl]amino}-N-methyl-1'H-spiro[cyclopropane-1,4'-isoquinoline]-2'(3'H)-carboxamide;

7'-{[6-(2-chloro-6-fluorophenyl)-5-oxo-5,6-dihydroimidazo[1,2-a]pyrimido[5,4-e]pyrimidin-2-yl]amino}-N-(propan-2-yl)-1'H-spiro[cyclopropane-1,4'-isoquinoline]-2'(3'H)-carboxamide;

6-(2,6-dichlorophenyl)-2-{[2-(2-fluoro ethyl)-4,4-dimethyl-1,2,3,4-tetrahydroisoquinolin-7-yl]amino}imidazo[1,2-a]pyrimido[5,4-e]pyrimidin-5(6H)-one;

6-(2,6-dichlorophenyl)-2-({4-[6-(methylsulfonyl)-2,6-diazaspiro[3.3]hept-2-yl]phenyl}amino)imidazo[1,2-a]pyrimido[5,4-e]pyrimidin-5(6H)-one;

6-(2,6-dichlorophenyl)-2-{[2-(pyrrolidin-1-yl)-2,3-dihydro-1H-inden-5-yl]amino}imidazo[1,2-a]pyrimido[5,4-e]pyrimidin-5(6H)-one;

6-(2,6-dichlorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one;

6-(2,6-dichlorophenyl)-2-[(4,4-dimethyl-1,2,3,4-tetrahydroisoquinolin-7-yl)amino]imidazo[1,2-a]pyrimido[5,4-e]pyrimidin-5(6H)-one;

6-(2,6-dichlorophenyl)-2-{[4-(piperidin-4-ylamino)phenyl]amino}imidazo[1,2-a]pyrimido[5,4-e]pyrimidin-5(6H)-one;

6-(2-chloro-6-fluorophenyl)-2-{[4-(1-methylpiperidin-4-yl)phenyl]amino}imidazo[1,2-a]pyrimido[5,4-e]pyrimidin-5(6H)-one;

2-[(2-acetyl-4,4-dimethyl-1,2,3,4-tetrahydroisoquinolin-7-yl)amino]-6-(2-chloro-6-fluorophenyl)imidazo[1,2-a]pyrimido[5,4-e]pyrimidin-5(6H)-one;

6-(2-chloro-6-fluorophenyl)-2-{[2-(cyclopropylcarbonyl)-4,4-dimethyl-1,2,3,4-tetrahydroisoquinolin-7-yl]amino}imidazo[1,2-a]pyrimido[5,4-e]pyrimidin-5(6H)-one;

6-(2-chloro-6-fluorophenyl)-2-{[4,4-dimethyl-2-(methylsulfonyl)-1,2,3,4-tetrahydroisoquinolin-7-yl]amino}imidazo[1,2-a]pyrimido[5,4-e]pyrimidin-5(6H)-one;

2-{[4-(2,6-diazaspiro[3.4]oct-2-yl)phenyl]amino}-6-(2,6-dichlorophenyl)imidazo[1,2-a]pyrimido[5,4-e]pyrimidin-5(6H)-one;

2-{[4-(2,7-diazaspiro[3.5]non-2-yl)phenyl]amino}-6-(2,6-dichlorophenyl)imidazo[1,2-a]pyrimido[5,4-e]pyrimidin-5(6H)-one;

6-(2,6-dichlorophenyl)-2-({4-[(3S)-3-(dimethylamino)pyrrolidin-1-yl]phenyl}amino)imidazo[1,2-a]pyrimido[5,4-e]pyrimidin-5(6H)-one;

6-(2-chloro-6-fluorophenyl)-2-{[2-(hydroxyacetyl)-4,4-dimethyl-1,2,3,4-tetrahydroisoquinolin-7-yl]amino}imidazo[1,2-a]pyrimido[5,4-e]pyrimidin-5(6H)-one;

7-{[6-(2-chloro-6-fluorophenyl)-5-oxo-5,6-dihydroimidazo[1,2-a]pyrimido[5,4-e]pyrimidin-2-yl]amino}-4,4-dimethyl-3,4-dihydroisoquinoline-2(1H)-sulfonamide;

2-[(2-acetyl-4,4-dimethyl-1,2,3,4-tetrahydroisoquinolin-7-yl)amino]-6-(2,6-dichlorophenyl)imidazo[1,2-a]pyrimido[5,4-e]pyrimidin-5(6H)-one;

6-(2,6-dichlorophenyl)-2-{[4,4-dimethyl-2-(methylsulfonyl)-1,2,3,4-tetrahydroisoquinolin-7-yl]amino}imidazo[1,2-a]pyrimido[5,4-e]pyrimidin-5(6H)-one;

6-(2,6-dichlorophenyl)-2-{[2-(ethylsulfonyl)-4,4-dimethyl-1,2,3,4-tetrahydroisoquinolin-7-yl]amino}imidazo[1,2-a]pyrimido[5,4-e]pyrimidin-5(6H)-one;

2-({4-[(1-acetylpiperidin-4-yl)amino]phenyl}amino)-6-(2,6-dichlorophenyl)imidazo[1,2-a]pyrimido[5,4-e]pyrimidin-5(6H)-one;

6-(2,6-dichlorophenyl)-2-[(4-{[1-(methylsulfonyl)piperidin-4-yl]amino}phenyl)amino]imidazo[1,2-a]pyrimido[5,4-e]pyrimidin-5(6H)-one;

6-(2,6-dichlorophenyl)-2-{[4-(9-methyl-3,9-diazaspiro[5.5]undec-3-yl)phenyl]amino}imidazo[1,2-a]pyrimido[5,4-e]pyrimidin-5(6H)-one;

6-(2,6-dichlorophenyl)-2-({4-[6-(methylsulfonyl)-2,6-diazaspiro[3.4]oct-2-yl]phenyl}amino)imidazo[1,2-a]pyrimido[5,4-e]pyrimidin-5(6H)-one;

6-(2-chlorophenyl)-2-({4-[(8aS)-hexahydropyrrolo[1,2-a]pyrazin-2(1H)-yl]phenyl}amino)imidazo[1,2-a]pyrimido[5,4-e]pyrimidin-5(6H)-one;

6-(2,6-dichlorophenyl)-2-({4-[(3aR,6aR)-5-methylhexahydropyrrolo[3,4-b]pyrrol-1(2H)-yl]phenyl}amino)imidazo[1,2-a]pyrimido[5,4-e]pyrimidin-5(6H)-one;

6-(2,6-dichlorophenyl)-2-[(4-{[2-(dimethylamino)ethyl](ethyl)amino}phenyl)amino]imidazo[1,2-a]pyrimido[5,4-e]pyrimidin-5(6H)-one;

6-(2,6-dichlorophenyl)-2-[(4-{propan-2-yl[2-(propan-2-ylamino)ethyl]amino}phenyl)amino]imidazo[1,2-a]pyrimido[5,4-e]pyrimidin-5(6H)-one;

2-[(2-acetyl-1,2,3,4-tetrahydroisoquinolin-7-yl)amino]-6-(2,6-dichlorophenyl)imidazo[1,2-a]pyrimido[5,4-e]pyrimidin-5(6H)-one;

6-(2,6-dichlorophenyl)-2-{[2-(methylsulfonyl)-1,2,3,4-tetrahydroisoquinolin-6-yl]amino}imidazo[1,2-a]pyrimido[5,4-e]pyrimidin-5(6H)-one;

2-[(2-acetyl-1,2,3,4-tetrahydroisoquinolin-6-yl)amino]-6-(2,6-dichlorophenyl)imidazo[1,2-a]pyrimido[5,4-e]pyrimidin-5(6H)-one;

6-(2-chlorophenyl)-2-{[4-(4-methylpiperazin-1-yl)phenyl]amino}imidazo[1,2-a]pyrimido[5,4-e]pyrimidine-5(6H)-thione;

6-(2-chlorophenyl)-5-imino-N-[4-(4-methylpiperazin-1-yl)phenyl]-5,6-dihydroimidazo[1,2-a]pyrimido[5,4-e]pyrimidin-2-amine;

6-(2-chlorophenyl)-2-[(2,4,4-trimethyl-1,2,3,4-tetrahydroisoquinolin-7-yl)amino]imidazo[1,2-a]pyrimido[5,4-e]pyrimidine-5(6H)-thione;

6-(2-chlorophenyl)-5-imino-N-(2,4,4-trimethyl-1,2,3,4-tetrahydroisoquinolin-7-yl)-5,6-dihydroimidazo[1,2-a]pyrimido[5,4-e]pyrimidin-2-amine;

6-(3-fluorophenyl)-2-{[4-(4-methylpiperazin-1-yl)phenyl]amino}imidazo[1,2-a]pyrimido[5,4-e]pyrimidin-5(6H)-one;

6-(3-chlorophenyl)-2-{[4-(4-methylpiperazin-1-yl)phenyl]amino}imidazo[1,2-a]pyrimido[5,4-e]pyrimidin-5(6H)-one;

6-(2,4-dimethoxyphenyl)-2-{[4-(4-methylpiperazin-1-yl)phenyl]amino}imidazo[1,2-a]pyrimido[5,4-e]pyrimidin-5(6H)-one;

6-(2-chlorophenyl)-2-{[5-(4-ethylpiperazin-1-yl)pyridin-2-yl]amino}imidazo[1,2-a]pyrimido[5,4-e]pyrimidin-5(6H)-one;

6-[2-chloro-4-(trifluoromethyl)phenyl]-2-{[4-(4-methylpiperazin-1-yl)phenyl]amino}imidazo[1,2-a]pyrimido[5,4-e]pyrimidin-5(6H)-one;

2-{[4-(4-methylpiperazin-1-yl)phenyl]amino}-6-[2-(trifluoromethoxy)phenyl]imidazo[1,2-a]pyrimido[5,4-e]pyrimidin-5(6H)-one;

4-{[6-(2-chlorophenyl)-5-oxo-5,6-dihydroimidazo[1,2-a]pyrimido[5,4-e]pyrimidin-2-yl]amino}benzoic acid;

2-[(4-bromophenyl)amino]-6-(2-chlorophenyl)imidazo[1,2-a]pyrimido[5,4-e]pyrimidin-5(6H)-one;

6-(3-methoxy-2-methylphenyl)-2-(phenylamino)imidazo[1,2-a]pyrimido[5,4-e]pyrimidin-5(6H)-one;

2-{[4-(1,4-diazepan-1-yl)-3-methylphenyl]amino}-6-(2,6-dichlorophenyl)imidazo[1,2-a]pyrimido[5,4-e]pyrimidin-5(6H)-one;

2-{[4-(4-methylpiperazin-1-yl)phenyl]amino}-6-(propan-2-yl)imidazo[1,2-a]pyrimido[5,4-e]pyrimidin-5(6H)-one;

6-(2-chlorophenyl)-2-{[3,5-difluoro-4-(4-methylpiperazin-1-yl)phenyl]amino}imidazo[1,2-a]pyrimidin-5(6H)-one;

6-(2-chlorophenyl)-2-{[4-(trifluoromethyl)phenyl]amino}imidazo[1,2-a]pyrimido[5,4-e]pyrimidin-5(6H)-one;

6-(2-chlorophenyl)-2-{[4-(1,3-thiazol-4-yl)phenyl]amino}imidazo[1,2-a]pyrimido[5,4-e]pyrimidin-5(6H)-one;

6-(2-chlorophenyl)-2-{[4-(1,3-thiazol-2-yl)phenyl]amino}imidazo[1,2-a]pyrimido[5,4-e]pyrimidin-5(6H)-one;

6-(2-chlorophenyl)-2-{[4-(1,8-naphthyridin-2-yl)phenyl]amino}imidazo[1,2-a]pyrimido[5,4-e]pyrimidin-5(6H)-one;

6-(2-chlorophenyl)-2-({4-[(2S)-2-(trifluoromethyl)pyrrolidin-1-yl]phenyl}amino)imidazo[1,2-a]pyrimido[5,4-e]pyrimidin-5(6H)-one;

2-{[3-chloro-4-(4-methylpiperazin-1-yl)-5-(trifluoromethyl)phenyl]amino}-6-(2-chlorophenyl)imidazo[1,2-a]pyrimido[5,4-e]pyrimidin-5(6H)-one;

6-(2-chlorophenyl)-2-{[3-chloro-4-(piperazin-1-yl)-5-(trifluoromethyl)phenyl]amino}imidazo[1,2-a]pyrimido[5,4-e]pyrimidin-5(6H)-one;

6-(2-chlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidine-5(6H)-thione;

2-{[7-{[6-(2-chlorophenyl)-5-oxo-5,6-dihydroimidazo[1,2-a]pyrimido[5,4-e]pyrimidin-2-yl]amino}-4,4-dimethyl-3,4-dihydroisoquinolin-2(1H)-yl]methyl}benzonitrile;

6-(2-chlorophenyl)-2-{[4,4-dimethyl-2-(4-propoxybenzyl)-1,2,3,4-tetrahydroisoquinolin-7-yl]amino}imidazo[1,2-a]pyrimido[5,4-e]pyrimidin-5(6H)-one;

6-(2-chlorophenyl)-2-({2-[3-fluoro-5-(trifluoromethyl)benzyl]-4,4-dimethyl-1,2,3,4-tetrahydroisoquinolin-7-yl}amino)imidazo[1,2-a]pyrimido[5,4-e]pyrimidin-5(6H)-one;

6-(2-chlorophenyl)-2-[(4-{2-[(2R)-2-methylpyrrolidin-1-yl]ethyl}phenyl)amino]imidazo[1,2-a]pyrimido[5,4-e]pyrimidin-5(6H)-one;

6-(2-chlorophenyl)-2-({4-[2-(morpholin-4-yl)-1,3-thiazol-4-yl]phenyl}amino)imidazo[1,2-a]pyrimido[5,4-e]pyrimidin-5(6H)-one; and 6-(2-chlorophenyl)-2-({4-[2-(6-methylquinolin-2-yl)ethyl] phenyl}amino)imidazo[1,2-a]pyrimido[5,4-e]pyrimidin-5(6H)-one.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, aralyphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like. Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Schemes

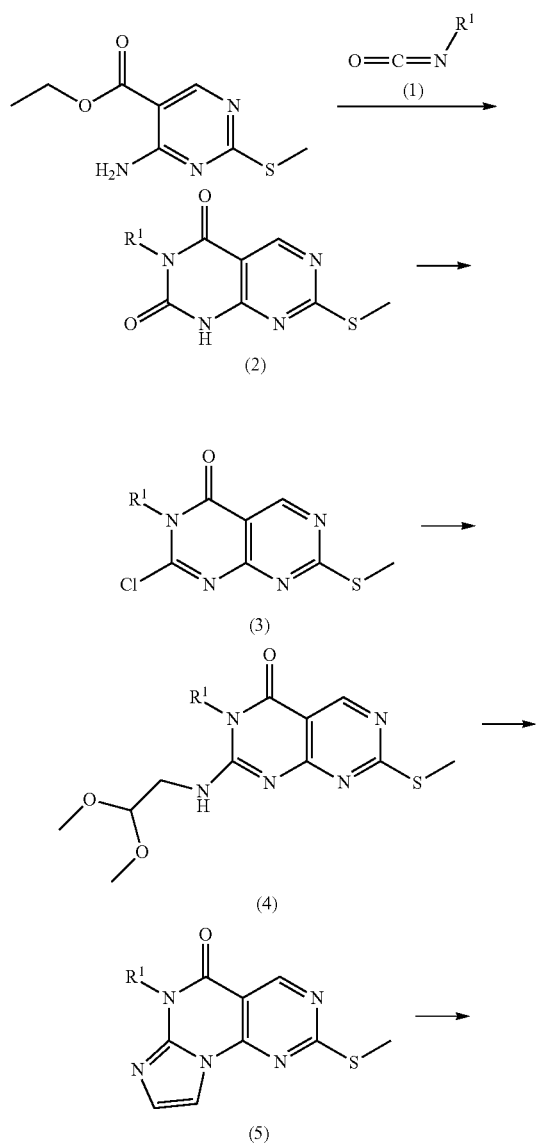

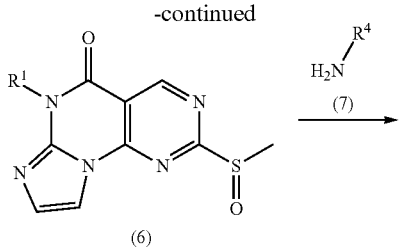

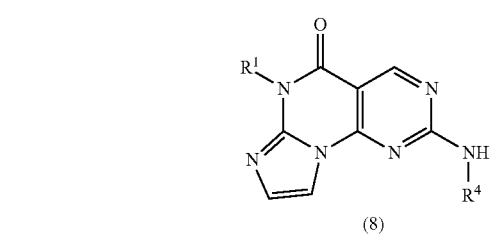

As shown in Scheme 1, ethyl 4-amino-2-(methylthio)pyrimidine-5-carboxylate (prepared as described in US 2005/0020590) can be reacted with a base such as, but not limited to, sodium hydride, followed by compounds of formula (1), wherein $R^1$ is as described herein, to provide compounds of formula (2). The reaction is typically performed at low temperature in a solvent such as, but not limited to, N,N-dimethylformamide. Compounds of formula (2) can be reacted with phosphorus oxychloride in the presence of a base such as, but not limited to, N,N-diisopropylethylamine, to provide compounds of formula (3). 2,2-Dimethoxyethanamine can be reacted with compounds of formula (3) at an elevated temperature to provide compounds of formula (4). The reaction is typically performed in a solvent such as but not limited to acetonitrile. Compounds of formula (4) can be reacted with an acid such as, but not limited to, concentrated hydrochloric acid to provide compounds of formula (5). The reaction is typically performed at elevated temperature in a solvent such as, but not limited to, acetonitrile and may be conducted in a single mode microwave oven. Compounds of formula (6) can be prepared by reacting compounds of formula (5) with meta-chloroperoxybenzoic acid. The reaction is typically performed at ambient temperature in a solvent such as but not limited to dichloromethane. Compounds of formula (6) can be reacted with compounds of formula (7), wherein $R^4$ is as described herein, to provide compounds of formula (8), which are representative of the compounds of this invention. The reaction is typically performed at elevated temperature and may not require the use of a solvent.

Scheme 2

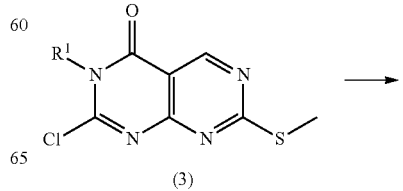

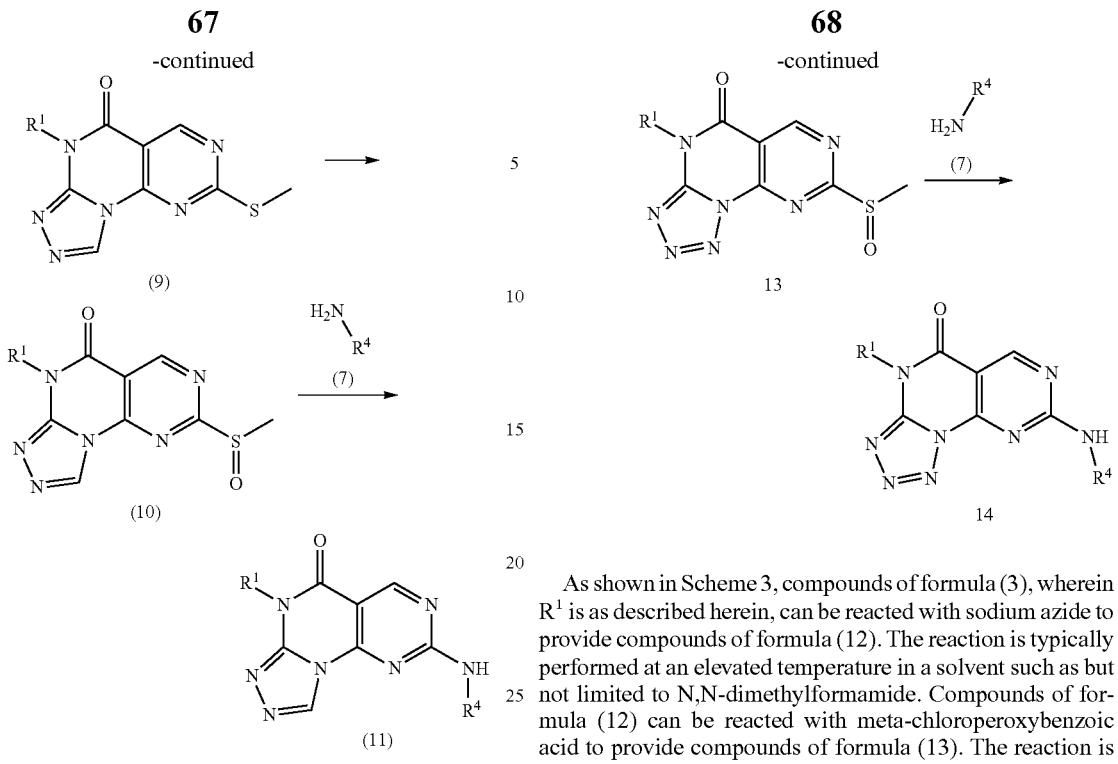

Compounds of formula (3), wherein $R^1$ is as described herein, can be reacted with formylhydrazide to provide compounds of formula (9). The reaction is typically performed in a solvent such as but not limited to acetonitrile, at elevated temperature. Additionally, the reaction may be performed in a microwave oven. Compounds of formula (9) can be reacted with meta-chloroperoxybenzoic acid to provide compounds of formula (10). The reaction is typically performed at ambient temperature in a solvent such as but not limited to dichloromethane. Compounds of formula (10) can be reacted with compounds of formula (7), wherein $R^4$ is as described herein, to provide compounds of formula (11), which are representative of the compounds of this invention. The reaction is typically performed at elevated temperature and may not require the use of a solvent.

Scheme 3

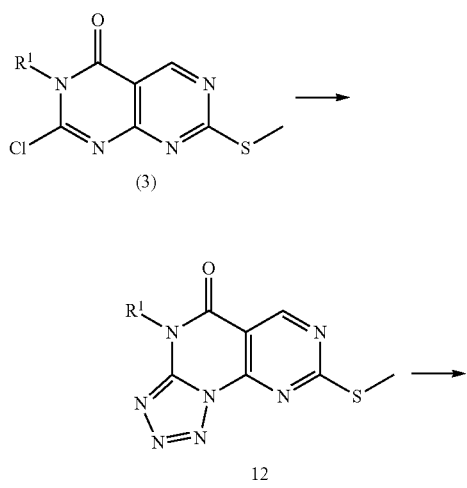

As shown in Scheme 3, compounds of formula (3), wherein $R^1$ is as described herein, can be reacted with sodium azide to provide compounds of formula (12). The reaction is typically performed at an elevated temperature in a solvent such as but not limited to N,N-dimethylformamide. Compounds of formula (12) can be reacted with meta-chloroperoxybenzoic acid to provide compounds of formula (13). The reaction is typically performed at ambient temperature in a solvent such as but not limited to dichloromethane. Compounds of formula (13) can be reacted with compounds of formula (7), wherein $R^4$ is as described herein, to provide compounds of formula (14), which are representative of the compounds of this invention. The reaction is typically performed at elevated temperature and may not require the use of a solvent.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperitoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all wee-1 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

In one group of embodiments, diseases and conditions of humans or other animals that can be treated with inhibitors of kinases, include, but are not limited to, tumors that are deficient in the p53 protein. The p53 protein is a tumor suppressor protein that is encoded in humans by the TP53 gene. The p53 protein regulates the cell cycle and therefore functions as a tumor suppressor that is involved in preventing cancer. Inhibition of Wee1 kinases sensitizes tumor cells to DNA damage and/or cell cycle perturbation, especially tumors that have lost their $G_1$-phase checkpoint due to a deficiency in the p53 protein.

A discussion of the loss of expression of Wee1 and how it relates to deficiency in the p53 protein can be found in *Annual Review of Biochemistry*, 2004, 73:39-85.

Involvement of mutations in the p53 gene and human tumor types can be found in *Nature*, 1989, 342:705-708.

A discussion of Wee1 kinase and p53 deficient tumor cells can be found in *Molecular Cancer Therapy*, 2009, 8:11.

A discussion of p53 and Wee1 kinases and anti-cancer therapies can be found in *BMC Cancer* 2006, 6:292.

A discussion of Wee1 kinase and p53 deficient tumor cells can be found in *Current Clinical Pharmacology*, 2010, 5:186-191.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxy-nucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(41R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(41R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine)(ONCOVIN®; P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

6-(2-chlorophenyl)-2-{[4-(4-methylpiperazin-1-yl)phenyl]amino}imidazo[1,2-a]pyrimido[5,4-e]pyrimidin-5(6H)-one Example 1A 3-(2-chlorophenyl)-7-(methylthio)pyrimido[4,5-d]pyrimidine-2,4(1H,3H)-dione NaH (5.26 g, 131 mmol) was added to a solution of ethyl 4-amino-2-(methylthio)pyrimidine-5-carboxylate (20.0 g, 94 mmol, US 2005/0020590) in N,N-dimethylformamide (700 mL) at 0° C. After 10 minutes, 1-chloro-2-isocyanatobenzene (15.9 mL, 131 mmol) was added dropwise to the mixture. The reaction was warmed to room temperature and stirred for 6 hours. The reaction mixture was diluted with brine (200 mL) and water (1000 mL) and extracted with ether (700 mL 2×). The aqueous layer was acidified with 5% citric acid (until pH=4-5), treated with brine, and extracted with ethyl acetate (2×). The combined organic layers were washed with water (2×), dried over MgSO$_4$, filtered, and concentrated to remove most of the solvent. The mixture was filtered, and the solid was washed with cold ethyl acetate, and oven dried to provide the title compound.

Example 1B

2-chloro-3-(2-chlorophenyl)-7-(methylthio)pyrimido[4,5-d]pyrimidin-4(3H)-one A mixture of Example 1A (15.9 g, 49.6 mmol) in $POCl_3$ (55 ml, 590 mmol) and diisopropylethylamine (55 ml, 315 mmol) was heated at 90° C. for 1.5 hours. The reaction mixture was concentrated. The residue was treated with ice and saturated $NaHCO_3$ carefully and then extracted with ethyl acetate. The insoluble material suspended in the two layers was filtered, washed with ether and water, and oven dried to provide the title compound. The two layers in the filtrate were separated. The aqueous layer was washed with ethyl acetate. The combined organic layers were dried over $MgSO_4$, filtered, concentrated, and triturated (twice) with ethyl acetate/ether to provide additional title compound.

Example 1C

3-(2-chlorophenyl)-2-(2,2-dimethoxyethylamino)-7-(methylthio)pyrimido[4,5-d]pyrimidin-4(3H)-one A mixture of 2,2-dimethoxyethanamine (0.744 g, 7.08 mmol) and Example 1B (1.20 g, 3.54 mmol) in acetonitrile (20 mL) was heated at 80° C. for 40 minutes. The mixture was concentrated, treated with $NaHCO_3$, and extracted with ethyl acetate (2×). The combined organic layers were dried over $MgSO_4$, filtered, and concentrated to provide the title compound.

Example 1D

4-(2-Chloro-phenyl)-8-methylsulfanyl-4H-3,4,7,9,9b-pentaaza-cyclopenta[a]naphthalen-5-one Example 1C (0.558 g) in acetonitrile (8 mL) was treated with concentrated HCl (0.10 mL). The mixture was heated in a Biotage microwave reactor at 160° C. for 15 minutes. The solvent was removed. The residue was treated with saturated $NaHCO_3$ and extracted with ethyl acetate (2×). The combined organic layers were dried over $MgSO_4$, filtered, concentrated, and purified on a 40 g column using the ISCO Companion flash system eluting with $CH_2Cl_2$/ethyl acetate (4:6 to 3:7) to provide the title compound.

Example 1E

4-(2-Chloro-phenyl)-8-methanesulfinyl-4H-3,4,7,9,9b-pentaaza-cyclopenta[a]naphthalen-5-one A mixture of meta-chloroperoxybenzoic acid (0.502 g, 2.24 mmol) and Example 1D (0.700 g, 2.04 mmol) in $CH_2Cl_2$ (40 mL) was stirred for 2 hours. The reaction mixture was diluted with $CH_2Cl_2$ and washed with saturated aqueous $NaHCO_3$ and saturated aqueous $Na_2S_2O_3$. The organic layer was dried over $MgSO_4$, filtered, and concentrated to provide the title compound.

Example 1F

6-(2-chlorophenyl)-2-{[4-(4-methylpiperazin-1-yl)phenyl]amino}imidazo[1,2-a]pyrimido[5,4-e]pyrimidin-5(6H)-one A mixture of Example 1E (45.0 mg, 0.125 mmol) and 4-(4-methylpiperazin-1-yl)aniline (52.6 mg, 0.275 mmol) was pre-mixed and heated in a vial at 90° C. for 1 hour. After cooling, the residue was treated with saturated $NaHCO_3$/brine and extracted with ethyl acetate (2×). The combined organic layers were dried over $MgSO_4$, filtered, concentrated, and purified by reverse-phase HPLC performed on a Zorbax RX-C18 column (250×21.2 mm, 7 μm particle size) using a gradient of 15% to 100% methanol: 0.1% aqueous trifluoroacetic acid over 48 minutes at a flow rate of 15 mL/minute to provide the title compound as a trifluoroacetic acid salt. $^1$H NMR (400 MHz, $CD_3OD$) δ ppm 2.97 (s, 3H), 3.08 (t, J=11.60 Hz, 2H), 3.22-3.34 (m, 2H), 3.61 (d, J=11.90 Hz, 2H), 3.84 (d, J=12.51 Hz, 2H), 6.95-7.17 (m, 3H), 7.47-7.64 (m, 3H), 7.64-7.88 (m, 4H), 9.06 (s, 1H). MS (ESI$^+$) m/z 487.3 (M+H)$^+$.

Example 2

2-anilino-6-(2-chlorophenyl)imidazo[1,2-a]pyrimido[5,4-e]pyrimidin-5(6H)-one A mixture of Example 1E (70.0 mg, 0.195 mmol) and aniline (39.1 μl, 0.428 mmol) was heated in a capped vial at 90° C. for 1 hour. After cooling, the residue was treated with saturated $NaHCO_3$/brine and extracted with ethyl acetate (2×). The combined organic layers were dried over $MgSO_4$, filtered, concentrated, and purified on a 12 g column using the ISCO Companion flash system eluting with $CH_2Cl_2$/ethyl acetate (8:2 to 7:3) to provide the title compound. $^1$H NMR (400 MHz, DMSO-$d_6$) δ ppm 7.08 (d, J=1.83 Hz, 1H), 7.14 (t, J=7.48 Hz, 1H), 7.42 (t, J=7.63 Hz, 2H), 7.54-7.59 (m, 2H), 7.61-7.66 (m, 1H), 7.70-7.74 (m, 1H), 7.79-7.90 (m, 3H), 9.14 (s, 1H), 10.78 (s, 1H). MS (ESI$^+$) m/z 389.2 (M+H)$^+$.

Example 3

6-(2-chlorophenyl)-2-(pyridin-4-ylamino)imidazo[1,2-a]pyrimido[5,4-e]pyrimidin-5(6H)-one A mixture of Example 1E (60.0 mg, 0.167 mmol) and pyridin-4-amine (34.5 mg, 0.367 mmol) was heated in a capped vial at 100° C. for 3 hours. The crude compound was purified by HPLC as described in Example 1F to provide the title compound as a trifluoroacetic acid salt. $^1$H NMR (400 MHz, DMSO-$d_6$) δ ppm 7.18 (d, J=1.83 Hz, 1H), 7.50-7.68 (m, 3H), 7.69-7.80 (m, 1H), 8.13 (d, J=1.83 Hz, 1H), 8.40 (d, J=7.32 Hz, 2H), 8.75 (d, J=7.32 Hz, 2H), 9.41 (s, 1H), 12.11 (s, 1H). MS (APCI$^+$) m/z 390.2 (M+H)$^+$.

Example 4

6-(2-chlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one Example 4 was prepared as described in Example 1F, substituting 4-(4-methylpiperazin-1-yl)aniline with 2'-methyl-2',3'-dihydro-1'H-spiro[cyclopropane-1,4'-isoquinolin]-7'-amine (WO 2009/151997). $^1$H NMR (400 MHz, $CD_3OD$) δ ppm 0.97-1.60 (m, 4H), 3.09 (s, 3H), 3.26 (d, J=13.12 Hz, 1H), 3.66 (d, J=12.21 Hz, 1H), 4.46-4.59 (m, 1H), 4.72 (d, J=14.65 Hz, 1H), 6.96 (d, J=8.24 Hz, 1H), 7.06 (d, J=1.83 Hz, 1H), 7.52-7.61 (m, 3H), 7.66-7.71 (m, 2H), 7.76 (s, 1H), 7.87 (d, J=1.83 Hz, 1H), 9.16 (s, 1H). MS (ESI$^+$) m/z 484.2 (M+H)$^+$.

Example 5

6-(2-chlorophenyl)-2-(5,6,7,8-tetrahydronaphthalen-2-ylamino)imidazo[1,2-a]pyrimido[5,4-e]pyrimidin-5(6H)-one Example 5 was prepared as described in Example 1F, substituting 4-(4-methylpiperazin-1-yl)aniline with 5,6,7,8-tetrahydronaphthalen-2-amine. $^1$H NMR (400 MHz, DMSO-$d_6$) δ ppm 1.63-1.90 (m, 4H), 2.63-2.89 (m, 4H), 7.05-7.12 (m, 2H), 7.51-7.59 (m, 4H), 7.61-7.65 (m, 1H), 7.69-7.75 (m, 2H), 9.10 (s, 1H), 10.64 (s, 1H). MS (ESI$^+$) m/z 443.3 (M+H)$^+$.

Example 6

6-(2-chlorophenyl)-2-{[3-(4-methylpiperazin-1-yl)phenyl]amino}imidazo[1,2-a]pyrimido[5,4-e]pyrimidin-5(6H)-one A mixture of Example 1E (60.0 mg, 0.167 mmol) and 3-(4-methylpiperazin-1-yl)aniline (65.4 mg, 0.342 mmol) was heated in a capped vial at 90° C. for 40 minutes. The crude compound was purified by HPLC as described in Example 1F to provide the title compound as a trifluoroacetic acid salt. $^1$H NMR (400 MHz, CD$_3$OD) δ ppm 2.98 (s, 3H), 3.11 (t, J=12.51 Hz, 2H), 3.25-3.34 (m, 2H), 3.63 (d, J=11.60 Hz, 2H), 3.89 (d, J=13.12 Hz, 2H), 6.85 (d, J=7.02 Hz, 1H), 7.06 (d, J=2.14 Hz, 1H), 7.26-7.48 (m, 3H), 7.53-7.61 (m, 3H), 7.65-7.72 (m, 1H), 7.82 (s, 1H), 9.14 (s, 1H). MS (ESI$^+$) m/z 487.3 (M+H)$^+$.

Example 7

6-(2-chlorophenyl)-2-[(4-cyclohexylphenyl)amino]imidazo[1,2-a]pyrimido[5,4-e]pyrimidin-5(6H)-one Example 7 was prepared as described in Example 2, substituting aniline with 4-cyclohexylaniline. $^1$H NMR (400 MHz, CDCl$_3$) δ ppm 1.35-1.50 (m, 4H), 1.70-1.81 (m, 2H), 1.83-1.95 (m, 4H), 2.46-2.60 (m, 1H), 7.08 (d, J=1.53 Hz, 1H), 7.28 (d, J=8.54 Hz, 2H), 7.46-7.51 (m, 3H), 7.56-7.66 (m, 3H), 7.71 (d, J=1.53 Hz, 1H), 7.93 (s, 1H), 9.24 (s, 1H). MS (ESI$^+$) m/z 471.3 (M+H)$^+$.

Example 8

6-(2-chlorophenyl)-2-{[4-(piperidin-1-yl)phenyl]amino}imidazo[1,2-a]pyrimido[5,4-e]pyrimidin-5(6H)-one Example 8 was prepared as described in Example 1F, substituting 4-(4-methylpiperazin-1-yl)aniline with 4-(piperidin-1-yl)aniline. $^1$H NMR (400 MHz, DMSO-$d_6$) δ ppm 1.55-1.74 (m, 2H), 1.79-1.98 (m, 4H), 3.33-3.57 (m, 4H), 7.10 (d, J=1.83 Hz, 1H), 7.53-7.61 (m, 4H), 7.62-7.66 (m, 1H), 7.72 (dd, J=7.48, 1.98 Hz, 1H), 7.85 (s, 1H), 7.94 (d, J=7.63 Hz, 2H), 9.16 (s, 1H), 10.91 (s, 1H). MS (ESI$^+$) m/z 472.3 (M+H)$^+$.

Example 9

6-(2-chlorophenyl)-2-{[4-(pyrrolidin-1-ylmethyl)phenyl]amino}imidazo[1,2-a]pyrimido[5,4-e]pyrimidin-5(6H)-one Example 9 was prepared as described in Example 1F, substituting 4-(4-methylpiperazin-1-yl)aniline with 4-(pyrrolidin-1-ylmethyl)aniline. $^1$H NMR (400 MHz, CD$_3$OD) δ ppm 1.92-2.09 (m, 2H), 2.12-2.36 (m, 2H), 3.07-3.28 (m, 2H), 3.41-3.64 (m, 2H), 4.38 (s, 2H), 7.07 (d, J=1.83 Hz, 1H), 7.47-7.62 (m, 5H), 7.66-7.72 (m, 1H), 7.88 (d, J=1.83 Hz, 1H), 7.96 (d, J=8.54 Hz, 2H), 9.19 (s, 1H). MS (ESI$^+$) m/z 472.0 (M+H)$^+$.

Example 10

6-(2-chlorophenyl)-2-{[4-(morpholin-4-yl)phenyl]amino}imidazo[1,2-a]pyrimido[5,4-e]pyrimidin-5(6H)-one Example 10 was prepared as described in Example 1F, substituting 4-(4-methylpiperazin-1-yl)aniline with 4-morpholinoaniline. $^1$H NMR (400 MHz, DMSO-$d_6$) δ ppm 3.09-3.20 (m, 4H), 3.75-3.82 (m, 4H), 7.00-7.12 (m, 3H), 7.53-7.66 (m, 4H), 7.70-7.83 (m, 3H), 9.08 (s, 1H), 10.66 (s, 1H). MS (ESI$^+$) m/z 474.3 (M+H)$^+$.

Example 11

6-(2-chlorophenyl)-2-{[3-(pyrrolidin-1-ylmethyl)phenyl]amino}imidazo[1,2-a]pyrimido[5,4-e]pyrimidin-5(6H)-one A mixture of Example 1E (50.0 mg, 0.139 mmol) and 3-(pyrrolidin-1-ylmethyl)aniline (49.0 mg, 0.278 mmol) was heated in a capped vial at 110° C. for 1 hour. The crude material was purified by HPLC as described in Example 1F to provide the tile compound as a trifluoroacetic acid salt. $^1$H NMR (400 MHz, CD$_3$OD) δ ppm 1.96-2.10 (m, 2H), 2.14-2.31 (m, 2H), 3.18-3.28 (m, 2H), 3.49-3.65 (m, 2H), 4.44 (s, 2H), 7.07 (d, J=1.83 Hz, 1H), 7.31 (d, J=7.32 Hz, 1H), 7.50-7.63 (m, 4H), 7.66-7.73 (m, 1H), 7.83-8.08 (m, 3H), 8.01 (s, 1H), 9.21 (s, 1H). MS (ESI$^+$) m/z 472.2 (M+H)$^+$.

Example 12

2-[(1-acetyl-2,3-dihydro-1H-indol-6-yl)amino]-6-(2-chlorophenyl)imidazo[1,2-a]pyrimido[5,4-e]pyrimidin-5(6H)-one A mixture of Example 1E (50.0 mg, 0.139 mmol), 1-(6-aminoindolin-1-yl)ethanone (36.7 mg, 0.208 mmol), and para-toluenesulfonic acid monohydrate (13 mg, 0.069 mmol) in acetonitrile (2 mL) was heated at 160° C. for 30 minutes in a Biotage microwave reactor. The reaction mixture was concentrated and purified by HPLC as described in Example 1F to provide the title compound as a trifluoroacetic acid salt. $^1$H NMR (400 MHz, DMSO-$d_6$) δ ppm 2.22 (s, 3H), 3.13 (t, J=8.39 Hz, 2H), 4.15 (t, J=8.39 Hz, 2H), 7.10 (d, J=6.41 Hz, 1H), 7.14-7.25 (m, 2H), 7.51-7.60 (m, 2H), 7.61-7.66 (m, 1H), 7.72 (dd, J=7.17, 1.98 Hz, 1H), 8.39 (s, 1H), 9.11 (s, 1H), 9.41 (s, 1H), 10.82 (s, 1H). MS (ESI$^+$) m/z 472.3 (M+H)$^+$.

Example 13

2-{[4-(4-acetylpiperazin-1-yl)phenyl]amino}-6-(2-chlorophenyl)imidazo[1,2-a]pyrimido[5,4-e]pyrimidin-5(6H)-one Example 13 was prepared as described in Example 1F, substituting 4-(4-methylpiperazin-1-yl)aniline with 1-(4-(4-aminophenyl)piperazin-1-yl)ethanone. $^1$H NMR (400 MHz, DMSO-$d_6$) δ ppm 2.06 (s, 3H), 3.15 (d, J=27.16 Hz, 4H), 3.61

(s, brd, 4H), 7.01-7.14 (m, 3H), 7.50-7.66 (m, 4H), 7.69-7.84 (m, 3H), 9.08 (s, 1H), 10.67 (s, 1H). MS (ESI$^+$) m/z 515.3 (M+H)$^+$.

Example 14

6-(2-methylphenyl)-2-{[4-(4-methylpiperazin-1-yl)phenyl]amino}imidazo[1,2-a]pyrimido[5,4-e]pyrimidin-5(6H)-one

Example 14A 7-(methylthio)-3-o-tolylpyrimido[4,5-d]pyrimidine-2,4(1H,3H)-dione Example 14A (0.15 g) was prepared as described in Example 1A, substituting 1-chloro-2-isocyanatobenzene with 1-isocyanato-2-methylbenzene. MS (ESI$^+$) m/z 301.1 (M+H)$^+$.

Example 14B 2-chloro-7-(methylthio)-3-o-tolylpyrimido[4,5-d]pyrimidin-4(3H)-one Example 14B (0.25 g) was prepared as described in Example 1B, substituting Example 1A with Example 14A. MS (ESI$^+$) m/z 319.0 (M+H)$^+$.

Example 14C 2-(2,2-dimethoxyethylamino)-7-(methylthio)-3-o-tolylpyrimido[4,5-d]pyrimidin-4(3H)-one Example 14C (0.3 g) was prepared as described in Example 1C, substituting Example 1B with Example 14B. MS (ESI$^+$) m/z 388.4 (M+H)$^+$.

Example 14D

8-Methylsulfanyl-4-o-tolyl-4H-3,4,7,9,9b-pentaaza-cyclopenta[a]naphthalen-5-one

Example 14D (0.15 g) was prepared as described in Example 1D, substituting Example 1C with Example 14C. MS (ESI$^+$) m/z 323.9 (M+H)$^+$.

Example 14E

8-Methanesulfinyl-4-(2-methylphenyl)-4H-3,4,7,9,9b-pentaaza-cyclopenta[a]naphthalen-5-one Example 14E (0.1 g) was prepared as described in Example 1E, substituting Example 1D with Example 14D. MS (ESI$^+$) m/z 340.0 (M+H)$^+$.

Example 14F 6-(2-methylphenyl)-2-{[4-(4-methylpiperazin-1-yl)phenyl]amino}imidazo[1,2-a]pyrimido[5,4-e]pyrimidin-5(6H)-one Example 14G (0.1 g) was prepared as described in Example 1F, substituting Example 1E with Example 14E. $^1$H NMR (300 MHz, DMSO-d$_6$) δ ppm 1.98-2.13 (m, 3H) 2.79-3.05 (m, 5H) 3.06-3.33 (m, 2H) 3.83 (d, J=12.69 Hz, 2H) 6.87-7.25 (m, 3H) 7.21-7.53 (m, 5H) 7.56-7.89 (m, 3H) 8.87-9.23 (m, 1H) 9.62 (s, 1H) 10.61 (s, 1H). MS (ESI$^+$) m/z 340.0 (M+H)$^+$.

Example 15

2-{[4-(4-methylpiperazin-1-yl)phenyl]amino}-6-[2-(trifluoromethyl)phenyl]imidazo[1,2-a]pyrimido[5,4-e]pyrimidin-5(6H)-one

Example 15A 7-(methylthio)-3-(2-(trifluoromethyl)phenyl)pyrimido[4,5-d]pyrimidine-2,4(1H,3H)-dione Example 15A (0.2 g) was prepared as described in Example 1A, substituting 1-chloro-2-isocyanatobenzene with 1-isocyanato-2-(trifluoromethyl)benzene. MS (ESI$^+$) m/z 355.1 (M+H)$^+$.

Example 15B 2-chloro-7-(methylthio)-3-(2-(trifluoromethyl)phenyl)pyrimido[4,5-d]pyrimidin-4(3H)-one Example 15B (0.2 g) was prepared as described in Example 1B, substituting Example 1A with Example 15A. MS (ESI$^+$) m/z 372.56 (M+H)$^+$.

Example 15C 2-(2,2-dimethoxyethylamino)-7-(methylthio)-3-(2-(trifluoromethyl)phenyl)pyrimido[4,5-d]pyrimidin-4(3H)-one Example 15C (0.28 g) was prepared as described in Example 1C, substituting Example 1B with Example 15B. MS (ESI$^+$) m/z 442.4 (M+H)$^+$.

Example 15D

8-Methylsulfanyl-4-(2-trifluoromethyl-phenyl)-4H-3,4,7,9,9b-pentaaza-cyclopenta[a]naphthalen-5-one Example 15D (0.1 g) was prepared as described in Example 1D, substituting Example 1C with Example 15C. MS (ESI$^+$) m/z 378.2 (M+H)$^+$.

Example 15E

8-Methanesulfinyl-4-(2-trifluoromethyl-phenyl)-4H-3,4,7,9,9b-pentaaza-cyclopenta[a]naphthalen-5-one Example 15E (0.05 g) was prepared as described in Example 1E, substituting Example 1D with Example 15D. MS (ESI$^+$) m/z 393.99 (M+H)$^+$.

Example 15F

2-{[4-(4-methylpiperazin-1-yl)phenyl]amino}-6-[2-(trifluoromethyl)phenyl]imidazo[1,2-a]pyrimido[5,4-e]pyrimidin-5(6H)-one Example 15F (0.02 g) was prepared as described in Example 1F, substituting Example 1E with Example 15E. $^1$H NMR (300 MHz, DMSO-d$_6$) δ ppm 3.17 (s, 2H) 3.52 (s, 2H) 3.83 (d, J=11.87 Hz, 2H) 6.97-7.16 (m, 3H) 7.49-7.84 (m, 6H) 7.85-8.02 (m, 2H) 9.08 (s, 1H) 9.60 (s, 1H) 10.68 (s, 5H). MS (ESI⁺) m/z 521.2 (M+H)⁺.

Example 16

6-(2-methoxyphenyl)-2-{[4-(4-methylpiperazin-1-yl)phenyl]amino}imidazo[1,2-a]pyrimido[5,4-e]pyrimidin-5(6H)-one Example 16A 3-(2-methoxyphenyl)-7-(methylthio)pyrimido[4,5-d]pyrimidine-2,4(1H,3H)-dione Example 16A (0.22 g) was prepared as described in Example 1A, substituting 1-chloro-2-isocyanatobenzene with 1-isocyanato-2-methoxybenzene. MS (ESI⁺) m/z 317.1 (M+H)⁺.

Example 16B 2-chloro-3-(2-methoxyphenyl)-7-(methylthio)pyrimido[4,5-d]pyrimidin-4(3H)-one Example 16B (0.23 g) was prepared as described in Example 1B, substituting Example 1A with Example 16A. MS (ESI⁺) m/z 334.55 (M+H)⁺.

Example 16C 2-(2,2-dimethoxyethylamino)-3-(2-methoxyphenyl)-7-(methylthio)pyrimido[4,5-d]pyrimidin-4(3H)-one Example 16C (0.28 g) was prepared as described in Example 1C, substituting Example 1B with Example 16B. MS (ESI⁺) m/z 404.3 (M+H)⁺.

Example 16D 4-(2-Methoxy-phenyl)-8-methylsulfanyl-4H-3,4,7,9,9b-pentaaza-cyclopenta[a]naphthalen-5-one Example 16D (0.1 g) was prepared as described in Example 1D, substituting Example 1C with Example 16C. MS (ESI⁺) m/z 341.2 (M+H)⁺.

Example 16E

8-Methanesulfinyl-4-(2-methoxy-phenyl)-4H-3,4,7,9,9b-pentaaza-cyclopenta[a]naphthalen-5-one Example 16E (0.05 g) was prepared as described in Example 1E, substituting Example 1D with Example 16D. MS (ESI⁺) m/z 356.03 (M+H)⁺.

Example 16F 6-(2-methoxyphenyl)-2-{[4-(4-methylpiperazin-1-yl)phenyl]amino}imidazo[1,2-a]pyrimido[5,4-e]pyrimidin-5(6H)-one Example 16F (0.015 g) was prepared as described in Example 1F, substituting Example 1E with Example 16E. ¹H NMR (300 MHz, DMSO-d₆) δ ppm 2.80-3.04 (m, 5H) 3.07-3.29 (m, 2H) 3.54 (d, J=11.90 Hz, 2H) 3.66-3.77 (m, 3H) 3.83 (d, J=13.09 Hz, 2H) 6.98-7.15 (m, 5H) 7.23 (d, J=7.14 Hz, 1H) 7.37 (dd, J=7.93, 1.59 Hz, 1H) 7.44-7.54 (m, 1H) 7.72 (s, 3H) 9.05 (s, 1H) 9.59 (s, 1H) 10.61 (s, 1H). MS (ESI⁺) m/z 483.3 (M+H)⁺.

Example 17

6-(2-chlorophenyl)-2-{[2-methoxy-4-(4-methylpiperazin-1-yl)phenyl]amino}imidazo[1,2-a]pyrimido[5,4-e]pyrimidin-5(6H)-one Example 17 was prepared as described in Example 1F, substituting 4-(4-methylpiperazin-1-yl)aniline with 2-methoxy-4-(4-methylpiperazin-1-yl)aniline. ¹H NMR (400 MHz, CD₃OD) δ ppm 2.98 (s, 3H), 3.10 (t, J=12.51 Hz, 2H), 3.23-3.35 (m, 2H), 3.63 (d, J=11.60 Hz, 2H), 3.83-3.97 (m, 5H), 6.68 (s, 1H), 6.77 (d, J=2.14 Hz, 1H), 7.04 (s, 1H), 7.48-7.63 (m, 3H), 7.66-7.72 (m, 1H), 7.72-8.15 (m, 2H), 9.07 (s, 1H). MS (ESI⁺) m/z 517.3 (M+H)⁺.

Example 18

6-(2-chlorophenyl)-2-[(1-methyl-1,2,3,4-tetrahydroquinolin-7-yl)amino]imidazo[1,2-a]pyrimido[5,4-e]pyrimidin-5(6H)-one A mixture of Example 1E (60.0 mg, 0.167 mmol) and 1-methyl-1,2,3,4-tetrahydroquinolin-7-amine (48.7 mg, 0.300 mmol) was heated in a capped vial at 90° C. for 1 hour. After cooling, the residue was treated with dimethylsulfoxide/methanol (2 mL). The precipitate was filtered, washed with methanol and water, and oven-dried to provide the title compound. ¹H NMR (400 MHz, DMSO-d₆) δ ppm 1.77-1.99 (m, 2H), 2.69 (t, J=6.26 Hz, 2H), 2.90 (s, 3H), 3.11-3.28 (m, 2H), 6.92 (d, J=7.93 Hz, 1H), 7.02 (d, J=7.32 Hz, 1H), 7.07 (s, 1H), 7.18 (s, 1H), 7.50-7.65 (m, 3H), 7.69-7.74 (m, 2H), 9.09 (s, 1H), 10.53 (s, 1H). MS (ESI⁺) m/z 458.2 (M+H)⁺.

Example 19

6-(2-chlorophenyl)-2-[(3-oxo-3,4-dihydro-2H-1,4-benzoxazin-6-yl)amino]imidazo[1,2-a]pyrimido[5,4-e]pyrimidin-5(6H)-one A mixture of Example 1E (60.0 mg, 0.167 mmol), N,N-diisopropylethylamine (0.058 mL, 0.334 mmol), and 6-amino-2H-benzo[b][1,4]oxazin-3(4H)-one (49.3 mg, 0.300 mmol) in N,N-dimethylformamide (1.5 mL) was stirred at room temperature for 2 hours. The reaction mixture was treated with saturated NaHCO₃/brine and extracted with ethyl acetate (2×). The combined organic layers were dried over MgSO₄, filtered, concentrated, and purified by HPLC as described in Example 1F to provide the title compound as a trifluoroacetic acid salt. ¹H NMR (500 MHz, DMSO-d₆) δ ppm 4.57 (s, 2H), 6.99 (d, J=7.93 Hz, 1H), 7.08-7.13 (m, 1H), 7.16-7.21 (m, 1H), 7.53-7.60 (m, 2H), 7.62-7.65 (m, 1H), 7.70-7.74 (m, 1H), 7.87 (s, 1H), 8.16 (s, 1H), 9.11 (s, 1H), 10.79 (s, 1H). MS (ESI⁺) m/z 460.2 (M+H)⁺.

Example 20 tert-butyl 7-{[6-(2-chlorophenyl)-5-oxo-5,6-dihydroimidazo[1,2-a]pyrimido[5,4-e]pyrimidin-2-yl]amino}-3,4-dihydroisoquinoline-2(1H)-carboxylate A mixture of Example 1E (0.900 g, 2.501 mmol) and tert-butyl 7-amino-3,4-dihydroisoquinoline-2(1H)-carboxylate (0.994 g, 4.00 mmol) was heated in a capped vial at 90°

C. for 1 hour. The reaction mixture were suspended and stirred in ethyl acetate. The solids were filtered and washed with ethyl acetate. The filter cake was stirred in saturated aqueous NaHCO$_3$, filtered, washed with water, and oven-dried to provide the title compound. The filtrate was diluted with ethyl acetate and washed with saturated NaHCO$_3$. The organic layer was dried over MgSO$_4$, filtered, concentrated, and purified on an 80 g column using the ISCO Companion flash system eluting with CH$_2$Cl$_2$/ethyl acetate (6:4 to 5:5) to provide the title compound. $^1$H NMR (300 MHz, DMSO-d$_6$) δ ppm 1.44 (s, 9H), 2.77 (t, J=5.75 Hz, 2H), 3.58 (t, J=5.75 Hz, 2H), 4.54 (s, 2H), 7.07 (d, J=1.59 Hz, 1H), 7.21 (d, J=8.72 Hz, 1H), 7.53-7.66 (m, 5H), 7.69-7.74 (m, 1H), 7.76 (d, J=1.59 Hz, 1H), 9.12 (s, 1H), 10.71 (s, 1H). MS (ESI$^+$) m/z 544.1 (M+H)$^+$.

Example 21

6-(2-chlorophenyl)-2-(1,2,3,4-tetrahydroisoquinolin-7-ylamino)imidazo[1,2-a]pyrimido[5,4-e]pyrimidin-5(6H)-one A mixture of Example 20 (0.357 g, 0.656 mmol) and trifluoroacetic acid (0.506 mL, 6.56 mmol) in CH$_2$Cl$_2$ (6 mL) was stirred at room temperature for 6 hours. The reaction mixture was concentrated and purified by HPLC as described in Example 1F to provide the title compound as a trifluoroacetic acid salt. $^1$H NMR (300 MHz, CD$_3$OD) δ ppm 3.14 (t, J=6.35 Hz, 2H), 3.54 (t, J=6.35 Hz, 2H), 4.43 (s, 2H), 7.07 (d, J=1.98 Hz, 1H), 7.31 (d, J=8.33 Hz, 1H), 7.52-7.63 (m, 3H), 7.66-7.72 (m, 2H), 7.76 (s, 1H), 7.87 (d, J=1.98 Hz, 1H), 9.18 (s, 1H). MS (ESI$^+$) m/z 444.2 (M+H)$^+$.

Example 22

6-(2-chlorophenyl)-2-{[3-methyl-4-(4-methylpiperazin-1-yl)phenyl]amino}imidazo[1,2-a]pyrimido[5,4-e]pyrimidin-5(6H)-one A mixture of Example 1E (60.0 mg, 0.167 mmol) and 3-methyl-4-(4-methylpiperazin-1-yl)aniline (54.8 mg, 0.267 mmol) was heated in a capped vial at 95° C. for 1 hour. The crude material was purified by HPLC as described in Example 1F to provide the title compound as a trifluoroacetic acid salt. $^1$H NMR (400 MHz, DMSO-d$_6$) δ ppm 2.31 (s, 3H), 2.90 (s, 3H), 2.96 (t, J=12.05 Hz, 2H), 3.22 (d, J=11.29 Hz, 2H), 3.53 (d, J=11.29 Hz, 2H), 7.08 (d, J=1.53 Hz, 1H), 7.15 (d, J=7.63 Hz, 1H), 7.53-7.65 (m, 4H), 7.72 (dd, J=7.48, 1.98 Hz, 1H), 7.77 (s, 1H), 9.11 (s, 1H), 9.78 (s, 1H), 10.71 (s, 1H). MS (ESI$^+$) m/z 501.2 (M+H)$^+$.

Example 23

6-allyl-2-{[4-(4-methylpiperazin-1-yl)phenyl]amino}imidazo[1,2-a]pyrimido[5,4-e]pyrimidin-5(6H)-one Example 23A 3-allyl-7-(methylthio)pyrimido[4,5-d]pyrimidine-2,4(1H,3H)-dione Example 23A (0.25 g) was prepared as described in Example 1A, substituting 1-chloro-2-isocyanatobenzene with allyl isocyanate. MS (ESI$^+$) m/z 250.5 (M+H)$^+$.

Example 23B 3-allyl-2-chloro-7-(methylthio)pyrimido[4,5-d]pyrimidin-4(3H)-one

Example 23B (0.3 g) was prepared as described in Example 1B, substituting Example 1A with Example 23A. MS (ESI$^+$) m/z 269.2 (M+H)$^+$.

Example 23C 3-allyl-2-(2,2-dimethoxyethylamino)-7-(methylthio)pyrimido[4,5-d]pyrimidin-4(3H)-one Example 23C (0.28 g) was prepared as described in Example 1C, substituting Example 1B with Example 23B. MS (ESI$^+$) m/z 338.3 (M+H)$^+$.

Example 23D

4-Allyl-8-methylsulfanyl-4H-3,4,7,9,9b-pentaaza-cyclopenta[a]naphthalen-5-one

Example 23D (0.05 g) was prepared as described in Example 1D, substituting Example 1C with Example 23C. MS (ESI$^+$) m/z 341.2 (M+H)$^+$.

Example 23E

4-Allyl-8-methanesulfinyl-4H-3,4,7,9,9b-pentaaza-cyclopenta[a]naphthalen-5-one

Example 23E (0.04 g) was prepared as described in Example 1E, substituting Example 1D with Example 23D. MS (ESI$^+$) m/z 289.9 (M+H)$^+$.

Example 23F 6-allyl-2-{[4-(4-methylpiperazin-1-yl)phenyl]amino}imidazo[1,2-a]pyrimido[5,4-e]pyrimidin-5(6H)-one Example 23F (0.02 g) was prepared as described in Example 1F, substituting Example 1E with Example 23E. $^1$H NMR (300 MHz, DMSO-d$_6$) δ ppm 2.92 (d, 5H) 3.18 (d, J=10.51 Hz, 2H) 3.64-3.96 (m, 2H) 4.51-4.88 (m, 2H) 4.99-5.37 (m, 2H) 5.75-6.16 (m, 1H) 6.95-7.13 (m, 3H) 7.18 (d, J=1.70 Hz, 1H) 7.52-7.90 (m, 3H) 8.87-9.17 (m, 1H) 9.59 (s, 1H) 10.52 (s, 1H). MS (ESI$^+$) m/z 417.2 (M+H)$^+$.

Example 24

6-cyclohexyl-2-{[4-(4-methylpiperazin-1-yl)phenyl]amino}imidazo[1,2-a]pyrimido[5,4-e]pyrimidin-5(6H)-one Example 24A 3-cyclohexyl-7-(methylthio)pyrimido[4,5-d]pyrimidine-2,4(1H,3H)-dione Example 24A (0.22 g) was prepared as described in Example 1A, substituting 1-chloro-2-isocyanatobenzene with cyclohexyl isocyanate. MS (ESI$^+$) m/z 292.48 (M+H)$^+$.

Example 24B 2-chloro-3-cyclohexyl-7-(methylthio)pyrimido[4,5-d]pyrimidin-4(3H)-one Example 24B (0.21 g) was prepared as described in Example 1B, substituting Example 1A with Example 24A. MS (ESI$^+$) m/z 310.92 (M+H)$^+$.

Example 24C 3-cyclohexyl-2-(2,2-dimethoxyethylamino)-7-(methylthio)pyrimido[4,5-d]pyrimidin-4(3H)-one Example 24C (0.25 g) was prepared as described in Example 1C, substituting Example 1B with Example 24B. MS (ESI$^+$) m/z 380.4 (M+H)$^+$.

Example 24D

4-Cyclohexyl-8-methylsulfanyl-4H-3,4,7,9,9b-pentaaza-cyclopenta[a]naphthalen-5-one Example 24D (0.137 g) was prepared as described in Example 1D, substituting Example 1C with Example 24C. MS (ESI$^+$) m/z 315.1 (M+H)$^+$.

Example 24E

4-Cyclohexyl-8-methanesulfinyl-4H-3,4,7,9,9b-pentaaza-cyclopenta[a]naphthalen-5-one Example 24E (0.14 g) was prepared as described in Example 1E, substituting Example 1D with Example 24D. MS (ESI$^+$) m/z 332.3 (M+H)$^+$.

Example 24F 6-cyclohexyl-2-{[4-(4-methylpiperazin-1-yl)phenyl]amino}imidazo[1,2-a]pyrimido[5,4-e]pyrimidin-5(6H)-one Example 24F (0.055 g) was prepared as described in Example 1F, substituting Example 1E with Example 24E. $^1$H NMR (300 MHz, DMSO-d$_6$) δ ppm 1.07-1.52 (m, 4H) 1.66 (s, 4H) 1.83 (s, 2H) 2.54-2.71 (m, 2H) 2.79-3.04 (m, 5H) 3.05-3.32 (m, 2H) 3.81 (d, J=13.09 Hz, 2H) 4.80-5.07 (m, 1H) 6.89-7.14 (m, 3H) 7.19 (d, J=1.98 Hz, 1H) 7.51-7.84 (m, 3H) 8.87-9.14 (m, 1H) 9.62 (s, 1H) 10.48 (s, 1H). MS (ESI$^+$) m/z 459.03 (M+H)$^+$.

Example 25

6-(2-chlorophenyl)-9-methyl-2-{[4-(4-methylpiperazin-1-yl)phenyl]amino}imidazo[1,2-a]pyrimido[5,4-e]pyrimidin-5(6H)-one

Example 25A 3-(2-chlorophenyl)-7-(methylthio)-2-(2-oxopropylamino)pyrimido[4,5-d]pyrimidin-4(3H)-one A mixture of 1-aminopropan-2-one (0.031 g, 0.425 mmol) and Example 1B (0.120 g, 0.354 mmol) in acetonitrile (7 mL) was heated at 80° C. for 40 minutes. The mixture was concentrated, treated with saturated aqueous NaHCO$_3$, and extracted with ethyl acetate (2×). The combined organic layers were dried over MgSO$_4$, filtered, and concentrated to provide the title compound.

Example 25B 4-(2-Chloro-phenyl)-1-methyl-8-methylsulfanyl-4H-3,4,7,9,9b-pentaaza-cyclopenta[a]naphthalen-5-one Example 25A (0.115 g) in acetonitrile (1.5 mL) was treated with concentrated HCl (0.03 mL) and the mixture heated in a Biotage MW at 160° C. for 40 minutes. The solvent was evaporated. The residue was treated with saturated aqueous NaHCO$_3$ and extracted with ethyl acetate (2×). The combined organic layers were dried over MgSO$_4$, filtered, concentrated, and purified on a 12 g column using the ISCO Companion flash system eluting with CH$_2$Cl$_2$/ethyl acetate to provide the title compound.

Example 25C 4-(2-Chloro-phenyl)-8-methanesulfinyl-1-methyl-4H-3,4,7,9,9b-pentaaza-cyclopenta[a]naphthalen-5-one A mixture of meta-chloroperoxybenzoic acid (0.021 g, 0.092 mmol) and Example 25B (0.030 g, 0.084 mmol) in dichloromethane (4 mL) was stirred for 2 hours. The reaction solution was diluted with dichloromethane and washed with saturated aqueous NaHCO$_3$ and Na$_2$S$_2$O$_3$. The organic layer was dried over MgSO$_4$ and concentrated to provide the title compound.

Example 25D 6-(2-chlorophenyl)-9-methyl-2-{[4-(4-methylpiperazin-1-yl)phenyl]amino}imidazo[1,2-a]pyrimido[5,4-e]pyrimidin-5(6H)-one A mixture of Example 25C (24.5 mg, 0.066 mmol) and 4-(4-methylpiperazin-1-yl)aniline (27.6 mg, 0.144 mmol) was heated in a vial at 90° C. for 1 hour. The crude material was purified by HPLC as described in Example 1F to provide the title compound as a trifluoroacetic acid salt. $^1$H NMR (400 MHz, CD$_3$OD) δ ppm 2.65 (s, 3H), 2.98 (s, 3H), 3.06 (t, J=12.82 Hz, 2H), 3.24-3.33 (m, 2H), 3.62 (d, J=11.90 Hz, 2H), 3.85 (d, J=12.82 Hz, 2H), 6.72 (s, 1H), 7.07 (d, J=8.54 Hz, 2H), 7.49-7.62 (m, 5H), 7.63-7.72 (m, 1H), 9.11 (s, 1H). MS (ESI$^+$) m/z 501.3 (M+H)$^+$.

Example 26

6-(2-chlorophenyl)-2-{[4-(4-methylpiperazin-1-yl)phenyl]amino}pyrimido[5,4-e][1,2,4]triazolo[4,3-a]pyrimidin-5(6H)-one

Example 26A 4-(2-Chloro-phenyl)-8-methylsulfanyl-4H-2,3,4,7,9,9b-hexaaza-cyclopenta[a]naphthalen-5-one A mixture of Example 1B (0.150 g, 0.442 mmol) and formohydrazide (0.066 g, 1.11 mmol) in acetonitrile (7 mL) was heated at 150° C. for 15 minutes in a Biotage microwave reactor. The solid was filtered. The filtrate was concentrated, treated with saturated aqueous NaHCO$_3$ and extracted with ethyl acetate (2×). The combined organic layers were dried over MgSO$_4$, filtered, concentrated, and purified on a 12 g column using the ISCO Companion flash system eluting with CH$_2$Cl$_2$/ethyl acetate (3:7 to 2:8) to provide the title compound.

Example 26B 4-(2-Chloro-phenyl)-8-methanesulfinyl-4H-2,3,4,7,9,9b-hexaaza-cyclopenta[a]naphthalen-5-one The title compound was prepared as described in Example 1E, substituting Example 1D with Example 26A.

Example 26C 6-(2-chlorophenyl)-2-{[4-(4-methylpiperazin-1-yl)phenyl]amino}pyrimido[5,4-e][1,2,4]triazolo[4,3-a]pyrimidin-5(6H)-one A mixture of Example 26B (10.0 mg, 0.028 mmol) and 4-(4-methylpiperazin-1-yl)aniline (11.7 mg, 0.061 mmol) was heated in a vial at 90° C. for 1 hour. The crude material was purified by HPLC as described in Example 1F to provide the title compound as a trifluoroacetic acid salt. $^1$H NMR (400 MHz, CD$_3$OD) δ ppm 2.99 (s, 3H), 3.03-3.16 (m, 2H), 3.24-3.38 (m, 2H), 3.50-3.71 (m, 2H), 3.78-3.98 (m, 2H), 7.02-7.19 (m, 2H), 7.50-7.63 (m, 3H), 7.63-7.81 (m, 3H), 9.10-9.22 (m, 2H). MS (ESI$^+$) m/z 488.3 (M+H)$^+$.

Example 27

6-(2-chlorophenyl)-9-methyl-2-{[4-(4-methylpiperazin-1-yl)phenyl]amino}pyrimido[5,4-e][1,2,4]triazolo[4,3-a]pyrimidin-5(6H)-one

Example 27A 4-(2-Chloro-phenyl)-1-methyl-8-methylsulfanyl-4H-2,3,4,7,9,9b-hexaaza-cyclopenta[a]naphthalen-5-one A mixture of Example 1B (0.150 g, 0.442 mmol) and acetohydrazide (0.072 g, 0.973 mmol) in acetonitrile (5 mL) was heated at 150° C. for 15 minutes in a Biotage microwave reactor. The solid was filtered. The filtrate was concentrated, treated with saturated aqueous NaHCO$_3$ and extracted with ethyl acetate (2×). The combined organic layers were dried over MgSO$_4$, filtered, concentrated, and purified on a 12 g column using the ISCO Companion flash system eluting with CH$_2$Cl$_2$/ethyl acetate (3:7 to 2:8) to provide the title compound.

Example 27B 4-(2-Chloro-phenyl)-8-methanesulfinyl-1-methyl-4H-2,3,4,7,9,9b-hexaaza-cyclopenta[a]naphthalen-5-one The title compound was prepared as described in Example 1E, substituting Example 1D with Example 27A.

Example 27C 6-(2-chlorophenyl)-9-methyl-2-{[4-(4-methylpiperazin-1-yl)phenyl]amino}pyrimido[5,4-e][1,2,4]triazolo[4,3-a]pyrimidin-5(6H)-one A mixture of Example 27B (44.7 mg, 0.119 mmol) and 4-(4-methylpiperazin-1-yl)aniline (50.2 mg, 0.262 mmol) was heated in a vial at 90° C. for 1 hour. The crude material was purified by HPLC as described in Example 1F to provide the title compound as a trifluoroacetic acid salt. 1H NMR (400 MHz, CD$_3$OD) δ ppm 2.80 (s, 2H), 2.98 (s, 4H), 3.06 (t, J=12.66 Hz, 2H), 3.25-3.34 (m, 2H), 3.62 (d, J=10.68 Hz, 2H), 3.86 (d, J=11.90 Hz, 2H), 6.91-7.16 (m, 2H), 7.46-7.65 (m, 5H), 7.66-7.73 (m, 1H), 9.12 (s, 1H). MS (APCI$^+$) m/z 502.2 (M+H)$^+$.

Example 28

4-(2-chlorophenyl)-8-{[4-(4-methylpiperazin-1-yl)phenyl]amino}pyrimido[5,4-e]tetrazolo[1,5-a]pyrimidin-5(4H)-one

Example 28A 4-(2-Chloro-phenyl)-8-methylsulfanyl-4H-1,2,3,4,7,9,9b-heptaaza-cyclopenta[a]naphthalen-5-one A mixture of Example 1B (0.175 g, 0.516 mmol) and sodium azide (0.037 g, 0.568 mmol) in N,N-dimethylformamide (5 mL) was heated at 70° C. for 1 hour. The reaction mixture was diluted with water and brine and extracted with ethyl acetate (2×). The combined organic layers were washed with brine (2×), dried over MgSO$_4$, filtered, concentrated, and purified on a 12 g column using the ISCO Companion flash system eluting with CH$_2$Cl$_2$/ethyl acetate (95:5 to 90:10) to provide the title compound.

Example 28B 4-(2-Chloro-phenyl)-8-methanesulfinyl-4H-1,2,3,4,7,9,9b-heptaaza-cyclopenta[a]naphthalen-5-one The title compound was prepared as described in Example 1E, substituting Example 1D with Example 28A.

Example 28C 4-(2-chlorophenyl)-8-{[4-(4-methylpiperazin-1-yl)phenyl]amino}pyrimido[5,4-e]tetrazolo[1,5-a]pyrimidin-5(4H)-one A mixture of Example 28B (65.4 mg, 0.181 mmol) and 4-(4-methylpiperazin-1-yl)aniline (76 mg, 0.398 mmol) was heated in a vial at 90° C. for 1 hour. After cooling, the residue was treated with saturated aqueous NaHCO$_3$/brine and extracted with ethyl acetate (2×). The combined organic layers were dried over MgSO$_4$, filtered, concentrated, and purified by HPLC as described in Example 1F to provide the title compound as a trifluoroacetic acid salt. $^1$H NMR (300 MHz, DMSO-d$_6$) δ ppm 2.87 (s, 3H), 2.92-3.05 (m, 2H), 3.11-3.24 (m, 2H), 3.54 (d, J=12.29 Hz, 2H), 3.75-3.94 (m, 2H), 6.92-7.23 (m, 2H), 7.51-7.72 (m, 4H), 7.76-7.89 (m, 2H), 9.58 (s, 1H), 10.95-11.10 (m, 1H). MS (ESI$^+$) m/z 489.0 (M+H)$^+$.

Example 29

6-(2-chlorophenyl)-2-({4-[4-(propan-2-yl)piperazin-1-yl]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(4-isopropylpiperazin-1-yl)aniline. $^1$H NMR (400 MHz, CD$_3$OD) δ 1.43 (d, J=6.7 Hz, 6H), 3.07 (t, J=12.0 Hz, 2H), 3.38-3.23 (m, 2H), 3.63-3.57 (m, 3H), 3.89 (d, J=12.8 Hz, 2H), 7.10-7.04 (m, 3H), 7.61-7.52 (m, 3H), 7.76-7.63 (m, 3H), 7.80-7.72 (m, 1H), 9.10 (s, 1H). MS (ESI$^+$) m/z 515.2 (M+H)$^+$.

Example 30

6-(2-chlorophenyl)-2-({4-[4-(cyclohexylmethyl) piperazin-1-yl]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(4-(cyclohexylmethyl)piperazin-1-yl)aniline. $^1$H NMR (400 MHz, CD$_3$OD) δ 1.17-1.01 (m, 2H), 1.48-1.19 (m, 3H), 2.00-1.67 (m, 6H), 3.08 (d, J=6.9 Hz, 2H), 3.16 (d, J=11.1 Hz, 2H), 3.35-3.22 (m, 2H), 3.67 (d, J=11.1 Hz, 2H), 3.83 (d, J=13.4 Hz, 2H), 7.10-7.05 (m, 3H), 7.62-7.53 (m, 3H), 7.90-7.63 (m, 4H), 9.10 (s, 1H). MS (ESI$^+$) m/z 569.3 (M+H)$^+$.

Example 31

3-{[4-(4-{[6-(2-chlorophenyl)-5-oxo-5,6-dihydroimidazo[1,2-a]pyrimido[5,4-e]pyrimidin-2-yl]amino}phenyl)piperazin-1-yl]methyl}benzonitrile The title compound was prepared as described in Example 1F, substituting 4-(4-methylpiperazin-1-yl)aniline with 3-((4-(4-aminophenyl)piperazin-1-yl)methyl)benzonitrile. $^1$H NMR (400 MHz, CD$_3$OD) δ 3.58-3.26 (m, 8H), 4.49 (s, 2H), 7.08-7.02 (m, 3H), 7.59-7.52 (m, 3H), 7.79-7.65 (m, 4H), 7.93-7.85 (m, 3H), 7.96 (t, J=1.4 Hz, 1H), 9.07 (s, 1H). MS (ESI$^+$) m/z 588.2 (M+H)$^+$.

Example 32

2-{[3-chloro-4-(4-methylpiperazin-1-yl)phenyl]amino}-6-(2-chlorophenyl)imidazo[1,2-a]pyrimido[5,4-e]pyrimidin-5(6H)-one The title compound was prepared as described in Example 1F, substituting 4-(4-methylpiperazin-1-yl)aniline with 3-chloro-4-(4-methylpiperazin-1-yl)aniline. $^1$H NMR (400 MHz, CD$_3$OD) δ 3.00 (s, 3H), 3.21-3.07 (m, 2H), 3.39-3.33 (m, 2H), 3.58-3.49 (m, 2H), 3.69-3.59 (m, 2H), 7.07 (d, J=1.9 Hz, 1H), 7.37-7.21 (m, 1H), 7.66-7.53 (m, 3H), 7.83-7.64 (m, 3H), 8.01 (d, J=2.3 Hz, 1H), 9.15 (bs, 1H). MS (ESI$^+$) m/z 521.2 (M+H)$^+$.

Example 33

6-(2-chlorophenyl)-2-({3-fluoro-4-[4-(propan-2-yl)piperazin-1-yl]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 3-fluoro-4-(4-isopropylpiperazin-1-yl)aniline. $^1$H NMR (400 MHz, CD$_3$OD) δ 1.43 (d, J=6.7 Hz, 6H), 3.15 (t, J=11.8 Hz, 2H), 3.44-3.31 (m, 2H), 3.71-3.53 (m, 5H), 7.07 (d, J=1.5 Hz, 1H), 7.14 (t, J=8.4 Hz, 1H), 7.61-7.51 (m, 4H), 7.71-7.66 (m, 1H), 7.75 (d, J=14.5 Hz, 1H), 7.83 (s, 1H), 9.15 (s, 1H). MS (ESI$^+$) m/z 533.2 (M+H)$^+$.

Example 34

6-(2-chlorophenyl)-2-[(2-methyl-1,2,3,4-tetrahydroisoquinolin-7-yl)amino]imidazo[1,2-a]pyrimido[5,4-e]pyrimidin-5(6H)-one A solution of Example 21 (0.120 g, 0.179 mmol) in tetrahydrofuran (4 ml) was treated with triethylamine (0.124 ml, 0.893 mmol) and CH$_3$I (0.034 ml, 0.536 mmol). The reaction mixture was stirred for 4 hours. The mixture was diluted with ethyl acetate and washed with saturated NaHCO$_3$ and brine. The organic layer was dried over MgSO$_4$, filtered, concentrated, and purified by reverse-phase HPLC performed on a Zorbax RX-C18 column (250×21.2 mm, 7 μm particle size) using a gradient of 15% to 100% methanol: 0.1% aqueous trifluoroacetic acid over 48 minutes at a flow rate of 15 mL/minute to provide the title compound as a trifluoroacetic acid salt. $^1$H NMR (400 MHz, CD$_3$OD) δ 3.09 (s, 3H), 3.28-3.20 (m, 2H), 3.49-3.41 (m, 1H), 3.84-3.75 (m, 1H), 4.46-4.38 (m, 1H), 4.68-4.60 (m, 1H), 7.07 (d, J=1.9 Hz, 1H), 7.34 (d, J=8.3 Hz, 1H), 7.63-7.48 (m, 3H), 7.73-7.66 (m, 2H), 7.78 (s, 1H), 7.88 (d, J=1.8 Hz, 1H), 9.18 (s, 1H). MS (ESI$^+$) m/z 458.1 (M+H)$^+$.

Example 35

6-(2-chlorophenyl)-2-({4-[2-(dimethylamino)ethoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(2-(dimethylamino)ethoxy)aniline. $^1$H NMR (400 MHz, CD$_3$OD) δ 3.00 (s, 6H), 3.65-3.58 (m, 2H), 4.38 (t, J=4.7 Hz, 2H), 7.12-7.03 (m, 3H), 7.62-7.52 (m, 3H), 7.82-7.65 (m, 4H), 9.11 (s, 1H). MS (ESI$^+$) m/z 476.2 (M+H)$^+$.

Example 36

6-(2-chlorophenyl)-2-({4-[2-(morpholin-4-yl)ethoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(2-morpholinoethoxy)aniline. $^1$H NMR (400 MHz, CD$_3$OD) δ 3.38-3.26 (m, 2H), 3.70-3.52 (m, 4H), 3.91-3.78 (m, 2H), 4.14-4.00 (m, 2H), 4.45-4.39 (m, 2H), 7.10-7.03 (m, 3H), 7.62-7.53 (m, 3H), 7.90-7.66 (m, 4H), 9.10 (bs, 1H). MS (ESI$^+$) m/z 518.2 (M+H)$^+$.

Example 37

6-(2-chlorophenyl)-2-{[3-methyl-4-(4-methyl-1,4-diazepan-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 3-methyl-4-(4-methyl-1,4-diazepan-1-yl)aniline. $^1$H NMR (400 MHz, CD$_3$OD) δ 2.30-2.14 (m, 2H), 2.39 (s, 3H), 3.01 (s, 3H), 3.22-3.17 (m, 2H), 3.51-3.25 (m, 3H), 3.68-3.54 (m, 3H), 7.06 (d, J=1.8 Hz, 1H), 7.25-7.17 (m, 1H), 7.63-7.50 (m, 4H), 7.70-7.67 (m, 2H), 7.81 (s, 1H), 9.12 (s, 1H). MS (ESI$^+$) m/z 515.2 (M+H)$^+$.

Example 38

6-(2-chlorophenyl)-2-{[4-(1-methylpiperidin-4-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 4-(1-methylpiperidin-4-yl)aniline. $^1$H NMR (400 MHz, CD$_3$OD) δ 1.11 (d, J=6.5 Hz, 3H), 1.78-1.64 (m, 2H), 1.96-1.86 (m, 1H), 2.13-2.04 (m, 2H), 3.72-3.62 (m, 4H), 7.07 (d, J=1.9 Hz, 1H), 7.62-7.53 (m, 3H), 7.73-7.66 (m, 3H), 7.90 (d, J=1.9 Hz, 1H), 8.10-8.03 (m, 2H), 9.20 (s, 1H). MS (ESI$^+$) m/z 486.0 (M+H)$^+$.

Example 39

2-{[4-(4-methylpiperazin-1-yl)phenyl]amino}-6-phenylimidazo[1,2-a]pyrimido[5,4-e]pyrimidin-5(6H)-one

Example 39A

7-(methylthio)-3-phenylpyrimido[4,5-d]pyrimidine-2,4(1H,3H)-dione

The title compound (0.22 g) was prepared as described in Example 1A, substituting 1-chloro-2-isocyanatobenzene with isocyanatobenzene. MS (ESI$^+$) m/z 287.1 (M+H)$^+$.

Example 39B

2-chloro-7-(methylthio)-3-phenylpyrimido[4,5-d]pyrimidin-4(3H)-one

The title compound (0.20 g) was prepared as described in Example 1B, substituting Example 1A with Example 39A. MS (ESI$^+$) m/z 304.8 (M+H)$^+$.

Example 39C

2-(2,2-dimethoxyethylamino)-7-(methylthio)-3-phenylpyrimido[4,5-d]pyrimidin-4(3H)-one The title compound (0.23 g) was prepared as described in Example 1C, substituting Example 1B with Example 39B. MS (ESI$^+$) m/z 374.05 (M+H)$^+$.

Example 39D

8-Methylsulfanyl-4-phenyl-4H-3,4,7,9,9b-pentaaza-cyclopenta[a]naphthalen-5-one The title compound (0.17 g) was prepared as described in Example 1D, substituting Example 1C with Example 39C. MS (ESI$^+$) m/z 309.9 (M+H)$^+$.

Example 39E

8-Methanesulfinyl-4-phenyl-4H-3,4,7,9,9b-pentaaza-cyclopenta[a]naphthalen-5-one The title compound (0.17 g) was prepared as described in Example 1E, substituting Example 1D with Example 39D. MS (ESI$^+$) m/z 325.9 (M+H)$^+$.

Example 39F

2-{[4-(4-methylpiperazin-1-yl)phenyl]amino}-6-phenylimidazo[1,2-a]pyrimido[5,4-e]pyrimidin-5(6H)-one The title compound (0.075 g) was prepared as described in Example 1F, substituting Example 1E with Example 39E. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.82-3.04 (m, 5H) 3.06-3.30 (m, 2H) 3.54 (d, J=11.87 Hz, 4H) 7.01-7.14 (m, 3H) 7.38-7.62 (m, 6H) 7.74 (s, 2H) 9.06 (s, 1H) 9.65 (s, 1H) 10.58 (s, 1H). MS (ESI$^+$) m/z 453.3 (M+H)$^+$.

Example 40

6-(2-chloro-4-methylphenyl)-2-{[4-(4-methylpiperazin-1-yl)phenyl]amino}imidazo[1,2-a]pyrimido[5,4-e]pyrimidin-5(6H)-one

Example 40A

3-(2-chloro-4-methylphenyl)-7-(methylthio)pyrimido[4,5-d]pyrimidine-2,4(1H,3H)-dione7

The title compound (0.54 g) was prepared as described in Example 1A, substituting 1-chloro-2-isocyanatobenzene with 2-chloro-1-isocyanato-4-methylbenzene. MS (ESI$^+$) m/z 335.1 (M+H)$^+$.

Example 40B

2-chloro-3-(2-chloro-4-methylphenyl)-7-(methylthio)pyrimido[4,5-d]pyrimidin-4(3H)-one The title compound (0.30 g) was prepared as described in Example 1B, substituting Example 1A with Example 40A. MS (ESI$^+$) m/z 353.0 (M+H)$^+$.

Example 40C

3-(2-chloro-4-methylphenyl)-2-(2,2-dimethoxyethylamino)-7-(methylthio)pyrimido[4,5-d]pyrimidin-4(3H)-one The title compound (0.35 g) was prepared as described in Example 1C, substituting Example 1B with Example 40B. MS (ESI$^+$) m/z 422.13 (M+H)$^+$.

Example 40D

4-(2-Chloro-4-methyl-phenyl)-8-methylsulfanyl-4H-3,4,7,9,9b-pentaaza-cyclopenta[a]naphthalen-5-one The title compound (0.29 g) was prepared as described in Example 1D, substituting Example 1C with Example 40C. MS (ESI$^+$) m/z 358.12 (M+H)$^+$.

Example 40E 4-(2-Chloro-4-methyl-phenyl)-8-methanesulfinyl-4H-3,4,7,9,9b-pentaaza-cyclopenta[a]naphthalen-5-one The title compound (0.29 g) was prepared as described in Example 1E, substituting Example 1D with Example 40D. MS (ESI$^+$) m/z 373.9 (M+H)$^+$.

Example 40F 6-(2-chloro-4-methylphenyl)-2-{[4-(4-methylpiperazin-1-yl)phenyl]amino}imidazo[1,2-a]pyrimido[5,4-e]pyrimidin-5(6H)-one The title compound (0.2 g) was prepared as described in Example 1F, substituting Example 1E with Example 40E. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.42 (s, 3H) 2.80-3.06 (m, 5H) 3.08-3.31 (m, 2H) 3.54 (d, J=11.87 Hz, 2H) 3.69-3.93 (m, 2H) 6.99-7.15 (m, 3H) 7.34 (d, J=6.78 Hz, 1H) 7.42-7.51 (m, 1H) 7.53 (s, 1H) 7.64-7.82 (m, 3H) 9.08 (s, 1H) 9.67 (s, 1H) 10.65 (s, 1H). MS (ESI$^+$) m/z 501.2 (M+H)$^+$.

Example 41

4-{[6-(2-chlorophenyl)-5-oxo-5,6-dihydroimidazo[1,2-a]pyrimido[5,4-e]pyrimidin-2-yl]amino}-N-cyclohexylbenzamide

Example 41A

4-[4-(2-Chloro-phenyl)-5-oxo-4,5-dihydro-3,4,7,9,9b-pentaaza-cyclopenta[a]naphthalen-8-ylamino]-benzoic acid A mixture of Example 1E (200.0 mg, 0.556 mmol), tert-butyl 4-aminobenzoate (129 mg, 0.667 mmol), and concentrated HCl (0.08 mL, 2.63 mmol) was heated at 160° C. for 30 minutes in a Biotage microwave reactor. The solvent was decanted. The remaining residue was treated with water, sonicated, filtered, washed with water, and oven-dried to provide the title compound as an HCl salt.

Example 41B

4-{[6-(2-chlorophenyl)-5-oxo-5,6-dihydroimidazo[1,2-a]pyrimido[5,4-e]pyrimidin-2-yl]amino}-N-cyclohexylbenzamide A mixture of Example 41A (60.0 mg, 0.128 mmol), 1-ethyl-3-[3-(dimethylamino)propyl]-carbodiimide hydrochloride (36.8 mg, 0.192 mmol), 1-hydroxybenzotriazole hydrate (29.4 mg, 0.192 mmol), triethylamine (0.071 mL, 0.511 mmol), and cyclohexylamine (0.022 mL, 0.192 mmol) in N,N-dimethylformamide (2 mL) was stirred for 24 hours. Water was added to the reaction solution. The solid was filtered, washed with water, and oven-dried to provide the title compound. $^1$H NMR (400 MHz, DMSO-d$_6$) δ 1.20-1.09 (m, 2H), 1.43-1.23 (m, 4H), 1.62 (d, J=12.3 Hz, 1H), 1.93-1.67 (m, 4H), 3.84-3.74 (m, 1H), 7.10 (t, J=3.8 Hz, 1H), 7.67-7.51 (m, 3H), 7.76-7.69 (m, 1H), 7.99-7.84 (m, 5H), 8.10 (d, J=7.9 Hz, 1H), 9.18 (s, 1H). MS (ESI$^+$) m/z 514.2 (M+H)$^+$.

Example 42

6-(2-chlorophenyl)-2-({4-[(4-methylpiperazin-1-yl)carbonyl]phenyl}amino)imidazo[1,2-a]pyrimido[5,4-e]pyrimidin-5(6H)-one A mixture of Example 41A (60.0 mg, 0.128 mmol), benzotriazol-1-yloxytripyrrolidinophosphonium hexafluorophosphate (100 mg, 0.192 mmol), triethylamine (0.071 mL, 0.511 mmol), and 1-methylpiperazine (0.021 mL, 0.192 mmol) in N,N-dimethylformamide (2 mL) was stirred for 5 hours. The reaction mixture was diluted with 20% brine and extracted with ethyl acetate (twice). The combined organic layers were washed with 20% brine, dried over MgSO$_4$, filtered, and concentrated. The residue was purified by HPLC (see protocol in Example 1F) to provide the title compound as a trifluoroacetic acid salt. $^1$H NMR (400 MHz, CD$_3$OD) δ 2.96 (s, 3H), 3.60-3.14 (m, 6H), 4.56-4.31 (m, 2H), 7.07 (d, J=1.9 Hz, 1H), 7.63-7.54 (m, 5H), 7.73-7.66 (m, 1H), 7.90 (d, J=1.9 Hz, 1H), 8.00-7.94 (m, 2H), 9.18 (s, 1H). MS (ESI$^+$) m/z 515.2 (M+H)$^+$.

Example 43

6-(2-chlorophenyl)-2-{[4-(1H-pyrazol-4-yl)phenyl]amino}imidazo[1,2-a]pyrimido[5,4-e]pyrimidin-5(6H)-one

Example 43A 8-(4-Bromo-phenylamino)-4-(2-chloro-phenyl)-4H-3,4,7,9,9b-pentaaza-cyclopenta[a]naphthalen-5-one A mixture of Example 1E (250.0 mg, 0.695 mmol) and 4-bromoaniline (191 mg, 1.112 mmol) was heated at 90° C. for 1 hour. While warm, the residue was treated with saturated aqueous NaHCO$_3$ solution and extracted with ethyl acetate (twice). The combined organic layers were dried over MgSO$_4$, filtered, and concentrated. The residue was triturated with a small amount of ethyl acetate. The solids were filtered, washed with ethyl acetate/hexane, and oven-dried to provide the title compound.

Example 43B 6-(2-chlorophenyl)-2-{[4-(1H-pyrazol-4-yl)phenyl]amino}imidazo[1,2-a]pyrimido[5,4-e]pyrimidin-5(6H)-one A mixture of Example 43A (45.0 mg, 0.096 mmol), 1-boc-pyrazole-4-boronic acid pinacol ester (31.1 mg, 0.106 mmol), bis(triphenylphosphine)palladium(II) dichloride (3.38 mg, 4.81 µmol), and 1M sodium carbonate (0.077 mL, 0.077 mmol) in dimethoxyethane/ethanol/water (7:2:3, 1.2 mL) was heated at 150° C. for 15 minutes in a Biotage microwave reactor. The solvents were evaporated, and the residue was purified by HPLC (see protocol in Example 1F) to provide the title compound as a trifluoroacetic acid salt. $^1$H NMR (400 MHz, DMSO-d$_6$) δ 7.09 (d, J=1.8 Hz, 1H), 7.75-7.54 (m, 7H), 7.90-7.78 (m, 3H), 8.05 (s, 2H), 9.13 (s, 1H), 10.80 (bs, 1H). MS (ESI$^+$) m/z 455.1 (M+H)$^+$.

Example 44

6-(2-chlorophenyl)-2-({4-[2-(diethylamino)ethoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(2-(diethylamino)ethoxy)aniline. $^1$H NMR (400 MHz, CD$_3$OD) δ 1.44-1.29 (m, 6H), 3.45-3.33 (m, 4H), 3.66-3.60 (m, 2H), 4.38 (t, J=4.7 Hz, 2H), 7.12-7.03 (m, 3H), 7.62-7.53 (m, 3H), 7.89-7.66 (m, 4H), 9.10 (bs, 1H). MS (ESI$^+$) m/z 504.1 (M+H)$^+$.

Example 45

6-(2-chlorophenyl)-2-{[4-(pyridin-3-yl)phenyl]amino}imidazo[1,2-a]pyrimido[5,4-e]pyrimidin-5(6H)-one The title compound was prepared as described in Example 43B, substituting 1-boc-pyrazole-4-boronic acid pinacol ester with pyridin-3-ylboronic acid. $^1$H NMR (500 MHz, CD$_3$OD) δ 7.09 (d, J=1.9 Hz, 1H), 7.62-7.52 (m, 3H), 7.73-7.67 (m, 1H), 7.96-7.87 (m, 3H), 8.16-8.06 (m, 3H), 8.78 (d, J=5.6 Hz, 1H), 8.93-8.87 (m, 1H), 9.19 (bs, 1H), 9.22 (s, 1H). MS (ESI$^+$) m/z 466.2 (M+H)$^+$.

Example 46

4-{[6-(2-chlorophenyl)-5-oxo-5,6-dihydroimidazo[1,2-a]pyrimido[5,4-e]pyrimidin-2-yl]amino}-N-(trans-4-hydroxycyclohexyl)benzamide The title compound was prepared as described in Example 41B, substituting cyclohexylamine with trans-4-aminocyclohexanol.HCl. $^1$H NMR (400 MHz, DMSO-d$_6$) δ 1.31 (dq, J=23.1, 10.3 Hz, 4H), 1.84 (t, J=13.1 Hz, 4H), 3.17 (s, 2H), 3.45-3.37 (m, 1H), 3.79-3.67 (m, 1H), 7.09 (t, J=2.1 Hz, 1H), 7.67-7.49 (m, 3H), 7.74-7.71 (m, 1H), 7.92 (q, J=8.8 Hz, 4H), 8.08 (d, J=7.9 Hz, 1H), 9.20 (s, 1H), 10.96 (s, 1H). MS (ESI$^+$) m/z 530.2 (M+H)$^+$.

Example 47

4-{[6-(2-chlorophenyl)-5-oxo-5,6-dihydroimidazo[1,2-a]pyrimido[5,4-e]pyrimidin-2-yl]amino}-N-ethylbenzamide The title compound was prepared as described in Example 41B, substituting cyclohexylamine with ethanamine. $^1$H NMR (400 MHz, DMSO-d$_6$) δ 1.14 (t, J=7.2 Hz, 3H), 3.35-3.25 (m, 2H), 7.12-7.07 (m, 1H), 7.67-7.52 (m, 4H), 7.76-7.68 (m, 1H), 7.98-7.87 (m, 4H), 8.39 (t, J=5.5 Hz, 1H), 9.19 (s, 1H), 10.97 (bs, 1H). MS (ESI$^+$) m/z 460.2 (M+H)$^+$.

Example 48

6-(2-chlorophenyl)-2-({4-[(4-hydroxypiperidin-1-yl)carbonyl]phenyl}amino)imidazo[1,2-a]pyrimido[5,4-e]pyrimidin-5(6H)-one The title compound was prepared as described in Example 42, substituting 1-methylpiperazine with piperidin-4-ol. $^1$H NMR (400 MHz, CD$_3$OD) δ 1.63-1.44 (m, 2H), 2.02-1.81 (m, 2H), 3.43-3.28 (m, 2H), 3.85-3.70 (m, 1H), 3.97-3.86 (m, 1H), 4.26-4.10 (m, 1H), 7.08 (d, J=1.9 Hz, 1H), 7.49 (d, J=8.4 Hz, 2H), 7.62-7.53 (m, 3H), 7.73-7.66 (m, 1H), 7.99-7.86 (m, 3H), 9.19 (s, 1H). MS (ESI$^+$) m/z 516.2 (M+H)$^+$.

Example 49

4-{[6-(2-chlorophenyl)-5-oxo-5,6-dihydroimidazo[1,2-a]pyrimido[5,4-e]pyrimidin-2-yl]amino}-N-(pyridin-4-yl)benzamide A mixture of Example 41A (60.0 mg, 0.128 mmol), pyridin-4-amine (18.05 mg, 0.192 mmol), triethylamine (0.071 mL, 0.511 mmol), and O-(7-azabenzotriazol-1-yl)-N,N,N',N'-tetramethyluronium hexafluorophosaphate (72.9 mg, 0.192 mmol) in N,N-dimethylformamide (2 mL) was stirred for 3.5 hours. Water was added to the mixture. The solids formed were filtered, washed with water, and purified by HPLC (see protocol in Example 1F) to provide the title compound as a trifluoroacetic acid salt. $^1$H NMR (400 MHz, CD$_3$OD) δ 7.08 (d, J=1.9 Hz, 1H), 7.63-7.51 (m, 3H), 7.72-7.65 (m, 1H), 7.90 (d, J=1.9 Hz, 1H), 8.10-8.00 (m, 4H), 8.41-8.34 (m, 2H), 8.67-8.61 (m, 2H), 9.21 (s, 1H). MS (ESI$^+$) m/z 509.2 (M+H)$^+$.

Example 50

6-(2-chlorophenyl)-2-({4-[3-(diethylamino)propoxy]-3-fluorophenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(3-(diethylamino)propoxy)-3-fluoroaniline. $^1$H NMR (400 MHz, CD$_3$OD) δ 1.36 (t, J=7.3 Hz, 6H), 2.29-2.18 (m, 2H), 3.33-3.27 (m, 4H), 3.44-3.36 (m, 2H), 4.20 (t, J=5.6 Hz, 2H), 7.20-7.05 (m, 2H), 7.63-7.51 (m, 4H), 7.83-7.66 (m, 3H), 9.14 (bs, 1H). MS (ESI$^+$) m/z 536.0 (M+H)$^+$.

Example 51

6-(2-chlorophenyl)-2-({3-fluoro-4-[2-(4-methylpiperazin-1-yl)ethoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 3-fluoro-4-(2-(4-methylpiperazin-1-yl)ethoxy)aniline. $^1$H NMR (400 MHz, CD$_3$OD) δ 2.90 (s, 3H), 3.23-3.16 (m, 6H), 3.44-3.35 (m, 4H), 4.31 (t, J=4.9 Hz, 2H), 7.08 (d, J=1.9 Hz, 1H), 7.21-7.14 (m, 1H), 7.63-7.53 (m, 4H), 7.84-7.66 (m, 3H), 9.15 (bs, 1H). MS (ESI$^+$) m/z 549.2 (M+H)$^+$.

Example 52

6-(2-chlorophenyl)-2-{[2-(2-methoxyethyl)-1,2,3,4-tetrahydroisoquinolin-7-yl]amino}imidazo[1,2-a]pyrimido[5,4-e]pyrimidin-5(6H)-one A mixture of Example 21 (0.050 g, 0.074 mmol), triethylamine (0.070 ml) and 1-bromo-2-methoxyethane (40 μl) in tetrahydrofuran (1.5 ml) was stirred at 65° C. overnight. The reaction mixture was concentrated and purified by HPLC (see protocol in Example 1F) to provide the title compound as a trifluoroacetic acid salt. $^1$H NMR (400 MHz, CD$_3$OD) δ 3.27-3.08 (m, 2H), 3.45 (s, 3H), 3.58-3.50 (m, 2H), 3.95-3.77 (m, 4H), 4.71-4.44 (m, 2H), 7.07 (d, J=1.9 Hz, 1H), 7.33 (d, J=8.2 Hz, 1H), 7.62-7.51 (m, 3H), 7.74-7.65 (m, 2H), 7.77 (s, 1H), 7.87 (d, J=1.5 Hz, 1H), 9.17 (s, 1H). MS (ESI⁺) m/z 502.1 (M+H)⁺.

Example 53

6-(2-chlorophenyl)-2-[(2,4,4-trimethyl-1,2,3,4-tetrahydroisoquinolin-7-yl)amino]imidazo[1,2-a]pyrimido[5,4-e]pyrimidin-5(6H)-one The title compound was prepared as described in Example 1F, substituting 4-(4-methylpiperazin-1-yl)aniline with 2,4,4-trimethyl-1,2,3,4-tetrahydroisoquinolin-7-amine. $^1$H NMR (400 MHz, CD$_3$OD) δ 1.48 (s, 6H), 3.12 (s, 3H), 3.58-3.34 (m, 4), 4.61-4.40 (m, 4H), 7.07 (d, J=1.9 Hz, 1H), 7.62-7.53 (m, 4H), 7.77-7.66 (m, 3H), 7.88 (d, J=1.9 Hz, 1H), 9.17 (s, 1H). MS (ESI⁺) m/z 486.2 (M+H)⁺.

Example 54

6-(3-hydroxy-2-methylphenyl)-2-(phenylamino)imidazo[1,2-a]pyrimido[5,4-e]pyrimidin-5(6H)-one

Example 54A 3-(3-methoxy-2-methylphenyl)-7-(methylthio)pyrimido[4,5-d]pyrimidine-2,4(1H,3H)-dione Example 54A (0.48 g) was prepared as described in Example 1A, substituting 1-chloro-2-isocyanatobenzene with 1-isocyanato-3-methoxy-2-methylbenzene. MS (ESI⁺) m/z 331.1 (M+H)⁺.

Example 54B 2-chloro-3-(3-methoxy-2-methylphenyl)-7-(methylthio)pyrimido[4,5-d]pyrimidin-4(3H)-one The title compound (0.5 g) was prepared as described in Example 1B, substituting Example 1A with Example 54A. MS (ESI⁺) m/z 349.0 (M+H)⁺.

Example 54C 2-(2,2-dimethoxyethylamino)-3-(3-methoxy-2-methylphenyl)-7-(methylthio)pyrimido[4,5-d]pyrimidin-4(3H)-one The title compound (0.59 g) was prepared as described in Example 1C, substituting Example 1B with Example 54B. MS (ESI⁺) m/z 417.1 (M+H)⁺.

Example 54D 4-(3-Methoxy-2-methyl-phenyl)-8-methylsulfanyl-4H-3,4,7,9,9b-pentaaza-cyclopenta[a]naphthalen-5-one The title compound (0.47 g) was prepared as described in Example 1D, substituting Example 1C with Example 54C. MS (ESI⁺) m/z 354.2 (M+H)⁺.

Example 54E

8-Methanesulfinyl-4-(3-methoxy-2-methyl-phenyl)-4H-3,4,7,9,9b-pentaaza-cyclopenta[a]naphthalen-5-one The title compound (0.14 g) was prepared as described in Example 1E, substituting Example 1D with Example 54D. MS (ESI⁺) m/z 370.18 (M+H)⁺.

Example 54F

The title compound (0.075 g) was prepared as described in Example 1F, substituting 4-(4-methylpiperazin-1-yl)aniline with aniline and substituting Example 1E with Example 54E. MS (ESI⁺) m/z 399.2 (M+H)⁺.

Example 54G 6-(3-hydroxy-2-methylphenyl)-2-(phenylamino)imidazo[1,2-a]pyrimido[5,4-e]pyrimidin-5(6H)-one To a suspension of Example 54F (70 mg, 0.176 mmol) in 2 ml dichloromethane was added borontrifluoride-dimethylsulfide (0.129 ml, 1.230 mmol). The reaction was allowed to stir overnight, and was quenched with methanol, and concentrated. Chromatography was performed on a Analogix 280 with an SF 12-24 column, 35-100% ethyl acetate/hexane gradient over 30 minutes to provide the title compound. $^1$H NMR (300 MHz, DMSO-d$_6$) δ 1.68-1.97 (m, 3H) 6.78 (d, J=6.74 Hz, 1H) 6.93 (d, J=7.93 Hz, 1H) 7.05 (d, J=1.59 Hz, 1H) 7.07-7.20 (m, 2H) 7.42 (t, J=7.93 Hz, 2H) 7.71-7.98 (m, 3H) 9.11 (s, 1H) 9.64 (s, 1H) 10.69 (s, 1H). MS (ESI⁺) m/z 385.2 (M+H)⁺.

Example 55

6-(2,6-dichlorophenyl)-2-{[4-(4-methylpiperazin-1-yl)phenyl]amino}imidazo[1,2-a]pyrimido[5,4-e]pyrimidin-5(6H)-one

Example 55A 3-(2,6-dichlorophenyl)-7-(methylthio)pyrimido[4,5-d]pyrimidine-2,4(1H,3H)-dione The title compound (10 g) was prepared as described in Example 1A, substituting 1-chloro-2-isocyanatobenzene with 1,3-dichloro-2-isocyanatobenzene. MS (ESI⁺) m/z 355.19 (M+H)⁺.

Example 55B 2-chloro-3-(2,6-dichlorophenyl)-7-(methylthio)pyrimido[4,5-d]pyrimidin-4(3H)-one The title compound (5.4 g) was prepared as described in Example 1B, substituting Example 1A with Example 55A. MS (ESI⁺) m/z 372.54 (M+H)⁺.

Example 55C 3-(2,6-dichlorophenyl)-2-(2,2-dimethoxyethylamino)-7-(methylthio)pyrimido[4,5-d]pyrimidin-4(3H)-one The title compound (6.4 g) was prepared as described in Example 1C, substituting Example 1B with Example 55B. MS (ESI⁺) m/z 442.19. (M+H)⁺.

Example 55D 4-(2,6-Dichloro-phenyl)-8-methylsulfanyl-4H-3,4,7,9,9b-pentaaza-cyclopenta[a]naphthalen-5-one The title compound (4.6 g) was prepared as described in Example 1D, substituting Example 1C with Example 55C. MS (ESI$^+$) m/z 378.2 (M+H)$^+$.

Example 55E 4-(2,6-Dichloro-phenyl)-8-methanesulfinyl-4H-3,4,7,9,9b-pentaaza-cyclopenta[a]naphthalen-5-one The title compound (0.5 g) was prepared as described in Example 1E, substituting Example 1D with Example 55D. MS (ESI$^+$) m/z 370.18 (M+H)$^+$.

Example 55F 6-(2,6-dichlorophenyl)-2-{[4-(4-methylpiperazin-1-yl)phenyl]amino}imidazo[1,2-a]pyrimido[5,4-e]pyrimidin-5(6H)-one The title compound (0.06 g) was prepared as described in Example 1F, substituting Example 1E with Example 55E. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.80-3.05 (m, 5H) 3.19 (d, J=11.53 Hz, 2H) 3.46-3.61 (m, 4H) 6.88-7.29 (m, 3H) 7.42-7.99 (m, 6H) 9.12 (s, 1H) 9.62 (s, 1H) 10.77 (s, 1H). MS (ESI$^+$) m/z 521.2 (M+H)$^+$.

Example 56

2-[(4-aminophenyl)amino]-6-(2-chlorophenyl)imidazo[1,2-a]pyrimido[5,4-e]pyrimidin-5(6H)-one

Example 56A

{4-[4-(2-Chloro-phenyl)-5-oxo-4,5-dihydro-3,4,7,9,9b-pentaaza-cyclopenta[a]naphthalen-8-ylamino]-phenyl}-carbamic acid tert-butyl ester A mixture of Example 1E (330.0 mg, 0.917 mmol) and tert-butyl 4-aminophenylcarbamate (306 mg, 1.468 mmol) was heated in a capped vial at 100° C. for 1 hour. The residue was dissolved in ethyl acetate and washed with saturated aqueous NaHCO$_3$. The organic layer was dried over MgSO$_4$, filtered, concentrated, and purified on a 40 g column using the ISCO Companion flash system eluting with hexane/ethyl acetate (5:5 to 4:6) to provide the title compound.

Example 56B

2-[(4-aminophenyl)amino]-6-(2-chlorophenyl)imidazo[1,2-a]pyrimido[5,4-e]pyrimidin-5(6H)-one A mixture of Example 56A (0.260 g, 0.516 mmol) and trifluoroacetic acid (0.397 mL, 5.16 mmol) in CH$_2$Cl$_2$ (5 mL) was stirred at 40° C. for 4 hours. The reaction mixture was concentrated and purified by HPLC (see protocol in Example 1F) to provide the title compound as a trifluoroacetic acid salt.

The salt was treated with saturated aqueous NaHCO$_3$ followed by filtration and drying to give a free base form of the title compound. $^1$H NMR (400 MHz, DMSO-d$_6$) δ 3.96 (s, 2H), 7.09 (d, J=1.8 Hz, 1H), 7.38-7.23 (m, 2H), 7.66-7.52 (m, 3H), 7.76-7.69 (m, 1H), 7.96-7.91 (m, 3H), 9.16 (s, 1H), 10.73-10.68 (m, 1H). MS (ESI$^+$) m/z 404.2 (M+H)$^+$.

Example 57

N-(4-{[6-(2-chlorophenyl)-5-oxo-5,6-dihydroimidazo[1,2-a]pyrimido[5,4-e]pyrimidin-2-yl]amino}phenyl)acetamide A mixture of Example 56B (35.0 mg, 0.087 mmol), acetic acid (7.44 μL, 0.130 mmol), triethylamine (0.048 mL, 0.347 mmol), and O-(7-azabenzotriazol-1-yl)-N,N,N',N'-tetramethyluronium hexafluorophosaphate (49.4 mg, 0.130 mmol) in tetrahydrofuran (2 mL) was stirred for 4 hours. The reaction mixture was concentrated and purified by HPLC (see protocol in Example 1F) to provide the title compound as a trifluoroacetic acid salt. $^1$H NMR (400 MHz, CD$_3$OD) δ 2.13 (s, 3H), 7.11 (d, J=1.9 Hz, 1H), 7.63-7.51 (m, 5H), 7.73-7.66 (m, 3H), 7.87 (s, 1H), 9.14 (bs, 1H). MS (ESI$^+$) m/z 446.2 (M+H)$^+$.

Example 58

N-(4-{[6-(2-chlorophenyl)-5-oxo-5,6-dihydroimidazo[1,2-a]pyrimido[5,4-e]pyrimidin-2-yl]amino}phenyl)cyclopentanecarboxamide The title compound was prepared as described in Example 57, substituting acetic acid with cyclopentanecarboxylic acid. $^1$H NMR (400 MHz, DMSO-d$_6$) δ 1.91-1.50 (m, 8H), 2.82-2.74 (m, 1H), 7.06 (d, J=1.8 Hz, 1H), 7.87-7.53 (m, 9H), 9.10 (s, 1H), 9.88 (s, 1H), 10.73 (bs, 1H). MS (ESI$^+$) m/z 500.2 (M+H)$^+$.

Example 59

N-(4-{[6-(2-chlorophenyl)-5-oxo-5,6-dihydroimidazo[1,2-a]pyrimido[5,4-e]pyrimidin-2-yl]amino}phenyl)-4-hydroxycyclohexanecarboxamide The title compound was prepared as described in Example 57, substituting acetic acid with 4-hydroxycyclohexanecarboxylic acid. $^1$H NMR (400 MHz, CD$_3$OD) δ 1.40-1.26 (m, 1H), 1.78-1.55 (m, 3H), 2.15-1.78 (m, 4H), 2.48-2.24 (m, 1H), 3.61-3.51 (m, 0.5H), 4.00-3.94 (m, 0.5H), 7.12 (t, J=1.7 Hz, 1H), 7.63-7.52 (m, 5H), 7.73-7.67 (m, 3H), 7.88 (s, 1H), 9.14 (bs, 1H). MS (ESI$^+$) m/z 530.2 (M+H)$^+$.

Example 60

N-(4-{[6-(2-chlorophenyl)-5-oxo-5,6-dihydroimidazo[1,2-a]pyrimido[5,4-e]pyrimidin-2-yl]amino}phenyl)-1-methylpiperidine-4-carboxamide The title compound was prepared as described in Example 57, substituting acetic acid with 1-methylpiperidine-4-carboxylic acid. $^1$H NMR (400 MHz, CD$_3$OD) δ 2.32-1.95 (m, 4H), 2.74-2.64 (m, 1H), 2.94-2.88 (m, 3H), 3.07 (td, J=13.0, 3.1 Hz, 2H), 3.66-3.58 (m, 2H), 7.06 (d, J=1.9 Hz, 1H), 7.64-7.52 (m, 5H), 7.78-7.66 (m, 3H), 7.87-7.78 (m, 1H), 9.15 (bs, 1H). MS (ESI$^+$) m/z 529.1 (M+H)$^+$.

Example 61

N-(4-{[6-(2-chlorophenyl)-5-oxo-5,6-dihydroimidazo[1,2-a]pyrimido[5,4-e]pyrimidin-2-yl]amino}phenyl)pyridine-4-carboxamide The title compound was prepared as described in Example 57, substituting acetic acid with isonicotinic acid. $^1$H NMR (400 MHz, DMSO-d$_6$) δ 7.08 (d, J=1.8 Hz, 1H), 7.67-7.52 (m, 3H), 7.74-7.71 (m, 1H), 7.98-7.69 (m, 7H), 8.87-8.81 (m, 2H), 9.14 (s, 1H), 10.61 (s, 1H), 10.82 (bs, 1H). MS (ESI$^+$) m/z 509.2 (M+H)$^+$.

Example 62

6-(2,6-dimethylphenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one

Example 62A

3-(2,6-dimethylphenyl)-7-(methylthio)pyrimido[4,5-d]pyrimidine-2,4(1H,3H)-dione The title compound (0.21 g) was prepared as described in Example 1A, substituting 1-chloro-2-isocyanatobenzene with 1,3-dimethyl-2-isocyanatobenzene. MS (ESI$^+$) m/z 315.14 (M+H)$^+$.

Example 62B

2-chloro-3-(2,6-dimethylphenyl)-7-(methylthio)pyrimido[4,5-d]pyrimidin-4(3H)-one The title compound (0.41 g) was prepared as described in Example 1B, substituting Example 1A with Example 62A. MS (ESI$^+$) m/z 333.06 (M+H)$^+$.

Example 62C

2-(2,2-dimethoxyethylamino)-3-(2,6-dimethylphenyl)-7-(methylthio)pyrimido[4,5-d]pyrimidin-4(3H)-one The title compound (6.4 g) was prepared as described in Example 1C, substituting Example 1B with Example 62B. MS (ESI$^+$) m/z 401.71. (M+H)$^+$.

Example 62D

4-(2,6-Dimethyl-phenyl)-8-methylsulfanyl-4H-3,4,7,9,9b-pentaaza-cyclopenta[a]naphthalen-5-one The title compound (0.4 g) was prepared as described in Example 1D, substituting Example 1C with Example 62C. MS (ESI$^+$) m/z 337.6 (M+H)$^+$.

Example 62E

4-(2,6-Dimethyl-phenyl)-8-methylsulfinyl-4H-3,4,7,9,9b-pentaaza-cyclopenta[a]naphthalen-5-one The title compound (0.17 g) was prepared as described in Example 1E, substituting Example 1D with Example 62D. MS (ESI$^+$) m/z 354.17 (M+H)$^+$.

Example 62F

6-(2,6-dimethylphenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one The title compound (0.07 g) was prepared as described in Example 1F, substituting 4-(4-methylpiperazin-1-yl)aniline with 2'-methyl-2',3'-dihydro-1'H-spiro[cyclopropane-1,4'-isoquinolin]-7'-amine and substituting Example 1E with Example 62E. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 0.78-1.48 (m, 4H) 1.86-2.12 (m, 6H) 2.96 (d, J=4.36 Hz, 3H) 3.14-3.36 (m, 1H) 3.45-3.69 (m, 1H) 4.41-4.87 (m, 2H) 6.95 (d, J=8.33 Hz, 1H) 7.09 (d, J=1.59 Hz, 1H) 7.20-7.28 (m, 2H) 7.27-7.39 (m, 1H) 7.57-7.88 (m, 3H) 9.14 (s, 1H) 10.25 (s, 1H) 10.80 (s, 1H). MS (ESI$^+$) m/z 478.2 (M+H)$^+$.

Example 63

2-({4-[4-(3-chlorobenzyl)piperazin-1-yl]phenyl}amino)-6-(2-chlorophenyl)imidazo[1,2-a]pyrimido[5,4-e]pyrimidin-5(6H)-one The title compound was prepared as described in Example 1F, substituting 4-(4-methylpiperazin-1-yl)aniline with 4-(4-(3-chlorobenzyl)piperazin-1-yl)aniline. $^1$H NMR (400 MHz, CD$_3$OD) δ 3.60-3.10 (m, 8H), 4.42 (s, 1H), 7.08-7.00 (m, 3H), 7.61-7.46 (m, 7H), 7.87-7.62 (m, 4H), 9.07 (bs, 1H). MS (ESI$^+$) m/z 597.1 (M+H)$^+$.

Example 64

6-(2-chlorophenyl)-2-({4-[4-(2-methoxyethyl)piperazin-1-yl]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(4-(2-methoxyethyl)piperazin-1-yl)aniline. $^1$H NMR (500 MHz, CD$_3$OD) δ 3.22-3.09 (m, 2H), 3.39-3.27 (m, 2H), 3.48-3.42 (m, 5H), 3.75-3.65 (m, 2H), 3.77 (t, J=5.0 Hz, 2H), 3.89-3.77 (m, 2H), 7.10-7.02 (m, 3H), 7.61-7.51 (m, 3H), 7.90-7.65 (m, 4H), 9.08 (bs, 1H). MS (ESI$^+$) m/z 531.2 (M+H)$^+$.

Example 65

6-(2-chlorophenyl)-2-{[3-methoxy-4-(4-methylpiperazin-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 3-methoxy-4-(4-methylpiperazin-1-yl)aniline. $^1$H NMR (500 MHz, CD$_3$OD) δ 2.98 (s, 3H), 3.10-3.00 (m, 2H), 3.37-3.23 (m, 2H), 3.64-3.52 (m, 4H), 3.91 (s, 3H), 7.05-6.97 (m, 1H), 7.07 (d, J=1.7 Hz, 1H), 7.45-7.31 (m, 1H), 7.47 (d, J=2.3 Hz, 1H), 7.64-7.52 (m, 3H), 7.71-7.68 (m, 1H), 7.90-7.77 (m, 1H), 9.11 (s, 1H). MS (ESI$^+$) m/z 517.1 (M+H)$^+$.

Example 66

6-(2-chlorophenyl)-2-({3-methoxy-4-[4-(propan-2-yl)piperazin-1-yl]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 4-(4-isopropylpiperazin-1-yl)-3-methoxyaniline. The reaction temperature was set at 100° C. $^1$H NMR (400 MHz, DMSO-$d_6$) δ 1.32 (d, J=6.5 Hz, 6H), 2.56 (s, 3H), 3.01-2.90 (m, 2H), 3.26-3.13 (m, 2H), 3.60-3.48 (m, 5H), 7.11-6.97 (m, 2H), 7.51-7.38 (m, 1H), 7.66-7.40 (m, 4H), 7.73-7.71 (m, 1H), 7.78 (s, 1H), 9.12 (s, 1H), 9.41 bs, 1H), 10.72 (bs, 1H). MS (ESI$^+$) m/z 545.2 (M+H)$^+$.

Example 67

6-(2-chlorophenyl)-2-({3-methoxy-4-[2-(4-methylpiperazin-1-yl)ethoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 3-methoxy-4-(2-(4-methylpiperazin-1-yl)ethoxy)aniline. $^1$H NMR (400 MHz, CD$_3$OD) δ 2.91 (s, 3H), 3.43-3.33 (m, 10H), 3.91 (s, 3H), 4.28 (t, J=4.9 Hz, 2H), 7.09-7.01 (m, 2H), 7.39-7.25 (m, 1H), 7.49 (d, J=2.5 Hz, 1H), 7.63-7.53 (m, 3H), 7.72-7.66 (m, 1H), 7.98-7.78 (m, 1H), 9.13 (bs, 1H). MS (ESI$^+$) m/z 561.2 (M+H)$^+$.

Example 68

6-(3-hydroxyphenyl)-2-(phenylamino)imidazo[1,2-a]pyrimido[5,4-e]pyrimidin-5(6H)-one

Example 68A 3-(3-(allyloxy)phenyl)-7-(methylthio)pyrimido[4,5-d]pyrimidine-2,4(1H,3H)-dione The title compound (0.21 g) was prepared as described in Example 1A, substituting 1-chloro-2-isocyanatobenzene with 1-(allyloxy)-3-isocyanatobenzene. MS (ESI$^+$) m/z 341. (M–H)$^+$.

Example 68B 3-(3-(allyloxy)phenyl)-2-chloro-7-(methylthio)pyrimido[4,5-d]pyrimidin-4(3H)-one The title compound (0.09 g) was prepared as described in Example 1B, substituting Example 1A with Example 68A. MS (ESI$^+$) m/z 361.14 (M+H)$^+$.

Example 68C 3-(3-(allyloxy)phenyl)-2-(2,2-dimethoxyethylamino)-7-(methylthio)pyrimido[4,5-d]pyrimidin-4(3H)-one The title compound (0.12 g) was prepared as described in Example 1C, substituting Example 1B with Example 68B. MS (ESI$^+$) m/z 429.1. (M+H)$^+$.

Example 68D 4-(3-Allyloxy-phenyl)-8-methylsulfanyl-4H-3,4,7,9,9b-pentaaza-cyclopenta[a]naphthalen-5-one The title compound (0.4 g) was prepared as described in Example 1D, substituting Example 1C with Example 68C. MS (ESI$^+$) m/z 366.17 (M+H)$^+$.

Example 68E 4-(3-Allyloxy-phenyl)-8-methylsulfinyl-4H-3,4,7,9,9b-pentaaza-cyclopenta[a]naphthalen-5-one The title compound (0.0.75 g) was prepared as described in Example 1E, substituting Example 1D with Example 68D. MS (ESI$^+$) m/z 382.1 (M+H)$^+$.

Example 68F

The title compound (0.042 g) was prepared as described in Example 1F, substituting 4-(4-methylpiperazin-1-yl)aniline with aniline and Example 1E with Example 68E. MS (ESI$^+$) m/z 411.1 (M+H)$^+$

Example 68G 6-(3-hydroxyphenyl)-2-(phenylamino)imidazo[1,2-a]pyrimido[5,4-e]pyrimidin-5(6H)-one The title compound (0.03 g) was prepared as described in Example 54G, substituting Example 54F with Example 68F. $^1$H NMR (300 MHz, DMSO-$d_6$) δ 3.17 (s, 1H) 6.77-6.96 (m, 3H) 7.04-7.20 (m, 2H) 7.27-7.48 (m, 3H) 7.86 (d, J=8.33 Hz, 3H) 9.12 (s, 1H) 10.71 (s, 1H). MS (ESI$^+$) m/z 371.2 (M+H)$^+$.

Example 69

6-(2-chlorophenyl)-2-[(4-methylphenyl)amino]imidazo[1,2-a]pyrimido[5,4-e]pyrimidin-5(6H)-one A mixture of Example 1E (132.0 mg, 0.367 mmol) and p-toluidine (86 mg, 0.807 mmol) was heated in a capped vial at 90° C. for 1 hour. After cooling, the residue was treated with saturated aqueous NaHCO$_3$ and brine and extracted with ethyl acetate (twice). The combined organic layers were dried over MgSO$_4$, filtered, concentrated, and purified on a 12 g column using the ISCO Companion flash system eluting with CH$_2$Cl$_2$/ethyl acetate (8:2 to 7:3) to provide the title compound. $^1$H NMR (400 MHz, CDCl$_3$) δ 2.39 (s, 3H), 7.08 (d, J=1.8 Hz, 1H), 7.26-7.23 (m, 2H), 7.49-7.47 (m, 3H), 7.57-7.55 (m, 2H), 7.66-7.61 (m, 1H), 7.72-7.67 (m, 1H), 7.88-7.72 (m, 1H), 9.24 (s, 1H). MS (ESI$^+$) m/z 403.2 (M+H)$^+$.

Example 70

6-(2-chlorophenyl)-2-{[4-(piperidin-2-yl)phenyl]amino}imidazo[1,2-a]pyrimido[5,4-e]pyrimidin-5(6H)-one A mixture of Example 1E (0.048 g, 0.133 mmol) and tert-butyl 2-(4-aminophenyl)piperidine-1-carboxylate (0.059 g, 0.213 mmol) was heated in a capped vial at 120° C. for 1 hour. The reaction mixture was treated with ethyl acetate and washed with saturated NaHCO$_3$. The organic layer was dried over MgSO$_4$, filtered, and concentrated. The residue was dissolved in CH$_2$Cl$_2$ (2 mL) and treated with trifluoroacetic acid (0.103 ml, 1.334 mmol). The mixture was stirred at 35° C. for 5 hours, concentrated, and purified by HPLC (see protocol in Example 1F) to provide the title compound as a trifluoroacetic acid salt. $^1$H NMR (500 MHz, CD$_3$OD) δ 1.89-1.72 (m, 2H), 2.16-1.96 (m, 4H), 3.25-3.16 (m, 1H), 3.51-3.43 (m, 1H), 4.29-4.22 (m, 1H), 7.08 (d, J=1.9 Hz, 1H), 7.62-7.50 (m, 5H), 7.72-7.66 (m, 1H), 7.97-7.86 (m, 3H), 9.19 (s, 1H). MS (ESI$^+$) m/z 472.2 (M+H)$^+$.

Example 71

6-(2-chlorophenyl)-2-{[4-(pyrrolidin-2-yl)phenyl]amino}imidazo[1,2-a]pyrimido[5,4-e]pyrimidin-5(6H)-one A mixture of Example 1E (0.048 g, 0.133 mmol) and tert-butyl 2-(4-aminophenyl)pyrrolidine-1-carboxylate (0.056 g, 0.213 mmol) was heated in a capped vial at 130° C. for 30 minutes. The reaction mixture was treated with ethyl acetate and washed with saturated aqueous NaHCO$_3$. The organic layer was dried over MgSO$_4$, filtered, and concentrated. The residue was dissolved in CH$_2$Cl$_2$ (2 mL) and treated with trifluoroacetic acid (0.103 ml, 1.334 mmol). The mixture was stirred at 35° C. overnight, concentrated, and purified by HPLC (see protocol in Example 1F) to provide the title compound as a trifluoroacetic acid salt. $^1$H NMR (500 MHz, CD$_3$OD) δ 2.36-2.19 (m, 3H), 2.57-2.47 (m, 1H), 3.53-3.41 (m, 2H), 4.69-4.62 (m, 1H), 7.08 (d, J=1.9 Hz, 1H), 7.62-7.51 (m, 5H), 7.72-7.66 (m, 1H), 7.88 (d, J=1.9 Hz, 1H), 7.97-7.92 (m, 2H), 9.19 (s, 1H). MS (ESI$^+$) m/z 458.2 (M+H)$^+$.

Example 72

6-(2-chlorophenyl)-2-{[4-(pyrrolidin-3-yl)phenyl]amino}imidazo[1,2-a]pyrimido[5,4-e]pyrimidin-5(6H)-one A mixture of Example 1E (0.048 g, 0.133 mmol) and tert-butyl 3-(4-aminophenyl)pyrrolidine-1-carboxylate (0.056 g, 0.213 mmol) was heated in a capped vial at 90° C. for 1 hour. The reaction mixture was treated with ethyl acetate and washed with saturated aqueous NaHCO$_3$. The organic layer was dried over MgSO$_4$, filtered, and concentrated. The residue was dissolved in CH$_2$Cl$_2$ (2 mL) and treated with trifluoroacetic acid (0.103 ml, 1.334 mmol). The mixture was stirred at 35° C. for 5 hrs, concentrated, and purified by HPLC (see protocol in Example 1F) to provide the title compound as a trifluoroacetic acid salt. $^1$H NMR (500 MHz, CD$_3$OD) δ 2.24-2.05 (m, 1H), 2.49 (dtd, J=10.2, 7.1, 3.1 Hz, 1H), 3.21 (dd, J=24.8, 13.8 Hz, 1H), 3.46-3.37 (m, 1H), 3.61-3.52 (m, 2H), 3.73 (dd, J=11.4, 7.9 Hz, 1H), 7.07 (d, J=1.8 Hz, 1H), 7.40-7.39 (m, 2H), 7.62-7.51 (m, 3H), 7.73-7.66 (m, 1H), 7.86-7.81 (m, 3H), 9.15 (s, 1H). MS (ESI$^+$) m/z 458.2 (M+H)$^+$.

Example 73

6-(2,6-dichlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one The title compound (0.02 g) was prepared as described in Example 1F, substituting 4-(4-methylpiperazin-1-yl)aniline with 2'-methyl-2',3'-dihydro-1'H-spiro[cyclopropane-1,4'-isoquinolin]-7'-amine and Example 1E with Example 55E. The crude material was triturated with 1:1 DMSO/methanol, filtered and dried under high vacuum. $^1$H NMR (300 MHz, DMSO-d$_6$) δ 0.76-1.01 (m, 4H) 2.27-2.38 (m, 3H) 2.46 (s, 2H) 3.63 (s, 2H) 6.77 (d, J=8.33 Hz, 1H) 7.11 (d, J=1.59 Hz, 1H) 7.49 (s, 1H) 7.56-7.69 (m, 2H) 7.71-7.83 (m, 3H) 9.14 (s, 1H) 10.77 (s, 1H) MS (ESI+) m/z 518.1 (M+H)$^+$.

Example 74

6-(2,6-dichlorophenyl)-2-{[3-methyl-4-(4-methyl-1,4-diazepan-1-yl)phenyl]amino}imidazo[1,2-a]pyrimido[5,4-e]pyrimidin-5(6H)-one The title compound (0.04 g) was prepared as described in Example 1F, substituting 4-(4-methylpiperazin-1-yl)aniline with 3-methyl-4-(4-methyl-1,4-diazepan-1-yl)aniline and Example 1E with Example 55E. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.00-2.22 (m, 2H) 2.21-2.42 (m, 5H) 2.91 (d, J=4.76 Hz, 3H) 3.10 (t, J=6.54 Hz, 2H) 3.21-3.36 (m, 4H) 6.97-7.38 (m, 2H) 7.38-7.99 (m, 6H) 9.14 (s, 1H) 9.51 (s, 1H) 10.76 (s, 1H). MS (ESI+) m/z 549.1 (M+H)$^+$.

Example 75

6-(2-chlorophenyl)-2-{[4-(piperazin-1-yl)-3-(trifluoromethyl)phenyl]amino}imidazo[1,2-a]pyrimido[5,4-e]pyrimidin-5(6H)-one A mixture of Example 1E (0.060 g, 0.167 mmol) and tert-butyl 4-(4-amino-2-(trifluoromethyl)phenyl)piperazine-1-carboxylate (0.092 g, 0.267 mmol) was heated in a capped vial at 130° C. for 1 hour. The reaction mixture was treated with ethyl acetate and washed with saturated aqueous NaHCO$_3$. The organic layer was dried over MgSO$_4$, filtered, and concentrated. The crude material was purified on a 12 g column using the ISCO Companion flash system eluting with CH$_2$Cl$_2$/ethyl acetate (9:1 to 7:3) to give the desired intermediate. The intermediate was dissolved in CH$_2$Cl$_2$ (2 mL) and treated with trifluoroacetic acid (0.128 ml, 1.668 mmol). The mixture was stirred at 40° C. for 4 hours, concentrated, and purified by HPLC (see protocol in Example 1F) to provide the title compound as a trifluoroacetic acid salt. $^1$H NMR (400 MHz, CD$_3$OD) δ 3.25-3.11 (m, 4H), 3.47-3.33 (m, 4H), 7.09 (d, J=1.6 Hz, 1H), 7.64-7.42 (m, 4H), 7.75-7.64 (m, 1H), 7.83 (s, 1H), 8.06 (d, J=7.1 Hz, 1H), 8.37 (bs, 1H), 9.21 (s, 1H). MS (ESI$^+$) m/z 541.1 (M+H)$^+$.

Example 76

6-(2-chlorophenyl)-2-({4-[(2S)-pyrrolidin-2-ylmethoxy]phenyl}amino)imidazo[1,2-a]pyrimido[5,4-e]pyrimidin-5(6H)-one A mixture of Example 1E (0.060 g, 0.167 mmol) and (S)-tert-butyl 2-((4-aminophenoxy)methyl)pyrrolidine-1-carboxylate (0.078 g, 0.267 mmol) was heated in a capped vial at 90° C. for 1 hour. The reaction mixture was treated with ethyl acetate and washed with saturated aqueous NaHCO$_3$. The organic layer was dried over MgSO$_4$, filtered, and concentrated. The crude material was purified on a 12 g column using the ISCO Companion flash system eluting with CH₂Cl₂/ethyl acetate (7:3 to 6:4) to give the desired intermediate. The intermediate was dissolved in CH₂Cl₂ (2 mL) and treated with trifluoroacetic acid (0.128 ml, 1.668 mmol). The mixture was stirred at 35° C. for 5 hours, concentrated, and purified by HPLC (see protocol in Example 1F) to provide the title compound as a trifluoroacetic acid salt. $^1$H NMR (400 MHz, CD₃OD) δ 1.99-1.89 (m, 1H), 2.21-2.03 (m, 2H), 2.33-2.25 (m, 1H), 3.3.40-3.34 (m, 2H), 4.18-3.96 (m, 2H), 4.37 (dd, J=10.5, 3.3 Hz, 1H), 7.10-7.03 (m, 3H), 7.62-7.53 (m, 3H), 7.87-7.64 (m, 4H), 9.12 (s, 1H). MS (ESI⁺) m/z 488.1 (M+H)⁺.

Example 77

6-(2-chlorophenyl)-2-({2-methyl-4-[3-(4-methylpiperazin-1-yl)propoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 2-methyl-4-(3-(4-methylpiperazin-1-yl)propoxy)aniline. The reaction temperature was set at 100° C. $^1$H NMR (400 MHz, CD₃OD) δ 2.31-2.12 (m, 4H), 2.91 (s, 3H), 3.22-3.13 (m, 2H), 3.36-3.26 (m, 2H), 3.49-3.38 (m, 4H), 4.13 (t, J=5.8 Hz, 2H), 6.93-6.79 (m, 2H), 7.12-7.03 (m, 1H), 7.46-7.23 (m, 1H), 7.62-7.51 (m, 3.5H), 7.72-7.65 (m, 1H), 7.95-7.87 (m, 0.5H), 9.15-8.95 (m, 1H). MS (ESI⁺) m/z 559.2 (M+H)⁺.

Example 78

6-(2-chlorophenyl)-2-{[4-(morpholin-4-ylmethyl)phenyl]amino}imidazo[1,2-a]pyrimido[5,4-e]pyrimidin-5(6H)-one A mixture of Example 1E (0.060 g, 0.167 mmol) and 4-(morpholinomethyl)aniline (0.051 g, 0.267 mmol) was heated in a capped vial at 90° C. for 1 hour. The crude material was purified by HPLC (see protocol in Example 1F). The TFA salt was treated with saturated aqueous NaHCO₃ and extracted into ethyl acetate. The organic layer was dried over MgSO₄, filtered, concentrated, and purified on a 12 g column using the ISCO Companion flash system eluting with methanol/ethyl acetate (5:95 to 10:90) to provide the title compound. $^1$H NMR (400 MHz, CD₃OD) δ 2.56-2.39 (m, 4H), 3.54 (s, 2H), 3.73-3.67 (m, 4H), 7.05 (d, J=1.9 Hz, 1H), 7.43-7.36 (m, 2H), 7.61-7.52 (m, 3H), 7.70-7.67 (m, 1H), 7.80-7.73 (m, 2H), 7.86 (s, 1H), 9.15 (s, 1H). MS (ESI⁺) m/z 488.0 (M+H)⁺.

Example 79

6-(2-chlorophenyl)-2-{[4-(1H-imidazol-1-ylmethyl)phenyl]amino}imidazo[1,2-a]pyrimido[5,4-e]pyrimidin-5(6H)-one A mixture of Example 1E (0.060 g, 0.167 mmol) and 4-((1H-imidazol-1-yl)methyl)aniline (0.046 g, 0.267 mmol) was heated in a capped vial at 100° C. for 1 hour. The reaction mixture was treated with ethyl acetate and washed with saturated aqueous NaHCO₃. The organic layer was dried over MgSO₄, filtered, and concentrated. The crude material was purified on a 12 g column using the ISCO Companion flash system eluting with methanol/ethyl acetate (5:95 to 10:90) to provide the title compound. $^1$H NMR (400 MHz, CD₃OD) δ 5.23 (s, 2H), 7.00 (s, 1H), 7.04 (d, J=1.9 Hz, 1H), 7.14 (s, 1H), 7.35-7.29 (m, 2H), 7.61-7.51 (m, 3H), 7.71-7.64 (m, 1H), 7.87-7.75 (m, 4H), 9.14 (s, 1H). MS (ESI⁺) m/z 468.8 (M+H)⁺.

Example 80

6-(2-chlorophenyl)-2-{[4-(1H-imidazol-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 4-(1H-imidazol-1-yl)aniline. The reaction temperature was set at 100° C. $^1$H NMR (400 MHz, CD₃OD) δ 7.09 (d, J=1.8 Hz, 1H), 7.63-7.50 (m, 3H), 7.72-7.66 (m, 1H), 7.79-7.77 (m, 3H), 7.93 (d, J=1.9 Hz, 1H), 8.09 (t, J=1.7 Hz, 1H), 8.13 (d, J=8.9 Hz, 2H), 9.24 (s, 1H), 9.46 (s, 1H). MS (ESI⁺) m/z 455.2 (M+H)⁺.

Example 81

6-(2-chlorophenyl)-2-{[6-(piperazin-1-yl)pyridin-3-yl]amino}imidazo[1,2-a]pyrimido[5,4-e]pyrimidin-5(6H)-one A mixture of Example 1E (0.060 g, 0.167 mmol) and tert-butyl 4-(5-aminopyridin-2-yl)piperazine-1-carboxylate (0.074 g, 0.267 mmol) was heated in a capped vial at 100° C. for 1 hour. The reaction mixture was treated with ethyl acetate and washed with saturated aqueous NaHCO₃. The organic layer was dried, filtered, and concentrated. The crude material was purified on a 12 g column using the ISCO Companion flash system eluting with hexane/ethyl acetate (2:8 to 1:9) to give the desired intermediate. The intermediate was dissolved in CH₂Cl₂ (2 mL) and treated with trifluoroacetic acid (0.128 ml, 1.668 mmol). The reaction mixture was stirred at 40° C. for 2.5 hours, concentrated, and purified by HPLC (see protocol in Example 1F) to provide the title compound as a trifluoroacetic acid salt. $^1$H NMR (400 MHz, CD₃OD) δ 3.41-3.38 (m, 4H), 3.90-3.83 (m, 4H), 7.08 (d, J=1.9 Hz, 1H), 7.21-7.14 (m, 1H), 7.63-7.53 (m, 3H), 7.73-7.66 (m, 1H), 7.90-7.82 (m, 1H), 8.16 (dd, J=9.2, 2.7 Hz, 1H), 8.75-8.58 (m, 1H), 9.16 (s, 1H). MS (ESI⁺) m/z 474.2 (M+H)⁺.

Example 82

6-(2-chlorophenyl)-2-({3-[3-(4-methylpiperazin-1-yl)propoxy]phenyl}amino)imidazo[1,2-a]pyrimido[5,4-e]pyrimidin-5(6H)-one The title compound was prepared as described in Example 1F, substituting 4-(4-methylpiperazin-1-yl)aniline with 3-(3-(4-methylpiperazin-1-yl)propoxy)aniline. The reaction temperature was set at 100° C. $^1$H NMR (400 MHz, CD₃OD) δ 2.25-2.12 (m, 2H), 2.90 (s, 3H), 3.19 (t, J=7.5 Hz, 2H), 3.35-3.27 (m, 4H), 3.53-3.42 (m, 4H), 4.16 (t, J=5.8 Hz, 2H), 6.75 (d, J=6.5 Hz, 1H), 7.08 (d, J=1.9 Hz, 1H), 7.41-7.24 (m, 2H), 7.63-7.49 (m, 4H), 7.73-7.66 (m, 1H), 7.85 (s, 1H), 9.17 (s, 1H). MS (ESI⁺) m/z 545.3 (M+H)⁺.

Example 83

6-(2-chlorophenyl)-2-({3-[3-(piperidin-1-yl)propoxy]phenyl}amino)imidazo[1,2-a]pyrimido[5,4-e]pyrimidin-5(6H)-one A mixture of Example 1E (0.060 g, 0.167 mmol) and 3-(3-(piperidin-1-yl)propoxy)aniline (0.047 g), and concentrated HCl (3 drops) in acetonitrile was heated at 170° C. for 20 minutes in a Biotage microwave reactor. The reaction mixture was concentrated and purified by HPLC (see protocol in Example 1F) to provide the title compound as a trifluoroacetic acid salt. $^1$H NMR (400 MHz, CD$_3$OD) δ 1.91-1.45 (m, 4H), 1.98 (d, J=14.6 Hz, 2H), 2.27 (td, J=11.3, 5.7 Hz, 2H), 2.98 (dt, J=12.6, 6.3 Hz, 2H), 3.36-3.33 (m, 2H), 3.63-3.59 (m, 2H), 4.24-4.04 (m, 2H), 6.75 (d, J=6.7 Hz, 1H), 7.07 (d, J=1.8 Hz, 1H), 7.32-7.27 (m, 2H), 7.65-7.40 (m, 4H), 7.73-7.64 (m, 1H), 7.84 (s, 1H), 9.16 (s, 1H). MS (ESI$^+$) m/z 530.2 (M+H)$^+$.

Example 84

6-(2,6-dichlorophenyl)-2-(phenylamino)imidazo[1,2-a]pyrimido[5,4-e]pyrimidin-5(6H)-one The title compound (0.025 g) was prepared as described in Example 1F, substituting 4-(4-methylpiperazin-1-yl)aniline with aniline and Example 1E with Example 55E. Chromatography was performed with an Analogix 280 with an SF 12-24 column, using 15% to 75% ethyl acetate/hexane gradient over 30 minutes. $^1$H NMR (300 MHz, DMSO-d$_6$) δ 7.08-7.21 (m, 2H) 7.43 (t, J=7.80 Hz, 2H) 7.59-7.68 (m, 1H) 7.72-7.79 (m, 2H) 7.86 (s, 3H) 9.17 (s, 1H) 10.69-10.97 (m, J=8.14 Hz, 1H). MS (ESI+) m/z 423.2 (M+H)$^+$.

Example 85

6-(2-chlorophenyl)-2-({3-methoxy-4-[2-(propan-2-ylamino)ethoxy]phenyl}amino)imidazo[1,2-a]pyrimido[5,4-e]pyrimidin-5(6H)-one The title compound was prepared as described in Example 81, substituting tert-butyl 4-(5-aminopyridin-2-yl)piperazine-1-carboxylate with tert-butyl 2-(4-amino-2-methoxyphenoxy)ethyl(isopropyl)carbamate. The mobile phase for the flash column was CH$_2$Cl$_2$/ethyl acetate (8:2 to 7:3). $^1$H NMR (400 MHz, CD$_3$OD) δ 1.40 (d, J=6.5 Hz, 6H), 3.45 (t, J=4.7 Hz, 2H), 3.55-3.48 (m, 1H), 3.94 (s, 3H), 4.30-4.24 (m, 2H), 7.09-7.02 (m, 2H), 7.40-7.25 (m, 1H), 7.64-7.50 (m, 4H), 7.71-7.68 (m, 1H), 7.80 (bs, 1H), 9.12 (bs, 1H). MS (ESI$^+$) m/z 520.2 (M+H)$^+$.

Example 86

6-(2-chlorophenyl)-2-({3-chloro-4-[2-(propan-2-ylamino)ethoxy]phenyl}amino)imidazo[1,2-a]pyrimido[5,4-e]pyrimidin-5(6H)-one The title compound was prepared as described in Example 81, substituting tert-butyl 4-(5-aminopyridin-2-yl)piperazine-1-carboxylate with tert-butyl 2-(4-amino-2-chlorophenoxy)ethyl(isopropyl)carbamate. The mobile phase for the flash column was CH$_2$Cl$_2$/ethyl acetate (8:2 to 7:3). $^1$H NMR (400 MHz, CD$_3$OD) δ 1.41 (d, J=6.5 Hz, 6H), 3.65-3.50 (m, 3H), 4.37 (t, J=4.8 Hz, 2H), 7.07 (d, J=1.9 Hz, 1H), 7.24-7.17 (m, 1H), 7.62-7.53 (m, 3H), 7.70-7.68 (m, 2H), 7.79 (bs, 1H), 8.00 (s, 1H), 9.15 (bs, 1H). MS (ESI$^+$) m/z 524.1 (M+H)$^+$.

Example 87

6-(2-chlorophenyl)-2-{[4-(hydroxymethyl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with (4-aminophenyl)methanol. The reaction temperature was set at 120° C. $^1$H NMR (400 MHz, DMSO-d$_6$) δ 4.50 (s, 2H), 7.10-7.05 (m, 1H), 7.38-7.36 (m, 1H), 7.64-7.53 (m, 4H), 7.73-7.69 (m, 1H), 7.81 (bs, 2H), 9.13 (s, 1H), 10.75 (s, 1H). MS (ESI$^+$) m/z 419.2 (M+H)$^+$.

Example 88

6-(2-chlorophenyl)-2-{[4-(1H-pyrazol-1-ylmethyl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 4-((1H-pyrazol-1-yl)methyl)aniline. The reaction temperature was set at 100° C. $^1$H NMR (400 MHz, DMSO-d$_6$) δ 5.33 (s, 2H), 6.28 (t, J=2.0 Hz, 1H), 7.07 (d, J=1.8 Hz, 1H), 7.32-7.26 (m, 2H), 7.47 (d, J=1.8 Hz, 1H), 7.66-7.51 (m, 3H), 7.73-7.71 (m, 1H), 7.87-7.76 (m, 4H), 9.13 (s, 1H), 10.79 (bs, 1H). MS (ESI$^+$) m/z 469.2 (M+H)$^+$.

Example 89

6-(2-chlorophenyl)-2-{[4-(1H-pyrazol-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 4-(1H-pyrazol-1-yl)aniline. The reaction temperature was set at 100° C. $^1$H NMR (400 MHz, DMSO-d$_6$) δ 6.55 (t, J=2.0 Hz, 1H), 7.09 (d, J=1.8 Hz, 1H), 7.67-7.52 (m, 3H), 7.75-7.71 (m, 2H), 8.04-7.86 (m, 5H), 8.46 (d, J=2.5 Hz, 1H), 9.16 (s, 1H), 10.91 (bs, 1H). MS (ESI$^+$) m/z 455.2 (M+H)$^+$.

Example 90

6-(2-chlorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one A mixture of Example 1E (0.500 g, 1.390 mmol) and tert-butyl 7'-amino-1'H-spiro[cyclopropane-1,4'-isoquinoline]-2'(3'H)-carboxylate (0.610 g, 2.224 mmol) was heated in a capped vial at 100° C. for 1 hour. The reaction mixture was treated with ethyl acetate and washed with saturated aqueous NaHCO$_3$. The organic layer was dried over MgSO$_4$, filtered, and concentrated. The crude material was purified on a 40 g column using the ISCO Companion flash system eluting with hexane/ethyl acetate (4:6 to 3:7) to give the desired intermediate. The intermediate was dissolved in CH$_2$Cl$_2$ (6 mL) and treated with trifluoroacetic acid (0.857 ml, 11.12 mmol). The reaction mixture was stirred at 35° C. for 2 hours, concentrated, and purified by HPLC (see protocol in Example 1F) to provide the title compound as a trifluoroacetic acid salt. $^1$H NMR (400 MHz, CD$_3$OD) δ 1.17-1.12 (m, 2H), 1.27-1.24 (m, 2H), 3.37 (s, 2H), 4.54 (s, 2H), 6.99-6.91 (m, 1H), 7.07 (d, J=1.9 Hz, 1H), 7.63-7.53 (m, 3H), 7.75-7.66 (m, 3H), 7.87 (bs, 1H), 9.16 (s, 1H). MS (ESI$^+$) m/z 470.2 (M+H)$^+$.

Example 91

2-[(2'-acetyl-2',3'-dihydro-1'H-spiro[cyclopropane-1,4'-isoquinolin]-7'-yl)amino]-6-(2-chlorophenyl)imidazo[1,2-a]pyrimido[5,4-e]pyrimidin-5(6H)-one A solution of Example 90 (0.100 g, 0.143 mmol), acetic acid (0.012 mL, 0.215 mmol), benzotriazol-1-yloxytripyrrolidinophosphonium hexafluorophosphate (0.112 g, 0.215 mmol), and triethylamine (0.100 mL, 0.716 mmol) in tetrahydrofuran (5 mL) was stirred overnight. The resulting suspension was diluted with ethyl acetate and washed with saturated aqueous $NaHCO_3$. The suspension was filtered and concentrated. The residue was treated with DMSO/methanol (1:1) with several drops of trifluoroacetic acid. The suspension was diluted with saturated aqueous $NaHCO_3$, filtered, washed with water, and oven-dried to provide the title compound. $^1H$ NMR (400 MHz, DMSO-$d_6$) δ 1.13-0.91 (m, 4H), 2.12 (s, 1.7H), 2.20 (s, 1.3H), 3.62-3.59 (m, 2H), 4.89-4.79 (m, 2H), 6.99-6.93 (m, 1H), 7.14 (t, J=2.1 Hz, 1H), 7.87-7.57 (m, 7H), 9.18 (s, 1H), 10.79 (bs, 1H). MS ($ESI^+$) m/z 512.2 $(M+H)^+$.

Example 92

6-(2-chlorophenyl)-2-[(1-methyl-1,2,3,4-tetrahydroquinolin-6-yl)amino]imidazo[1,2-a]pyrimido[5,4-e]pyrimidin-5(6H)-one The title compound was prepared as described in Example 1F, substituting 4-(4-methylpiperazin-1-yl)aniline with 1-methyl-1,2,3,4-tetrahydroquinolin-6-amine. The reaction temperature was set at 100° C. $^1H$ NMR (400 MHz, $CD_3OD$) δ 2.27-2.17 (m, 2H), 3.08-2.78 (m, 2H), 3.24, (s, 3H), 3.64-3.50 (m, 2H), 7.08 (d, J=1.9 Hz, 1H), 7.50-7.29 (m, 1H), 7.63-7.51 (m, 3H), 7.73-7.66 (m, 2H), 7.80 (d, J=8.3 Hz, 1H), 7.86 (d, J=1.9 Hz, 1H), 9.17 (s, 1H). MS ($ESI^+$) m/z 458.2 $(M+H)^+$.

Example 93

6-(2-chlorophenyl)-2-({1-[2-(dimethylamino)ethyl]-2,3-dihydro-1H-indol-5-yl}amino)imidazo[1,2-a]pyrimido[5,4-e]pyrimidin-5(6H)-one The title compound was prepared as described in Example 1F, substituting 4-(4-methylpiperazin-1-yl)aniline with 1-(2-(dimethylamino)ethyl)indolin-5-amine. The reaction temperature was set at 100° C. $^1H$ NMR (400 MHz, $CD_3OD$) δ 2.98 (s, 6H), 3.12-3.02 (m, 2H), 3.55-3.37 (m, 6H), 6.78-6.72 (m, 1H), 7.05 (d, J=1.8 Hz, 1H), 7.61-7.42 (m, 5H), 7.88-7.66 (m, 2H), 9.08 (s, 1H). MS ($ESI^+$) m/z 501.2 $(M+H)^+$.

Example 94

6-(2-chlorophenyl)-2-{[2-(dimethylamino)-2,3-dihydro-1H-inden-5-yl]amino}imidazo[1,2-a]pyrimido[5,4-e]pyrimidin-5(6H)-one The title compound was prepared as described in Example 1F, substituting 4-(4-methylpiperazin-1-yl)aniline with $N^2,N^2$-dimethyl-2,3-dihydro-1H-indene-2,5-diamine. The reaction temperature was set at 100° C. $^1H$ NMR (400 MHz, $CD_3OD$) δ 2.95 (s, 6H), 3.31-3.11 (m, 2H), 3.61-3.39 (m, 2H), 4.22-4.13 (m, 1H), 7.06 (d, J=1.9 Hz, 1H), 7.32 (d, J=7.9 Hz, 1H), 7.63-7.51 (m, 4H), 7.72-7.64 (m, 1H), 7.87-7.81 (m, 2H), 9.14 (s, 1H). MS ($ESI^+$) m/z 472.2 $(M+H)^+$.

Example 95

6-(2-chloro-6-fluorophenyl)-2-{[4-(4-methylpiperazin-1-yl)phenyl]amino}imidazo[1,2-a]pyrimido[5,4-e]pyrimidin-5(6H)-one Example 95A 3-(2-chloro-6-fluorophenyl)-7-(methylthio)pyrimido[4,5-d]pyrimidine-2,4(1H,3H)-dione The title compound was prepared as described in Example 1A, substituting 1-chloro-2-isocyanatobenzene with 1-chloro-3-fluoro-2-isocyanatobenzene (2 hour reaction time).

Example 95B 2-chloro-3-(2-chloro-6-fluorophenyl)-7-(methylthio)pyrimido[4,5-d]pyrimidin-4(3H)-one A mixture of Example 95A (0.960 g, 2.83 mmol) in $POCl_3$ (3.5 ml, 37.5 mmol) and diisopropylethylamine (DIEA) (3.5 ml, 20.04 mmol) was heated at 90° C. for 1.5 hours. After concentrating the reaction mixture, the residue was treated with ice and aqueous $NaHCO_3$ solution and extracted with ethyl acetate. The organic layer was dried over $MgSO_4$, filtered, concentrated and purified on a 40 g silica column using the ISCO Companion flash system eluting with hexane/ethyl acetate (7:3 to 6:4) to provide the title compound.

Example 95C 4-(2-chloro-6-fluorophenyl)-8-methylsulfanyl-4H-3,4,7,9,9b-pentaaza-cyclopenta[a]naphthalen-5-one The title compound was prepared as described in Examples 1C and 1D, substituting Example 1B with Example 95B in Example 1C. The title compound was purified through trituration using ethyl acetate instead of through a flash column in the second step.

Example 95D 4-(2-Chloro-6-fluorophenyl)-8-methanesulfinyl-4H-3,4,7,9,9b-pentaaza-cyclopenta[a]naphthalen-5-one The title compound was prepared as described in Example 1E, substituting Example 1D with Example 95C.

Example 95E 6-(2-chloro-6-fluorophenyl)-2-{[4-(4-methylpiperazin-1-yl)phenyl]amino}imidazo[1,2-a]pyrimido[5,4-e]pyrimidin-5(6H)-one A mixture of Example 95D (0.060 g, 0.159 mmol) and 4-(4-methylpiperazin-1-yl)aniline (0.049 g, 0.254 mmol) was mixed and heated at 100° C. for 0.5 hr. The crude material was purified by HPLC (see protocol in Example 1F) to provide the title compound as a trifluoroacetic acid salt. $^1H$ NMR (400 MHz, $CD_3OD$) δ 2.98 (s, 3H), 3.16-3.01 (m, 2H), 3.36-3.21 (m, 2H), 3.63-3.61 (m, 2H), 3.87-3.84 (m, 2H), 7.17-6.95 (m, 3H), 7.38 (dd, J=12.8, 4.7 Hz, 1H), 7.53 (d, J=8.2 Hz, 1H), 7.97-7.57 (m, 4H), 9.08 (s, 1H). MS ($ESI^+$) m/z 505.2 $(M+H)^+$.

Example 96

6-(2-chloro-6-fluorophenyl)-2-{[3-methyl-4-(4-methyl-1,4-diazepan-1-yl)phenyl]amino}imidazo[1,2-a]pyrimido[5,4-e]pyrimidin-5(6H)-one The title compound was prepared as described in Example 95E, substituting 4-(4-methylpiperazin-1-yl)aniline with 3-methyl-4-(4-methyl-1,4-diazepan-1-yl)aniline. $^1$H NMR (400 MHz, CD$_3$OD) δ 2.30-2.09 (m, 2H), 2.41 (s, 3H), 3.01 (s, 3H), 3.48-3.17 (m, 6H), 3.66-3.56 (m, 2H), 7.08 (d, J=1.9 Hz, 1H), 7.24-7.10 (m, 1H), 7.43-7.34 (m, 1H), 7.67-7.50 (m, 4H), 7.90-7.76 (m, 1H), 9.14 (bs, 1H). MS (ESI$^+$) m/z 533.2 (M+H)$^+$.

Example 97

6-(2-chloro-6-fluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one The title compound was prepared as described in Example 95E, substituting 4-(4-methylpiperazin-1-yl)aniline with 2,4,4-trimethyl-1,2,3,4-tetrahydroisoquinolin-7-amine. $^1$H NMR (400 MHz, CD$_3$OD) δ 1.48 (s, 6H), 3.12 (s, 3H), 3.41-3.28 (m, 1H), 3.61-3.49 (m, 1H), 4.64-4.37 (m, 2H), 7.09 (d, J=1.8 Hz, 1H), 7.43-7.31 (m, 1H), 7.68-7.50 (m, 3H), 7.75 (s, 2H), 7.89 (d, J=1.7 Hz, 1H), 9.18 (s, 1H). MS (ESI$^+$) m/z 504.2 (M+H)$^+$.

Example 98

6-(2,6-difluorophenyl)-2-{[4-(4-methylpiperazin-1-yl)phenyl]amino}imidazo[1,2-a]pyrimido[5,4-e]pyrimidin-5(6H)-one

Example 98A

3-(2,6-difluorophenyl)-7-(methylthio)pyrimido[4,5-d]pyrimidine-2,4(1H,3H)-dione The title compound (0.3 g) was prepared as described in Example 1A, substituting 1-chloro-2-isocyanatobenzene with 1,3-difluoroisocyanatobenzene. MS (ESI$^+$) m/z 323.1 (M+H)$^+$.

Example 98B

2-chloro-3-(2,6-difluorophenyl)-7-(methylthio)pyrimido[4,5-d]pyrimidin-4(3H)-one Example 98B (0.31 g) was prepared as described in Example 1B, substituting Example 1A with Example 98A. MS (ESI$^+$) m/z 341.2 (M+H)$^+$.

Example 98C

3-(2,6-difluorophenyl)-2-(2,2-dimethoxyethylamino)-7-(methylthio)pyrimido[4,5-d]pyrimidin-4(3H)-one The title compound (0.3 g) was prepared as described in Example 1C, substituting Example 1B with Example 98B. MS (ESI$^+$) m/z 409.4 (M+H)$^+$.

Example 98D

4-(2,6-difluoro-phenyl)-8-methylsulfanyl-4H-3,4,7,9,9b-pentaaza-cyclopenta[a]naphthalen-5-one The title compound (0.47 g) was prepared as described in Example 1D, substituting Example 1C with Example 98C. MS (ESI$^+$) m/z 346.28 (M+H)$^+$.

Example 98E

4-(2,6-difluoro-phenyl)-8-methylsulfinyl-4H-3,4,7,9,9b-pentaaza-cyclopenta[a]naphthalen-5-one The title compound (0.1 g) was prepared as described in Example 1E, substituting Example 1D with Example 98D. MS (ESI$^+$) m/z 361.68 (M+H)$^+$.

Example 98F

6-(2,6-difluorophenyl)-2-{[4-(4-methylpiperazin-1-yl)phenyl]amino}imidazo[1,2-a]pyrimido[5,4-e]pyrimidin-5(6H)-one The title compound (0.015 g) was prepared as described in Example 1F, substituting Example 1E with Example 98E. The crude material was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.80-3.04 (m, 5H) 3.07-3.29 (m, 2H) 3.83 (d, J=13.09 Hz, 4H) 7.12 (d, J=1.59 Hz, 3H) 7.40 (t, J=8.33 Hz, 2H) 7.56-7.83 (m, 4H) 9.09 (s, 1H) 9.57 (s, 1H) 10.73 (s, 1H). MS (ESI$^+$) m/z 489.2 (M+H)$^+$.

Example 99

6-(2-chlorophenyl)-2-{[2-(2-hydroxyethyl)-1,2,3,4-tetrahydroisoquinolin-7-yl]amino}imidazo[1,2-a]pyrimido[5,4-e]pyrimidin-5(6H)-one The title compound was prepared as described in Example 1F, substituting 4-(4-methylpiperazin-1-yl)aniline with 2-(7-amino-3,4-dihydroisoquinolin-2(1H)-yl)ethanol. The reaction temperature was set at 100° C. $^1$H NMR (400 MHz, CD$_3$OD) δ 2.75 (t, J=6.0 Hz, 2H), 2.97-2.84 (m, 4H), 3.77 (s, 2H), 3.81 (t, J=6.0 Hz, 2H), 7.05 (d, J=1.9 Hz, 1H), 7.48-7.13 (m, 1H), 7.61-7.48 (m, 5H), 7.71-7.65 (m, 1H), 7.88-7.78 (m, 1H), 9.13 (s, 1H). MS (ESI$^+$) m/z 488.3 (M+H)$^+$.

Example 100

6-(2-chlorophenyl)-2-{[3-(hydroxymethyl)-4-(4-methyl-1,4-diazepan-1-yl)phenyl]amino}imidazo[1,2-a]pyrimido[5,4-e]pyrimidin-5(6H)-one

Example 100A

(2-(4-methyl-1,4-diazepan-1-yl)-5-nitrophenyl)methanol

A mixture of (2-fluoro-5-nitrophenyl)methanol (4.500 g, 26.3 mmol), diisopropylethylamine (6.89 mL, 39.4 mmol), and 1-methyl-1,4-diazepane (4.25 mL, 34.2 mmol) in acetonitrile (150 mL) was refluxed for 24 hours. The solvent was evaporated. The residue was treated with saturated aqueous NaHCO$_3$ and extracted with ethyl acetate (twice). The combined organic layers were dried over MgSO$_4$ and filtered. The title compound was crystallized from the organic layers.

Example 100B (5-amino-2-(4-methyl-1,4-diazepan-1-yl)phenyl) methanol

Ethanol (30 mL) was added to Pd/C (0.040 g, 0.038 mmol) in a flask purged with N$_2$. Example 100A (0.400 g, 1.508 mmol) was added to the above mixture. The reaction was stirred under H$_2$ using a balloon for 6 hours. The reaction mixture was filtered through diatomaceous earth and concentrated to provide the title compound.

Example 100C 6-(2-chlorophenyl)-2-{[3-(hydroxymethyl)-4-(4-methyl-1,4-diazepan-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with Example 100B. The reaction temperature was set at 100° C. for 0.5 hour. $^1$H NMR (400 MHz, CD$_3$OD) δ 2.35-2.17 (m, 2H), 3.00 (s, 3H), 3.50-3.23 (m, 6H), 3.64-3.54 (m, 2H), 4.80 (bs, 2H), 7.07 (d, J=1.9 Hz, 1H), 7.33-7.23 (m, 1H), 7.62-7.52 (m, 3H), 7.72-7.63 (m, 2H), 7.95-7.87 (m, 1H), 8.16 (bs, 1H), 9.14 (s, 1H). MS (ESI$^+$) m/z 531.2 (M+H)$^+$.

Example 101

6-(2-chlorophenyl)-2-{[4-(hexahydropyrrolo[1,2-a] pyrazin-2(1H)-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with 4-(hexahydropyrrolo[1,2-a]pyrazin-2(1H)-yl)aniline. The reaction temperature was set at 100° C. for 0.5 hour. $^1$H NMR (400 MHz, CD$_3$OD) δ 2.39-2.07 (m, 4H), 3.18-2.89 (m, 3H), 3.59-3.36 (m, 4H), 3.86-3.69 (m, 1H), 4.18-3.89 (m, 1H), 7.12-7.03 (m, 3H), 7.64-7.48 (m, 3H), 7.74-7.65 (m, 3H), 7.95-7.77 (m, 1H), 9.09 (bs, 1H). MS (ESI$^+$) m/z 513.3 (M+H)$^+$.

Example 102

6-(2-chlorophenyl)-2-[(4-hydroxy-3-methylphenyl) amino]imidazo[1,2-a]pyrimido[5,4-e]pyrimidin-5 (6H)-one The title compound was prepared as described in Example 1F, substituting 4-(4-methylpiperazin-1-yl)aniline with 4-amino-2-methylphenol. The reaction temperature was set at 100° C. for 0.5 hour. $^1$H NMR (400 MHz, CD$_3$OD) δ 2.24 (s, 3H), 6.84-6.76 (m, 1H), 7.08 (d, J=1.9 Hz, 1H), 7.48-7.28 (m, 2H), 7.62-7.52 (m, 4H), 7.79-7.65 (m, 1H), 9.09 (s, 1H). MS (ESI$^+$) m/z 419.3 (M+H)$^+$.

Example 103

6-(2-chlorophenyl)-2-({4-[3-(diethylamino)propoxy]-3-methylphenyl}amino)imidazo[1,2-a]pyrimido[5,4-e]pyrimidin-5(6H)-one A mixture of Example 102 (0.050 g, 0.119 mmol), PPh$_3$ on polymer support (3 mmol/g, 0.213 g), di-tert-butyl azodicarboxylate (0.147 g), and 3-(diethylamino)propan-1-ol (0.096 mL) in tetrahydrofuran (2.5 mL) was stirred for 2 days. The reaction mixture was diluted with ethyl acetate and filtered through diatomaceous earth. The concentrate was purified by HPLC (see protocol in Example 1F) to provide the title compound as a trifluoroacetic acid salt. $^1$H NMR (500 MHz, CD$_3$OD) δ 1.40-1.34 (m, 6H), 1.50-1.44 (m, 2H), 2.31-2.22 (m, 5H), 3.29-3.20 (m, 2H), 3.44-3.37 (m, 2H), 4.19-4.12 (m, 2H), 7.01-6.93 (m, 1H), 7.06 (d, J=1.9 Hz, 1H), 7.61-7.49 (m, 5H), 7.88-7.62 (m, 2H), 9.11 (s, 1H). MS (ESI$^+$) m/z 532.2 (M+H)$^+$.

Example 104

6-(2-chlorophenyl)-2-{[3-methyl-4-(piperazin-1-yl) phenyl]amino}imidazo[1,2-a]pyrimido[5,4-e]pyrimidin-5(6H)-one The title compound was prepared following the general procedure described in Example 81, substituting tert-butyl 4-(5-aminopyridin-2-yl)piperazine-1-carboxylate with tert-butyl 4-(4-amino-2-methylphenyl)piperazine-1-carboxylate. $^1$H NMR (500 MHz, CD$_3$OD) δ 2.39 (s, 3H), 3.17-3.15 (m, 4H), 3.46-3.36 (m, 4H), 7.07 (d, J=1.9 Hz, 1H), 7.21-7.12 (m, 1H), 7.62-7.49 (m, 4H), 7.92-7.64 (m, 3H), 9.12 (s, 1H). MS (ESI$^+$) m/z 487.2 (M+H)$^+$.

Example 105

6-(2-chlorophenyl)-2-{[4-(1,4-diazepan-1-yl)-3-methylphenyl]amino}imidazo[1,2-a]pyrimido[5,4-e] pyrimidin-5(6H)-one Example 105A 1-(2-methyl-4-nitrophenyl)-1,4-diazepane The title compound was prepared as described in Example 100A, substituting (2-fluoro-5-nitrophenyl)methanol and 1-methyl-1,4-diazepane with 1-fluoro-2-methyl-4-nitrobenzene and 1,4-diazepane (0.7 more equivalent), respectively.

Example 105B 4-(1,4-diazepan-1-yl)-3-methylaniline

The title compound was prepared as described in Example 100B, substituting Example 100A with Example 105B.

Example 105C 6-(2-chlorophenyl)-2-{[4-(1,4-diazepan-1-yl)-3-methylphenyl]amino}imidazo[1,2-a]pyrimido[5,4-e] pyrimidin-5(6H)-one A mixture of Example 1E (0.075 g, 0.208 mmol), Example 105B (0.051 g, 0.250 mmol), and 4 drops of trifluoroacetic acid in acetonitrile (4.5 mL) was heated at 70° C. overnight. The reaction mixture was concentrated and purified by HPLC (see protocol in Example 1F) to provide the title compound as a trifluoroacetic acid salt. $^1$H NMR (500 MHz, DMSO-$d_6$) δ 2.08-1.99 (m, 2H), 2.32 (s, 3H), 3.12-3.05 (m, 2H), 3.30-3.25 (m, 4H), 3.36-3.30 (m, 2H), 7.08 (d, J=1.8 Hz, 1H), 7.21-7.14 (m, 1H), 7.65-7.52 (m, 4H), 7.77-7.69 (m, 2H), 8.78 (bs, 2H), 9.10 (s, 1H), 10.72-10.54 (m, 1H). MS (ESI$^+$) m/z 501.2 (M+H)$^+$.

Example 106

6-(2-chlorophenyl)-2-(2,3,4,5-tetrahydro-1H-2-benzazepin-7-ylamino)imidazo[1,2-a]pyrimido[5,4-e]pyrimidin-5(6H)-one The title compound was prepared as described in Example 105C, substituting Example 105B with 2,3,4,5-tetrahydro-1H-benzo[c]azepin-7-amine. $^1$H NMR (400 MHz, CD$_3$OD) δ 2.09-2.01 (m, 2H), 3.15-3.09 (m, 2H), 3.53-3.47 (m, 2H), 4.40 (s, 2H), 7.08 (d, J=1.9 Hz, 1H), 7.45-7.39 (m, 1H), 7.62-7.53 (m, 3H), 7.74-7.66 (m, 2H), 7.87-7.77 (m, 2H), 9.18 (s, 1H). MS (ESI$^+$) m/z 458.2 (M+H)$^+$.

Example 107

6-(2-chlorophenyl)-2-[(3-methyl-2,3,4,5-tetrahydro-1H-3-benzazepin-7-yl)amino]imidazo[1,2-a]pyrimido[5,4-e]pyrimidin-5(6H)-one The title compound was prepared as described in Example 1F, substituting 4-(4-methylpiperazin-1-yl)aniline with 3-methyl-2,3,4,5-tetrahydro-1H-benzo[d]azepin-7-amine. The reaction temperature was set at 100° C. for 0.5 hour. $^1$H NMR (400 MHz, DMSO-$d_6$) δ 2.88 (d, J=4.5 Hz, 3H), 3.29-2.98 (m, 6H), 3.69-3.60 (m, 2H), 7.08 (d, J=1.8 Hz, 1H), 7.31-7.24 (m, 1H), 7.75-7.52 (m, 7H), 7.79 (s, 1H), 9.96 (bs, 1H), 10.77 (bs, 1H). MS (ESI$^+$) m/z 472.2 (M+H)$^+$.

Example 108

6-(2-chlorophenyl)-2-[(1,1,2-trimethyl-1,2,3,4-tetrahydroisoquinolin-7-yl)amino]imidazo[1,2-a]pyrimido[5,4-e]pyrimidin-5(6H)-one The title compound was prepared as described in Example 1F, substituting 4-(4-methylpiperazin-1-yl)aniline with 1,1,2-trimethyl-1,2,3,4-tetrahydroisoquinolin-7-amine. The reaction temperature was set at 100° C. for 0.5 hour. $^1$H NMR (400 MHz, CD$_3$OD) δ 1.77 (s, 3H), 1.86 (s, 3H), 3.01 (s, 3H), 3.32-3.13 (m, 2H), 3.83-3.51 (m, 2H), 7.06 (d, J=1.9 Hz, 1H), 7.30 (t, J=11.8 Hz, 1H), 7.63-7.47 (m, 3H), 7.72-7.65 (m, 1H), 7.87-7.73 (m, 3H), 9.18 (s, 1H). MS (ESI$^+$) m/z 486.1 (M+H)$^+$.

Example 109

6-(2,6-dichlorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one

Example 109A tert-butyl 7'-{[6-(2,6-dichlorophenyl)-5-oxo-5,6-dihydroimidazo[1,2-a]pyrimido[5,4-e]pyrimidin-2-yl]amino}-1'H-spiro[cyclopropane-1,4'-isoquinoline]-2'(3'H)-carboxylate To Example 55D (1225 mg, 3.24 mmol) and m-chloroperoxybenzoic acid (871 mg, 3.89 mmol) was added 15 mL of dichloromethane. The reaction was stirred for 15 minutes and tert-butyl 7'-amino-1'H-spiro[cyclopropane-1,4'-isoquinoline]-2'(3'H)-carboxylate (1066 mg, 3.89 mmol) was added. The reaction was stirred at room temperature for 25 minutes, diluted with ethyl acetate, washed with saturated aqueous NaHCO$_3$, water, and brine, dried over MgSO$_4$, filtered, and concentrated. Chromatography was performed with an Analogix 280 with an SF 25-80 column at a 10% to 60% ethyl acetate/hexane gradient over 30 minutes to provide the title compound. MS (ESI$^+$) m/z 604.2 (M+H)$^+$.

Example 109B 6-(2,6-dichlorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one To a solution of Example 109A (0.12 g, 0.2 mmol) in 3 ml dichloromethane was added excess TFA. The reaction mixture was stirred at room temperature for one hour. The mixture was concentrated and the crude material was dried over high vacuum to provide the title compound. $^1$H NMR (300 MHz, DMSO-$d_6$) δ 0.87-1.27 (m, 4H) 3.18-3.38 (m, 2H) 4.34-4.58 (m, 2H) 6.94 (d, J=8.48 Hz, 1H) 7.13 (d, J=1.70 Hz, 1H) 7.39-8.01 (m, 6H) 8.91-9.45 (m, 3H) 10.88 (s, 1H). MS (ESI$^+$) m/z 504.2 (M+H)$^+$.

Example 110

6-(2,6-dichlorophenyl)-2-{[3-methyl-4-(piperazin-1-yl)phenyl]amino}imidazo[1,2-a]pyrimido[5,4-e]pyrimidin-5(6H)-one

Example 110A tert-butyl 4-(4-{[6-(2,6-dichlorophenyl)-5-oxo-5,6-dihydroimidazo[1,2-a]pyrimido[5,4-e]pyrimidin-2-yl]amino}-2-methylphenyl)piperazine-1-carboxylate The title compound (0.198 g) was prepared as described in Example 109A, with the addition of diisopropylethylamine (0.103 g, 0.793 mmol) and substituting tert-butyl 7'-amino-1'H-spiro[cyclopropane-1,4'-isoquinoline]-2'(3'H)-carboxylate with tert-butyl 4-(4-amino-2-methylphenyl)piperazine-1-carboxylate. Chromatography was performed with an Analogix 280 with an SF 12-24 column, 10% to 70% ethyl acetate/hexane gradient over 30 minutes. MS (ESI$^+$) m/z 621.0 (M+H)$^+$.

Example 110B 6-(2,6-dichlorophenyl)-2-{[3-methyl-4-(piperazin-1-yl)phenyl]amino}imidazo[1,2-a]pyrimido[5,4-e]pyrimidin-5(6H)-one The title compound (0.015 g) was prepared as described in Example 109B, substituting Example 109A with Example 110A. $^1$H NMR (300 MHz, DMSO-$d_6$) δ 2.21-2.39 (m, 3H) 2.96-3.11 (m, J=4.76 Hz, 4H) 3.19-3.35 (m, 4H) 7.05-7.22

(m, 2H) 7.53-7.70 (m, 2H) 7.70-7.86 (m, 4H) 8.71 (s, 2H) 9.14 (s, 1H) 10.79 (s, 1H). MS (ESI$^+$) m/z 521.2 (M+H)$^+$.

Example 111

6-(2,6-dichlorophenyl)-2-(1,2,3,4-tetrahydroisoquinolin-7-ylamino)imidazo[1,2-a]pyrimido[5,4-e]pyrimidin-5(6H)-one

Example 111A tert-butyl 7-{[6-(2,6-dichlorophenyl)-5-oxo-5,6-dihydroimidazo[1,2-a]pyrimido[5,4-e]pyrimidin-2-yl]amino}-3,4-dihydroisoquinoline-2(1H)-carboxylate The title compound (0.11 g) was prepared as described in Example 109A, with the addition of diisopropylethylamine (0.103 g, 0.793 mmol) and substituting tert-butyl 7'-amino-1'H-spiro[cyclopropane-1,4'-isoquinoline]-2'(3'H)-carboxylate with tert-butyl 7-amino-3,4-dihydroisoquinoline-2(1H)-carboxylate. Chromatography was performed with an Analogix 280 with an SF 12-24 column, 10% to 60% ethyl acetate/hexane gradient over 30 minutes. MS (ESI$^+$) m/z 578.3 (M+H)$^+$.

Example 111B 6-(2,6-dichlorophenyl)-2-{[3-methyl-4-(piperazin-1-yl)phenyl]amino}imidazo[1,2-a]pyrimido[5,4-e]pyrimidin-5(6H)-one The title compound (0.015 g) was prepared as described in Example 109B, substituting Example 109A with Example 111A. $^1$H NMR (300 MHz, DMSO-d$_6$) δ 2.90-3.08 (m, 2H) 3.32-3.52 (m, 2H) 4.36 (s, 2H) 7.13 (d, J=1.59 Hz, 1H) 7.29 (d, J=8.73 Hz, 1H) 7.57-7.73 (m, 3H) 7.73-7.80 (m, 2H) 7.85 (s, 1H) 9.00 (s, 2H) 9.18 (s, 1H) 10.90 (s, 1H). MS (ESI$^+$) m/z 478.2 (M+H)$^+$.

Example 112

6-(2-chlorophenyl)-2-{[3-ethyl-4-(4-methylpiperazin-1-yl)phenyl]amino}imidazo[1,2-a]pyrimido[5,4-e]pyrimidin-5(6H)-one

Example 112A 1-methyl-4-(4-nitro-2-vinylphenyl)piperazine

A mixture of 1-(2-bromo-4-nitrophenyl)-4-methylpiperazine (0.900 g, 3.00 mmol), tetrakis(triphenylphosphine)palladium(0) (0.104 g, 0.090 mmol), and tributyl(vinyl)tin (0.964 mL, 3.30 mmol) in 1,4-dioxane (30 mL) was degassed and heated at 105° C. overnight. After cooling, the suspension was filtered, concentrated, and purified on a 40 g column using the ISCO Companion flash system eluting with methanol/ethyl acetate (5:95 to 10:90) to provide the title compound.

Example 112B 3-ethyl-4-(4-methylpiperazin-1-yl)aniline

Example 112A (0.558 g) in ethanol (20 mL) and tetrahydrofuran (5 ml) was added to 5% Pd—C (wet) catalyst in a 50 ml pressure bottle and stirred for 16 hours at 30 psi of hydrogen at room temperature. The reaction mixture was filtered through diatomaceous earth and concentrated to provide the title compound.

Example 112C 6-(2-chlorophenyl)-2-{[3-ethyl-4-(4-methylpiperazin-1-yl)phenyl]amino}imidazo[1,2-a]pyrimido[5,4-e]pyrimidin-5(6H)-one The title compound was prepared as described in Example 1F, substituting 4-(4-methylpiperazin-1-yl)aniline with Example 112B. The reaction temperature was set at 100° C. for 0.5 hour. $^1$H NMR (400 MHz, CD$_3$OD) δ 1.35-1.27 (m, 3H), 2.85-2.75 (m, 2H), 2.99 (s, 3H), 3.25-3.10 (m, 4H), 3.38-3.34 (m, 2H), 3.64-3.56 (m, 2H), 7.06 (d, J=1.9 Hz, 1H), 7.23 (d, J=7.1 Hz, 1H), 7.62-7.52 (m, 3H), 7.87-7.63 (m, 4H), 9.12 (s, 1H). MS (ESI$^+$) m/z 515.3 (M+H)$^+$.

Example 113

6-(2-chlorophenyl)-2-{[2-(cyclohexylmethyl)-4,4-dimethyl-1,2,3,4-tetrahydroisoquinolin-7-yl]amino}imidazo[1,2-a]pyrimido[5,4-e]pyrimidin-5(6H)-one

Example 113A 2-(cyclohexylmethyl)-4,4-dimethyl-7-nitro-1,2,3,4-tetrahydroisoquinoline Sodium cyanotrihydroborate (0.600 g, 9.55 mmol) was added to a solution of 4,4-dimethyl-7-nitro-1,2,3,4-tetrahydroisoquinoline (0.600 g, 2.91 mmol), acetic acid (0.210 mL, 3.66 mmol) and cyclohexanecarbaldehyde (0.4 g, 3.57 mmol) in methanol (40 mL). The reaction mixture was stirred at 35° C. for 16 hours. The reaction was neutralized with saturated sodium bicarbonate solution, and the mixture was concentrated under reduced pressure. The residue was diluted with water and extracted with ethyl acetate (3×50 mL). The combined organic layers were washed with brine, dried over Na$_2$SO$_4$, filtered, and concentrated. The crude product was purified with silica gel column chromatography (3% ethyl acetate/petroleum ether) to provide the title compound.

Example 113B 2-(cyclohexylmethyl)-4,4-dimethyl-1,2,3,4-tetrahydroisoquinolin-7-amine Example 113A (0.7 g, 2.315 mmol) was added to Pd/C (10%, 0.1 g, 0.094 mmol) in methanol (50 mL). The mixture was degassed and purged with hydrogen. The reaction mixture was stirred for 5 hours under hydrogen. The crude material was purified with silica gel column chromatography (50:1 CH$_2$Cl$_2$/methanol) to provide the title compound. LC-MS: m/e=273 (M+H)$^+$. $^1$H NMR (400 MHz, CDCl$_3$), δ 7.08 (d, J=8.4 Hz, 1H), 6.53 (dd, J=8.4 Hz, 2.4 Hz, 1H), 6.33 (d, J=2.0 Hz, 1H), 3.49 (br, 2H), 3.44 (s, 2H), 2.32 (s, 2H), 2.20 (d, J=7.2 Hz, 2H), 1.84 (d, J=12.8 Hz, 2H), 1.66-1.72 (m, 3H), 1.53-1.60 (m, 1H), 1.24 (s, 6H), 1.15-1.28 (m, 2H), 0.83-0.92 (m, 2H).

Example 113C 6-(2-chlorophenyl)-2-{[2-(cyclohexylmethyl)-4,4-dimethyl-1,2,3,4-tetrahydroisoquinolin-7-yl]amino}imidazo[1,2-a]pyrimido[5,4-e]pyrimidin-5(6H)-one A mixture of Example 1E (0.065 g, 0.181 mmol), Example 113B (0.059 g, 0.217 mmol), and trifluoroacetic acid (0.028 mL, 0.361 mmol) in acetonitrile (3 mL) was heated at 70° C. for 1 hour. The reaction mixture was concentrated and purified by HPLC (see protocol in Example 1F) to provide the title compound as a trifluoroacetic acid salt. $^1$H NMR (400 MHz, CD$_3$OD) δ 1.36-1.04 (m, 3H), 1.54-1.35 (m, 8H), 1.87-1.71 (m, 5H), 2.12-2.04 (m, 1H), 3.26-3.18 (m, 3H), 3.73-3.58 (m, 1H), 4.60-4.42 (m, 2H), 7.06 (d, J=1.8 Hz, 1H), 7.62-7.53 (m, 4H), 7.78-7.62 (m, 3H), 7.88 (d, J=1.9 Hz, 1H), 9.17 (s, 1H). MS (ESI$^+$) m/z 568.3 (M+H)$^+$.

Example 114

6-(2,6-dichlorophenyl)-2-{[2-(dimethylamino)-2,3-dihydro-1H-inden-5-yl]amino}imidazo[1,2-a]pyrimido[5,4-e]pyrimidin-5(6H)-one The title compound (0.045 g) was prepared as described in Example 109A, with the addition of diisopropylethylamine (0.098 g, 0.53 mmol) and substituting tert-butyl 7'-amino-1'H-spiro[cyclopropane-1,4'-isoquinoline]-2'(3'H)-carboxylate with N$^2$,N$^2$-dimethyl-2,3-dihydro-1H-indene-2,5-diamine. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). $^1$H NMR (300 MHz, DMSO-d$_6$) δ 2.85 (d, J=4.41 Hz, 6H) 3.00-3.48 (m, 4H) 4.13 (dd, J=14.75, 7.29 Hz, 1H) 7.00-7.21 (m, 1H) 7.20-7.43 (m, 1H) 7.45-7.99 (m, 6H) 9.16 (s, 1H) 9.83 (s, 1H) 10.86 (s, 1H). MS (ESI$^+$) m/z 506.2 (M+H)$^+$.

Example 115

6-(2,6-dichlorophenyl)-2-({4-[4-(propan-2-yl)piperazin-1-yl]phenyl}amino)imidazo[1,2-a]pyrimido[5,4-e]pyrimidin-5(6H)-one The title compound (0.09 g) was prepared as described in Example 109A, with the addition of diisopropylethylamine (0.103 g, 0.79 mmol) and substituting tert-butyl 7'-amino-1'H-spiro[cyclopropane-1,4'-isoquinoline]-2'(3'H)-carboxylate with 4-(4-isopropylpiperazin-1-yl)aniline. The crude material was triturated with ethyl acetate to provide the title compound. $^1$H NMR (300 MHz, DMSO-d$_6$) δ 1.01 (d, J=6.44 Hz, 6H) 2.54-2.66 (m, 5H) 3.12 (s, 4H) 7.63 (d, J=2.03 Hz, 1H) 7.65 (s, 1H) 7.74 (s, 5H) 7.76 (s, 1H) 7.83 (s, 1H) 9.09 (s, 1H) 10.70 (s, 1H). MS (ESI$^+$) m/z 549.2 (M+H)$^+$.

Example 116

6-(2,6-dichlorophenyl)-2-{[4-(hexahydropyrrolo[1,2-a]pyrazin-2(1H)-yl)phenyl]amino}imidazo[1,2-a]pyrimido[5,4-e]pyrimidin-5(6H)-one The title compound was prepared as described in Example 109A, with the addition of diisopropylethylamine (0.103 g, 0.79 mmol) and substituting tert-butyl 7'-amino-1'H-spiro[cyclopropane-1,4'-isoquinoline]-2'(3'H)-carboxylate with 4-(hexahydropyrrolo[1,2-a]pyrazin-2(1H)-yl)aniline. The crude material was triturated with ethyl acetate to provide the title compound. $^1$H NMR (300 MHz, DMSO-d$_6$) δ 1.38 (dd, J=10.91, 6.94 Hz, 1H) 1.54-1.95 (m, 3H) 1.97-2.17 (m, 2H) 2.16-2.34 (m, 1H) 2.41 (t, J=10.51 Hz, 1H) 2.66-2.83 (m, 1H) 2.97-3.13 (m, 2H) 3.70 (dd, J=44.81, 11.10 Hz, 2H) 7.02 (d, J=8.33 Hz, 2H) 7.10 (d, J=1.59 Hz, 1H) 7.43-7.95 (m, 6H) 9.10 (s, 1H) 10.70 (s, 1H). MS (ESI$^+$) m/z 547.3 (M+H)$^+$.

Example 117

6-(2-chlorophenyl)-2-{[2-(2-ethylbutyl)-4,4-dimethyl-1,2,3,4-tetrahydroisoquinolin-7-yl]amino}imidazo[1,2-a]pyrimido[5,4-e]pyrimidin-5(6H)-one

Example 117A 2-(2-ethylbutyl)-4,4-dimethyl-1,2,3,4-tetrahydroisoquinolin-7-amine The title compound was prepared as described in Example 113A and Example 113B, substituting cyclohexanecarbaldehyde with 2-ethylbutanal. LC-MS: m/e=261 (M+H)$^+$. $^1$H NMR (400 MHz, CDCl$_3$), δ 7.08 (d, J=8.4 Hz, 1H), 6.53 (dd, J=8.4 Hz, 2.4 Hz, 1H), 6.32 (d, J=2.4 Hz, 1H), 3.48 (br, 2H), 3.44 (s, 2H), 2.33 (s, 2H), 2.24 (d, J=7.6 Hz, 2H), 1.50-1.53 (m, 1H), 1.31-1.44 (m, 4H), 1.25 (s, 6H), 0.87 (t, J=7.4 Hz, 6H).

Example 117B 6-(2-chlorophenyl)-2-{[2-(2-ethylbutyl)-4,4-dimethyl-1,2,3,4-tetrahydroisoquinolin-7-yl]amino}imidazo[1,2-a]pyrimido[5,4-e]pyrimidin-5(6H)-one The title compound was prepared as described in Example 113C, substituting Example 113B with Example 117A. $^1$H NMR (500 MHz, CD$_3$OD) δ 1.01 (t, J=7.4 Hz, 6H), 1.69-1.37 (m, 10H), 2.04-1.99 (m, 1H), 3.29 (s, 3H), 3.68-3.56 (m, 1H), 4.67-4.49 (m, 2H), 7.05 (d, J=1.9 Hz, 1H), 7.62-7.52 (m, 4H), 7.77-7.66 (m, 2H), 7.87 (d, J=1.9 Hz, 1H), 9.16 (s, 1H). MS (ESI$^+$) m/z 556.3 (M+H)$^+$.

Example 118

6-(2,6-dichlorophenyl)-2-({4-[2-(4-methylpiperazin-1-yl)ethyl]phenyl}amino)imidazo[1,2-a]pyrimido[5,4-e]pyrimidin-5(6H)-one To Example 55D (75 mg, 0.198 mmol) and m-chloroperoxybenzoic acid (51.1 mg, 0.228 mmol) was added 2 mL dichloromethane. The reaction was stirred for 15 minutes and was concentrated. The crude material was dissolved in 2 mL acetonitrile, followed by addition of 4-(2-(4-methylpiperazin-1-yl)ethyl)aniline (50.0 mg, 0.228 mmol) and trifluoroacetic acid (45 mg, 0.4 mmol). The reaction was heated to 50° C. for 1.5 hours, then cooled to room temperature overnight. The reaction was diluted with ethyl acetate and washed with saturated aqueous NaHCO$_3$, water, and brine, dried over MgSO$_4$, filtered, and concentrated. The crude material was dissolved in methanol and treated with 2M HCl in diethyl ether. The mixture was stirred until solids begins to form, and was then diluted with ether. The mixture was stirred for 10 minutes and filtered to provide the title compound. $^1$H NMR (300 MHz, DMSO-$d_6$) δ 2.84 (s, 3H) 3.05 (s, 2H) 3.22-3.52 (m, 6H) 3.59-3.75 (m, 4H) 7.12 (d, J=2.03 Hz, 1H) 7.34 (d, J=8.48 Hz, 2H) 7.47-8.12 (m, 6H) 9.17 (s, 1H) 10.86 (s, 1H) 11.61 (s, 1H). MS (ESI$^+$) m/z 549.3 (M+H)$^+$.

Example 119

6-(2,6-dichlorophenyl)-2-({1-[2-(dimethylamino) ethyl]-2,3-dihydro-1H-indol-5-yl}amino)imidazo[1, 2-a]pyrimido[5,4-e]pyrimidin-5(6H)-one To Example 55D (70.0 mg, 0.185 mmol) and m-chloroperoxybenzoic acid (47.7 mg, 0.213 mmol) was added CH$_2$Cl$_2$ (2 mL). The reaction was stirred for 15 minutes. The solvent was evaporated. The residue was dissolved in acetonitrile (2.000 mL) and treated with 1-(2-(dimethylamino)ethyl)indolin-5-amine (43.7 mg, 0.213 mmol) followed by trifluoroacetic acid (0.029 mL, 0.370 mmol). The mixture was heated at 60° C. for 2 hours. Most of the solvent was evaporated. The resulting mixture was diluted with ethyl acetate, washed with saturated aqueous NaHCO$_3$, water, and brine. The organic layer was dried over MgSO$_4$, filtered, concentrated, and purified by HPLC (see protocol in Example 1F) to provide the title compound as a trifluoroacetic acid salt. $^1$H NMR (400 MHz, CD$_3$OD) δ 2.98 (d, J=5.7 Hz, 6H), 3.14-3.02 (m, 2H), 3.72-3.37 (m, 6H), 6.81-6.70 (m, 1H), 7.06 (d, J=1.8 Hz, 1H), 7.61-7.44 (m, 3H), 7.70-7.61 (m, 2H), 7.89-7.74 (m, 1H), 9.09 (s, 1H). MS (ESI$^+$) m/z 535.2 (M+H)$^+$.

Example 120

6-(2,6-dichlorophenyl)-2-{[3-ethyl-4-(4-methylpiperazin-1-yl)phenyl]amino}imidazo[1,2-a]pyrimido [5,4-e]pyrimidin-5(6H)-one The title compound was prepared as described in Example 119, substituting 1-(2-(dimethylamino)ethyl)indolin-5-amine with Example 112B. $^1$H NMR (400 MHz, CD$_3$OD) δ 1.35-1.22 (m, 3H), 2.86-2.69 (m, 2H), 3.00 (s, 3H), 3.38-3.10 (m, 6H), 3.64-3.56 (m, 2H), 7.08 (d, J=1.8 Hz, 1H), 7.27-7.12 (m, 1H), 7.57 (dd, J=9.1, 7.0 Hz, 1H), 7.94-7.63 (m, 5H), 9.15 (bs, 1H). MS (ESI$^+$) m/z 549.2 (M+H)$^+$.

Example 121

6-(2,6-dichlorophenyl)-2-{[3-(hydroxymethyl)-4-(4-methyl-1,4-diazepan-1-yl)phenyl]amino}imidazo[1, 2-a]pyrimido[5,4-e]pyrimidin-5(6H)-one The title compound was prepared as described in Example 119, substituting 1-(2-(dimethylamino)ethyl)indolin-5-amine with Example 100B. $^1$H NMR (400 MHz, CD$_3$OD) δ 2.26-2.10 (m, 2H), 3.01 (s, 3H), 3.26-3.19 (m, 2H), 3.68-3.33 (m, 6H), 4.80-4.77 (m, 2H), 7.08 (d, J=1.9 Hz, 1H), 7.33-7.26 (m, 1H), 7.58 (dd, J=9.1, 7.0 Hz, 1H), 7.70-7.63 (m, 3H), 7.94 (d, J=1.9 Hz, 1H), 8.20 (bs, 1H), 9.17 (s, 1H). MS (ESI$^+$) m/z 565.2 (M+H)$^+$.

Example 122

6-(2,6-dichlorophenyl)-2-(1,2,3,4-tetrahydroisoquinolin-6-ylamino)imidazo[1,2-a]pyrimido[5,4-e] pyrimidin-5(6H)-one The title compound (0.068 g) was prepared as described in Example 109A, substituting tert-butyl 7'-amino-1'H-spiro [cyclopropane-1,4'-isoquinoline]-2'(3'H)-carboxylate with tert-butyl 6-amino-3,4-dihydroisoquinoline-2(1H)-carboxylate. The crude material was dissolved in a small amount of dichloromethane and treated with TFA for 1 hour. The solvent was removed and the compound taken up in a small amount of methanol and treated with excess 2N HCl/diethyl ether for 1 hour. The suspension was diluted with 50 mL diethyl ether and the solid filtered and dried. $^1$H NMR (300 MHz, DMSO-$d_6$) δ 2.98-3.16 (m, 2H) 3.28-3.48 (m, 2H) 4.18-4.31 (m, 2H) 7.13 (d, J=1.70 Hz, 1H) 7.20-7.32 (m, 1H) 7.54-7.87 (m, 6H) 9.18 (s, 1H) 9.25 (s, 3H) 10.88 (s, 1H). MS (ESI$^+$) m/z 478.29 (M+H)$^+$.

Example 123

6-(2,6-dichloro-4-fluorophenyl)-2-{[4-(4-methylpiperazin-1-yl)phenyl]amino}imidazo[1,2-a]pyrimido [5,4-e]pyrimidin-5(6H)-one Example 123A 4-(2,6-dichloro-4-fluorophenyl)-8-methylsulfanyl-4H-3,4,7,9,9b-pentaaza-cyclopenta[a]naphthalen-5-one The title compound was prepared following the general procedures described in Examples 1A through Example 1D, substituting 1-chloro-2-isocyanatobenzene with 1,3-dichloro-5-fluoro-2-isocyanatobenzene in Example 1A, and with a shortened reaction time (2 hours). Common techniques were used to modify the reaction workup and purification processes. Modifications to Example 1A: during the workup the aqueous layer was acidified and the product precipitated out. Modifications to Example 1B: the desired product was purified on a silica column using the ISCO Companion flash system eluting with CH$_2$Cl$_2$/hexane (90:10 to 95:5). Modifications to Example 1D: the desired product was isolated through trituration with ethyl acetate followed by washing with aqueous NaHCO$_3$.

Example 123B 6-(2,6-dichloro-4-fluorophenyl)-2-{[4-(4-methylpiperazin-1-yl)phenyl]amino}imidazo[1,2-a]pyrimido [5,4-e]pyrimidin-5(6H)-one To Example 123A (60.0 mg, 0.151 mmol) and m-chloroperoxybenzoic acid (40.7 mg, 0.182 mmol) was added 1,2-dichloroethane (2 ml). The reaction mixture was stirred for 15 minutes. The mixture was treated with 4-(4-methylpiperazin-1-yl)aniline (34.8 mg, 0.182 mmol) and trifluoroacetic acid (0.023 ml, 0.303 mmol) and heated to 60° C. for 1.5 hours. The reaction mixture was concentrated and purified by HPLC (see protocol in Example 1F) to provide the title compound as a trifluoroacetic acid salt. $^1$H NMR (400 MHz, CD$_3$OD) δ 2.98 (s, 3H), 3.15-3.02 (m, 2H), 3.40-3.21 (m, 2H), 3.63 (d, J=11.2 Hz, 2H), 3.86 (d, J=12.5 Hz, 2H), 7.12-7.05 (m, 3H), 7.57 (d, J=8.2 Hz, 2H), 7.90-7.67 (m, 3H), 9.11 (s, 1H). MS (ESI$^+$) m/z 539.2 (M+H)$^+$.

Example 124

6-(2,6-dichloro-4-fluorophenyl)-2-{[3-methyl-4-(4-methyl-1,4-diazepan-1-yl)phenyl]amino}imidazo[1, 2-a]pyrimido[5,4-e]pyrimidin-5(6H)-one The title compound was prepared as described in Example 123B, substituting 4-(4-methylpiperazin-1-yl)aniline with 3-methyl-4-(4-methyl-1,4-diazepan-1-yl)aniline. An aqueous workup was done before HPLC. $^1$H NMR (400 MHz, CD$_3$OD) δ 2.28-2.14 (m, 2H), 2.45-2.37 (m, 2H), 2.65 (s, 3H), 3.01 (s, 3H), 3.25-3.17 (m, 2H), 3.74-3.32 (m, 4H), 7.09 (d, J=1.8 Hz, 1H), 7.21 (bs, 1H), 7.99-7.50 (m, 5H), 9.14 (s, 1H). MS (ESI$^+$) m/z 567.2 (M+H)$^+$.

Example 125

6-(2,6-dichloro-4-fluorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one The title compound was prepared as described in Example 123B, substituting 4-(4-methylpiperazin-1-yl)aniline with 2'-methyl-2',3'-dihydro-1'H-spiro[cyclopropane-1,4'-isoquinolin]-7'-amine. An aqueous workup was done before HPLC purification. $^1$H NMR (400 MHz, CD$_3$OD) δ 1.48-1.08 (m, 4H), 3.09 (s, 3H), 3.35-3.22 (m, 1H), 3.67 (d, J=12.6 Hz, 1H), 4.76-4.52 (m, 2H), 6.96 (d, J=8.3 Hz, 1H), 7.10 (d, J=1.8 Hz, 1H), 7.57 (d, J=8.1 Hz, 2H), 7.76-7.62 (m, 2H), 7.89 (d, J=1.7 Hz, 1H), 9.18 (s, 1H). MS (ESI$^+$) m/z 536.1 (M+H)$^+$.

Example 126

6-(2,6-dichloro-4-fluorophenyl)-2-{[2-(dimethylamino)-2,3-dihydro-1H-inden-5-yl]amino}imidazo[1,2-a]pyrimido[5,4-e]pyrimidin-5(6H)-one The title compound was prepared as described in Example 123B, substituting 4-(4-methylpiperazin-1-yl)aniline with N$^2$,N$^2$-dimethyl-2,3-dihydro-1H-indene-2,5-diamine. An aqueous workup was done before HPLC purification. $^1$H NMR (400 MHz, CD$_3$OD) δ 2.96 (s, 6H), 3.26-3.16 (m, 2H), 3.56-3.41 (m, 2H), 4.22-4.13 (m, 1H), 7.09 (d, J=1.9 Hz, 1H), 7.36-7.30 (m, 1H), 7.68-7.50 (m, 3H), 7.90-7.78 (m, 2H), 9.15 (s, 1H).

Example 127

6-(2,6-dichlorophenyl)-2-({4-[(4-methylpiperazin-1-yl)methyl]phenyl}amino)imidazo[1,2-a]pyrimido[5,4-e]pyrimidin-5(6H)-one To Example 55D (75 mg, 0.198 mmol) and m-chloroperoxybenzoic acid (53.3 mg, 0.238 mmol) was added 2 mL dichlormethane. The reaction was stirred for 15 minutes when 4-((4-methylpiperazin-1-yl)methyl)aniline (48.9 mg, 0.238 mmol) followed by trifluoroacetic acid (0.031 ml, 0.397 mmol). The mixture was stirred at 50° C. for 1 hour, and at room temperature overnight. The mixture was diluted with ethyl acetate, washed with saturated aqueous NaHCO$_3$, water, and brine, dried over MgSO$_4$, filtered and concentrated. The crude material was dissolved in methanol, and treated with 2N HCl in diethyl ether for 1 hour. The mixture was diluted with diethyl ether and filtered. The solid was triturated with 1:1 DMSO/methanol solution, diluted with ethyl acetate, filtered, and dried over high-vacuum to provide the title compound. $^1$H NMR (501 MHz, DMSO-d$_6$) δ 2.53 (s, 2H) 2.78 (s, 2H) 3.15 (s, 3H) 3.19-3.50 (m, 4H) 3.91 (s, 2H) 7.09 (d, J=1.18 Hz, 1H) 7.47 (d, J=7.58 Hz, 2H) 7.55-7.64 (m, 1H) 7.66-7.74 (m, 2H) 7.80 (d, J=1.66 Hz, 2H) 7.86 (d, J=8.06 Hz, 2H) 9.16 (s, 1H). MS (ESI$^+$) m/z 534.9 (M+H)$^+$.

Example 128

6-(2,6-dichlorophenyl)-2-({4-[(3R,5S)-3,5-dimethylpiperazin-1-yl]-3-fluorophenyl}amino)imidazo[1,2-a]pyrimido[5,4-e]pyrimidin-5(6H)-one The title compound (0.09 g) was prepared as described in Example 109A, substituting tert-butyl 7'-amino-1'H-spiro[cyclopropane-1,4'-isoquinoline]-2'(3'H)-carboxylate with 4-((3S,5R)-3,5-dimethylpiperazin-1-yl)-3-fluoroaniline. The final compound was dissolved in 2 mL methanol and treated with excess 2M HCl/diethyl ether for 1 hour. The solid material was filtered and dried over high-vac to provide the title compound as the HCL salt. $^1$H NMR (300 MHz, DMSO-d$_6$) δ 1.20-1.41 (m, 6H) 2.63-2.90 (m, 2H) 3.35-3.55 (m, 4H) 7.06-7.30 (m, 2H) 7.51-7.85 (m, 6H) 8.71 (s, 1H) 9.18 (s, 1H) 9.32 (s, 1H) 10.91 (s, 1H). MS (ESI$^+$) m/z 552.5.0 (M+H)$^+$.

Example 129

6-(2,6-dichlorophenyl)-2-{[3,5-difluoro-4-(piperazin-1-yl)phenyl]amino}imidazo[1,2-a]pyrimido[5,4-e]pyrimidin-5(6H)-one

Example 129A tert-butyl 4-(4-{[6-(2,6-dichlorophenyl)-5-oxo-5,6-dihydroimidazo[1,2-a]pyrimido[5,4-e]pyrimidin-2-yl]amino}-2,6-difluorophenyl)piperazine-1-carboxylate The title compound (0.039 g) was prepared as described in Example 109A, substituting tert-butyl 7'-amino-1'H-spiro[cyclopropane-1,4'-isoquinoline]-2'(3'H)-carboxylate with tert-butyl 4-(4-amino-2,6-difluorophenyl)piperazine-1-carboxylate. The crude reaction mixture was triturated with ethyl acetate to provide the title compound. MS (ESI$^+$) m/z 642.93 (M+H)$^+$.

Example 129B 6-(2,6-dichlorophenyl)-2-{[3,5-difluoro-4-(piperazin-1-yl)phenyl]amino}imidazo[1,2-a]pyrimido[5,4-e]pyrimidin-5(6H)-one The title compound (0.03 g) was prepared as described in Example 109B, substituting Example 109A with Example 129A. The TFA salt was dissolved in methanol, treated with excess 2M HCl in diethyl ether and stirred until a solid began to form. The mixture was diluted with ether, and stirred for 10 minutes before filtering the solid to provide the title compound. $^1$H NMR (300 MHz, DMSO-d$_6$) δ 3.21 (d, 4H) 3.29 (d, 4H) 7.15 (d, J=1.59 Hz, 1H) 7.49-7.72 (m, 3H) 7.71-7.90 (m, 3H) 8.77 (s, 2H) 9.24 (s, 1H) 11.06 (s, 1H). MS (ESI$^+$) m/z 543.2 (M+H)$^+$.

Example 130

6-(2-chlorophenyl)-2-{[2-(cyclopropylmethyl)-4,4-dimethyl-1,2,3,4-tetrahydroisoquinolin-7-yl]amino}imidazo[1,2-a]pyrimido[5,4-e]pyrimidin-5(6H)-one

Example 130A 2-(cyclopropylmethyl)-4,4-dimethyl-1,2,3,4-tetrahydroisoquinolin-7-amine The title compound was prepared as described in Example 113A and Example 113B, substituting cyclohexanecarbaldehyde with cyclopropanecarbaldehyde. LC-MS: m/e=231 (M+H)$^+$. $^1$H NMR (400 MHz, CDCl$_3$), δ 7.09 (d, J=8.4 Hz, 1H), 6.54 (dd, J=8.0 Hz, 2.4 Hz, 1H), 6.35 (d, J=2.4 Hz, 1H), 3.55 (br, 2H), 3.49 (s, 2H), 2.46 (s, 2H), 2.35 (d, J=2.4 Hz, 2H), 1.26 (s, 6H), 0.88-1.00 (m, 1H), 0.51-0.56 (m, 2H), 0.15-0.18 (m, 2H).

Example 130B 6-(2-chlorophenyl)-2-{[2-(cyclopropylmethyl)-4,4-dimethyl-1,2,3,4-tetrahydroisoquinolin-7-yl]amino}imidazo[1,2-a]pyrimido[5,4-e]pyrimidin-5(6H)-one A mixture of Example 1E (65.0 mg, 0.181 mmol), Example 130A (49.9 mg, 0.217 mmol), and 2,2,2-trifluoroacetic acid (0.028 mL, 0.361 mmol) in acetonitrile (2 mL) was heated at 60° C. for 1.5 hours. The mixture was concentrated, and the remaining solution was diluted with ethyl acetate and washed with saturated aqueous NaHCO$_3$, brine, and water, dried over MgSO$_4$, filtered, concentrated, and purified by HPLC (see protocol in Example 1F) to provide the title compound as a trifluoroacetic acid salt. $^1$H NMR (500 MHz, CD$_3$OD) δ 0.54 (d, J=4.2 Hz, 2H), 0.86 (s, 2H), 1.34-1.23 (m, 1H), 1.49 (s, 3H), 1.53 (s, 3H), 3.44-3.11 (m, 2H), 3.76-3.66 (m, 1H), 4.68-4.44 (m, 2H), 7.06 (d, J=1.6 Hz, 1H), 7.63-7.44 (m, 4H), 7.82-7.63 (m, 3H), 7.88 (s, 1H), 9.17 (s, 1H). MS (ESI$^+$) m/z 526.2 (M+H)$^+$.

Example 131

6-(2-chlorophenyl)-2-{[4,4-dimethyl-2-(pyridin-3-ylmethyl)-1,2,3,4-tetrahydroisoquinolin-7-yl]amino}imidazo[1,2-a]pyrimido[5,4-e]pyrimidin-5(6H)-one Example 131A 4,4-dimethyl-2-(pyridin-3-ylmethyl)-1,2,3,4-tetrahydroisoquinolin-7-amine The title compound was prepared as described in Example 113A and Example 113B, substituting cyclohexanecarbaldehyde with 2-(pyridin-3-yl)acetaldehyde in Example 113A (T=10° C.). LC-MS: m/e=268 (M+H)$^+$. $^1$H NMR (400 MHz, CDCl$_3$) δ 8.53 (s, 1H), 8.45 (dd, J=4.6 Hz, 1.0 Hz, 1H), 7.69 (d, J=7.6 Hz, 1H), 7.17-7.20 (m, 1H), 7.02 (d, J=8.4 Hz, 1H), 6.48 (dd, J=8.4 Hz, 2.4 Hz, 1H), 6.22 (d, J=2.4 Hz, 1H), 3.56 (s, 2H), 3.46 (s, 2H), 2.31 (s, 2H), 1.16 (s, 6H).

Example 131B 6-(2-chlorophenyl)-2-{[4,4-dimethyl-2-(pyridin-3-ylmethyl)-1,2,3,4-tetrahydroisoquinolin-7-yl]amino}imidazo[1,2-a]pyrimido[5,4-e]pyrimidin-5(6H)-one The title compound was prepared as described in Example 130B, substituting Example 130A with Example 131A. $^1$H NMR (500 MHz, CD$_3$OD) δ 1.43 (s, 6H), 3.36-3.35 (m, 2H), 4.45 (s, 2H), 4.61 (s, 2H), 7.07 (d, J=1.8 Hz, 1H), 7.62-7.47 (m, 4H), 7.97-7.64 (m, 5H), 8.33-8.26 (m, 1H), 8.81-8.76 (m, 1H), 8.88 (bs, 1H), 9.17 (s, 1H). MS (ESI$^+$) m/z 563.1 (M+H)$^+$.

Example 132

6-(2-chlorophenyl)-2-{[4,4-dimethyl-2-(thiophen-3-ylmethyl)-1,2,3,4-tetrahydroisoquinolin-7-yl]amino}imidazo[1,2-a]pyrimido[5,4-e]pyrimidin-5(6H)-one Example 132A 4,4-dimethyl-2-(thiophen-3-ylmethyl)-1,2,3,4-tetrahydroisoquinolin-7-amine The title compound was prepared as described in Example 113A and Example 113B, substituting cyclohexanecarbaldehyde with thiophene-3-carbaldehyde. LC-MS: m/e=273 (M+H)$^+$. $^1$H NMR (400 MHz, CDCl$_3$), δ 7.26-7.28 (m, 1H), 7.17 (s, 1H), 7.12 (d, J=5.2 Hz, 1H), 7.09 (d, J=8.4 Hz, 1H), 6.54 (dd, J=8.4 Hz, 2.4 Hz, 1H), 6.31 (d, J=2.4 Hz, 1H), 3.64 (s, 2H), 3.52 (s, 2H), 3.50 (br, 2H), 2.37 (s, 2H), 1.23 (s, 6H).

Example 132B 6-(2-chlorophenyl)-2-{[4,4-dimethyl-2-(thiophen-3-ylmethyl)-1,2,3,4-tetrahydroisoquinolin-7-yl]amino}imidazo[1,2-a]pyrimido[5,4-e]pyrimidin-5(6H)-one The title compound was prepared as described in Example 130B, substituting Example 130A with Example 132A. $^1$H NMR (500 MHz, CD$_3$OD) δ 1.44 (s, 6H), 3.48-3.30 (m, 2H), 4.62-4.39 (m, 4H), 7.06 (s, 1H), 7.34 (d, J=5.0 Hz, 1H), 7.63-7.51 (m, 4H), 7.87-7.63 (m, 6H), 9.17 (s, 1H). MS (ESI$^+$) m/z 568.2 (M+H)$^+$.

Example 133

6-(2-chlorophenyl)-2-[(1,1,2-trimethyl-1,2,3,4-tetrahydroisoquinolin-6-yl)amino]imidazo[1,2-a]pyrimido[5,4-e]pyrimidin-5(6H)-one The title compound was prepared as described in Example 130B, substituting Example 130A with 1,1,2-trimethyl-1,2,3,4-tetrahydroisoquinolin-6-amine. $^1$H NMR (500 MHz, CD$_3$OD) δ 1.75 (s, 3H), 1.85 (s, 3H), 3.01 (s, 3H), 3.36-3.17 (m, 2H), 3.78-3.58 (m, 2H), 7.07 (d, J=1.9 Hz, 1H), 7.62-7.46 (m, 4H), 7.88-7.66 (m, 4H), 9.17 (s, 1H). MS (ESI$^+$) m/z 486.2 (M+H)$^+$.

Example 134

6-(2,6-dichlorophenyl)-2-{[4-(pyrrolidin-2-yl)phenyl]amino}imidazo[1,2-a]pyrimido[5,4-e]pyrimidin-5(6H)-one Example 134A tert-butyl 2-(4-{[6-(2,6-dichlorophenyl)-5-oxo-5,6-dihydroimidazo[1,2-a]pyrimido[5,4-e]pyrimidin-2-yl]amino}phenyl)pyrrolidine-1-carboxylate The title compound (0.012 g) was prepared as described in Example 109A, substituting tert-butyl 7'-amino-1'H-spiro[cyclopropane-1,4'-isoquinoline]-2'(3'H)-carboxylate with tert-butyl 2-(4-aminophenyl)pyrrolidine-1-carboxylate. MS (ESI$^+$) m/z 591.93 (M+H)$^+$.

Example 134B 6-(2,6-dichlorophenyl)-2-{[4-(pyrrolidin-2-yl)phenyl]amino}imidazo[1,2-a]pyrimido[5,4-e]pyrimidin-5(6H)-one The title compound (0.01 g) was prepared as described in Example 109B, substituting Example 109A with Example 134A. The TFA salt was dissolved in methanol, treated with excess 2M HCl in diethyl ether and stirred until a solid began to form. The mixture was diluted with ether, stirred for 10 minutes and filtered to give the title compound. $^1$H NMR (300 MHz, DMSO-$d_6$) δ 1.88-2.21 (m, 3H) 2.23-2.46 (m, 1H) 3.18-3.43 (m, 2H) 4.55 (s, 1H) 7.14 (d, J=1.98 Hz, 2H) 7.42-7.71 (m, 3H) 7.70-7.82 (m, 2H) 7.90 (s, 2H) 8.56-9.09 (m, 1H) 9.20 (s, 1H) 9.93 (s, 1H) 10.98 (s, 1H). MS (ESI$^+$) m/z 429.2 (M+H)$^+$.

Example 135

6-(2,6-dichlorophenyl)-2-{[4-(piperidin-2-yl)phenyl]amino}imidazo[1,2-a]pyrimido[5,4-e]pyrimidin-5(6H)-one

Example 135A tert-butyl 2-(4-{[6-(2,6-dichlorophenyl)-5-oxo-5,6-dihydroimidazo[1,2-a]pyrimido[5,4-e]pyrimidin-2-yl]amino}phenyl)piperidine-1-carboxylate The title compound (0.012 g) was prepared as described in Example 109A, substituting tert-butyl 7'-amino-1'H-spiro[cyclopropane-1,4'-isoquinoline]-2'(3'H)-carboxylate with tert-butyl 2-(4-aminophenyl)piperidine-1-carboxylate. MS (ESI$^+$) m/z 605.98 (M+H)$^+$.

Example 135B 6-(2,6-dichlorophenyl)-2-{[4-(piperidin-2-yl)phenyl]amino}imidazo[1,2-a]pyrimido[5,4-e]pyrimidin-5(6H)-one The title compound (0.095 g) was prepared as described in Example 109B, substituting Example 109A with Example 135A. The TFA salt was dissolved in methanol, treated with excess 2M HCl in diethyl ether and stirred until a solid began to form. The mixture was diluted with ether, stirred for 10 minutes and filtered to provide the title compound. $^1$H NMR (300 MHz, DMSO-$d_6$) δ 1.90 (d, J=15.47 Hz, 6H) 2.95-3.19 (m, 1H) 3.24-3.45 (m, J=7.01 Hz, 1H) 4.22 (s, 1H) 7.14 (d, J=1.98 Hz, 1H) 7.50-7.70 (m, 3H) 7.71-7.81 (m, 2H) 7.90 (d, J=7.93 Hz, 3H) 8.98 (s, 2H) 9.20 (s, 1H) 10.97 (s, 1H). MS (ESI$^+$) m/z 506.2 (M+H)$^+$.

Example 136

2-{[3-chloro-4-(4-methylpiperazin-1-yl)phenyl]amino}-6-(2,6-dichlorophenyl)imidazo[1,2-a]pyrimido[5,4-e]pyrimidin-5(6H)-one The title compound (0.075 g) was prepared as described in Example 127, substituting 4-((4-methylpiperazin-1-yl)methyl)aniline with 3-chloro-4-(4-methylpiperazin-1-yl)aniline. The crude material was triturated with ethyl acetate to provide the title compound. $^1$H NMR (300MHz, DMSO-$d_6$) δ 2.23 (d, 4H) 2.97 (d, 4H) 7.13 (d, J=1.36 Hz, 1H) 7.24 (d, J=8.82 Hz, 1H) 7.56-7.69 (m, 1H) 7.71-7.83 (m, 3H) 7.88 (d, J=2.37 Hz, 1H) 9.04-9.27 (m, 1H) 10.66-11.05 (m, 1H). MS (ESI$^+$) m/z 555.2 (M+H)$^+$.

Example 137

6-(2,6-dichlorophenyl)-2-({3-methoxy-4-[4-(propan-2-yl)piperazin-1-yl]phenyl}amino)imidazo[1,2-a]pyrimido[5,4-e]pyrimidin-5(6H)-one The title compound (0.065 g) was prepared as described in Example 127, substituting 4-((4-methylpiperazin-1-yl)methyl)aniline with 4-(4-isopropylpiperazin-1-yl)-3-methoxyaniline. The crude material was triturated with ethyl acetate to provide the title compound. $^1$H NMR (300 MHz, DMSO-$d_6$) δ 0.89-1.10 (m, 6H) 2.59 (s, 4H) 2.65-2.77 (m, 1H) 2.97 (s, 4H) 3.71-3.93 (m, 3H) 6.95 (s, 1H) 7.11 (d, J=1.70 Hz, 1H) 7.37 (s, 1H) 7.47-7.56 (m, 1H) 7.57-7.69 (m, 1H) 7.72-7.84 (m, 3H) 9.13 (s, 1H) 10.74 (s, 1H). MS (ESI$^+$) m/z 642.93 (M+H)$^+$.

Example 138

6-(2-chlorophenyl)-2-{[4-(4-hydroxypiperidin-1-yl)phenyl]amino}imidazo[1,2-a]pyrimido[5,4-e]pyrimidin-5(6H)-one The title compound was prepared as described in Example 130B, substituting Example 130A with 1-(4-aminophenyl)piperidin-4-ol. No aqueous workup was used before HPLC. $^1$H NMR (400 MHz, CD$_3$OD) δ 2.09-1.92 (m, 2H), 2.31-2.19 (m, 2H), 3.68-3.58 (m, 2H), 3.91-3.82 (m, 2H), 4.15-4.07 (m, 1H), 7.08 (d, J=1.9 Hz, 1H), 7.63-7.53 (m, 3H), 7.73-7.66 (m, 3H), 7.92 (d, J=1.9 Hz, 1H), 8.10-8.04 (m, 2H), 9.22 (s, 1H). MS (ESI$^+$) m/z 488.3 (M+H)$^+$.

Example 139

6-(2-chloro-6-fluorophenyl)-2-{[2-(dimethylamino)-2,3-dihydro-1H-inden-5-yl]amino}imidazo[1,2-a]pyrimido[5,4-e]pyrimidin-5(6H)-one The title compound was prepared as described in Example 130B, substituting Example 1E and Example 130A with Example 95D and N$^2$,N$^2$-dimethyl-2,3-dihydro-1H-indene-2,5-diamine, respectively. No aqueous workup was used before HPLC. $^1$H NMR (500 MHz, CD$_3$OD) δ 2.96 (s, 6H), 3.30-3.16 (m, 2H), 3.55-3.41 (m, 2H), 4.21-4.14 (m, 1H), 7.07 (d, J=1.9 Hz, 1H), 7.43-7.29 (m, 2H), 7.67-7.51 (m, 3H), 7.87-7.81 (m, 2H), 9.14 (bs, 1H). MS (ESI$^+$) m/z 490.2 (M+H)$^+$.

Example 140

6-(2-chloro-6-fluorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidin-5(6H)-one The title compound was prepared as described in Example 130B, substituting Example 1E and Example 130A Example 95D and 2'-methyl-2',3'-dihydro-1'H-spiro[cyclopropane-1,4'-isoquinolin]-7'-amine, respectively. $^1$H NMR (500 MHz, CD$_3$OD) δ 1.13-1.04 (m, 1H), 1.27-1.13 (m, 2H), 1.52-1.44 (m, 1H), 3.09 (s, 3H), 3.32-3.23 (m, 1), 3.70-3.62 (m, 1H), 4.78-4.49 (m, 2H), 6.99-6.92 (m, 1H), 7.08 (d, J=1.9 Hz, 1H), 7.43-7.35 (m, 1H), 7.54 (d, J=8.2 Hz, 1H), 7.78-7.58 (m, 3H), 7.88 (s, 1H), 9.17 (s, 1H). MS (ESI$^+$) m/z 502.2 (M+H)$^+$.

Example 141

6-(2-chloro-6-fluorophenyl)-2-{[4-(1,4-diazepan-1-yl)-3-methylphenyl]amino}imidazo[1,2-a]pyrimido[5,4-e]pyrimidin-5(6H)-one The title compound was prepared as described in Example 130B, substituting Example 1E and Example 130A with Example 95D and Example 105B, respectively. No aqueous workup was used before HPLC. $^1$H NMR (500 MHz, CD$_3$OD) δ 2.16 (dt, J=11.5, 5.9 Hz, 2H), 2.38 (s, 3H), 3.18 (dt, J=7.3, 3.7 Hz, 2H), 3.40 (s, 4H), 3.52-3.43 (m, 2H), 7.07 (d, J=1.8 Hz, 1H), 7.20 (bs, 1H), 7.38 (td, J=8.9, 1.2 Hz, 1H), 7.67-7.47 (m, 4H), 7.89-7.68 (m, 1H), 9.12 (s, 1H). MS (ESI$^+$) m/z 519.2 (M+H)$^+$.

Example 142

2-[(2'-methyl-2',3'-dihydro-1'H-spiro[cyclopropane-1,4'-isoquinolin]-7'-yl)amino]-6-(propan-2-yl)imidazo[1,2-a]pyrimido[5,4-e]pyrimidin-5(6H)-one Example 142A 3-isopropyl-7-(methylthio)pyrimido[4,5-d]pyrimidine-2,4(1H,3H)-dione The title compound (0.4 g) was prepared as described in Example 1A, substituting 1-chloro-2-isocyanatobenzene with 2-isocyanatopropane. MS (ESI$^+$) m/z 253.0 (M+H)$^+$.

Example 142B 2-chloro-3-isopropyl-7-(methylthio)pyrimido[4,5-d]pyrimidin-4(3H)-one The title compound (0.4 g) was prepared as described in Example 1B, substituting Example 1A with Example 142A. MS (ESI$^+$) m/z 271.06 (M+H)$^+$.

Example 142C 2-(2,2-dimethoxyethylamino)-3-isopropyl-7-(methylthio)pyrimido[4,5-d]pyrimidin-4(3H)-one The title compound (0.45 g) was prepared as described in Example 1C, substituting Example 1B with Example 142B. MS (ESI$^+$) m/z 340.3 (M+H)$^+$.

Example 142D 2-(methylsulfanyl)-6-(propan-2-yl)imidazo[1,2-a]pyrimido[5,4-e]pyrimidin-5(6H)-one The title compound (0.35 g) was prepared as described in Example 1D, substituting Example 1C with Example 142C. MS (ESI$^+$) m/z 276.14 (M+H)$^+$.

Example 142E

2-[(2'-methyl-2',3'-dihydro-1'H-spiro[cyclopropane-1,4'-isoquinolin]-7'-yl)amino]-6-(propan-2-yl)imidazo[1,2-a]pyrimido[5,4-e]pyrimidin-5(6H)-one The title compound (0.085 g) was prepared as described in Example 127, substituting Example 55D with Example 142D and 4-((4-methylpiperazin-1-yl)methyl)aniline with 2'-methyl-2',3'-dihydro-1'H-spiro[cyclopropane-1,4'-isoquinolin]-7'-amine. The crude material was triturated with ethyl acetate to provide the title compound. $^1$H NMR (300 MHz, DMSO-d$_6$) δ 0.72-1.01 (m, 4H) 1.40-1.66 (m, 6H) 2.25-2.40 (m, 3H) 2.42-2.47 (m, 2H) 3.53-3.71 (m, 2H) 5.24-5.45 (m, 1H) 6.74 (d, J=8.72 Hz, 1H) 7.20 (d, J=1.59 Hz, 1H) 7.46 (s, 1H) 7.55 (s, 1H) 7.69 (d, J=1.59 Hz, 1H) 9.04 (s, 1H) 10.48 (s, 1H). MS (ESI$^+$) m/z 416.2 (M+H)$^+$.

Example 143

6-(2,6-dichlorophenyl)-2-{[4-(3-oxopiperazin-1-yl)phenyl]amino}imidazo[1,2-a]pyrimido[5,4-e]pyrimidin-5(6H)-one The title compound (0.03 g) was prepared as described in Example 109A, substituting tert-butyl 7'-amino-1'H-spiro[cyclopropane-1,4'-isoquinoline]-2'(3'H)-carboxylate with 4-(4-aminophenyl)piperazin-2-one. The crude material was triturated with ethyl acetate to provide the title compound. $^1$H NMR (300 MHz, DMSO-d$_6$) δ 3.36-3.49 (m, 2H) 3.63-3.80 (m, 2H) 6.85-7.32 (m, 3H) 7.45-7.96 (m, 6H) 8.05 (s, 1H) 9.11 (s, 1H) 10.74 (s, 1H). MS (ESI$^+$) m/z 521.0 (M+H)$^+$.

Example 144

6-(2-chlorophenyl)-2-{[4,4-dimethyl-2-(propan-2-yl)-1,2,3,4-tetrahydroisoquinolin-7-yl]amino}imidazo[1,2-a]pyrimido[5,4-e]pyrimidin-5(6H)-one Example 144A 2-isopropyl-4,4-dimethyl-1,2,3,4-tetrahydroisoquinolin-7-amine The title compound was prepared as described in Example 113A and Example 113B, substituting cyclohexanecarbaldehyde with acetone. LC-MS: m/e=219 (M+H)$^+$. $^1$H NMR (400 MHz, CDCl$_3$), δ 7.07 (d, J=8.0 Hz, 1H), 6.53 (dd, J=8.4 Hz, 2.8 Hz, 1H), 6.34 (d, J=2.4 Hz, 1H), 3.59 (s, 2H), 3.48 (br, 2H), 2.82-2.88 (m, 1H), 2.39 (s, 2H), 1.23 (s, 6H), 1.08 (d, J=6.4 Hz, 6H).

Example 144B 6-(2-chlorophenyl)-2-{[4,4-dimethyl-2-(propan-2-yl)-1,2,3,4-tetrahydroisoquinolin-7-yl]amino}imidazo[1,2-a]pyrimido[5,4-e]pyrimidin-5(6H)-one The title compound was prepared as described in Example 130B, substituting Example 130A with Example 144A. No aqueous workup was used before HPLC. $^1$H NMR (400 MHz, CD$_3$OD) δ 1.51-1.48 (m, 12H), 3.33-3.20 (m, 1H), 3.55-3.52 (m, 1H), 3.76 (dt, J=13.2, 6.5 Hz, 1H), 4.45-4.41 (m, 1H), 4.65-4.61 (m, 1H), 7.06 (d, J=1.8 Hz, 1H), 7.63-7.45 (m, 4H), 7.72-7.64 (m, 1H), 7.77 (bs, 2H), 7.89-7.88 (m, 1H), 9.16 (s, 1H). MS (ESI$^+$) m/z 514.2 (M+H)$^+$.

Example 145

6-(2-chlorophenyl)-2-{[4,4-dimethyl-2-(4,4,4-trifluorobutyl)-1,2,3,4-tetrahydroisoquinolin-7-yl]amino}imidazo[1,2-a]pyrimido[5,4-e]pyrimidin-5(6H)-one

Example 145A 4,4-dimethyl-2-(4,4,4-trifluorobutyl)-1,2,3,4-tetrahydroisoquinolin-7-amine The title compound was prepared as described in Example 113A and Example 113B, substituting cyclohexanecarbaldehyde with 4,4,4-trifluorobutanal. LC-MS: m/e=287 (M+H)$^+$. $^1$H NMR (400 MHz, CDCl$_3$), δ 7.09 (d, J=8.4 Hz, 1H), 6.54 (dd, J=8.0, 2.4 Hz, 1H), 6.33 (d, J=2.0 Hz, 1H), 3.51 (br, 2H), 3.47 (s, 2H), 2.48 (t, J=6.8 Hz, 2H), 2.36 (s, 2H), 2.19-2.25 (m, 2H), 1.77-1.81 (m, 2H), 1.25 (s, 6H).

Example 145B 6-(2-chlorophenyl)-2-{[4,4-dimethyl-2-(4,4,4-trifluorobutyl)-1,2,3,4-tetrahydroisoquinolin-7-yl]amino}imidazo[1,2-a]pyrimido[5,4-e]pyrimidin-5(6H)-one The title compound was prepared as described in Example 130B, substituting Example 130A with Example 145A. No aqueous workup was used before HPLC. $^1$H NMR (400 MHz, CD$_3$OD) δ 1.50 (s, 6H), 2.18 (bs, 2H), 2.47-2.31 (m, 2H), 3.63-3.37 (m, 4H), 4.55 (bs, 2H), 7.05 (d, J=1.9 Hz, 1H), 7.62-7.53 (m, 4H), 7.77-7.66 (m, 3H), 7.88 (d, J=1.9 Hz, 1H), 9.17 (s, 1H). MS (ESI$^+$) m/z 582.3 (M+H)$^+$.

Example 146

6-(2-chlorophenyl)-2-[(1,1,2-trimethyl-2,3-dihydro-1H-isoindol-5-yl)amino]imidazo[1,2-a]pyrimido[5,4-e]pyrimidin-5(6H)-one The title compound was prepared as described in Example 130B, substituting Example 130A with 1,1,2-trimethylisoindolin-5-amine. $^1$H NMR (400 MHz, CD$_3$OD) δ 1.55 (s, 3H), 1.83 (s, 3H), 3.03 (s, 3H), 4.66-4.57 (m, 1H), 4.91-4.77 (m, 1H), 7.07 (d, J=1.9 Hz, 1H), 7.45-7.43 (m, 1H), 7.63-7.52 (m, 3H), 7.73-7.64 (m, 1H), 7.79 (bs, 1H), 7.89 (d, J=1.9 Hz, 1H), 8.00 (s, 1H), 9.19 (s, 1H). MS (ESI$^+$) m/z 472.2 (M+H)$^+$.

Example 147

6-(2-chlorophenyl)-2-[(1,1,2,3,3-pentamethyl-2,3-dihydro-1H-isoindol-5-yl)amino]imidazo[1,2-a]pyrimido[5,4-e]pyrimidin-5(6H)-one The title compound was prepared as described in Example 130B, substituting Example 130A with 1,1,2,3,3-pentamethylisoindolin-5-amine. $^1$H NMR (500 MHz, CD$_3$OD) δ 1.72-1.65 (m, 6H), 1.91-1.74 (m, 6H), 2.99 (s, 3H), 7.08 (d, J=1.9 Hz, 1H), 7.49-7.43 (m, 1H), 7.62-7.51 (m, 3H), 7.72-7.66 (m, 1H), 7.92-7.80 (m, 3H), 9.21 (s, 1H). MS (ESI$^+$) m/z 500.2 (M+H)$^+$.

Example 148

6-(2,6-dichlorophenyl)-2-{[3-methoxy-4-(4-methylpiperazin-1-yl)phenyl]amino}imidazo[1,2-a]pyrimido[5,4-e]pyrimidin-5(6H)-one The title compound (0.105 g) was prepared as described in Example 127, substituting 4-((4-methylpiperazin-1-yl)methyl)aniline with 3-methoxy-4-(4-methylpiperazin-1-yl)aniline. The crude material was dissolved in dichloromethane and an equal amount of trifluoroacetic acid. After stirring for one hour, the mixture was concentrated. The crude material was dissolved with methanol and treated with excess 2N HCl in diethyl ether. The mixture was diluted further with ether, stirred and filtered to provide the title compound. $^1$H NMR (300 MHz, DMSO-d$_6$) δ 2.77-2.89 (m, 3H) 2.91-3.09 (m, 2H) 3.11-3.32 (m, 2H) 3.43-3.55 (m, 4H) 3.80-3.90 (m, 3H) 6.97-7.07 (m, J=2.71 Hz, 1H) 7.12 (d, J=2.03 Hz, 1H) 7.37-7.49 (m, J=2.03 Hz, 1H) 7.55 (s, 1H) 7.58-7.70 (m, 1H) 7.71-7.84 (m, 3H) 9.15 (s, 1H) 10.30 (s, 1H) 10.79 (s, 1H). MS (ESI$^+$) m/z 551.2. (M+H)$^+$.

Example 149

6-(2,6-dichlorophenyl)-2-({4-[3-(diethylamino)propoxy]-3-fluorophenyl}amino)imidazo[1,2-a]pyrimido[5,4-e]pyrimidin-5(6H)-one The title compound (0.079 g) was prepared as described in Example 127, substituting 4-((4-methylpiperazin-1-yl)methyl)aniline with 4-(3-(diethylamino)propoxy)-3-fluoroaniline. The crude material was dissolved in dichloromethane and an equal amount of trifluoroacetic acid. The mixture was allowed to stir for 1 hour and was concentrated. The crude material was dissolved with methanol and treated with excess 2N HCl in diethyl ether. The mixture was diluted further with ether, stirred, and filtered to provide the title compound. $^1$H NMR (300 MHz, DMSO-d$_6$) δ 1.24 (d, 6H) 2.14 (d, 2H) 3.16 (d, 6H) 4.16 (d, 2H) 7.13 (d, J=1.59 Hz, 1H) 7.26 (t, J=8.93 Hz, 1H) 7.55-7.70 (m, 2H) 7.70-7.88 (m, 4H) 9.18 (s, 1H) 9.78 (s, 1H) 10.89 (s, 1H). MS (ESI$^+$) m/z 570.3 (M+H)$^+$.

Example 150

6-(2,6-dichlorophenyl)-2-[(1,1,2-trimethyl-1,2,3,4-tetrahydroisoquinolin-6-yl)amino]imidazo[1,2-a]pyrimido[5,4-e]pyrimidin-5(6H)-one To Example 55D (75 mg, 0.198 mmol) and m-chloroperoxybenzoic acid (53.3 mg, 0.238 mmol) was added 2 mL dichloromethane. The reaction was stirred for 15 minutes and 1,1,2-trimethyl-1,2,3,4-tetrahydroisoquinolin-6-amine (45 mg, 0.238 mmol) followed by trifluoroacetic acid (0.031 ml, 0.397 mmol) was added. The mixture was stirred at room temperature overnight, diluted with ethyl acetate, washed with saturated aqueous NaHCO$_3$, water, and brine, dried over MgSO$_4$ and concentrated. The crude material was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 1.60 (d, 3H)

1.76 (d, 3H) 2.83 (d, 3H) 3.05 (d, 1H) 3.32 (d, 1H) 3.55 (d, 2H) 7.14 (d, J=1.59 Hz, 1H) 7.51 (d, J=8.73 Hz, 1H) 7.57-7.91 (m, 6H) 9.19 (s, 1H) 10.61-11.08 (m, 2H). MS (ESI⁺) m/z 520.2 (M+H)⁺.

Example 151

2-({4-[(1S,4S)-2,5-diazabicyclo[2.2.1]hept-2-yl]phenyl}amino)-6-(2,6-dichlorophenyl)imidazo[1,2-a]pyrimido[5,4-e]pyrimidin-5(6H)-one The title compound (0.11 g) was prepared as described in Example 109A, substituting tert-butyl 7'-amino-1'H-spiro[cyclopropane-1,4'-isoquinoline]-2'(3'H)-carboxylate with (1S,4S)-tert-butyl 5-(4-aminophenyl)-2,5-diazabicyclo[2.2.1]heptane-2-carboxylate. The crude material was dissolved in 1:1 dichloromethane/TFA for 1 hour, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The resulting TFA salt was dissolved in methanol and treated with 2N HCl in diethyl ether for 20 minutes. The precipitate was diluted with diethyl ether and filtered to provide the title compound. ¹H NMR (300 MHz, DMSO-d₆) δ 1.83-2.23 (m, 2H) 3.16-3.38 (m, 2H) 3.49-3.73 (m, 2H) 4.29-4.70 (m, 2H) 6.61-6.83 (m, 2H) 7.11 (s, 1H) 7.43-7.58 (m, 1H) 7.58-7.68 (m, 1H) 7.68-7.84 (m, 4H) 8.71 (s, 1H) 9.09 (s, 1H) 9.28 (s, 1H) 10.69 (s, 1H). MS (ESI⁺) m/z 519(M+H)⁺.

Example 152

6-(2,6-dichlorophenyl)-2-[(2,4,4-trimethyl-1,2,3,4-tetrahydroisoquinolin-7-yl)amino]imidazo[1,2-a]pyrimido[5,4-e]pyrimidin-5(6H)-one The title compound (0.095 g) was prepared as described in Example 150, substituting 1,1,2-trimethyl-1,2,3,4-tetrahydroisoquinolin-6-amine with 2,4,4-trimethyl-1,2,3,4-tetrahydroisoquinolin-7-amine. The crude material was triturated with ethyl acetate, dissolved in methanol, treated with excess 2M HCl in diethyl ether and stirred until a solid began to form. The mixture was diluted with ether, stirred for 10 minutes, and filtered to provide the title compound. ¹H NMR (300 MHz, DMSO-d₆) δ 1.32-1.38 (m, 3H) 1.42-1.47 (m, 3H) 2.95-3.03 (m, 3H) 3.13-3.34 (m, 2H) 4.28-4.58 (m, 2H) 7.07-7.19 (m, 1H) 7.49-7.91 (m, 7H) 9.18 (s, 1H) 10.03 (s, 1H) 10.92 (s, 1H). MS (ESI⁺) m/z 520.2 (M+H)⁺.

Example 153

6-(2,6-dichlorophenyl)-2-{[4-(4,4-difluoropiperidin-1-yl)phenyl]amino}imidazo[1,2-a]pyrimido[5,4-e]pyrimidin-5(6H)-one The title compound (0.08 g) was prepared as described in Example 109A, substituting tert-butyl 7'-amino-1'H-spiro[cyclopropane-1,4'-isoquinoline]-2'(3'H)-carboxylate with 4-(4,4-difluoropiperidin-1-yl)aniline. Chromatographic purification was performed with an Analogix280 with a SF 12-24 column, 10% to 70% ethyl acetate/hexane gradient over 30 minutes. ¹H NMR (300 MHz, DMSO-d₆) δ 1.92-2.21 (m, 4H) 3.33-3.40 (m, 4H) 6.94-7.20 (m, 3H) 7.48-7.96 (m, 6H) 9.04-9.18 (m, 1H) 10.60-10.83 (m, 1H). MS (ESI⁺) m/z 542.3 (M+H)⁺.

Example 154

6-(2,6-dichlorophenyl)-2-{[4-(3,3-difluoropiperidin-1-yl)phenyl]amino}imidazo[1,2-a]pyrimido[5,4-e]pyrimidin-5(6H)-one The title compound (0.09 g) was prepared as described in Example 109A, substituting tert-butyl 7'-amino-1'H-spiro[cyclopropane-1,4'-isoquinoline]-2'(3'H)-carboxylate with 4-(3,3-difluoropiperidin-1-yl)aniline. Chromatographic purification was performed with an Analogix280 with a SF 12-24 column, 10% to 70% ethyl acetate/hexane gradient over 30 minutes. ¹H NMR (300 MHz, DMSO-d₆) δ 1.71-1.92 (m, 2H) 1.93-2.16 (m, 2H) 3.22 (d, J=4.75 Hz, 2H) 3.43 (q, J=12.09 Hz, 2H) 6.94-7.22 (m, 3H) 7.49-7.98 (m, 6H) 9.11 (s, 1H) 10.73 (s, 1H) MS (ESI⁺) m/z 542.3 (M+H)⁺.

Example 155

6-(2,6-dichlorophenyl)-2-({3-fluoro-4-[4-(propan-2-yl)piperazin-1-yl]phenyl}amino)imidazo[1,2-a]pyrimido[5,4-e]pyrimidin-5(6H)-one The title compound (0.06 g) was prepared as described in Example 150, substituting tert-butyl 7'-amino-1'H-spiro[cyclopropane-1,4'-isoquinoline]-2'(3'H)-carboxylate with 3-fluoro-4-(4-isopropylpiperazin-1-yl)aniline. The crude material was triturated with ethyl acetate, filtered and dried under high vacuum to provide the title compound. ¹H NMR (300 MHz, DMSO-d₆) δ 1.00 (t, J=7.34 Hz, 6H) 2.55-2.64 (m, 4H) 2.65-2.75 (m, 1H) 3.00 (s, 4H) 6.93-7.29 (m, 2H) 7.52-7.96 (m, 6H) 9.16 (s, 1H) 10.87 (s, 1H). MS (ESI⁺) m/z 567.2 (M+H)⁺.

Example 156

6-(2,6-dichlorophenyl)-2-{[4-(piperazin-1-yl)-3-(trifluoromethyl)phenyl]amino}imidazo[1,2-a]pyrimido[5,4-e]pyrimidin-5(6H)-one Example 156A tert-butyl 4-[4-{[6-(2,6-dichlorophenyl)-5-oxo-5,6-dihydroimidazo[1,2-a]pyrimido[5,4-e]pyrimidin-2-yl]amino}-2-(trifluoromethyl)phenyl]piperazine-1-carboxylate The title compound (0.09 g) was prepared as described in Example 109A, substituting tert-butyl 7'-amino-1'H-spiro[cyclopropane-1,4'-isoquinoline]-2'(3'H)-carboxylate with tert-butyl 4-(4-amino-2-(trifluoromethyl)phenyl)piperazine-1-carboxylate. Chromatography was performed with an Analogix 280 with a SF12-24 column, 10% to 70% ethyl acetate/hexane gradient over 30) to provide the title compound. MS (ESI+) m/z 675.1 (M+H)+.

Example 156B 6-(2,6-dichlorophenyl)-2-{[4-(piperazin-1-yl)-3-(trifluoromethyl)phenyl]amino}imidazo[1,2-a]pyrimido[5,4-e]pyrimidin-5(6H)-one The title compound (0.08 g) was prepared as described in Example 109B, substituting Example 109A with Example 156A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 3.09 (d, J=4.41 Hz, 4H) 3.15-3.28 (m, 4H) 7.16 (d, J=1.70 Hz, 1H) 7.52-7.72 (m, 2H) 7.70-7.88 (m, 3H) 8.17 (s, 2H) 8.97 (s, 2H) 9.22 (s, 1H) 11.11 (s, 1H). MS (ESI$^+$) m/z 575.2 (M+H)$^+$.

Example 157

6-(2-chlorophenyl)-2-{[4-(4-methylpiperazin-1-yl)-3-(propan-2-yl)phenyl]amino}imidazo[1,2-a]pyrimido[5,4-e]pyrimidin-5(6H)-one

Example 157A 1-methyl-4-(4-nitro-2-(prop-1-en-2-yl)phenyl)piperazine

A mixture of 1-(2-bromo-4-nitrophenyl)-4-methylpiperazine (0.810 g, 2.70 mmol), tetrakis(triphenylphosphine)palladium(0) (0.094 g, 0.081 mmol), and tributyl(prop-1-en-2-yl)stannane (0.983 g, 2.97 mmol) in 1,4-dioxane (30 mL) was degassed and heated at 105° C. overnight. After cooling, the suspension was filtered, concentrated, and purified on a 40 g column using the ISCO Companion flash system eluting with methanol/ethyl acetate (5:95 to 10:90) to provide the title compound.

Example 157B 3-isopropyl-4-(4-methylpiperazin-1-yl)aniline

Ra—Ni water slurry (10 mg) and tetrahydrofuran (10 ml)/trifluoroethanol (10 mL) were added to Example 157A (20 mg, 0.077 mmol) in a 50 ml pressure bottle. The mixture was stirred for 16 hours at 30 psi of hydrogen at room temperature. The reaction mixture was filtered and concentrated to provide the title compound.

Example 157C 6-(2-chlorophenyl)-2-{[4-(4-methylpiperazin-1-yl)-3-(propan-2-yl)phenyl]amino}imidazo[1,2-a]pyrimido[5,4-e]pyrimidin-5(6H)-one The title compound was prepared as described in Example 130B, substituting Example 130A with Example 157B. No aqueous workup was used before HPLC purification. $^1$H NMR (400 MHz, CD$_3$OD) δ 1.29 (s, 3H), 1.30 (s, 3H), 3.00 (s, 3H), 3.24-3.07 (m, 4H), 3.42-3.26 (m, 2H), 3.61-3.58 (m, 3H), 7.06 (d, J=1.8 Hz, 1H), 7.27 (d, J=7.1 Hz, 1H), 7.62-7.46 (m, 3H), 7.74-7.65 (m, 3H), 7.82 (bs, 1H), 9.14 (s, 1H). MS (ESI$^+$) m/z 529.3 (M+H)$^+$.

Example 158

2-{[4-(4-acetylpiperazin-1-yl)phenyl]amino}-6-(2-chloro-6-fluorophenyl)imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 1-(4-(4-aminophenyl)piperazin-1-yl)ethanone, respectively. $^1$H NMR (400 MHz, CD$_3$OD) δ 2.18 (s, 3H), 3.41-3.33 (m, 4H), 3.87-3.74 (m, 4H), 7.09 (d, J=1.9 Hz, 1H), 7.29-7.23 (m, 2H), 7.44-7.34 (m, 1H), 7.57-7.47 (m, 1H), 7.63 (td, J=8.3, 5.7 Hz, 1H), 7.83-7.74 (m, 2H), 7.90-7.85 (m, 1H), 9.16 (s, 1H). MS (ESI$^+$) m/z 533.3 (M+H)$^+$.

Example 159

6-(2-chloro-6-fluorophenyl)-2-[(4,4-dimethyl-1,2,3,4-tetrahydroisoquinolin-7-yl)amino]imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 4,4-dimethyl-1,2,3,4-tetrahydroisoquinolin-7-amine, respectively. $^1$H NMR (400 MHz, CD$_3$OD) δ 1.37 (s, 3H), 1.41 (s, 3H), 4.21-4.09 (m, 2H), 5.25-5.23 (m, 2H), 7.08 (t, J=1.8 Hz, 1H), 7.30-7.20 (m, 2H), 7.42-7.34 (m, 1H), 7.56-7.50 (m, 1H), 7.65-7.59 (m, 2H), 7.99 (dd, J=4.0, 2.0 Hz, 1H), 9.15 (d, J=5.0 Hz, 1H). MS (ESI$^+$) m/z 490.3 (M+H)$^+$.

Example 160

6-(2,6-dichloro-4-fluorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one

Example 160A tert-butyl 7'-{[6-(2,6-dichloro-4-fluorophenyl)-5-oxo-5,6-dihydroimidazo[1,2-c]pyrimido[5,4-e]pyrimidin-2-yl]amino}-1'H-spiro[cyclopropane-1,4'-isoquinoline]-2'(3'H)-carboxylate A mixture of Example 123A (600.0 mg, 1.514 mmol) and m-chloroperoxybenzoic acid (407 mg, 1.817 mmol) in CH$_2$Cl$_2$ (14 ml) was stirred for 20 minutes. tert-Butyl 7'-amino-1'H-spiro[cyclopropane-1,4'-isoquinoline]-2'(3'H)-carboxylate (499 mg, 1.817 mmol) was added to the reaction mixture. After 25 minutes, the reaction mixture was diluted with ethyl acetate, washed with saturated aqueous NaHCO$_3$, and brine. The organic layer was dried over MgSO$_4$, filtered, concentrated, and purified on a 40 g column using the ISCO Companion flash system eluting with hexane/ethyl acetate (6:4 to 4:6) to provide the title compound.

Example 160B 6-(2,6-dichloro-4-fluorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one To a solution of Example 160A (0.855 g, 1.374 mmol) in CH$_2$Cl$_2$ (10 ml) was added trifluoroacetic acid (1.058 ml, 13.74 mmol). The reaction mixture was stirred for 7 hrs and concentrated. The residue was dissolved in 5 mL of methanol and treated with 2M HCl in diethyl ether slowly until a precipitate started to form. Diethyl ether was added, and the suspension was stirred for 15 minutes, filtered, washed with ether, and oven-dried to provide the title compound as an HCl salt. $^1$H NMR (300 MHz, DMSO-$d_6$) δ 1.11 (s, 4H), 3.27 (dd, J=4.4, 2.2 Hz, 2H), 4.46 (s, 2H), 6.93 (d, J=9.0 Hz, 1H), 7.14 (d, J=1.8 Hz, 1H), 7.82-7.63 (m, 2H), 7.91-7.84 (m, 2H), 9.17 (s, 1H), 9.37 (bs, 1H), 10.90 (bs, 1H). MS (ESI$^+$) m/z 522.3 (M+H)$^+$.

Example 161

6-(2-chlorophenyl)-2-[(2-ethyl-4,4-dimethyl-1,2,3,4-tetrahydroisoquinolin-7-yl)amino]imidazo[1,2-a]pyrimido[5,4-e]pyrimidin-5(6H)-one

Example 161A 2-ethyl-4,4-dimethyl-7-nitro-1,2,3,4-tetrahydroisoquinoline

Bromoethane (0.75 g, 6.88 mmol) was added to a solution of 4,4-dimethyl-7-nitro-1,2,3,4-tetrahydroisoquinoline (1.4 g, 6.79 mmol) and $K_2CO_3$ (2 g, 14.47 mmol) in N,N-dimethylformamide (80 mL). The mixture was stirred at 50° C. for 4 hours. The solvent was removed under vacuum to give a residue which was purified by silica gel column chromatography eluting with 10% ethyl acetate/heptane to provide the title compound.

Example 161B 2-ethyl-4,4-dimethyl-1,2,3,4-tetrahydroisoquinolin-7-amine

The title compound was prepared as described in Example 113B, substituting Example 113A with Example 161A. LC-MS: m/e=205 (M+H)$^+$. $^1$H NMR (400 MHz, CDCl$_3$), δ 7.08 (d, J=8.4 Hz, 1H), 6.53 (dd, J=8.4 Hz, 2.4 Hz, 1H), 6.33 (d, J=2.4 Hz, 1H), 3.48 (s, 4H), 2.49 (q, J=6.8 Hz, 14.0 Hz, 2H), 2.36 (s, 2H), 1.25 (s, 6H), 1.14 (t, J=7.2 Hz, 3H).

Example 161C 6-(2-chlorophenyl)-2-[(2-ethyl-4,4-dimethyl-1,2,3,4-tetrahydroisoquinolin-7-yl)amino]imidazo[1,2-a]pyrimido[5,4-e]pyrimidin-5(6H)-one The title compound was prepared as described in Example 130B, substituting Example 130A with Example 161B. No aqueous workup was used before HPLC. $^1$H NMR (400 MHz, CD$_3$OD) δ 1.53-1.45 (m, 9H), 3.31-3.26 (m, 1H), 3.43 (q, J=7.3 Hz, 2H), 3.65-3.56 (m, 1H), 4.63-4.39 (m, 2H), 7.06 (d, J=1.9 Hz, 1H), 7.62-7.53 (m, 4H), 7.80-7.62 (m, 3H), 7.88 (d, J=1.9 Hz, 1H), 9.16 (s, 1H). MS (ESI$^+$) m/z 500.2 (M+H)$^+$.

Example 162

6-(2-chlorophenyl)-2-{[4,4-dimethyl-2-(2,2,2-trifluoroethyl)-1,2,3,4-tetrahydroisoquinolin-7-yl]amino}imidazo[1,2-a]pyrimido[5,4-e]pyrimidin-5(6H)-one

Example 162A 4,4-dimethyl-7-nitro-2-(2,2,2-trifluoroethyl)-1,2,3,4-tetrahydroisoquinoline 2,2,2-Trifluoroethyl trichloromethanesulfonate (1.8 g, 6.40 mmol) was added to a solution of 4,4-dimethyl-7-nitro-1,2,3,4-tetrahydroisoquinoline (0.8 g, 3.88 mmol) and sodium bicarbonate (0.66 g, 7.86 mmol) in N,N-dimethylformamide (50 mL). The reaction mixture was stirred at 60° C. for 16 hour. The mixture was concentrated, and CH$_2$Cl$_2$ (70 mL) and water (70 mL) were added to the residue. After separation, the aqueous layer was extracted with CH$_2$Cl$_2$ again. The combined organic layers were washed with saturated aqueous NaCl (1×150 mL), dried over Na$_2$SO$_4$, filtered, and concentrated to provide the title compound.

Example 162B 4,4-dimethyl-2-(2,2,2-trifluoroethyl)-1,2,3,4-tetrahydroisoquinolin-7-amine The title compound was prepared as described in Example 113B, substituting Example 113A with Example 161A. LC-MS: m/e=259 (M+H)$^+$. $^1$H NMR (400 MHz, CDCl$_3$), δ 7.09 (d, J=8.4 Hz, 1H), 6.50 (dd, J=8.4 Hz, 2.4 Hz, 1H), 6.30 (d, J=2.4 Hz, 1H), 3.75 (s, 2H), 3.51 (br, 2H), 3.10 (q, J=9.6 Hz, 2H), 2.62 (s, 2H), 1.26 (s, 6H).

Example 162C 6-(2-chlorophenyl)-2-{[4,4-dimethyl-2-(2,2,2-trifluoroethyl)-1,2,3,4-tetrahydroisoquinolin-7-yl]amino}imidazo[1,2-a]pyrimido[5,4-e]pyrimidin-5(6H)-one The title compound was prepared as described in Example 130B, substituting Example 130A with Example 162B. No aqueous workup was used before HPLC. $^1$H NMR (400 MHz, CD$_3$OD) δ 1.33 (s, 6H), 2.72 (s, 2H), 3.29-3.22 (m, 2H), 3.89 (s, 2H), 7.06 (d, J=1.5 Hz, 1H), 7.44-7.38 (m, 2H), 7.64-7.48 (m, 4H), 7.72-7.64 (m, 1H), 7.83 (s, 1H), 9.19 (d, J=43.2 Hz, 1H). MS (ESI+) m/z 554.3 (M+H)$^+$.

Example 163

6-(2-chlorophenyl)-2-({2-[4-(1H-imidazol-1-yl)benzyl]-4,4-dimethyl-1,2,3,4-tetrahydroisoquinolin-7-yl}amino)imidazo[1,2-a]pyrimido[5,4-e]pyrimidin-5(6H)-one

Example 163A 2-(4-(1H-imidazol-1-yl)benzyl)-4,4-dimethyl-7-nitro-1,2,3,4-tetrahydroisoquinoline The title compound was prepared as described in Example 113A, substituting cyclohexanecarbaldehyde with 4-(1H-imidazol-1-yl)benzaldehyde.

Example 163B 2-(4-(1H-imidazol-1-yl)benzyl)-4,4-dimethyl-1,2,3,4-tetrahydroisoquinolin-7-amine To a solution of Example 163A (1.45 g, 4.00 mmol) in 95% ethanol (20 mL) were added zinc (2 g, 30.6 mmol) and acetic acid (4 mL, 69.9 mmol). The reaction mixture was stirred for 4 hours at 50° C. Aqueous saturated NaHCO$_3$ solution (200 mL) and CH$_2$Cl$_2$ (200 mL) were added to the reaction mixture and the suspension was filtered. The aqueous layer was extracted with CH$_2$Cl$_2$ (200 mL). The combined organic layers were washed with saturated NaCl (1×300 mL), dried over Na$_2$SO$_4$, filtered, and concentrated. The crude material was purified using the Chemflash system using a 120 g C18 column eluting with 40-80% methanol in water (0.8 g (NH$_4$)$_2$CO$_3$ in 1 L of water) to provide the title compound. LC-MS: m/e=333 (M+H)$^+$. $^1$H NMR (400 MHz, DMSO-d$_6$), δ 8.25 (s, 1H), 7.73 (s, 1H), 7.62 (d, J=8.4 Hz, 2H), 7.49 (d, J=8.4 Hz, 2H), 7.11 (s, 1H), 6.97 (d, J=8.4 Hz, 1H), 6.41 (dd, J=8.4 Hz, 2.0 Hz, 1H), 6.16 (d, J=2.0 Hz, 1H), 4.76 (s, 2H), 3.62 (s, 2H), 3.43 (s, 2H), 2.31 (s, 2H), 1.15 (s, 6H).

Example 163C 6-(2-chlorophenyl)-2-({2-[4-(1H-imidazol-1-yl)benzyl]-4,4-dimethyl-1,2,3,4-tetrahydroisoquinolin-7-yl}amino)imidazo[1,2-a]pyrimido[5,4-e]pyrimidin-5 (6H)-one The title compound was prepared as described in Example 130B, substituting Example 130A with Example 163B. No aqueous workup was used before HPLC. $^1$H NMR (400 MHz, CD$_3$OD) δ 1.45 (s, 6H), 3.42 (s, 2H), 4.56 (bs, 2H), 4.69 (s, 2H), 7.06 (d, J=1.8 Hz, 1H), 7.62-7.51 (m, 4H), 7.81-7.66 (m, 4H), 7.94-7.85 (m, 5H), 8.13 (t, J=1.8 Hz, 1H), 9.18 (s, 1H), 9.48 (t, J=1.4 Hz, 1H). MS (ESI$^+$) m/z 628.3 (M+H)$^+$.

Example 164

2-({2-[(1-benzylpiperidin-4-yl)methyl]-4,4-dimethyl-1,2,3,4-tetrahydroisoquinolin-7-yl}amino)-6-(2-chlorophenyl)imidazo[1,2-a]pyrimido[5,4-e]pyrimidin-5(6H)-one

Example 164A 2-((1-benzylpiperidin-4-yl)methyl)-4,4-dimethyl-7-nitro-1,2,3,4-tetrahydroisoquinoline The title compound was prepared as described in Example 113A, substituting cyclohexanecarbaldehyde with 1-benzylpiperidine-4-carbaldehyde.

Example 164B 2-((1-benzylpiperidin-4-yl)methyl)-4,4-dimethyl-1,2,3,4-tetrahydroisoquinolin-7-amine The title compound was prepared as described in Example 163B, substituting Example 163A with Example 164A. LC-MS: m/e=364 (M+H)$^+$. $^1$H NMR (400 MHz, CDCl$_3$), δ 7.22-7.32 (m, 5H), 7.07 (d, J=8.4 Hz, 1H), 6.53 (dd, J=8.4 Hz, 2.4 Hz, 1H), 6.32 (d, J=2.4 Hz, 1H), 3.48-3.51 (m, 4H), 3.44 (s, 2H), 2.88 (d, J=9.2 Hz, 2H), 2.32 (s, 2H), 2.26 (d, J=7.2 Hz, 2H), 1.96 (t, J=7.2 Hz, 2H), 1.78 (d, J=12.4 Hz, 2H), 1.52-1.62 (m, 1H), 1.26-1.32 (m, 2H), 1.23 (s, 6H).

Example 164C 2-({2-[(1-benzylpiperidin-4-yl)methyl]-4,4-dimethyl-1,2,3,4-tetrahydroisoquinolin-7-yl}amino)-6-(2-chlorophenyl)imidazo[1,2-a]pyrimido[5,4-e]pyrimidin-5(6H)-one The title compound was prepared as described in Example 130B, substituting Example 130A with Example 164B. No aqueous workup was used before HPLC purification. $^1$H NMR (400 MHz, CD$_3$OD) δ 1.50 (s, 6H), 1.69 (dd, J=24.1, 12.1 Hz, 2H), 2.10 (d, J=14.1 Hz, 2H), 2.41 (bs, 1H), 3.10 (t, J=12.5 Hz, 2H), 3.38-3.31 (m, 2H), 3.60-3.47 (m, 4H), 4.35 (s, 2H), 4.55 (s, 2H), 7.06 (d, J=1.9 Hz, 1H), 7.63-7.39 (m, 9H), 7.81-7.64 (m, 3H), 7.88 (d, J=1.5 Hz, 1H), 9.17 (s, 1H). MS (ESI$^+$) m/z 659.2 (M+H)$^+$.

Example 165

2-[(2'-acetyl-2',3'-dihydro-1'H-spiro[cyclopropane-1,4'-isoquinolin]-7'-yl)amino]-6-(2,6-dichloro-4-fluorophenyl)imidazo[1,2-a]pyrimido[5,4-e]pyrimidin-5(6H)-one A solution Example 160B (0.080 g, 0.134 mmol), acetic acid (0.012 mL, 0.202 mmol), benzotriazol-1-yloxytripyrrolidinophosphonium hexafluorophosphate (0.105 g, 0.202 mmol), and triethylamine (0.094 mL, 0.672 mmol) in tetrahydrofuran (4 mL) was stirred overnight. The reaction mixture was diluted with ethyl acetate and washed with saturated aqueous NaHCO$_3$ and brine. The organic layer was dried over MgSO$_4$, filtered, concentrated, and purified on a 4 g column using the ISCO Companion flash system eluting with hexane/ethyl acetate (1:9) to 100% ethyl acetate to provide the title compound. $^1$H NMR (400 MHz, CD$_3$OD) δ 1.10-0.98 (m, 4H), 2.17 (s, 1.7H), 2.23 (s, 1.3H), 3.63 (d, J=4.0 Hz, 2H), 4.89 (s, 2H), 6.90 (bs, 1H), 7.08 (d, J=1.8 Hz, 1H), 7.63-7.45 (m, 4H), 7.86 (bs, 1H), 9.15 (bs, 1H). MS (ESI$^+$) m/z 564.2 (M+H)$^+$.

Example 166

6-(2,6-dichlorophenyl)-2-{[4-(4-hydroxypiperidin-1-yl)phenyl]amino}imidazo[1,2-a]pyrimido[5,4-e]pyrimidin-5(6H)-one The title compound (0.02 g) was prepared as described in Example 109A, substituting tert-butyl 7'-amino-1'H-spiro[cyclopropane-1,4'-isoquinoline]-2'(3'H)-carboxylate with 1-(4-aminophenyl)piperidin-4-ol. The final compound was triturated from the crude reaction mixture with dichloromethane/ethyl acetate. $^1$H NMR (300 MHz, DMSO-d$_6$) δ 1.21-1.32 (m, 1H) 1.57 (s, 2H) 1.86 (s, 2H) 2.80-3.06 (m, 4H) 7.11 (d, J=1.59 Hz, 2H) 7.46-7.99 (m, 7H) 9.12 (s, 1H) 10.55-10.94 (m, J=27.77 Hz, 1H). MS (ESI$^+$) m/z 522.2 (M+H)$^+$.

Example 167

2-[(4-cyclohexylphenyl)amino]-6-(2,6-dichlorophenyl)imidazo[1,2-a]pyrimido[5,4-e]pyrimidin-5(6H)-one The title compound (0.07 g) was prepared as described in Example 109A, substituting tert-butyl 7'-amino-1'H-spiro[cyclopropane-1,4'-isoquinoline]-2'(3'H)-carboxylate with 4-cyclohexylaniline. Chromatography was performed with an Analogix 280 with an SF 12-24 column, 10% to 70% ethyl acetate/hexane gradient over 30 minutes to provide the title compound. $^1$H NMR (300 MHz, DMSO-d$_6$) δ 1.31-1.51 (m, 5H) 1.63-1.90 (m, 6H) 7.11 (d, J=1.70 Hz, 1H) 7.27 (d, J=7.80 Hz, 2H) 7.49-7.95 (m, 6H) 9.14 (s, 1H) 10.80 (s, 1H). MS (ESI$^+$) m/z 505.4 (M+H)$^+$.

Example 168

6-(2,6-dichlorophenyl)-2-{[4-(pyrrolidin-3-yl)phenyl]amino}imidazo[1,2-a]pyrimido[5,4-e]pyrimidin-5(6H)-one

Example 168A tert-butyl 3-(4-{[6-(2,6-dichlorophenyl)-5-oxo-5,6-dihydroimidazo[1,2-a]pyrimido[5,4-e]pyrimidin-2-yl]amino}phenyl)pyrrolidine-1-carboxylate The title compound (0.09 g) was prepared as described in Example 109A, substituting tert-butyl 7'-amino-1'H-spiro[cyclopropane-1,4'-isoquinoline]-2'(3'H)-carboxylate with 4-(4-aminophenyl)piperazin-2-one. Chromatography was performed with an Analogix 280 with an SF 12-24 column, 10% to 70% ethyl acetate/hexane gradient over 30 minutes to provide the title compound. MS (ESI$^+$) m/z 591.9 (M+H)$^+$.

Example 168B 6-(2,6-dichlorophenyl)-2-{[4-(pyrrolidin-3-yl)phenyl]amino}imidazo[1,2-a]pyrimido[5,4-e]pyrimidin-5(6H)-one The title compound (0.085 g) was prepared as described in Example 109B, substituting Example 109A with Example 168A. The TFA salt was dissolved in methanol, treated with excess 2M HCl in diethyl ether and was stirred until a solid began to form. The mixture was diluted with diethyl ether, stirred for 10 minutes, and filtered. $^1$H NMR (300 MHz, DMSO-d$_6$) δ 1.93 (d, 1H) 2.37 (d, 1H) 3.06 (d, 1H) 3.17-3.34 (m, 3H) 7.13 (d, J=1.59 Hz, 1H) 7.40 (d, J=8.33 Hz, 2H) 7.57-7.70 (m, 1H) 7.70-7.98 (m, 5H) 9.17 (s, 3H) 10.89 (s, 1H). MS (ESI$^+$) m/z 492.2 (M+H)$^+$.

Example 169

6-(2,6-dichlorophenyl)-2-{[4-(morpholin-4-yl)phenyl]amino}imidazo[1,2-a]pyrimido[5,4-e]pyrimidin-5(6H)-one The title compound (0.085 g) was prepared as described in Example 109A, substituting tert-butyl 7'-amino-1'H-spiro[cyclopropane-1,4'-isoquinoline]-2'(3'H)-carboxylate with 4-morpholinoaniline. Chromatography was performed with an Analogix 280 with an SF 12-24 column, 50% to 100% ethyl acetate/hexane gradient over 30 minutes. $^1$H NMR (300 MHz, DMSO-d$_6$) δ3.11 (s, 4H) 3.65-3.83 (m, 4H) 7.01 (s, 2H) 7.11 (d, J=1.59 Hz, 1H) 7.45-7.96 (m, 6H) 9.10 (s, 1H) 10.73 (s, 1H). MS (ESI$^+$) m/z 508.3 (M+H)$^+$.

Example 170

6-(2,6-dichlorophenyl)-2-{[4,4-dimethyl-2-(2,2,2-trifluoroethyl)-1,2,3,4-tetrahydroisoquinolin-7-yl]amino}imidazo[1,2-a]pyrimido[5,4-e]pyrimidin-5(6H)-one The title compound (0.09 g) was prepared as described in Example 150, substituting 1,1,2-trimethyl-1,2,3,4-tetrahydroisoquinolin-6-amine with 4,4-dimethyl-2-(2,2,2-trifluoroethyl)-1,2,3,4-tetrahydroisoquinolin-7-amine. Chromatography was performed with an Analogix 280 with an SF 12-24 column, 10% to 70% ethyl acetate/hexane gradient over 30 minutes. $^1$H NMR (300 MHz, DMSO-d$_6$) δ 1.27 (s, 6H) 2.61-2.76 (m, 2H) 3.33-3.49 (m, 2H) 3.85 (s, 2H) 7.12 (d, J=1.59 Hz, 1H) 7.34-7.54 (m, J=8.33 Hz, 2H) 7.58-7.70 (m, 2H) 7.71-7.83 (m, 3H) 9.15 (s, 1H) 10.78 (s, 1H). MS (ESI$^+$) m/z 588.3 (M+H)$^+$.

Example 171

2-{[2'-(cyclopropylcarbonyl)-2',3'-dihydro-1'H-spiro[cyclopropane-1,4'-isoquinolin]-7'-yl]amino}-6-(2,6-dichloro-4-fluorophenyl)imidazo[1,2-a]pyrimido[5,4-e]pyrimidin-5(6H)-one The title compound was prepared as described in Example 165, substituting acetic acid with cyclopropanecarboxylic acid. The crude material was purified by HPLC (see protocol in Example 1F) to provide the title compound as a trifluoroacetic acid salt. $^1$H NMR (400 MHz, DMSO-d$_6$) δ 0.83-0.68 (m, 4H), 1.13-0.90 (m, 4H), 2.22-2.03 (m, 1H), 3.56 (s, 0.8H), 3.81 (s, 1.2H), 4.79 (s, 1.4H), 5.05 (s, 0.6H), 6.93-6.70 (m, 1H), 7.13 (d, J=1.8 Hz, 1H), 7.69-7.56 (m, 2H), 7.90-7.80 (m, 3H), 9.16 (s, 1H), 10.84 (bs, 1H). MS (ESI$^+$) m/z 590.2 (M+H)$^+$.

Example 172

6-(2,6-dichloro-4-fluorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one A mixture of Example 160B (0.065 g, 0.109 mmol), mesyl chloride (0.013 mL, 0.164 mmol), and triethylamine (0.076 mL, 0.546 mmol) in N,N-dimethylformamide (2 mL) was stirred for 2 hours. Water was added to the reaction mixture. The resulting solids were filtered, washed with water and further purified by HPLC (see protocol in Example 1F) to provide the title compound as a trifluoroacetic acid salt. $^1$H NMR (400 MHz, CD$_3$OD) δ 1.10-1.04 (m, 4H), 2.90 (s, 3H), 3.43 (s, 2H), 4.63 (s, 2H), 6.86 (bs, 1H), 7.09 (d, J=1.8 Hz, 1H), 7.66-7.51 (m, 4H), 7.84 (bs, 1H), 9.14 (s, 1H). MS (ESI$^+$) m/z 600.2 (M+H)$^+$.

Example 173

6-(2,6-dichloro-4-fluorophenyl)-2-{[6-(piperazin-1-yl)pyridin-3-yl]amino}imidazo[1,2-a]pyrimido[5,4-e]pyrimidin-5(6H)-one The title compound was prepared following the general procedures described in Example 160A and Example 160B, substituting tert-butyl 7'-amino-1'H-spiro[cyclopropane-1,4'-isoquinoline]-2'(3'H)-carboxylate with tert-butyl 4-(5-aminopyridin-2-yl)piperazine-1-carboxylate (64.9 mg, 0.233 mmol) in Example 160A. The deprotection step was run at 35° C. overnight and the final trifluoroacetic acid salt was not converted into an HCl salt. $^1$H NMR (400 MHz, CD$_3$OD) δ 3.38 (t, J=13.1, 8.1 Hz, 4H), 3.89-3.81 (m, 4H), 7.16-7.07 (m, 2H), 7.56 (s, 1H), 7.58 (s, 1H), 7.93-7.81 (m, 1H), 8.18-8.10 (m, 1H), 8.71-8.55 (m, 1H), 9.17 (s, 1H). MS (ESI$^+$) m/z 526.2 (M+H)$^+$.

Example 174

6-(2,6-dichlorophenyl)-2-{[4-(2-oxopiperazin-1-yl)
phenyl]amino}imidazo[1,2-a]pyrimido[5,4-e]pyrimi-
din-5(6H)-one

Example 174A tert-butyl 4-(4-{[6-(2,6-dichlorophenyl)-5-oxo-5,6-
dihydroimidazo[1,2-a]pyrimido[5,4-e]pyrimidin-2-
yl]amino}phenyl)-3-oxopiperazine-1-carboxylate The title compound (0.011 g) was prepared as described in Example 109A, substituting tert-butyl 7'-amino-1'H-spiro [cyclopropane-1,4'-isoquinoline]-2'(3'H)-carboxylate with tert-butyl 4-(4-aminophenyl)-3-oxopiperazine-1-carboxylate. Chromatography was performed with an Analogix 280 with an SF 12-24 column, 50% to 100% ethyl acetate/hexane gradient over 30 minutes to provide the title compound. MS (ESI$^+$) m/z 621.4 (M+H)$^+$.

Example 174B 6-(2,6-dichlorophenyl)-2-{[4-(2-oxopiperazin-1-yl)
phenyl]amino}imidazo[1,2-a]pyrimido[5,4-e]pyrimi-
din-5(6H)-one The title compound (0.1 g) was prepared as described in Example 109B, substituting Example 109A with Example 174A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 3.55 (d, 2H) 3.90 (d, 4H) 7.13 (d, J=1.70 Hz, 1H) 7.38 (d, J=8.82 Hz, 2H) 7.58-7.71 (m, 1H) 7.73-7.80 (m, 2H) 7.91 (s, 3H) 9.19 (s, 1H) 9.68 (s, 2H) 10.96 (s, 1H). MS (ESI$^+$) m/z 521.3 (M+H)$^+$.

Example 175

2-({4-[(1R,4R)-2,5-diazabicyclo[2.2.1]hept-2-yl]
phenyl}amino)-6-(2,6-dichlorophenyl)imidazo[1,2-
a]pyrimido[5,4-e]pyrimidin-5(6H)-one

Example 175A tert-butyl (1R,4R)-5-(4-{[6-(2,6-dichlorophenyl)-5-
oxo-5,6-dihydroimidazo[1,2-a]pyrimido[5,4-e]pyri-
midin-2-yl]amino}phenyl)-2,5-diazabicyclo[2.2.1]
heptane-2-carboxylate The title compound (0.11 g) was prepared as described in Example 109A, substituting tert-butyl 7'-amino-1'H-spiro [cyclopropane-1,4'-isoquinoline]-2'(3'H)-carboxylate with (1R,4R)-tert-butyl 5-(4-aminophenyl)-2,5-diazabicyclo [2.2.1]heptane-2-carboxylate. Chromatography was performed with an Analogix 280 with an SF 12-24 column, 40% to 100% ethyl acetate/hexane gradient over 30 minutes. MS (ESI$^+$) m/z 619.3 (M+H)$^+$.

Example 175B 2-({4-[(1R,4R)-2,5-diazabicyclo[2.2.1]hept-2-yl]
phenyl}amino)-6-(2,6-dichlorophenyl)imidazo[1,2-
a]pyrimido[5,4-e]pyrimidin-5(6H)-one The title compound (0.1 g) was prepared as described in Example 109B, substituting Example 109A with Example 175A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 2.00 (d, 2H) 3.22 (d, 2H) 3.64 (d, 2H) 4.44 (d, 1H) 4.61 (d, 1H) 6.75 (d, J=8.72 Hz, 2H) 7.11 (s, 1H) 7.41-7.93 (m, 6H) 8.75 (s, 1H) 9.09 (s, 1H) 9.35 (s, 1H) 10.70 (s, 1H). MS (ESI$^+$) m/z 519.2 (M+H)$^+$.

Example 176

6-(2,6-dichlorophenyl)-2-{[4-(4-methylpiperazin-1-
yl)-3-(propan-2-yl)phenyl]amino}imidazo[1,2-a]
pyrimido[5,4-e]pyrimidin-5(6H)-one The title compound (0.05 g) was prepared as described in Example 150, substituting 1,1,2-trimethyl-1,2,3,4-tetrahydroisoquinolin-6-amine with 3-isopropyl-4-(4-methylpiperazin-1-yl)aniline, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered. $^1$H NMR (300 MHz, DMSO-d$_6$) δ 1.15-1.33 (m, 6H) 2.73-2.94 (m, 3H) 2.99-3.16 (m, 4H) 3.16-3.30 (m, 2H) 3.40-3.50 (m, 2H) 6.96-7.37 (m, 2H) 7.47-7.91 (m, 6H) 9.15 (s, 1H) 10.30 (s, 1H) 10.80 (s, 1H). MS (ESI$^+$) m/z 526.2 (M+H)$^+$.

Example 177

6-(2,6-dichlorophenyl)-2-[(1,1,2,3,3-pentamethyl-2,
3-dihydro-1H-isoindol-5-yl)amino]imidazo[1,2-a]
pyrimido[5,4-e]pyrimidin-5(6H)-one The title compound (0.062 g) was prepared as described in Example 150, substituting 1,1,2-trimethyl-1,2,3,4-tetrahydroisoquinolin-6-amine with 3-isopropyl-4-(4-methylpiperazin-1-yl)aniline, and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes and filtered to provide the title compound. $^1$H NMR (300 MHz, DMSO-d$_6$) δ 1.55 (d, 6H) 1.82 (d, 6H) 2.86 (d, 3H) 7.14 (d, J=1.98 Hz, 1H) 7.42-7.53 (m, 1H) 7.58-7.69 (m, 1H) 7.75 (t, J=8.13 Hz, 4H) 7.82-7.98 (m, 1H) 9.20 (s, 1H) 9.96 (d, J=3.97 Hz, 1H) 11.00 (s, 1H). MS (ESI$^+$) m/z 534.2 (M+H)$^+$.

Example 178

6-(2,6-dichlorophenyl)-2-[(1,1,2-trimethyl-2,3-dihy-
dro-1H-isoindol-5-yl)amino]imidazo[1,2-a]pyrimido
[5,4-e]pyrimidin-5(6H)-one The title compound (0.045 g) was prepared as described in Example 150, substituting 1,1,2-trimethyl-1,2,3,4-tetrahydroisoquinolin-6-amine with 1,1,2-trimethylisoindolin-5- amine and purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 1.27-1.54 (m, 3H) 1.63-1.85 (m, 3H) 2.81-3.00 (m, 3H) 4.48-4.68 (m, 1H) 4.68-4.86 (m, 1H) 7.09-7.17 (m, 1H) 7.45 (d, J=8.48 Hz, 1H) 7.57-7.72 (m, 1H) 7.71-7.81 (m, 3H) 7.90 (d, J=12.21 Hz, 2H) 9.20 (s, 1H) 10.78 (s, 1H) 11.00 (s, 1H). MS (ESI$^+$) m/z 506.0 (M+H)$^+$.

Example 179

(3aS,10aS)-8-{[6-(2,6-dichlorophenyl)-5-oxo-5,6-dihydroimidazo[1,2-a]pyrimido[5,4-e]pyrimidin-2-yl]amino}-2,3,3a,5,10,10a-hexahydropyrrolo[3,4-c][1]benzazepin-4(1H)-one

Example 179A tert-butyl (3aS,10aS)-8-{[6-(2,6-dichlorophenyl)-5-oxo-5,6-dihydroimidazo[1,2-a]pyrimido[5,4-e]pyrimidin-2-yl]amino}-4-oxo-3,3a,4,5,10,10a-hexahydropyrrolo[3,4-c][1]benzazepine-2(1H)-carboxylate The title compound (0.1 g) was prepared as described in Example 109A, substituting tert-butyl 7'-amino-1'H-spiro[cyclopropane-1,4'-isoquinoline]-2'(3'H)-carboxylate with (3aS,10aS)-tert-butyl 8-amino-4-oxo-3,3a,4,5,10,10a-hexahydrobenzo[b]pyrrolo[3,4-e]azepine-2(1H)-carboxylate. The crude material was triturated with ethyl acetate to provide the title compound. MS (ESI$^+$) m/z 647.4 (M+H)$^+$.

Example 179B (3aS,10aS)-8-{[6-(2,6-dichlorophenyl)-5-oxo-5,6-dihydroimidazo[1,2-a]pyrimido[5,4-e]pyrimidin-2-yl]amino}-2,3,3a,5,10,10a-hexahydropyrrolo[3,4-c][1]benzazepin-4(1H)-one The title compound (0.09 g) was prepared as described in Example 109B, substituting Example 109A with Example 179A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 2.57-2.80 (m, 1H) 2.81-3.17 (m, 3H) 3.18-3.47 (m, 2H) 3.46-3.66 (m, 2H) 6.90-7.31 (m, 2H) 7.42-8.03 (m, 6H) 8.92-9.31 (m, 3H) 9.92 (s, 1H) 10.85 (s, 1H). MS (ESI$^+$) m/z 547.2 (M+H)$^+$.

Example 180

6-(2,6-dichlorophenyl)-2-{[4-(6-oxo-1,4,5,6-tetrahydropyridazin-3-yl)phenyl]amino}imidazo[1,2-a]pyrimido[5,4-e]pyrimidin-5(6H)-one The title compound (0.095 g) was prepared as described in Example 150, substituting 1,1,2-trimethyl-1,2,3,4-tetrahydroisoquinolin-6-amine with 6-(4-aminophenyl)-4,5-dihydropyridazin-3(2H)-one. The crude material was triturated with ethyl acetate to provide the title compound. $^1$H NMR (300 MHz, DMSO-$d_6$) δ 2.38-2.48 (m, 2H) 2.97 (t, J=8.13 Hz, 2H) 7.13 (d, J=1.59 Hz, 1H) 7.45-8.12 (m, 8H) 9.20 (s, 1H) 10.90 (s, 1H) 11.03 (s, 1H). MS (ESI$^+$) m/z 642.93 (M+H)$^+$.

Example 181

2-(1,2,3-benzothiadiazol-5-ylamino)-6-(2,6-dichlorophenyl)imidazo[1,2-a]pyrimido[5,4-e]pyrimidin-5(6H)-one The title compound (0.04 g) was prepared as described in Example 150, substituting 1,1,2-trimethyl-1,2,3,4-tetrahydroisoquinolin-6-amine with benzo[d][1,2,3]thiadiazol-5-amine. The crude material was triturated with ethyl acetate to provide the title compound. $^1$H NMR (500 MHz, DMSO-$d_6$) δ 7.17 (d, J=1.53 Hz, 1H) 7.59-7.70 (m, 1H) 7.78 (d, J=8.24 Hz, 2H) 7.88 (s, 1H) 8.08-8.32 (m, 1H) 8.43 (d, J=8.85 Hz, 1H) 9.27 (d, J=20.75 Hz, 2H) 11.32 (s, 1H). MS (ESI$^+$) m/z 480.9 (M+H)$^+$.

Example 182

2-(1,3-benzothiazol-6-ylamino)-6-(2,6-dichlorophenyl)imidazo[1,2-a]pyrimido[5,4-e]pyrimidin-5(6H)-one The title compound (0.035 g) was prepared as described in Example 150, substituting 1,1,2-trimethyl-1,2,3,4-tetrahydroisoquinolin-6-amine with 3-chloro-4-(4-methylpiperazin-1-yl)aniline. Chromatography was performed with an Analogix 280 with an SF 12-24 column, 50% to 100% ethyl acetate/hexane gradient over 30 minutes. $^1$H NMR (300 MHz, DMSO-$d_6$) δ 7.14 (d, J=1.98 Hz, 1H) 7.54-7.71 (m, 1H) 7.70-7.84 (m, 2H) 7.92 (d, J=7.93 Hz, 2H) 8.12 (d, J=8.73 Hz, 1H) 8.71 (s, 1H) 9.22 (s, 1H) 9.32 (s, 1H) 11.11 (s, 1H). MS (ESI$^+$) m/z 480.1 (M+H)$^+$.

Example 183

2-({4-[bis(2-methoxyethyl)amino]phenyl}amino)-6-(2-chlorophenyl)imidazo[1,2-a]pyrimido[5,4-e]pyrimidin-5(6H)-one

Example 183A

N,N-bis(2-methoxyethyl)-4-nitroaniline 1-fluoro-4-nitrobenzene (133 mg, 0.94 mmol), bis(2-methoxyethyl)amine (125 mg, 0.94 mmol) and potassium carbonate (143 mg, 1.04 mmol) were stirred in DMSO (2 mL) at 70° C. for 24 hours. The reaction mixture was poured into water, and the aqueous phase was extracted with ethyl acetate (2×25 mL). The combined organic extracts were washed with brine, dried over magnesium sulfate, filtered and concentrated to provide the title compound. MS (ESI$^+$) m/e 255.1 (M+H)$^+$.

Example 183B

N$^1$,N$^1$-bis(2-methoxyethyl)benzene-1,4-diamine

Example 183A (130 mg, 0.51 mmol) in ethanol (1.5 mL) was added to 5% Pd/C (wet, 13 mg) in a 10 mL carousel pressure bottle. The mixture was stirred under 30 psi of hydrogen at 50° C. for 1 hour. The mixture was filtered

Example 183C 2-({4-[bis(2-methoxyethyl)amino]phenyl}amino)-6-(2-chlorophenyl)imidazo[1,2-a]pyrimido[5,4-e]pyrimidin-5(6H)-one Example 1E (40 mg, 0.11 mmol), Example 183B (25 mg, 0.11 mmol) and trifluoroacetic acid (1 μL) were stirred in acetonitrile (3 mL) at room temperature for 24 hours. The reaction mixture was concentrated. The crude mixture was purified by RP-HPLC (Sunfire 50×250 mm 5 μM) using a gradient elution of 10/90 acetonitrile/0.1% TFA in water to 50/50 over 30 minutes at 254 nm to provide the title compound as the TFA salt. $^1$H NMR (400 MHz, DMSO-d$_6$, 90° C.) δ 10.14 (br s, 1H), 9.01 (s, 1H), 7.71 (m, 1H), 7.65 (m, 1H), 7.54 (m, 5H), 7.02 s, 1H)-6.79 (br, d, 2H), 3.57 (m, 8H), 3.29 (s, 6H). MS (ESI$^+$) m/e 520.1 (M+H)$^+$.

Example 184

6-(2-chlorophenyl)-2-[(3-cyclopropyl-2,3,4,5-tetrahydro-1H-3-benzazepin-7-yl)amino]imidazo[1,2-a]pyrimido[5,4-e]pyrimidin-5(6H)-one The title compound was prepared as described in Example 130B, substituting example 130A with 3-cyclopropyl-2,3,4,5-tetrahydro-1H-benzo[d]azepin-7-amine. No aqueous workup was used before HPLC. $^1$H NMR (400 MHz, CD$_3$OD) δ 1.19-1.00 (m, 4H), 2.98-2.89 (m, 1H), 3.39-3.04 (m, 6H), 4.00-3.88 (m, 2H), 7.06 (d, J=1.9 Hz, 1H), 7.33-7.26 (m, 1H), 7.63-7.53 (m, 3H), 7.71-7.66 (m, 3H), 7.84 (s, 1H), 9.14 (s, 1H). MS (ESI$^+$) m/z 498.2 (M+H)$^+$.

Example 185

6-(2-chlorophenyl)-2-{[3-(2,2-difluoroethyl)-2,3,4,5-tetrahydro-1H-3-benzazepin-7-yl]amino}imidazo[1,2-a]pyrimido[5,4-e]pyrimidin-5(6H)-one The title compound was prepared as described in Example 130B, substituting Example 130A with 3-(2,2-difluoroethyl)-2,3,4,5-tetrahydro-1H-benzo[d]azepin-7-amine. No aqueous workup was used before HPLC. $^1$H NMR (400 MHz, CD$_3$OD) δ 3.32-3.21 (m, 5H), 3.67-3.50 (bs, 4H), 3.84 (td, J=14.7, 3.7 Hz, 2H), 7.06 (d, J=1.9 Hz, 1H), 7.33-7.26 (m, 1H), 7.62-7.53 (m, 3H), 7.73-7.65 (m, 3H), 7.84 (d, J=0.7 Hz, 1H), 9.15 (s, 1H). MS (ESI$^+$) m/z 522.2 (M+H)$^+$.

Example 186

6-(2-chloro-4,6-difluorophenyl)-2-{[4-(4-methylpiperazin-1-yl)phenyl]amino}imidazo[1,2-a]pyrimido[5,4-e]pyrimidin-5(6H)-one

Example 186A 4-(2-chloro-4,6-difluorophenyl)-8-methylsulfanyl-4H-3,4,7,9,9b-pentaaza-cyclopenta[a]naphthalen-5-one The title compound was prepared following the general procedures described in Examples 1A through Example 1D, substituting 1-chloro-2-isocyanatobenzene with 1-chloro-3,5-difluoro-2-isocyanatobenzene in Example 1A with a shortened reaction time (2 hrs). Common techniques were used to modify the reaction workup and purification processes. Modifications to Example 1A: during the workup the aqueous layer was acidified and the product precipitated out. Modifications to Example 1B: the desired product was purified on a silica column using the ISCO Companion flash system eluting with CH$_2$Cl$_2$/hexane (90:10 to 95:5). Modifications to Example 1D: the desired product was isolated through trituration with ethyl acetate followed by washing with aqueous NaHCO$_3$ and diethyl ether.

Example 186B 6-(2-chloro-4,6-difluorophenyl)-2-{[4-(4-methylpiperazin-1-yl)phenyl]amino}imidazo[1,2-a]pyrimido[5,4-e]pyrimidin-5(6H)-one The title compound was prepared as described in Example 123B, substituting Example 123A with Example 186A. $^1$H NMR (400 MHz, CD$_3$OD) δ 2.98 (s, 3H), 3.19-3.00 (m, 2H), 3.33-3.27 (m, 2H), 3.67-3.59 (m, 2H), 3.89-3.82 (m, 2H), 7.13-7.03 (m, 3H), 7.33 (td, J=9.1, 2.8 Hz, 1H), 7.44 (dt, J=8.3, 2.2 Hz, 1H), 7.94-7.62 (m, 3H), 9.14-9.08 (m, 1H). MS (ESI$^+$) m/z 523.2 (M+H)$^+$.

Example 187

6-(2-chloro-4,6-difluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one The title compound was prepared as described in Example 123B, substituting Example 123A and 4-(4-methylpiperazin-1-yl)aniline with Example 186A and 2,4,4-trimethyl-1,2,3,4-tetrahydroisoquinolin-7-amine, respectively. $^1$H NMR (400 MHz, CD$_3$OD) δ 1.48 (s, 6H), 3.12 (s, 3H), 3.43-3.30 (m, 1H), 3.67-3.45 (m, 1H), 4.63-4.38 (m, 2H), 7.10 (d, J=1.8 Hz, 1H), 7.38-7.27 (m, 1H), 7.49-7.41 (m, 1H), 7.57 (d, J=8.2 Hz, 1H), 7.82-7.68 (m, 2H), 7.89 (d, J=1.5 Hz, 1H), 9.18 (s, 1H). MS (ESI$^+$) m/z 522.1 (M+H)$^+$.

Example 188

6-(2-chloro-4,6-difluorophenyl)-2-{[2-(dimethylamino)-2,3-dihydro-1H-inden-5-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 186A and N$^2$,N$^2$-dimethyl-2,3-dihydro-1H-indene-2,5-diamine, respectively. $^1$H NMR (400 MHz, CD$_3$OD) δ 2.96 (s, 6H), 3.32-3.18 (m, 2H), 3.56-3.40 (m, 2H), 4.22-4.14 (m, 1H), 7.08 (d, J=1.9 Hz, 1H), 7.37-7.28 (m, 2H), 7.46-7.43 (m, 1H), 7.60 (bs, 1H), 7.87-7.77 (m, 2H), 9.13 (s, 1H). MS (ESI$^+$) m/z 508.1 (M+H)$^+$.

Example 189

6-(2-chlorophenyl)-2-[(4-{[3-(morpholin-4-yl)propyl]amino}phenyl)amino]imidazo[1,2-a]pyrimido[5,4-e]pyrimidin-5(6H)-one

Example 189A

N-(3-morpholinopropyl)-4-nitroaniline

The title compound was prepared as described in Example 183A, substituting N-(3-aminopropyl)morpholine for bis(2-methoxyethyl)amine. MS (ESI$^+$) m/e 266.1 (M+H)$^+$.

Example 189B

N¹-(3-morpholinopropyl)benzene-1,4-diamine

The title compound was prepared as described in Example 183B substituting Example 189A for Example 183A. MS (ESI⁺) m/e 236.2 (M+H)⁺.

Example 189C 6-(2-chlorophenyl)-2-[(4-{[3-(morpholin-4-yl)propyl]amino}phenyl)amino]imidazo[1,2-a]pyrimido[5,4-e]pyrimidin-5(6H)-one The title compound was prepared as described in Example 183C substituting Example 189B for Example 183B. ¹H NMR (400 MHz, DMSO-d₆, 90° C.) δ 10.11 (s, 1H), 9.01 (s, 1H), 7.67 (m, 2H), 7.53 (m, 5H), 7.02 (s, 1H), 6.68 (d, 2H), 3.84 (m, 4H), 3.24 (m, 4H), 3.18 (m, 4H), 1.98 (m, 2H). MS (ESI⁺) m/e 531.2 (M+H)⁺.

Example 190

6-(2-chlorophenyl)-2-({4-[4-(pyrrolidin-1-yl)piperidin-1-yl]phenyl}amino)imidazo[1,2-a]pyrimido[5,4-e]pyrimidin-5(6H)-one

Example 190A 1-(4-nitrophenyl)-4-(pyrrolidin-1-yl)piperidine

The title compound was prepared as described in Example 183A substituting 4-(1-pyrrolidinyl)piperidine for bis(2-methoxyethyl)amine. MS (ESI⁺) m/e 276.1 (M+H)⁺.

Example 190B 4-(4-(pyrrolidin-1-yl)piperidin-1-yl)aniline

The title compound was prepared as described in Example 183B substituting Example 190A for Example 183A. MS (ESI⁺) m/e 236.2 (M+H)⁺.

Example 190C 6-(2-chlorophenyl)-2-({4-[4-(pyrrolidin-1-yl)piperidin-1-yl]phenyl}amino)imidazo[1,2-a]pyrimido[5,4-e]pyrimidin-5(6H)-one The title compound was prepared as described in Example 183C substituting Example 190B for Example 183B. ¹H NMR (400 MHz, DMSO-d₆, 90° C.) δ 10.25 (br s, 1H), 9.05 (s, 1H), 7.60 (m, 5H), 7.41 (m, 1H), 7.05 (m, 4H), 3.92 (m, 1H), 3.80 (br d, 2H), 2.81 (m, 3H), 1.93 (m, 11H). MS (ESI⁺) m/e 541.2 (M+H)⁺.

Example 191

6-(2-chlorophenyl)-2-({4-[4-(dimethylamino)piperidin-1-yl]phenyl}amino)imidazo[1,2-a]pyrimido[5,4-e]pyrimidin-5(6H)-one

Example 191A

N,N-dimethyl-1-(4-nitrophenyl)piperidin-4-amine

The title compound was prepared as described in Example 183A substituting 4-(dimethylamino)piperidine for bis(2-methoxyethyl)amine. MS (ESI⁺) m/e 250.1 (M+H)⁺.

Example 191B 1-(4-aminophenyl)-N,N-dimethylpiperidin-4-amine

The title compound was prepared as described in Example 183B substituting Example 191A for Example 183A. MS (ESI⁺) m/e 220.1 (M+H)⁺.

Example 191C 6-(2-chlorophenyl)-2-({4-[4-(dimethylamino)piperidin-1-yl]phenyl}amino)imidazo[1,2-a]pyrimido[5,4-e]pyrimidin-5(6H)-one The title compound was prepared as described in Example 183C substituting Example 191B for Example 183B. ¹H NMR (400 MHz, DMSO-d₆, 90° C.) δ 10.25 (s, 1H), 9.05 (s, 1H), 7.66 (m, 4H), 7.54 (m, 3H), 7.03 (m, 3H), 3.64 (m, 2H), 3.32 (m, 2H), 2.81 (s, 6H), 2.77 (m, 1H), 2.10 (m, 2H), 1.76 (m, 2H). MS (ESI⁺) m/e 515.1 (M+H)⁺.

Example 192

6-(2-chlorophenyl)-2-[(4-{[2-(1-methylpyrrolidin-2-yl)ethyl]amino}phenyl)amino]imidazo[1,2-a]pyrimido[5,4-e]pyrimidin-5(6H)-one

Example 192A

N-(2-(1-methylpyrrolidin-2-yl)ethyl)-4-nitroaniline

The title compound was prepared as described in Example 183A substituting 2-(2-aminoethyl)-1-methylpyrrolidine for bis(2-2-methoxyethyl)amine. MS (ESI⁺) m/e 250.2 (M+H)⁺.

Example 192B

N¹-(2-(1-methylpyrrolidin-2-yl)ethyl)benzene-1,4-diamine

The title compound was prepared as described in Example 183B substituting Example 192A for Example 183A. MS (ESI⁺) m/e 220.2 (M+H)⁺.

Example 192C 6-(2-chlorophenyl)-2-[(4-{[2-(1-methylpyrrolidin-2-yl)ethyl]amino}phenyl)amino]imidazo[1,2-a]pyrimido[5,4-e]pyrimidin-5(6H)-one The title compound was prepared as described in Example 183C substituting Example 192B for Example 183B. ¹H NMR (400 MHz, DMSO-d₆, 90° C.) δ 10.11 (br s, 1H), 9.01 (s, 1H), 7.67 (m, 2H), 7.53 (m, 5H), 7.01 (m, 1H), 6.68 (m, 2H), 3.18 (m, 5H), 2.82 (s, 3H), 2.32 (m, 1H), 2.16 (m, 1H), 1.99 (m, 2H), 1.80 (m, 2H). MS (ESI⁺) m/e 515.2 (M+H)⁺.

Example 193

4-(dimethylamino)cyclohexyl 4-{[6-(2,6-dichlorophenyl)-5-oxo-5,6-dihydroimidazo[1,2-a]pyrimido[5,4-e]pyrimidin-2-yl]amino}benzoate The title compound (0.05 g) was prepared as described in Example 150, substituting 1,1,2-trimethyl-1,2,3,4-tetrahydroisoquinolin-6-amine with 4-(dimethylamino)cyclohexyl 4-aminobenzoate HCl salt, and was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 1.85 (t, 8H) 2.73 (t, 6H) 3.23 (t, 1H) 7.15 (t, J=1.98 Hz, 1H) 7.58-7.70 (m, 1H) 7.73-7.81 (m, 2H) 7.87-8.29 (m, 5H) 9.11-9.45 (m, 1H) 10.11 (s, 1H) 11.21 (s, 1H). MS (ESI$^+$) m/z 591.2 (M+H)$^+$.

Example 194

6-(2,6-dichlorophenyl)-2-(1H-indazol-5-ylamino) imidazo[1,2-a]pyrimido[5,4-e]pyrimidin-5(6H)-one The title compound (0.095 g) was prepared as described in Example 109A, substituting tert-butyl 7'-amino-1'H-spiro [cyclopropane-1,4'-isoquinoline]-2'(3'H)-carboxylate with tert-butyl 5-amino-1H-indazole-1-carboxylate. Chromatography was performed on an Analogix 280 with an SF 12-24 column, 50% to 100% ethyl acetate/hexane gradient over 30 minutes. The crude compound was dissolved in dichloromethane and treated with excess TFA. The mixture was stirred for 30 minutes, and concentrated. The TFA salt was dissolved in methanol, treated with 2M HCl in diethyl ether for 30 minutes, diluted with ether, filtered, and dried under high-vac. $^1$H NMR (300 MHz, DMSO-$d_6$) δ 7.12 (d, J=1.98 Hz, 1H) 7.36-8.02 (m, 6H) 7.99-8.48 (m, 2H) 9.16 (s, 1H) 10.92 (s, 1H). MS (ESI$^+$) m/z 463.1 (M+H)$^+$.

Example 195

6-(2,6-dichlorophenyl)-2-({4-[(3S)-3-(propan-2-yl) piperazin-1-yl]phenyl}amino)imidazo[1,2-a]pyrimido[5,4-e]pyrimidin-5(6H)-one Example 195A tert-butyl (2S)-4-(4-{[6-(2,6-dichlorophenyl)-5-oxo-5,6-dihydroimidazo[1,2-a]pyrimido[5,4-e]pyrimidin-2-yl]amino}phenyl)-2-(propan-2-yl)piperazine-1-carboxylate The title compound (0.06 g) was prepared as described in Example 109A, substituting tert-butyl 7'-amino-1'H-spiro [cyclopropane-1,4'-isoquinoline]-2'(3'H)-carboxylate with (S)-tert-butyl 4-(4-aminophenyl)-2-isopropylpiperazine-1-carboxylate. Chromatography was performed on an Analogix 280 with an SF 12-24 column, 50% to 100% ethyl acetate/ hexane gradient over 30 minutes to give a yellow filprovide the title compound. MS (ESI$^+$) m/z 649.27 (M+H)$^+$.

Example 195B 6-(2,6-dichlorophenyl)-2-({4-[(3S)-3-(propan-2-yl) piperazin-1-yl]phenyl}amino)imidazo[1,2-a]pyrimido[5,4-e]pyrimidin-5(6H)-one The title compound (0.05 g) was prepared as described in Example 109B, substituting Example 109A with Example 195A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 0.95-1.20 (m, 6H) 1.85-2.13 (m, 1H) 2.66-3.27 (m, 4H) 3.25-3.46 (m, 1H) 3.77 (d, J=13.09 Hz, 2H) 7.12 (d, J=1.59 Hz, 3H) 7.36-8.04 (m, 6H) 9.12 (s, 3H) 10.78 (s, 1H). MS (ESI$^+$) m/z 549.2 (M+H)$^+$.

Example 196

6-(2,6-dichlorophenyl)-2-[(4-{1-[1-dimethylamino)-3-methylbutyl]cyclobutyl}phenyl)amino]imidazo[1,2-a]pyrimido[5,4-e]pyrimidin-5(6H)-one The title compound (0.06 g) was prepared as described in Example 150, substituting 1,1,2-trimethyl-1,2,3,4-tetrahydroisoquinolin-6-amine with 4-(1-(1-(dimethylamino)-3-methylbutyl)cyclobutyl)aniline. Chromatography was performed with an Analogix280 with an SF 12-24 column, 0% to 10% methanol/dichloromethane gradient over 40 minutes. The crude material was dissolved in methanol, treated with 2M HCl in diethyl ether, and filtered to provide the title compound. $^1$H NMR (300 MHz, DMSO-$d_6$) δ 1.01 (t, J=5.75 Hz, 6H) 1.27-1.56 (m, 2H) 1.60-2.03 (m, 3H) 2.15 (d, J=4.76 Hz, 3H) 2.34 (t, J=7.34 Hz, 2H) 2.61 (t, J=7.74 Hz, 2H) 2.73-2.88 (m, 3H) 3.75 (t, J=5.75 Hz, 1H) 7.14 (s, 1H) 7.47-7.70 (m, 3H) 7.71-7.82 (m, 2H) 7.92 (d, J=1.59 Hz, 3H) 9.00 (s, 1H) 9.20 (s, 1H) 10.98 (s, 1H). MS (ESI$^+$) m/z 589.9 (M+H)$^+$.

Example 197

6-(2,6-dichlorophenyl)-2-({4-[4-methyl-2-(methylamino)-1,3-thiazol-5-yl]phenyl}amino)imidazo[1,2-a]pyrimido[5,4-e]pyrimidin-5(6H)-one The title compound (0.09 g) was prepared as described in Example 150, substituting 1,1,2-trimethyl-1,2,3,4-tetrahydroisoquinolin-6-amine with 5-(4-aminophenyl)-N,4-dimethylthiazol-2-amine. The crude material was triturated with dichloromethane to provide the title compound. $^1$H NMR (300 MHz, DMSO-$d_6$) δ 2.19-2.31 (m, 3H) 2.71-2.91 (m, 3H) 7.12 (d, J=1.59 Hz, 1H) 7.33-7.53 (m, 3H) 7.58-7.69 (m, 1H) 7.72-7.80 (m, 2H) 7.89 (s, 3H) 9.18 (s, 1H) 10.94 (s, 1H). MS (ESI$^+$) m/z 549.1 (M+H)$^+$.

Example 198

6-(2,6-dichlorophenyl)-2-{[6-(piperazin-1-yl)pyridin-3-yl]amino}imidazo[1,2-a]pyrimido[5,4-e]pyrimidin-5(6H)-one Example 198A tert-butyl 4-(5-{[6-(2,6-dichlorophenyl)-5-oxo-5,6-dihydroimidazo[1,2-a]pyrimido[5,4-e]pyrimidin-2-yl]amino}pyridin-2-yl)piperazine-1-carboxylate The title compound (0.095 g) was prepared as described in Example 109A, substituting tert-butyl 7'-amino-1'H-spiro [cyclopropane-1,4'-isoquinoline]-2'(3'H)-carboxylate with tert-butyl 4-(5-aminopyridin-2-yl)piperazine-1-carboxylate. Chromatography was performed with an Analogix 280 with an SF 12-24 column, 40% to 100% ethyl acetate/hexane gradient over 30 minutes to provide the title compound. MS (ESI+) m/z 608.31 (M+H)+.

Example 198B 6-(2,6-dichlorophenyl)-2-{[6-(piperazin-1-yl)pyridin-3-yl]amino}imidazo[1,2-a]pyrimido[5,4-e]pyrimidin-5(6H)-one The title compound (0.09 g) was prepared as described in Example 109B, substituting Example 109A with Example 198A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 2.93-3.47 (m, 4H) 3.82 (s, 4H) 6.89-7.36 (m, 2H) 7.43-8.00 (m, 5H) 8.17 (s, 1H) 8.73 (s, 1H) 8.98-9.47 (m, J=32.13 Hz, 3H) 10.93 (s, 1H). MS (ESI$^+$) m/z 508.1 (M+H)$^+$.

Example 199

6-(2,6-dichlorophenyl)-2-(1H-indazol-6-ylamino)imidazo[1,2-a]pyrimido[5,4-e]pyrimidin-5(6H)-one

Example 199A tert-butyl 6-{[6-(2,6-dichlorophenyl)-5-oxo-5,6-dihydroimidazo[1,2-a]pyrimido[5,4-e]pyrimidin-2-yl]amino}-1H-indazole-1-carboxylate The title compound (0.08 g) was prepared as described in Example 109A, substituting tert-butyl 7'-amino-1'H-spiro[cyclopropane-1,4'-isoquinoline]-2'(3'H)-carboxylate with tert-butyl 6-amino-1H-indazole-1-carboxylate. Chromatography was performed with an Analogix 280 with an SF 12-24 column, 40% to 100% ethyl acetate/hexane gradient over 30 minutes to provide the title compound. MS (ESI$^+$) m/z 563.2 (M+H)$^+$.

Example 199B 6-(2,6-dichlorophenyl)-2-(1H-indazol-6-ylamino)imidazo[1,2-a]pyrimido[5,4-e]pyrimidin-5(6H)-one The title compound (0.08 g) was prepared as described in Example 109B, substituting Example 109A with Example 199A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 7.19 (s, 1H) 7.43 (dd, J=8.92, 1.78 Hz, 1H) 7.57-7.70 (m, 1H) 7.71-7.82 (m, 3H) 7.88-8.13 (m, 2H) 8.47 (s, 1H) 9.21 (s, 1H) 11.07 (s, 1H). MS (ESI$^+$) m/z 463.1 (M+H)$^+$.

Example 200

(1R)-octahydro-2H-quinolizin-1-yl 4-{[6-(2,6-dichlorophenyl)-5-oxo-5,6-dihydroimidazo[1,2-a]pyrimido[5,4-e]pyrimidin-2-yl]amino}benzoate The title compound (0.055 g) was prepared as described in Example 150, substituting 1,1,2-trimethyl-1,2,3,4-tetrahydroisoquinolin-6-amine with (1R)-octahydro-1H-quinolizin-1-yl 4-aminobenzoate, HCl salt and purified with an Analogix 280 with an SF 12-24 column, 0% to 6% methanol/dichloromethane gradient over 30 minutes. The crude material was dissolved in methanol, treated with 2M HCl in diethyl ether for 20 minutes, and filtered to provide the title compound. $^1$H NMR (300 MHz, DMSO-$d_6$) δ 1.35-2.12 (m, 10H) 2.10-2.33 (m, 1H) 2.88-3.13 (m, 2H) 3.41-3.53 (m, 2H) 4.87-5.13 (m, 1H) 7.15 (d, J=1.70 Hz, 1H) 7.59-7.71 (m, 1H) 7.73-7.81 (m, 2H) 8.06 (s, 4H) 9.25 (s, 1H) 10.36 (s, 1H) 11.23 (s, 1H). MS (ESI$^+$) m/z 604.2 (M+H)$^+$.

Example 201

2-[cyclopropyl(methyl)amino]ethyl 4-{[6-(2,6-dichlorophenyl)-5-oxo-5,6-dihydroimidazo[1,2-a]pyrimido[5,4-e]pyrimidin-2-yl]amino}benzoate The title compound (0.055 g) was prepared as described in Example 150, substituting 1,1,2-trimethyl-1,2,3,4-tetrahydroisoquinolin-6-amine with 2-(cyclopropyl(methyl)amino)ethyl 4-aminobenzoate, and was purified with an Analogix 280 with an SF 12-24 column, 0% to 7% methanol/dichloromethane gradient over 30 minutes. The crude material was dissolved in methanol, treated with 2M HCl in diethyl ether for 20 minutes, and filtered to provide the title compound. $^1$H NMR (300 MHz, DMSO-$d_6$) δ 0.69-1.23 (m, 4H) 2.83-3.12 (m, 4H) 3.55-3.81 (m, 2H) 4.55-4.77 (m, 2H) 7.16 (s, 1H) 7.49-7.88 (m, 3H) 7.88-8.27 (m, 5H) 9.26 (s, 1H) 10.09 (s, 1H) 11.23 (s, 1H). MS (ESI$^+$) m/z 564.0 (M+H)$^+$.

Example 202

6-(2,6-dichlorophenyl)-2-[(4-{[(1R,5S)-7-ethyl-3,7-diazabicyclo[3.3.1]non-3-yl]carbonyl}phenyl)amino]imidazo[1,2-a]pyrimido[5,4-e]pyrimidin-5(6H)-one The title compound (0.065 g) was prepared as described in Example 150, substituting 1,1,2-trimethyl-1,2,3,4-tetrahydroisoquinolin-6-amine with (4-aminophenyl)((1R,5S)-7-ethyl-3,7-diazabicyclo[3.3.1]nonan-3-yl)methanone, and was purified with an Analogix 280 with an SF 12-24 column, 0% to 7% methanol/dichloromethane gradient over 30 minutes. The crude material was dissolved in methanol, treated with 2M HCl in diethyl ether for 20 minutes, and filtered to provide the title compound. $^1$H NMR (300 MHz, DMSO-$d_6$) δ 1.20-1.39 (m, 3H) 1.60-1.98 (m, 2H) 2.12-2.41 (m, 2H) 3.14 (d, 7H) 3.68 (d, 2H) 4.03 (d, 2H) 7.15 (d, J=1.59 Hz, 1H) 7.32-8.11 (m, 7H) 8.30 (d, J=11.50 Hz, 1H) 9.22 (s, 1H) 11.08 (s, 1H). MS (ESI$^+$) m/z 603.1 (M+H)$^+$.

Example 203

6-(2-chlorophenyl)-2-{[3,5-difluoro-4-(piperazin-1-yl)phenyl]amino}imidazo[1,2-a]pyrimido[5,4-e]pyrimidin-5(6H)-one

Example 203A tert-butyl 4-(2,6-difluoro-4-nitrophenyl)piperazine-1-carboxylate The title compound was prepared as described in Example 183A substituting 3,4,5-trifluoronitrobenzene for 1-fluoro-4-nitrobenzene and 1-boc-piperazine for bis(2-methoxyethyl)amine. MS (ESI$^+$) m/e 344.1 (M+H)$^+$.

Example 203B tert-butyl 4-(4-amino-2,6-difluorophenyl)piperazine-1-carboxylate The title compound was prepared as described in Example 183B substituting Example 203A for Example 183A. MS (ESI$^+$) m/e 314.1 (M+H)$^+$.

Example 203C 6-(2-chlorophenyl)-2-{[3,5-difluoro-4-(piperazin-1-yl)phenyl]amino}imidazo[1,2-a]pyrimido[5,4-e]pyrimidin-5(6H)-one Example 1E (40 mg, 0.11 mmol) and Example 203B (41 mg, 0.13 mmol) were stirred in acetonitrile (3 mL) at room temperature for 24 hours. The reaction mixture was concentrated, and dissolved in 4 mL 1:1 TFA:dichloromethane. After 18 hours, the reaction was concentrated and purified by RP-HPLC (Sunfire 50×250 mm 5 μM) using a gradient elution of 5/95 acetonitrile/0.1% TFA in water to 40/60 over 30 minutes at 254 nm to provide the title compound as the TFA salt. $^1$H NMR (400 MHz, DMSO-$d_6$, 90° C.) δ 10.67 (s, 1H), 9.16 (s, 1H), 7.67 (m, 2H), 7.57 (m, 5H), 7.07 (s, 1H), 3.32 (m, 4H), 3.22 (m, 4H). MS (ESI$^+$) m/e 509.1 (M+H)$^+$.

Example 204

6-(2-chlorophenyl)-2-({4-[(8aR)-hexahydropyrrolo[1,2-a]pyrazin-2(1H)-yl]phenyl}amino)imidazo[1,2-a]pyrimido[5,4-e]pyrimidin-5(6H)-one

Example 204A (R)-2-(4-nitrophenyl)octahydropyrrolo[1,2-a]pyrazine

The title compound was prepared as described in Example 183A substituting (R)-1,4-diazabicyclo[4.3.0]nonane for bis(2-methoxyethyl)amine. MS (ESI$^+$) m/e 248.2 (M+H)$^+$.

Example 204B (R)-4-(hexahydropyrrolo[1,2-a]pyrazin-2(1H)-yl)aniline

The title compound was prepared as described in Example 183B substituting Example 204A for Example 183A. MS (ESI$^+$) m/e 218.0 (M+H)$^+$.

Example 204C 6-(2-chlorophenyl)-2-({4-[(8aR)-hexahydropyrrolo[1,2-a]pyrazin-2(1H)-yl]phenyl}amino)imidazo[1,2-a]pyrimido[5,4-e]pyrimidin-5(6H)-one The title compound was prepared as described in Example 183C substituting Example 204B for Example 183B. $^1$H NMR (400 MHz, DMSO-$d_6$, 90° C.) δ 10.28 (s, 1H), 9.05 (s, 1H), 7.70 (m, 4H), 7.55 (m, 3H), 7.04 (m, 3H), 3.50 (m, 9H), 2.19 (m, 1H), 2.06 (m, 2H), 1.85 (m, 1H). MS (ESI$^+$) m/e 513.2 (M+H)$^+$.

Example 205

2-(2',3'-dihydro-1'H-spiro[cyclopropane-1,4'-isoquinolin]-7'-ylamino)-6-(4-hydroxyphenyl)imidazo[1,2-a]pyrimido[5,4-e]pyrimidin-5(6H)-one

Example 205A 3-(4-(allyloxy)phenyl)-7-(methylthio)pyrimido[4,5-d]pyrimidine-2,4(1H,3H)-dione The title compound (0.95 g) was prepared as described in Example 1A, substituting 1-chloro-2-isocyanatobenzene with 1-(allyloxy)-4-isocyanatobenzene. The solid material in the workup was filtered to provide the title compound. MS (ESI$^+$) m/z 343.2 (M+H)$^+$.

Example 205B 3-(4-(allyloxy)phenyl)-2-chloro-7-(methylthio)pyrimido[4,5-d]pyrimidin-4(3H)-one The title compound (0.97 g) was prepared as described in Example 1B, substituting Example 1A with Example 205A. MS (ESI$^+$) m/z 361.19 (M+H)$^+$.

Example 205C 3-(4-(allyloxy)phenyl)-2-(2,2-dimethoxyethylamino)-7-(methylthio)pyrimido[4,5-d]pyrimidin-4(3H)-one The title compound (1 g) was prepared as described in Example 1C, substituting Example 1B with Example 205B. MS (ESI$^+$) m/z 430.28 (M+H)$^+$.

Example 205D 2-(methylsulfanyl)-6-[4-(prop-2-en-1-yloxy)phenyl]imidazo[1,2-a]pyrimido[5,4-e]pyrimidin-5(6H)-one The title compound (0.975 g) was prepared as described in Example 1D, substituting Example 1C with Example 205C. MS (ESI$^+$) m/z 366.1 (M+H)$^+$.

Example 205E 2-(methylsulfinyl)-6-[4-(prop-2-en-1-yloxy)phenyl]imidazo[1,2-a]pyrimido[5,4-e]pyrimidin-5(6H)-one The title compound (0.95 g) was prepared as described in Example 1E, substituting Example 1D with Example 205D. MS (ESI$^+$) m/z 382.2 (M+H)$^+$.

Example 205F tert-butyl 7'-({5-oxo-6-[4-(prop-2-en-1-yloxy)phenyl]-5,6-dihydroimidazo[1,2-a]pyrimido[5,4-e]pyrimidin-2-yl}amino)-1'H-spiro[cyclopropane-1,4'-isoquinoline]-2'(3'H)-carboxylate To a solution of Example 205E (125 mg, 0.328 mmol) in 4 mL acetonitrile was added tert-butyl 7'-amino-1'H-spiro[cyclopropane-1,4'-isoquinoline]-2'(3'H)-carboxylate (108 mg, 0.393 mmol). The reaction was heated to 60° C. overnight, cooled, diluted with ethyl acetate, washed with saturated aqueous NaHCO$_3$, water, and brine, dried over MgSO$_4$, filtered, and concentrated. The crude material was purified by chromatography with an Analogix 280 with an SF 24-40 column, 20% to 100% ethyl acetate/hexane gradient over 30 minutes to provide the title compound. MS (ESI$^+$) m/z 592.36 (M+H)$^+$.

Example 205G 2-(2',3'-dihydro-1'H-spiro[cyclopropane-1,4'-isoquinolin]-7'-ylamino)-6-(4-hydroxyphenyl)imidazo[1,2-a]pyrimido[5,4-e]pyrimidin-5(6H)-one The title compound (0.035 g) was prepared as described in Example 54G, substituting Example 54F with Example 205F.

The crude material was purified by preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 1.11 (s, 4H) 3.19-3.34 (m, 2H) 4.45 (s, 2H) 6.90 (t, J=9.32 Hz, 3H) 7.08 (d, J=1.98 Hz, 1H) 7.20 (d, J=8.72 Hz, 2H) 7.49-7.98 (m, 3H) 9.09 (s, 1H) 9.42 (s, 2H) 10.71 (s, 1H). MS (ESI$^+$) m/z 542.1 (M+H)$^+$.

Example 206

6-(2,6-dichlorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one To a solution of Example 109B (75 mg, 0.149 mmol) in 2 mL N,N-dimethylformamide was added diisopropylethylamine (0.130 ml, 0.744 mmol) followed by methanesulfonyl chloride (0.017 ml, 0.223 mmol). The reaction mixture was stirred at room temperature overnight, then diluted with ethyl acetate. The organics were washed with saturated aqueous NaHCO$_3$, water, and brine, dried over MgSO$_4$, filtered, and concentrated. The crude material was triturated with ethyl acetate, filtered and dried over high vacuum to provide the title compound. $^1$H NMR (300 MHz, DMSO-$d_6$) δ 0.85-1.12 (m, 4H) 1.99 (s, 2H) 2.86-3.02 (m, 3H) 4.55 (s, 2H) 6.90 (d, J=8.33 Hz, 1H) 7.13 (d, J=1.59 Hz, 1H) 7.44-7.94 (m, 6H) 9.16 (s, 1H) 10.84 (s, 1H). MS (ESI$^+$) m/z 582.1 (M+H)$^+$.

Example 207

2-[(2'-acetyl-2',3'-dihydro-1'H-spiro[cyclopropane-1,4'-isoquinolin]-7'-yl)amino]-6-(2,6-dichlorophenyl)imidazo[1,2-a]pyrimido[5,4-e]pyrimidin-5(6H)-one To a solution of Example 109B (200 mg, 0.397 mmol) in 5 mL N,N-dimethylformamide was added diisopropylethylamine (0.346 ml, 1.983 mmol) followed by acetic anhydride (0.041 ml, 0.436 mmol). The reaction mixture was stirred at room temperature overnight, then diluted with ethyl acetate. The organics were washed with saturated aqueous NaHCO$_3$, water, and brine, dried over MgSO$_4$, filtered, and concentrated. The crude material was purified by chromatography was performed with an Analogix 280 with an SF 25-40 column, 0% to 4% methanol/dichloromethane gradient over 30 minutes to provide the title compound. $^1$H NMR (300 MHz, DMSO-$d_6$) δ 1.02 (d, J=8.14 Hz, 4H) 2.10 (d, J=21.70 Hz, 3H) 3.46-3.64 (m, 2H) 4.75 (s, 2H) 6.75-7.04 (m, 1H) 7.12 (s, 1H) 7.44-7.90 (m, 6H) 9.16 (s, 1H) 10.80 (s, 1H). MS (ESI$^+$) m/z 546.2 (M+H)$^+$.

Example 208

6-(2-chlorophenyl)-2-{[4-(octahydro-2H-pyrido[1,2-a]pyrazin-2-yl)phenyl]amino}imidazo[1,2-a]pyrimido[5,4-e]pyrimidin-5(6H)-one Example 208A 2-(4-nitrophenyl)octahydro-1H-pyrido[1,2-a]pyrazine The title compound was prepared as described in Example 183A substituting (+/−)-1,4-diazabicyclo[4.4.0]decane for bis(2-methoxyethyl)amine. MS (ESI$^+$) m/e 262.2 (M+H)$^+$.

Example 208B 4-(dihydro-1H-pyrido[1,2-a]pyrazin-2(6H,7H,8H,9H,9aH)-yl)aniline

The title compound was prepared as described in Example 183B substituting Example 208A for Example 183A. MS (ESI$^+$) m/e 232.1 (M+H)$^+$.

Example 208C 6-(2-chlorophenyl)-2-{[4-(octahydro-2H-pyrido[1,2-a]pyrazin-2-yl)phenyl]amino}imidazo[1,2-a]pyrimido[5,4-e]pyrimidin-5(6H)-one The title compound was prepared as described in Example 183C substituting Example 208B for Example 183B. $^1$H NMR (400 MHz, DMSO-$d_6$, 90° C.) δ 10.29 (s, 1H), 9.05 (s, 1H), 7.68 (m, 4H), 7.54 (m, 3H), 7.05 (m, 3H), 3.81 (m, 2H), 3.45 (m, 4H), 3.02 (m, 2H), 2.65 (m, 1H), 1.85 (m, 4H), 1.56 (m, 2H). MS (ESI$^+$) m/e 527.2 (M+H)$^+$.

Example 209

6-(2-chloro-6-fluorophenyl)-2-[(1,1,2-trimethyl-2,3-dihydro-1H-isoindol-5-yl)amino]imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 1,1,2-trimethylisoindolin-5-amine, respectively. An aqueous workup was done before HPLC purification to provide the title compound. $^1$H NMR (400 MHz, CD$_3$OD) δ 1.55 (s, 3H), 1.80 (s, 3H), 3.03 (s, 3H), 4.90-4.77 (m, 1H), 4.66-4.57 (m, 1H), 7.09 (d, J=1.9 Hz, 1H), 7.50-7.30 (m, 2H), 7.56-7.48 (m, 1H), 7.63 (td, J=8.4, 5.8 Hz, 1H), 7.80 (bs, 1H), 7.90 (d, J=1.9 Hz, 1H), 8.00 (s, 1H), 9.20 (s, 1H). MS (ESI$^+$) m/z 490.1 (M+H)$^+$.

Example 210

6-(2-chloro-6-fluorophenyl)-2-[(1,1,2,3,3-pentamethyl-2,3-dihydro-1H-isoindol-5-yl)amino]imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 1,1,2,3,3-pentamethyl-isoindolin-5-amine, respectively. An aqueous workup was done before HPLC purification to provide the title compound. $^1$H NMR (400 MHz, CD$_3$OD) δ 1.67 (s, 3H), 1.70 (s, 3H), 1.85 (s, 3H), 1.88 (s, 3H), 2.98 (s, 3H), 7.10 (d, J=1.9 Hz, 1H), 7.42-7.32 (m, 1H), 7.49-7.42 (m, 1H), 7.57-7.50 (m, 1H), 7.63 (td, J=8.4, 5.8 Hz, 1H), 7.87 (bs, 2H), 9.22 (s, 1H). MS (ESI+) m/z 518.1 (M+H)+.

Example 211

6-(2-chlorophenyl)-2-({4-[4-(oxetan-3-yl)piperazin-1-yl]phenyl}amino)imidazo[1,2-a]pyrimido[5,4-e]pyrimidin-5(6H)-one

Example 211A tertbenzyl 4-(piperazin-1-yl)phenylcarbamate

To a solution of tert-butyl 4-(4-aminophenyl)piperazine-1-carboxylate (2.1 g, 7.6 mmol) in dioxane (20 ml) was added $K_2CO_3$ (1.1 g, 8 mmol) followed by benzyl carbonochloridate (1.38 ml, 9.0 mmol). The mixture was stirred at room temperature for 10 minutes. The reaction was quenched with water and extracted with ethyl acetate. The organic phase was concentrated and dissolved in $CH_2Cl_2$ (20 ml) followed by the addition of trifluoroacetic acid (2 ml). The mixture was stirred at room temperature overnight. The reaction was concentrated and purified by flash chromatography (10% methanol in dichloromethane) to provide the title compound. MS (DCI/$NH_3$) m/z 312 (M+H)+.

Example 211B 4-(4-(oxetan-3-yl)piperazin-1-yl)aniline

To a solution of Example 211A (1.0 g, 3.21 mmol) in methanol (20 ml) was added oxetan-3-one (278 mg, 3.8 mmol) and the mixture was stirred at 50° C. for 3 hours. The reaction mixture was treated with $NaCNBH_3$ (248 mg, 4.0 mmol) and stirred at 50° C. for three days. The reaction mixture was quenched with water and extracted with ethyl acetate. The organic phase was concentrated and dissolved in trifluoroacetic acid (2 ml). The mixture was stirred at 50° C. overnight. The residue was purified by flash chromatography (20% methanol in dichloromethane) to provide the title compound. $^1$H NMR (300 MHz, $CD_3OD$) δ 2.41-2.57 (m, 4H), 2.98-3.09 (m, 4H), 3.47-3.65 (m, 1H), 4.62 (t, J=6.27 Hz, 2H), 4.70 (q, J=6.33 Hz, 2H), 6.64-6.75 (m, 2H), 6.77-6.90 (m, 2H). MS (DCI/$NH_3$) m/z 234 (M+H)+.

Example 211C 6-(2-chlorophenyl)-2-({4-[4-(oxetan-3-yl)piperazin-1-yl]phenyl}amino)imidazo[1,2-a]pyrimido[5,4-e]pyrimidin-5(6H)-one The title compound was prepared as described in Example 130B, substituting Example 130A with Example 211B. No aqueous workup was performed before HPLC purification. $^1$H NMR (400 MHz, $CD_3OD$) δ 3.60-3.26 (m, 8H), 4.52-4.45 (m, 1H), 4.95-4.84 (m, 4H), 7.05 (d, J=2.0 Hz, 1H), 7.13-7.08 (m, 2H), 7.61-7.53 (m, 3H), 7.84-7.66 (m, 4H), 9.09 (s, 1H). MS (ESI+) m/z 529.2 (M+H)+.

Example 212

6-(2,6-dichloro-4-fluorophenyl)-2-[(2,4,4-trimethyl-1,2,3,4-tetrahydroisoquinolin-7-yl)amino]imidazo[1,2-a]pyrimido[5,4-e]pyrimidin-5(6H)-one The title compound was prepared as described in Example 123B, substituting 4-(4-methylpiperazin-1-yl)aniline with 2,4,4-trimethyl-1,2,3,4-tetrahydroisoquinolin-7-amine. An aqueous workup was done before HPLC purification. $^1$H NMR (400 MHz, $CD_3OD$) δ 1.46 (s, 6H), 3.12 (s, 3H), 3.66-3.31 (m, 2H), 4.64-4.38 (m, 2H), 7.10 (d, J=1.8 Hz, 1H), 7.61-7.53 (m, 3H), 7.81-7.69 (m, 2H), 7.90 (d, J=1.7 Hz, 1H), 9.19 (s, 1H). MS (ESI+) m/z 538.2 (M+H)+.

Example 213

6-(2,6-dichlorophenyl)-2-[(4-oxo-1,4-dihydrocinnolin-6-yl)amino]imidazo[1,2-a]pyrimido[5,4-e]pyrimidin-5(6H)-one The title compound (0.055 g) was prepared as described in Example 150, substituting 1,1,2-trimethyl-1,2,3,4-tetrahydroisoquinolin-6-amine with 6-aminocinnolin-4(1H)-one. Chromatography was performed with an Analogix 280 with an SF 12-24 column, using a 0% to 6% methanol/dichloromethane gradient over 30 minutes. $^1$H NMR (300 MHz, DMSO-$d_6$) δ 7.19 (s, 1H) 7.51-7.85 (m, 6H) 7.94 (s, 1H) 8.19 (dd, J=9.32, 2.58 Hz, 1H) 8.85 (s, 1H) 9.23 (s, 1H) 11.24 (s, 1H). MS (ESI+) m/z 491.1 (M+H)+.

Example 214

2-{[4-(4-acetylpiperazin-1-yl)phenyl]amino}-6-(2,6-dichlorophenyl)imidazo[1,2-a]pyrimido[5,4-e]pyrimidin-5(6H)-one The title compound (0.045 g) was prepared as described in Example 109A, substituting tert-butyl 7'-amino-1'H-spiro[cyclopropane-1,4'-isoquinoline]-2'(3'H)-carboxylate with 1-(4-(4-aminophenyl)piperazin-1-yl)ethanone. Chromatography was performed with an Analogix 280 with an SF 12-24 column, 0% to 5% methanol/dichloromethane gradient over 30 minutes to provide the title compound. $^1$H NMR (300 MHz, DMSO-$d_6$) δ 2.01-2.10 (m, 3H) 3.01-3.24 (m, 4H) 3.50-3.67 (m, 4H) 6.86-7.27 (m, 3H) 7.43-7.97 (m, 6H) 9.11 (s, 1H) 10.74 (s, 1H). MS (ESI+) m/z 549.2 (M+H)+.

Example 215

6-(2,6-dichlorophenyl)-2-({4-[4-(dimethylamino)piperidin-1-yl]phenyl}amino)imidazo[1,2-a]pyrimido[5,4-e]pyrimidin-5(6H)-one The title compound (0.06 g) was prepared as described in Example 150, substituting 1,1,2-trimethyl-1,2,3,4-tetrahydroisoquinolin-6-amine with 3-chloro-4-(4-methylpiperazin-1-yl)aniline. Chromatography was performed with an Analogix 280 with an SF 12-25 column, 0% to 10% methanol/dichloromethane gradient over 30 minutes, and at 10% methanol for 30 minutes to provide the title compound. $^1$H NMR (300 MHz, DMSO-$d_6$) δ 1.36-1.63 (m, 2H) 1.84 (s, 2H) 2.14-2.35 (m, 7H) 2.57-2.80 (m, 2H) 3.71 (d, J=12.21 Hz, 2H) 6.82-7.20 (m, 3H) 7.43-8.00 (m, 6H) 9.09 (s, 1H) 10.56-10.89 (m, 1H). MS (ESI+) m/z 549.1 (M+H)+.

Example 216 methyl 4-{[6-(2,6-dichlorophenyl)-5-oxo-5,6-dihydroimidazo[1,2-a]pyrimido[5,4-e]pyrimidin-2-yl]amino}benzoate The title compound (0.6 g) was prepared as described in Example 109A, substituting tert-butyl 7'-amino-1'H-spiro[cyclopropane-1,4'-isoquinoline]-2'(3'H)-carboxylate with methyl 4-aminobenzoate. The crude material was triturated with dichloromethane to provide the title compound. $^1$H NMR (300 MHz, DMSO-d$_6$) δ 3.67-3.99 (m, 3H) 7.14 (d, J=2.03 Hz, 1H) 7.49-7.90 (m, 3H) 8.04 (s, 5H) 9.24 (s, 1H) 11.19 (s, 1H). MS (ESI$^+$) m/z 481.2 (M+H)$^+$.

Example 217

6-(2-chlorophenyl)-2-{[3,5-dichloro-4-(piperazin-1-yl)phenyl]amino}imidazo[1,2-a]pyrimido[5,4-e]pyrimidin-5(6H)-one Example 217A tert-butyl 4-(2,6-dichloro-4-nitrophenyl)piperazine-1-carboxylate The title compound was prepared as described in Example 183A substituting 3,5-dichloro-4-fluoronitrobenzene for 1-fluoro-4-nitrobenzene and 1-boc-piperazine for bis(2-methoxyethyl)amine. MS (ESI$^+$) m/e 276.0 (M+H)$^+$.

Example 217B tert-butyl 4-(4-amino-2,6-dichlorophenyl)piperazine-1-carboxylate

Example 217A (216 mg, 0.57 mmol) was stirred vigorously in tetrahydrofuran (10 mL) under a stream of N$_2$. To the stirred solution was added platinum (IV) oxide (44 mg). The reaction was stirred for 24 hours at room temperature under a H$_2$ balloon. The reaction was filtered through diatomaceous earth to remove the catalyst and concentrated to provide the title compound. MS (ESI$^+$) m/e 346.1 (M+H)$^+$.

Example 217C 6-(2-chlorophenyl)-2-{[3,5-dichloro-4-(piperazin-1-yl)phenyl]amino}imidazo[1,2-a]pyrimido[5,4-e]pyrimidin-5(6H)-one The title compound was prepared as described in Example 203C substituting Example 217B for Example 203B. $^1$H NMR (500 MHz, DMSO-d$_6$) δ 10.99 (br s, 1H), 9.20 (s, 1H), 7.97 (s, 2H), 7.73 (m, 1H), 7.62 (m, 4H), 7.13 (s, 1H), 3.36 (m, 4H), 3.22 (m, 4H). MS (ESI$^+$) m/e 543.1 (M+H)$^+$.

Example 218

6-(2-chlorophenyl)-2-{[4-(imidazo[1,2-a]pyridin-2-yl)phenyl]amino}imidazo[1,2-a]pyrimido[5,4-e]pyrimidin-5(6H)-one The title compound was prepared as described in Example 183C substituting 4-imidizo[1,2-A]pyridin-2-ylaniline for Example 183B. $^1$H NMR (500 MHz, DMSO-d$_6$) δ 11.04 (br s, 1H), 9.20 (s, 1H), 8.82 (d, 1H), 8.66 (s, 1H), 8.04 (m, 4H), 7.89 (d, 2H), 7.79 (m, 1H), 7.73 (m, 1H), 7.62 (m, 3H), 7.37 (t, 1H), 7.12 (s, 1H).). MS (ESI$^+$) m/e 505.2 (M+H)$^+$.

Example 219

6-(2-chlorophenyl)-2-({4-[4-oxo-3-(propan-2-yl)-1,3-thiazolidin-2-yl]phenyl}amino)imidazo[1,2-a]pyrimido[5,4-e]pyrimidin-5(6H)-one The title compound was prepared as described in Example 183C substituting 2-(4-aminophenyl)-3-isopropylthiazolidin-4-one for Example 183B. $^1$H NMR (500 MHz, DMSO-d$_6$) δ 10.87 (br s, 1H), 9.15 (s, 1H), 7.89 (m, 3H), 7.12 (m, 1H), 7.60 (m, 3H), 7.49 (m, 2H), 7.09 (s, 1H), 5.89 (s, 1H), 3.94 (m, 2H), 3.58 (s, 1H), 1.20 (d, 3H), 0.90 (d, 3H). MS (ESI$^+$) m/e 532.2 (M+H)$^+$.

Example 220

6-(2-chlorophenyl)-2-{[4-(2,3-dihydroimidazo[2,1-b][1,3]thiazol-6-yl)phenyl]amino}imidazo[1,2-a]pyrimido[5,4-e]pyrimidin-5(6H)-one The title compound was prepared as described in Example 183C substituting 4-(2,3-dihydroimidazo[2,1-B][1,3]thiazol-6-yl)aniline for Example 183B. $^1$H NMR (500 MHz, DMSO-d$_6$) δ 10.91 (br s, 1H), 9.16 (s, 1H), 7.92 (m, 4H), 7.73 (m, 3H), 7.60 (m, 3H), 7.10 (s, 1H), 4.40 (t, 2H), 4.08 (t, 2H). MS (ESI$^+$) m/e 513.2 (M+H)$^+$.

Example 221

6-(2-chlorophenyl)-2-{[4-(5-methyl-4-oxo-1,3-thiazolidin-2-yl)phenyl]amino}imidazo[1,2-a]pyrimido[5,4-e]pyrimidin-5(6H)-one Example 221A 5-methyl-2-(4-nitrophenyl)thiazol-4-ol A mixture of 4-nitrobenzonitrile (5 g, 33.8 mmol), thioacetic acid (4.73 g, 44.6 mmol), and pyridine (0.8 mL) was heated to 100° C. for 2 hours. Ethanol was added to the partially cooled mixture and it was cooled to room temperature. The precipitate was collected and rinsed with ethanol and diethyl ether to provide the title compound.

Example 221B 2-(4-aminophenyl)-5-methylthiazolidin-4-one

Example 221A (2.3 g, 1 mmol) and 5% Pd/C (2 g) in methanol (100 mL) was subjected to hydrogen at 30 psi for 4 hours. The mixture was filtered through diatomaceous earth. The filtrate was concentrated and purified by flash chromatography (1% CH$_3$OH/CH$_2$Cl$_2$) to provide the title compound.

Example 221C 6-(2-chlorophenyl)-2-{[4-(5-methyl-4-oxo-1,3-thiazolidin-2-yl)phenyl]amino}imidazo[1,2-a]pyrimido[5,4-e]pyrimidin-5(6H)-one The title compound was prepared as described in Example 183C substituting Example 221B for Example 183B. $^1$H NMR (400 Mz, DMSO-d$_6$) δ 10.82 (br s, 1H), 9.13 (s, 1H), 8.95 (s, 1H) 7.86 (m, 3H), 7.70 (m, 1H), 7.57 (m, 3H), 7.45 (m, 2H), 7.06 (m, 1H), 3.93 (m, 1H), 1.45 (m, 3H). MS (ESI$^+$) m/e 504.1 (M+H)$^+$.

Example 222

6-(2-chlorophenyl)-2-{[4-(imidazo[2,1-b][1,3]thiazol-6-yl)phenyl]amino}imidazo[1,2-a]pyrimido[5,4-e]pyrimidin-5(6H)-one The title compound was prepared as described in Example 183C substituting 4-(imidazo[2,1-b]thiazol-6-yl)aniline for Example 183B. ¹H NMR (400 MHz, DMSO-d₆) δ 0.86 (br s, 1H), 9.15 (s, 1H), 8.22 (s, 1H), 7.95 (m, 6H), 7.73 (m, 1H), 7.60 (m, 3H), 7.30 (d, 1H), 7.09 (s, 1H). MS (ESI⁺) m/e 511.2 (M+H)⁺.

Example 223

6-(2-chlorophenyl)-2-{[4-(3-oxo-2,3-dihydro-1H-indazol-7-yl)phenyl]amino}imidazo[1,2-a]pyrimido[5,4-e]pyrimidin-5(6H)-one

Example 223A methyl 3-bromo-2-fluorobenzoate

To a solution of 3-bromo-2-fluorobenzoic acid (10 g, 0.045 mol) in N,N-dimethylformamide (50 mL) was added iodomethane (5 mL) dropwise. The reaction was heated to 50° C. for 24 hours. After the reaction was cooled and diluted with water (500 mL), ethyl acetate (200 mL) was added. The organic phase was separated, dried over MgSO₄, filtered, and concentrated to provide the title compound.

Example 223B methyl 4'-amino-2-fluorobiphenyl-3-carboxylate

To a solution of Example 223A (3.1 g, 13 mmol) in dimethoxyethane (25 mL) was added (4-aminophenyl)boronic acid (2.77 g, 16 mmol) and Na₂CO₃ (3.38 g, 31.2 mmol) in water (6 mL) followed by 1'-bis(diphenylphosphino)ferrocene-palladium(II)dichloride:dichloromethane:complex (652 mg, 0.8 mmol). The mixture was heated to 85° C. for 10 hours. After cooling to room temperature, the reaction mixture was partitioned between water and ethyl acetate. The organic phase was washed with water followed by brine then dried over magnesium sulfate. After filtration and concentration, the crude product was purified by flash chromatography (1%-100% ethyl acetate/hexane) to provide the title compound.

Example 223C 7-(4-aminophenyl)-1H-indazol-3(2H)-one

Example 223B (255 mg, 1.04 mmol), p-toluenesulfonic acid monohydrate (98 mg, 0.51 mmol) and hydrazine (1.1 mL) were irradiated in a microwave vial at 200° C. for 20 minutes. The crude mixture was purified by RP-HPLC to provide the title compound.

Example 223D 6-(2-chlorophenyl)-2-{[4-(3-oxo-2,3-dihydro-1H-indazol-7-yl)phenyl]amino}imidazo[1,2-a]pyrimido[5,4-e]pyrimidin-5(6H)-one The title compound was prepared as described in Example 183C substituting Example 223C for Example 183B. ¹H NMR (400 MHz, DMSO-d₆, 90° C.) δ 10.60 (br s, 1H), 9.41 (s, 1H), 7.98 (m, 2H), 7.83 (m, 1H), 7.75 (m, 2H), 7.67 (m, 1H), 7.58 (m, 4H), 7.42 (m, 1H), 7.08 (m, 2H). MS (ESI⁺) m/e 521.2 (M+H)⁺.

Example 224

6-(2-chloro-6-fluorophenyl)-2-{[2'-(2,2-difluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one

Example 224A

2',3'-dihydro-1'H-spiro[cyclopropane-1,4'-isoquinolin]-7'-amine

To a solution of tert-butyl 7'-amino-1'H-spiro[cyclopropane-1,4'-isoquinoline]-2'(3'H)-carboxylate (0.350 g, 1.276 mmol) in CH₂Cl₂ (8 ml) was added trifluoroacetic acid (0.983 ml, 12.76 mmol). The reaction was stirred overnight and concentrated to provide the title compound as a trifluoroacetic acid salt.

Example 224B

2'-(2,2-difluoroethyl)-2',3'-dihydro-1'H-spiro[cyclopropane-1,4'-isoquinolin]-7'-amine To a solution of Example 224A (245 mg, 0.850 mmol) in acetonitrile (10 mL) was added potassium carbonate (587 mg, 4.25 mmol). After 15 minutes, 1,1-difluoro-2-iodoethane (0.150 mL, 1.700 mmol) was added and the reaction mixture was heated at 80° C. in a capped vial for 5 hours. After cooling, the suspension was filtered. The filtrate was concentrated and purified on a 40 g column using the ISCO Companion flash system eluting with methanol/ethyl acetate (1:99) to provide the title compound.

Example 224C 6-(2-chloro-6-fluorophenyl)-2-{[2'-(2,2-difluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 224B, respectively. An aqueous workup was done before the HPLC purification. ¹H NMR (400 MHz, CD₃OD) δ 1.31-1.21 (m, 4H), 3.58 (s, 2H), 3.99-3.80 (m, 2H), 4.74 (s, 2H), 6.66-6.35 (m, 1H), 6.97-6.95 (m, 1H), 7.08 (d, J=1.8 Hz, 1H), 7.43-7.29 (m, 1H), 7.54 (dt, J=8.2, 1.2 Hz, 1H), 7.93-7.57 (m, 4H), 9.19-9.12 (m, 1H). MS (ESI⁺) m/z 552.2 (M+H)⁺.

Example 225

6-(2-chloro-6-fluorophenyl)-2-{[2'-(2-fluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one

Example 225A

2'-(2-fluoroethyl)-2',3'-dihydro-1'H-spiro[cyclopropane-1,4'-isoquinolin]-7'-amine The title compound was prepared as described in Example 224B, substituting 1,1-difluoro-2-iodoethane with 1-fluoro-2-iodoethane.

Example 225B 6-(2-chloro-6-fluorophenyl)-2-{[2'-(2-fluoroethyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 225A, respectively. An aqueous workup was done before the HPLC purification. $^1$H NMR (400 MHz, CD$_3$OD) δ 1.45-1.15 (m, 4H), 3.57 (bs, 2H), 3.82-3.69 (m, 2H), 4.74 (bs, 2H), 5.07-4.87 (m, 2H), 6.97 (d, J=8.2 Hz, 1H), 7.08 (d, J=1.9 Hz, 1H), 7.44-7.34 (m, 1H), 7.54 (dt, J=8.2, 1.2 Hz, 1H), 7.83-7.57 (m, 3H), 7.88 (d, J=1.4 Hz, 1H), 9.18 (s, 1H). MS (ESI$^+$) m/z 534.1 (M+H)$^+$.

Example 226

6-(2-chloro-6-fluorophenyl)-2-{[2-(diethylamino)-2,3-dihydro-1H-inden-5-yl]amino}imidazo[1,2-a]pyrimido[5,4-e]pyrimidin-5(6H)-one

Example 226A

N,N-diethyl-2,3-dihydro-1H-inden-2-amine

To a solution of 1H-inden-2(3H)-one (6.00 g, 45.4 mmol) in methanol (100 ml) was added diethylamine (6.64 g, 91 mmol), sodium cyanotrihydroborate (5.71 g, 91 mmol) and acetic acid (5.45 g, 91 mmol). The reaction mixture was stirred overnight and concentrated. The residue was diluted with methylene chloride, washed with saturated aqueous NaHCO$_3$ (2×50 mL), dried over Na$_2$SO$_4$, filtered, and concentrated. The resulting residue was dissolved in 1M aqueous HCl (100 ml), and extracted with methylene chloride (2×50 mL). The aqueous layer was treated with 6N aqueous NaOH solution until the pH=14 and was extracted with methylene chloride (4×100 mL). The combined organic layers were dried over Na$_2$SO$_4$, filtered, and concentrated to provide the title compound.

Example 226B

N,N-diethyl-5-nitro-2,3-dihydro-1H-inden-2-amine

To a solution of Example 226A (2.0 g, 10.57 mmol) in trifluoroacetic acid (80 ml, 1038 mmol) was added nitric acid (0.726 ml, 10.57 mmol) dropwise at 0° C. The mixture was stirred at 0-15° C. for 5 hours. The solution was poured into ice/water (20 mL) and the pH was adjusted to 10 with NH$_3$/H$_2$O. The mixture was extracted with methylene chloride (4×50 mL). The combined organic layers were dried over Na$_2$SO$_4$, filtered and concentrated to provide the title compound.

Example 226C

N$^2$,N$^2$-diethyl-2,3-dihydro-1H-indene-2,5-diamine

To a solution of Example 226B (2.0 g, 8.54 mmol) in methanol (50 ml) was added Pd/C (10%, 2 g). The mixture was bubbled with hydrogen and stirred overnight. The reaction mixture was filtered through a pad of diatomaceous earth and concentrated. The crude product was purified by HPLC (C18 column, mobile phase A: 10 mM NH$_4$HCO$_3$ in water, mobile phase B: acetonitrile, 50-75% B) to provide the title compound. MS m/z: 205 (M+H)$^+$. $^1$H NMR (400 MHz, CDCl$_3$): δ 6.95 (d, J=8.0 Hz, 1H), 6.54 (s, 1H), 6.46 (dd, J=7.6, 2.0 Hz, 1H), 3.61-3.54 (m, 1H), 2.97-2.91 (m, 2H), 2.83-2.73 (m, 2H), 2.64 (q, J=7.2 Hz, 4H), 1.05 (t, J=6.8 Hz, 6H).

Example 226D 6-(2-chloro-6-fluorophenyl)-2-{[2-(diethylamino)-2,3-dihydro-1H-inden-5-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 226C, respectively. An aqueous workup was done before the HPLC purification. $^1$H NMR (400 MHz, CD$_3$OD) δ 1.46-1.32 (m, 6H), 3.54-3.17 (m, 8H), 4.39-4.31 (m, 1H), 7.07 (d, J=1.9 Hz, 1H), 7.47-7.22 (m, 2H), 7.68-7.45 (m, 3H), 7.88-7.77 (m, 2H), 9.12 (bs, 1H). MS (ESI$^+$) m/z 518.2 (M+H)$^+$.

Example 227

6-(2-chloro-6-fluorophenyl)-2-{[2-(cyclopropylamino)-2,3-dihydro-1H-inden-5-yl]amino}imidazo[1,2-a]pyrimido[5,4-e]pyrimidin-5(6H)-one

Example 227A

N$^2$-cyclopropyl-2,3-dihydro-1H-indene-2,5-diamine

The title compound was prepared as described in Example 226A, Example 226B, and Example 226C, substituting diethylamine with cyclopropanamine. MS m/z: 221 (M+H)$^+$. $^1$H NMR (400 MHz, DMSO-d$_6$): δ 6.80 (d, J=8.0 Hz, 1H), 6.40 (s, 1H), 6.32 (dd, J=8.0, 6.0 Hz, 1H), 5.28-5.25 (m, 0.5H), 5.14-5.11 (m, 0.5H), 4.77 (s, 2H), 2.98-2.91 (m, 1H), 2.86-2.77 (m, 4H), 2.71-2.56 (m, 3H), 2.20-2.05 (m, 1H), 1.94-1.79 (m, 1H).

Example 227B 6-(2-chloro-6-fluorophenyl)-2-{[2-(cyclopropylamino)-2,3-dihydro-1H-inden-5-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 227A, respectively. An aqueous workup was done before the HPLC purification. $^1$H NMR (400 MHz, CD$_3$OD) δ 1.02-0.82 (m, 4H), 2.92-2.80 (m, 1H), 3.25-3.11 (m, 2H), 3.58-3.42 (m, 2H), 4.31-4.21 (m, 1H), 7.08 (d, J=1.9 Hz, 1H), 7.43-7.27 (m, 2H), 7.70-7.47 (m, 3H), 7.86-7.78 (m, 2H), 9.15 (s, 1H). MS (ESI$^+$) m/z 502.2 (M+H)$^+$.

Example 228

6-(2-chloro-6-fluorophenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one The title compound was prepared as described in Example 160A and Example 160B, substituting Example 123A with Example 95C.

Example 229

2-{[4-(1,4'-bipiperidin-1'-yl)phenyl]amino}-6-(2-chlorophenyl)imidazo[1,2-a]pyrimido[5,4-e]pyrimidin-5(6H)-one

Example 229A

1'-(4-nitrophenyl)-1,4'-bipiperidine

The title compound was prepared as described in Example 183A substituting 4-piperidinopiperidine for bis(2-methoxyethyl)amine. MS (ESI$^+$) m/e 290.1 (M+H)$^+$.

Example 229B 4-(1,4'-bipiperidin-1'-yl)aniline

The title compound was prepared as described in Example 183B substituting Example 229A for Example 183A. MS (ESI$^+$) m/e 260.2 (M+H)$^+$.

Example 229C

2-{[4-(1,4'-bipiperidin-1'-yl)phenyl]amino}-6-(2-chlorophenyl)imidazo[1,2-a]pyrimido[5,4-e]pyrimidin-5(6H)-one The title compound was prepared as described in Example 183C substituting Example 229B for Example 183B. $^1$H NMR (400 MHz, DMSO-d$_6$) δ 10.65 (br s, 1H), 9.08 (s, 1H), 7.72 (m, 3H), 7.58 (m, 4H), 7.07 (m, 3H), 3.87 (M, 2H), 3.47 (m, 4H), 2.95 (m, 2H), 2.73 (m, 2H), 2.10 (m, 2H), 1.78 (m, 6H), 1.42 (m, 1H). MS (ESI$^+$) m/e 555.2 (M+H)$^+$.

Example 230

6-(2-chlorophenyl)-2-({4-[(3R)-3-(dimethylamino)pyrrolidin-1-yl]phenyl}amino)imidazo[1,2-a]pyrimido[5,4-e]pyrimidin-5(6H)-one

Example 230A (R)—N,N-dimethyl-1-(4-nitrophenyl)pyrrolidin-3-amine

The title compound was prepared as described in Example 183A substituting (R)—N,N-dimethylpyrrolidin-3-amine for bis(2-methoxyethyl)amine. MS (ESI$^+$) m/e 236.2 (M+H)$^+$.

Example 230B (R)-1-(4-aminophenyl)-N,N-dimethylpyrrolidin-3-amine

The title compound was prepared as described in Example 183B substituting Example 230A for Example 183A.

Example 230C 6-(2-chlorophenyl)-2-({4-[(3R)-3-(dimethylamino)pyrrolidin-1-yl]phenyl}amino)imidazo[1,2-a]pyrimido[5,4-e]pyrimidin-5(6H)-one The title compound was prepared as described in Example 183C substituting Example 230B for Example 183B. $^1$H NMR (400 MHz, DMSO-d$_6$) δ 10.58 (br s, 1H), 9.05 (s, 1H), 7.73 (m, 3H), 7.58 (m, 4H), 7.06 (s, 1H), 6.72 (m, 2H), 4.02 (m, 1H), 3.62 (m, 1H), 3.45 (m, 2H), 3.27 (m, 1H), 2.87 (s, 6H), 2.45 (m, 1H), 2.21 (m, 1H). MS (ESI$^+$) m/e 501.2 (M+H)$^+$.

Example 231

6-(2-chlorophenyl)-2-({4-[3-(trifluoromethyl)piperidin-1-yl]phenyl}amino)imidazo[1,2-a]pyrimido[5,4-e]pyrimidin-5(6H)-one

Example 231A 1-(4-nitrophenyl)-3-(trifluoromethyl)piperidine

The title compound was prepared as described in Example 183A substituting 3-(trifluoromethyl)piperidine for bis(2-methoxyethyl)amine. MS (ESI$^+$) m/e 275.1 (M+H)$^+$.

Example 231B 4-(3-(trifluoromethyl)piperidin-1-yl)aniline

The title compound was prepared as described in Example 183B substituting Example 231A for Example 183A.

Example 231C 6-(2-chlorophenyl)-2-({4-[3-(trifluoromethyl)piperidin-1-yl]phenyl}amino)imidazo[1,2-a]pyrimido[5,4-e]pyrimidin-5(6H)-one The title compound was prepared as described in Example 183C substituting Example 231B for Example 183B. $^1$H NMR (400 MHz, DMSO-d$_6$) δ 10.65 (br s, 1H), 9.08 (s, 1H), 7.65 (m, 7H), 7.07 (m, 3H), 3.74 (m, 2H), 2.71 (m, 3H), 1.96 (m, 1H), 1.82 (m, 1H), 1.65 (m, 1H), 1.46 (m, 1H). MS (ESI$^+$) m/e 540.3 (M+H)$^+$.

Example 232

3-[4-(4-{[6-(2-chlorophenyl)-5-oxo-5,6-dihydroimidazo[1,2-a]pyrimido[5,4-e]pyrimidin-2-yl]amino}phenyl)piperazin-1-yl]propanenitrile

Example 232A 3-(4-(4-nitrophenyl)piperazin-1-yl)propanenitrile

The title compound was prepared as described in Example 183A substituting 3-(piperazin-1-yl)propanenitrile for bis(2-methoxyethyl)amine. MS (ESI$^+$) m/e 261.2 (M+H)$^+$.

Example 232B 3-(4-(4-aminophenyl)piperazin-1-yl)propanenitrile

The title compound was prepared as described in Example 183B substituting Example 232B for Example 183B.

Example 232C

3-[4-(4-{[6-(2-chlorophenyl)-5-oxo-5,6-dihydroimidazo[1,2-a]pyrimido[5,4-e]pyrimidin-2-yl]amino}phenyl)piperazin-1-yl]propanenitrile The title compound was prepared as described in Example 183C substituting Example 232B for Example 183B. $^1$H NMR (400 MHz, DMSO-$d_6$) δ 10.67 (br s, 1H), 9.08 (s, 1H) 7.64 (m, 7H), 7.07 (m, 3H), 3.55 (m, 4H), 3.07 (m, 4H). MS (ESI$^+$) m/e 526.3 (M+H)$^+$.

Example 233

3-[(4-{[6-(2-chlorophenyl)-5-oxo-5,6-dihydroimidazo[1,2-a]pyrimido[5,4-e]pyrimidin-2-yl]amino}phenyl)(cyclopropyl)amino]propanenitrile

Example 233A 3-(cyclopropyl(4-nitrophenyl)amino)propanenitrile

The title compound was prepared as described in Example 183A substituting 3-(cyclopropylamino)propanenitrile for bis(2-methoxyethyl)amine.

Example 233B 3-((4-aminophenyl)(cyclopropyl)amino)propanenitrile

The title compound was prepared as described in Example 183B substituting Example 233A for Example 183A.

Example 233C

3-[(4-{[6-(2-chlorophenyl)-5-oxo-5,6-dihydroimidazo[1,2-a]pyrimido[5,4-e]pyrimidin-2-yl]amino}phenyl)(cyclopropyl)amino]propanen The title compound was prepared as described in Example 183C substituting Example 233B for Example 183B. $^1$H NMR (400 MHz, DMSO-$d_6$) δ 10.62 (br s, 1H), 9.06 (s, 1H), 7.64 (m, 7H), 7.09 (m, 3H), 3.72 (m, 2H), 2.72 (m, 2H), 2.57 (m, 1H), 0.88 (m, 2H), 0.58 (m, 2H). MS (ESI$^+$) m/e 497.2 (M+H)$^+$.

Example 234

6-(2-chlorophenyl)-2-[(4-{[2-(dimethylamino)ethyl]amino}phenyl)amino]imidazo[1,2-a]pyrimido[5,4-e]pyrimidin-5(6H)-one

Example 234A

N$^1$,N$^1$-dimethyl-N$^2$-(4-nitrophenyl)ethane-1,2-diamine

The title compound was prepared as described in Example 183A substituting N$^1$,N$^1$-dimethylethane-1,2-diamine for bis(2-methoxyethyl)amine. MS (ESI$^+$) m/e 210.1 (M+H)$^+$.

Example 234B

N$^1$-(2-(dimethylamino)ethyl)benzene-1,4-diamine

The title compound was prepared as described in Example 183B substituting example 234A for Example 183A.

Example 234C 6-(2-chlorophenyl)-2-[(4-{[2-(dimethylamino)ethyl]amino}phenyl)amino]imidazo[1,2-a]pyrimido[5,4-e]pyrimidin-5(6H)-one The title compound was prepared as described in Example 183C substituting Example 234B for Example 183B. $^1$H NMR (400 MHz, DMSO-$d_6$) δ 10.55 (br s, 1H) 9.04 (s, 1H), 7.73 (m, 2H), 7.59 (m, 5H), 7.06 (s, 1H), 6.72 (m, 2H), 3.42 (m, 2H), 3.27 (m, 2H), 2.85 (s, 6H). MS (ESI$^+$) m/e 475.2 (M+H)$^+$.

Example 235

1-(4-{[6-(2-chlorophenyl)-5-oxo-5,6-dihydroimidazo[1,2-a]pyrimido[5,4-e]pyrimidin-2-yl]amino}phenyl)piperidine-4-carboxamide

Example 235A 1-(4-nitrophenyl)piperidine-4-carboxamide

The title compound was prepared as described in Example 183A substituting piperidine-4-carboxamide for bis(2-methoxyethyl)amine.

Example 235B 1-(4-aminophenyl)piperidine-4-carboxamide

The title compound was prepared as described in Example 183B substituting Example 235A for Example 182A.

Example 235C 1-(4-{[6-(2-chlorophenyl)-5-oxo-5,6-dihydroimidazo[1,2-a]pyrimido[5,4-e]pyrimidin-2-yl]amino}phenyl)piperidine-4-carboxamide The title compound was prepared as described in Example 183C substituting Example 235B for Example 183B. $^1$H NMR (400 MHz, DMSO-$d_6$) δ 10.62 (br s, 1H), 9.13 (s, 1H), 7.80 (m, 4H), 7.60 (m, 3H), 7.42 (m, 3H), 7.09 (s, 1H). 6.91 (s, 1H), 3.69 (m, 2H), 3.17 (m, 2H), 2.42 (m, 1H), 1.89 (m, 4H). MS (ESI$^+$) m/e 515.2 (M+H)$^+$.

Example 236

6-(2-chlorophenyl)-2-({4-[4-(morpholin-4-yl)piperidin-1-yl]phenyl}amino)imidazo[1,2-a]pyrimido[5,4-e]pyrimidin-5(6H)-one

Example 236A 4-(1-(4-nitrophenyl)piperidin-4-yl)morpholine

The title compound was prepared as described in Example 183A substituting 4-(piperidin-4-yl)morpholine for bis(2-methoxyethyl)amine. MS (ESI$^+$) m/e 292.1 (M+H)$^+$.

Example 236B 4-(4-morpholinopiperidin-1-yl)aniline

The title compound was prepared as described in Example 183B substituting Example 236A for Example 183A.

Example 236C 6-(2-chlorophenyl)-2-({4-[4-(morpholin-4-yl)piperidin-1-yl]phenyl}amino)imidazo[1,2-a]pyrimido[5,4-e]pyrimidin-5(6H)-one The title compound was prepared as described in Example 183C substituting Example 236B for Example 183B. The crude product was recrystallized from 1:1 DMSO:CH₃OH to provide the title compound as the free base. $^1$H NMR (400 MHz, DMSO-d$_6$, 120° C.) δ 10.02 (br s, 1H), 9.02 (s, 1H), 7.59 (m, 7H), 7.01 (s, 1H), 6.95 (d, 2H), 3.68 (m, 2H) 3.59 (m, 4H), 2.75 (m, 1H), 2.51 (m, 5H), 2.33 (m, 1H), 1.86 (m, 2H), 1.57 (m, 2H).

Example 237

6-(2,6-dichlorophenyl)-2-[(4-{[4-(dimethylamino)piperidin-1-yl]carbonyl}phenyl)amino]imidazo[1,2-a]pyrimido[5,4-e]pyrimidin-5(6H)-one

Example 237A

4-{[6-(2,6-dichlorophenyl)-5-oxo-5,6-dihydroimidazo[1,2-a]pyrimido[5,4-e]pyrimidin-2-yl]amino}benzoic acid To a suspension of Example 216 (0.6 g, 1.24 mmol) in 10 mL methanol and 3 mL water was added KOH (0.28 g, 4.99 mmol). The reaction was heated at 50 degrees overnight and at 60 degrees for 1.5 hours. The reaction mixture was cooled and concentrated. The crude material was suspended in ethyl acetate, acidified with 1M aqueous HCl, and the aqueous layer was extracted with dichloromethane (2×). The combined organics were washed with water and brine, dried over MgSO₄, filtered and concentrated. The material in the aqueous layer was filtered and the solid was dried to provide the title compound. MS (ESI⁺) m/z 467.2 (M+H)⁺.

Example 237B 6-(2,6-dichlorophenyl)-2-[(4-{[4-(dimethylamino)piperidin-1-yl]carbonyl}phenyl)amino]imidazo[1,2-a]pyrimido[5,4-e]pyrimidin-5(6H)-one To a solution of Example 237A (100 mg, 0.214 mmol) in 5 mL N,N-dimethylformamide was added 1-ethyl-3-[3-(dimethylamino)propyl]-carbodiimide hydrochloride (61.5 mg, 0.321 mmol), 1-hydroxybenzotriazole hydrate (49.2 mg, 0.321 mmol), diisopropylethylamine (0.075 ml, 0.428 mmol) followed by N,N-dimethylpiperidin-4-amine (0.036 ml, 0.257 mmol). The reaction mixture was held at room temperature overnight, and then diluted with ethyl acetate. The organics were washed with aqueous saturated NaHCO₃, water, and brine, then dried over MgSO₄, filtered, and concentrated. The compound was triturated from the crude reaction mixture to provide the title compound. $^1$H NMR (300 MHz, DMSO-d$_6$) δ 1.21-1.55 (m, 2H) 1.63-1.98 (m, 2H) 2.13-2.43 (m, 6H) 2.73-3.12 (m, 2H) 7.14 (d, J=1.59 Hz, 1H) 7.48 (d, J=8.73 Hz, 2H) 7.58-7.81 (m, 4H) 7.86-8.02 (m, 3H) 9.06-9.33 (m, 1H) 11.04 (s, 1H). MS (ESI⁺) m/z 477.1 (M+H)⁺.

Example 238

4-{[6-(2,6-dichlorophenyl)-5-oxo-5,6-dihydroimidazo[1,2-a]pyrimido[5,4-e]pyrimidin-2-yl]amino}-N-[4-(dimethylamino)cyclohexyl]benzamide The title compound (0.03 g) was prepared as described in Example 237B, substituting N,N-dimethylpiperidin-4-amine with N¹,N¹-dimethylcyclohexane-1,4-diamine. The compound was triturated from the crude reaction mixture with ethyl acetate. $^1$H NMR (300 MHz, DMSO-d$_6$) δ 1.59 (t, 4H) 2.03 (t, 4H) 2.57-2.78 (m, 6H) 3.08 (t, 1H) 3.78 (t, 1H) 7.14 (t, J=1.86 Hz, 1H) 7.52-7.72 (m, 1H) 7.70-7.83 (m, 2H) 7.93 (d, J=1.70 Hz, 5H) 8.22 (d, J=7.80 Hz, 1H) 9.22 (s, 1H) 11.05 (s, 1H). MS (ESI⁺) m/z 591.1 (M+H)⁺.

Example 239

4-{[6-(2,6-dichlorophenyl)-5-oxo-5,6-dihydroimidazo[1,2-a]pyrimido[5,4-e]pyrimidin-2-yl]amino}-N-(1-methylpiperidin-4-yl)benzamide The title compound (0.015 g) was prepared as described in Example 237B, substituting N,N-dimethylpiperidin-4-amine with 1-methylpiperidin-4-amine. The compound was triturated from the crude reaction mixture with ethyl acetate. $^1$H NMR (300 MHz, DMSO-d$_6$) δ 1.82 (d, J=54.75 Hz, 4H) 3.19-3.28 (m, 3H) 3.77-4.05 (m, 2H) 7.14 (d, J=1.98 Hz, 1H) 7.53-7.72 (m, 1H) 7.71-7.85 (m, 2H) 7.84-8.07 (m, 6H) 8.16-8.42 (m, 1H) 9.14-9.28 (m, 1H) 11.06 (s, 1H). MS (ESI⁺) m/z 563.1 (M+H)⁺.

Example 240

6-(2,6-dichlorophenyl)-2-({4-[4-(pyrrolidin-1-yl)piperidin-1-yl]phenyl}amino)imidazo[1,2-a]pyrimido[5,4-e]pyrimidin-5(6H)-one The title compound (0.07 g) was prepared as described in Example 150, substituting 1,1,2-trimethyl-1,2,3,4-tetrahydroisoquinolin-6-amine with 4-(4-(pyrrolidin-1-yl)piperidin-1-yl)aniline. The compound was triturated from the crude reaction mixture with ethyl acetate. $^1$H NMR (300 MHz, DMSO-d$_6$) δ 1.39-1.62 (m, 2H) 1.60-1.78 (m, 4H) 1.81-1.99 (m, 3H) 2.04-2.24 (m, 1H) 2.59-2.84 (m, 2H) 3.47-3.74 (m, 2H) 6.77-7.20 (m, 3H) 7.35-7.93 (m, 6H) 9.09 (s, 1H) 10.70 (s, 1H). MS (ESI⁺) m/z 575.2 (M+H)⁺.

Example 241

2-[(2'-acetyl-2',3'-dihydro-1'H-spiro[cyclopropane-1,4'-isoquinolin]-7'-yl)amino]-6-(2-chloro-6-fluorophenyl)imidazo[1,2-a]pyrimido[5,4-e]pyrimidin-5(6H)-one A solution of Example 228 (0.075 g, 0.134 mmol), acetic acid (0.011 ml, 0.201 mmol), benzotriazol-1-yloxytripyrrolidinophosphonium hexafluorophosphate (0.104 g, 0.201 mmol), and triethylamine (0.093 ml, 0.669 mmol) in N,N-dimethylformamide (2.5 ml) was stirred overnight. Water was added to the reaction mixture slowly. The resulting solids were filtered, washed with water and further purified by reverse-phase HPLC performed on a Zorbax RX-C18 column (250×21.2 mm, 7 µm particle size) using a gradient of 10% to 95% acetonitrile: 0.1% aqueous trifluoroacetic acid over 35 minutes at a flow rate of 15 mL/minute to provide the title compound as a trifluoroacetic acid salt. $^1$H NMR (400 MHz, CD₃OD) δ 1.10-0.98 (m, 4H), 2.17 (s, 1.7H), 2.23 (s, 1.3H), 3.62 (d, J=4.4 Hz, 2H), 4.86 (s, 2H), 6.94-6.85 (m, 1H), 7.07 (d, J=2.1 Hz, 1H), 7.42-7.34 (m, 1H), 7.70-7.46 (m, 4H), 7.84 (bs, 1H), 9.14 (bs, 1H). MS (ESI⁺) m/z 530.2 (M+H)⁺.

Example 242

6-(2-chloro-6-fluorophenyl)-2-{[2'-(cyclopropylcarbonyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 241, substituting acetic acid with cyclopropanecarboxylic acid. ¹H NMR (400 MHz, CD₃OD) δ 1.08-0.80 (m, 8H), 2.14-1.98 (m, 1H), 3.64 (s, 0.8H), 3.84 (s, 1.2H),), 4.88 (s, 1.2H), 5.09 (s, 0.8H), 6.93-6.86 (m, 1H), 7.07 (d, J=1.9 Hz, 1H), 7.42-7.34 (m, 1H), 7.70-7.46 (m, 4H), 7.89-7.77 (m, 1H), 9.14 (bs, 1H). MS (ESI⁺) m/z 556.2 (M+H)⁺.

Example 243

6-(2-chloro-6-fluorophenyl)-2-{[2'-(methylsulfonyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 172, substituting Example 160B with Example 228. ¹H NMR (400 MHz, CD₃OD) δ 1.17-0.99 (m, 4H), 2.90 (s, 3H), 3.44 (s, 2H), 4.64 (s, 2H), 6.94-6.81 (m, 1H), 7.08 (d, J=1.9 Hz, 1H), 7.42-7.34 (m, 1H), 7.70-7.47 (m, 4H), 7.85 (s, 1H), 9.16 (bs, 1H). MS (ESI⁺) m/z 566.2 (M+H)⁺.

Example 244

6-(2-chloro-6-fluorophenyl)-2-({4-[(8aR)-hexahydropyrrolo[1,2-a]pyrazin-2(1H)-yl]phenyl}amino)imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and (R)-4-(hexahydropyrrolo[1,2-a]pyrazin-2(1H)-yl)aniline, respectively. An aqueous workup was done before the HPLC purification. ¹H NMR (400 MHz, CD₃OD) δ 2.42-1.72 (m, 4H), 3.20-2.86 (m, 2H), 4.19-3.22 (m, 7H), 7.11-7.04 (m, 3H), 7.43-7.34 (m, 1H), 7.56-7.50 (m, 1H), 7.90-7.56 (m, 4H), 9.09 (bs, 1H). MS (ESI⁺) m/z 531.2 (M+H)⁺.

Example 245

2-({4-[(3R)-1-azabicyclo[2.2.2]oct-3-ylamino]phenyl}amino)-6-(2-chlorophenyl)imidazo[1,2-a]pyrimido[5,4-e]pyrimidin-5(6H)-one Example 245A (R)—N-(4-nitrophenyl)quinuclidin-3-amine The title compound was prepared as described in Example 183A substituting (R)-quinuclidin-3-amine for bis(methoxyethyl)amine. MS (ESI⁺) m/e 248.2 (M+H)⁺.

Example 245B (R)—N¹-(quinuclidin-3-yl)benzene-1,4-diamine

The title compound was prepared as described in Example 183B substituting Example 245A for Example 183A.

Example 245C 2-({4-[(3R)-1-azabicyclo[2.2.2]oct-3-ylamino]phenyl}amino)-6-(2-chlorophenyl)imidazo[1,2-a]pyrimido[5,4-e]pyrimidin-5(6H)-one The title compound was prepared as described in Example 183C substituting Example 245B for Example 183B. ¹H NMR (400 MHz, DMSO-d₆) δ 10.54 (br s, 1H), 9.04 (s, 1H), 7.73 (m, 2H), 7.59 (m, 5H), 7.06 (s, 1H), 6.70 (m, 2H), 3.85 (m, 1H), 3.74 (m, 1H), 3.25 (m, 4H), 2.94 (m, 1H), 2.22 (m, 1H), 2.10 (m, 1H), 1.94 (m, 2H), 1.71 (m, 1H). MS (ESI⁺) m/e 513.3 (M+H)⁺.

Example 246

6-(2-chlorophenyl)-2-[(4-{[2-(pyrrolidin-1-yl)ethyl]amino}phenyl)amino]imidazo[1,2-a]pyrimido[5,4-e]pyrimidin-5(6H)-one Example 246A 4-nitro-N-(2-(pyrrolidin-1-yl)ethyl)aniline The title compound was prepared as described in Example 183A substituting 2-(pyrrolidin-1-yl)ethanamine for bis(2-methoxyethyl)amine. MS (ESI⁺) m/e 236.2 (M+H)⁺.

Example 246B

N¹-(2-(pyrrolidin-1-yl)ethyl)benzene-1,4-diamine

The title compound was prepared as described in Example 183B substituting Example 246A for Example 183B.

Example 246C 6-(2-chlorophenyl)-2-[(4-{[2-(pyrrolidin-1-yl)ethyl]amino}phenyl)amino]imidazo[1,2-a]pyrimido[5,4-e]pyrimidin-5(6H)-one The title compound was prepared as described in Example 183C substituting Example 246B for Example 183B. ¹H NMR (400 MHz, DMSO-d₆, 90° C.) δ 10.14 (br s, 1H), 9.01 (s, 1H), 7.67 (m, 2H), 7.54 (m, 5H), 7.02 (m, 1H), 6.71 (d, 2H), 3.45 (m, 4H), 3.35 (m, 4H), 1.98 (m, 4H). MS (ESI⁺) m/e 501.2 (M+H)⁺.

Example 247

6-(2-chlorophenyl)-2-({4-[4-(pyridin-2-yl)piperazin-1-yl]phenyl}amino)imidazo[1,2-a]pyrimido[5,4-e]pyrimidin-5(6H)-one Example 247A 1-(4-nitrophenyl)-4-(pyridin-2-yl)piperazine The title compound was prepared as described in Example 183A substituting 1-(pyridin-2-yl)piperazine for bis(2-methoxyethyl)amine. MS (ESI⁺) m/e 285.1 (M+H)⁺.

Example 247B 4-(4-(pyridin-2-yl)piperazin-1-yl)aniline

The title compound was prepared as described in Example 183B substituting Example 247A for Example 183A.

Example 247C 6-(2-chlorophenyl)-2-({4-[4-(pyridin-2-yl)piperazin-1-yl]phenyl}amino)imidazo[1,2-a]pyrimido[5,4-e]pyrimidin-5(6H)-one The title compound was prepared as described in Example 183C substituting Example 247B for Example 183B. The crude product was recrystallized from 1:1 DMSO:CH$_3$OH to provide the title compound as the free base. $^1$H NMR (400 MHz, DMSO-d$_6$, 90° C.) δ 10.24 (br s, 1H), 9.04 (s, 1H), 8.13 (m, 1H), 7.68 (m, 4H), 7.54 (m, 4H), 7.03 (m, 3H), 6.84 (d, 1H), 6.64 (m, 1H), 3.67 (m, 4H), 3.27 (m, 4H). MS (ESI$^+$) m/e 550.3 (M+H)$^+$.

Example 248

6-(2-chlorophenyl)-2-[(4-{[2-(morpholin-4-yl)ethyl]amino}phenyl)amino]imidazo[1,2-a]pyrimido[5,4-e]pyrimidin-5(6H)-one

Example 248A

N-(2-morpholinoethyl)-4-nitroaniline

The title compound was prepared as described in Example 183A substituting 2-morpholinoethanamine for bis(2-methoxyethyl)amine. MS (ESI$^+$) m/e 252.2 (M+H)$^+$.

Example 248B

N$^1$-(2-morpholinoethyl)benzene-1,4-diamine

The title compound was prepared as described in Example 183B substituting Example 248A for Example 183A.

Example 248C 6-(2-chlorophenyl)-2-[(4-{[2-(morpholin-4-yl)ethyl]amino}phenyl)amino]imidazo[1,2-a]pyrimido[5,4-e]pyrimidin-5(6H)-one The title compound was prepared as described in Example 183C substituting Example 248B for Example 183B. $^1$H NMR (400 MHz, DMSO-d$_6$) δ 10.55 (br s, 1H), 9.04 (s, 1H), 7.72 (m, 2H), 7.61 (m, 5H), 7.06 (s, 1H), 6.73 (m, 2H), 3.86 (m, 4H), 3.53 (m, 4H), 3.31 (m, 4H). MS (ESI$^+$) m/e 517.2 (M+H)$^+$.

Example 249

6-(2-chlorophenyl)-2-({4-[(2S)-2-(pyrrolidin-1-ylmethyl)pyrrolidin-1-yl]phenyl}amino)imidazo[1,2-a]pyrimido[5,4-e]pyrimidin-5(6H)-one

Example 249A (S)-1-(4-nitrophenyl)-2-(pyrrolidin-1-ylmethyl)pyrrolidine

The title compound was prepared as described in Example 183A substituting (S)-1,2'-methylenedipyrrolidine for bis(2-methoxyethyl)amine. MS (ESI$^+$) m/e 276.2 (M+H)$^+$.

Example 249B (S)-4-(2-(pyrrolidin-1-ylmethyl)pyrrolidin-1-yl)aniline

The title compound was prepared as described in Example 183B substituting Example 249A for Example 183A.

Example 249C 6-(2-chlorophenyl)-2-({4-[(2S)-2-(pyrrolidin-1-ylmethyl)pyrrolidin-1-yl]phenyl}amino)imidazo[1,2-a]pyrimido[5,4-e]pyrimidin-5(6H)-one The title compound was prepared as described in Example 183C substituting Example 249B for Example 183B. $^1$H NMR (400 MHz, DMSO-d$_6$, 90° C.) δ 10.20 (br s, 1H), 9.02 (s, 1H), 7.59 (m, 7H), 7.03 (s, 1H), 6.74 (d, 2H), 4.12 (m, 1H), 3.45 (m, 5H), 3.25 (m, 3H), 2.05 (m, 8H). MS (ESI$^+$) m/e 541.1 (M+H)$^+$.

Example 250

6-(2-chlorophenyl)-2-[(4-{4-[3-(dimethylamino)propyl]piperazin-1-yl}phenyl)amino]imidazo[1,2-a]pyrimido[5,4-e]pyrimidin-5(6H)-one

Example 250A

N,N-dimethyl-3-(4-(4-nitrophenyl)piperazin-1-yl)propan-1-amine

The title compound was prepared as described in Example 183A substituting N,N-dimethyl-3-(piperazin-1-yl)propan-1-amine for bis(2-methoxyethyl)amine. MS (ESI$^+$) m/e 293.2 (M+H)$^+$.

Example 250B 4-(4-(3-(dimethylamino)propyl)piperazin-1-yl)aniline

The title compound was prepared as described in Example 183B substituting Example 250A for Example 183A.

Example 250C 6-(2-chlorophenyl)-2-[(4-{4-[3-(dimethylamino)propyl]piperazin-1-yl}phenyl)amino]imidazo[1,2-a]pyrimido[5,4-e]pyrimidin-5(6H)-one The title compound was prepared as described in Example 183C substituting Example 250B for Example 183B. $^1$H NMR (400 MHz, DMSO-d$_6$) δ 10.70 (br s, 1H), 9.09 (s, 1H), 7.64 (m, 7H), 7.09 (m, 3H), 3.46 (m, 4H), 3.16 (m, 8H), 2.82 (s, 6H), 2.11 (m, 2H). MS (ESI$^+$) m/e 558.2 (M+H)$^+$.

Example 251

6-(2-chlorophenyl)-2-({4-[(2R)-2-(methoxymethyl)pyrrolidin-1-yl]phenyl}amino)imidazo[1,2-a]pyrimido[5,4-e]pyrimidin-5(6H)-one

Example 251A (R)-2-(methoxymethyl)-1-(4-nitrophenyl)pyrrolidine

The title compound was prepared as described in Example 183A substituting (R)-2-(methoxymethyl)pyrrolidine for bis(2-methoxyethyl)amine. MS (ESI$^+$) m/e 237.1 (M+H)$^+$.

Example 251B (R)-4-(2-(methoxymethyl)pyrrolidin-1-yl)aniline

The title compound was prepared as described in Example 183B substituting Example 251A for Example 183A.

Example 251C 6-(2-chlorophenyl)-2-({4-[(2R)-2-(methoxymethyl) pyrrolidin-1-yl]phenyl}amino)imidazo[1,2-a]pyrimido[5,4-e]pyrimidin-5(6H)-one The title compound was prepared as described in Example 183C substituting Example 251B for Example 183B. $^1$H NMR (400 MHz, DMSO-$d_6$ $\delta$ 10.55 (br s, 1H), 9.03 (s, 1H), 7.63 (m, 7H), 7.05 (s, 1H), 6.70 (m, 2H), 3.84 (m, 1H), 3.41 (m, 2H), 3.30 (s, 3H), 3.23 (m, 1H), 3.07 (m, 1H), 1.95 (m, 4H). MS (ESI$^+$) m/e 502.2 (M+H)$^+$.

Example 252

1-(4-{[6-(2-chlorophenyl)-5-oxo-5,6-dihydroimidazo [1,2-a]pyrimido[5,4-e]pyrimidin-2-yl] amino}phenyl)-N,N-diethylpiperidine-3-carboxamide

Example 252A

N,N-diethyl-1-(4-nitrophenyl)piperidine-3-carboxamide

The title compound was prepared as described in Example 183A substituting N,N-diethylpiperidine-3-carboxamide for bis(2-methoxyethyl)amine. MS (ESI$^+$) m/e 306.1 (M+H)$^+$.

Example 252B 1-(4-aminophenyl)-N,N-diethylpiperidine-3-carboxamide

The title compound was prepared as described in Example 183B substituting Example 252A for Example 183A.

Example 252C 1-(4-{[6-(2-chlorophenyl)-5-oxo-5,6-dihydroimidazo [1,2-a]pyrimido[5,4-e]pyrimidin-2-yl] amino}phenyl)-N,N-diethylpiperidine-3-carboxamide The title compound was prepared as described in Example 183C substituting Example 252B for Example 183B. The crude product was recrystallized from 1:1 DMSO:CH$_3$OH to provide the title compound as the free base. $^1$H NMR (400 MHz, DMSO-$d_6$, 90° C.) $\delta$ 10.20 (s, 1H), 9.03 (s, 1H), 7.71 (s, 1H), 7.59 (m, 6H), 7.02 (s, 1H), 6.96 (d, 2H), 3.66 (m, 2H), 3.34 (m, 4H), 3.01 (m, 1H), 2.77 (m, 3H), 1.70 (m, 4H), 1.10 (m, 5H). MS (ESI$^+$) m/e 571.2 (M+H)$^+$.

Example 253

6-(2-chlorophenyl)-2-[(4-{[3-(2-oxopyrrolidin-1-yl) propyl]amino}phenyl)amino]imidazo[1,2-a]pyrimido[5,4-e]pyrimidin-5(6H)-one

Example 253A 1-(3-(4-nitrophenylamino)propyl)pyrrolidin-2-one

The title compound was prepared as described in Example 183A substituting 1-(3-aminopropyl)pyrrolidin-2-one for bis (2-methoxyethyl)amine. MS (ESI$^+$) m/e 264.2 (M+H)$^+$.

Example 253B 1-(3-(4-aminophenylamino)propyl)pyrrolidin-2-one

The title compound was prepared as described in Example 183B substituting Example 253A for Example 183B.

Example 253C 6-(2-chlorophenyl)-2-[(4-{[3-(2-oxopyrrolidin-1-yl) propyl]amino}phenyl)amino]imidazo[1,2-a]pyrimido[5,4-e]pyrimidin-5(6H)-one The title compound was prepared as described in Example 183C substituting Example 253B for Example 183B. $^1$H NMR (400 MHz, DMSO-$d_6$) $\delta$ 10.70 (br, s, 1H), 9.10 (s, 1H), 7.73 (m, 4H), 7.59 (m, 3H), 7.06 (m, 3H), 3.31 (m, 4H), 3.14 (t, 2H), 2.25 (t, 2H), 1.94 (m, 2H), 1.79 (m, 2H). MS (ESI$^+$) m/e 529.2 (M+H)$^+$.

Example 254

6-(2-chlorophenyl)-2-({4-[4-(4-fluorophenyl)piperazin-1-yl]phenyl}amino)imidazo[1,2-a]pyrimido[5,4-e]pyrimidin-5(6H)-one

Example 254A 1-(4-fluorophenyl)-4-(4-nitrophenyl)piperazine

The title compound was prepared as described in Example 183A substituting 1-(4-fluorophenyl)piperazine for bis(2-methoxyethyl)amine. MS (ESI$^+$) m/e 302.1 (M+H)$^+$.

Example 254B 4-(4-(4-fluorophenyl)piperazin-1-yl)aniline

The title compound was prepared as described in Example 183B substituting Example 254A for Example 183A.

Example 254C

The title compound was prepared as described in Example 183C substituting Example 254B for Example 183B. $^1$H NMR (400 MHz, DMSO-$d_6$) $\delta$ 10.67 (br s, 1H), 9.08 (s, 1H), 7.67 (m, 7H), 7.08 (m, 7H), 3.38 (m, 8H). MS (ESI$^+$) m/e 567.3 (M+H)$^+$.

Example 255

6-(2-chloro-6-fluorophenyl)-2-({4-[4-(dimethylamino)piperidin-1-yl]phenyl}amino)imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 1-(4-aminophenyl)-N,N-dimethylpiperidin-4-amine, respectively. An aqueous workup was done before the HPLC purification. $^1$H NMR (500 MHz, CD$_3$OD) δ 2.00-1.86 (m, 2H), 2.26-2.19 (m, 2H), 2.98-2.88 (m, 8H), 3.40 (tt, J=12.1, 3.9 Hz, 1H), 3.93-3.85 (m, 2H), 7.18-7.05 (m, 3H), 7.39 (t, J=8.7 Hz, 1H), 7.53 (d, J=8.2 Hz, 1H), 7.94-7.57 (m, 4H), 9.13 (s, 1H). MS (ESI$^+$) m/z 533.1 (M+H)$^+$.

Example 256

6-(2-chloro-6-fluorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one

Example 256A 2-((S)-3-fluoropyrrolidin-1-yl)-2,3-dihydro-1H-inden-5-amine

The title compound was prepared as described in Example 226A, Example 226B, and Example 226C, substituting diethylamine with (S)-3-fluoropyrrolidine. MS m/z: 221 (M+H)$^+$. 1HNMR (400 MHz, DMSO-d$_6$): δ 6.80 (d, J=8.0 Hz, 1H), 6.40 (s, 1H), 6.32 (dd, J=8.0, 6.0 Hz, 1H), 5.28-5.25 (m, 0.5H), 5.14-5.11 (m, 0.5H), 4.77 (s, 2H), 2.98-2.91 (m, 1H), 2.86-2.77 (m, 4H), 2.71-2.56 (m, 3H), 2.20-2.05 (m, 1H), 1.94-1.79 (m, 1H).

Example 256B 6-(2-chloro-6-fluorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 256A, respectively. An aqueous workup was done before the HPLC purification. $^1$H NMR (500 MHz, CD$_3$OD) δ 2.69-2.12 (m, 2H), 3.26-3.17 (m, 2H), 3.60-3.40 (m, 4H), 4.11-3.64 (m, 2H), 4.26 (bs, 1H), 5.58-5.41 (m, 1H), 7.07 (d, J=1.8 Hz, 1H), 7.47-7.24 (m, 2H), 7.69-7.45 (m, 3H), 7.91-7.76 (m, 2H), 9.13 (s, 1H). MS (ESI$^+$) m/z 534.2 (M+H)$^+$.

Example 257

6-(2-chloro-6-fluorophenyl)-2-({2-[(2-fluoroethyl)amino]-2,3-dihydro-1H-inden-5-yl}amino)imidazo[1,2-a]pyrimido[5,4-e]pyrimidin-5(6H)-one

Example 257A

N$^2$-(2-fluoroethyl)-2,3-dihydro-1H-indene-2,5-diamine

The title compound was prepared as described in Example 226A, Example 226B, and Example 226C, substituting diethylamine with 2-fluoroethanamine. MS m/z: 195 (M+H)$^+$. 1HNMR (400 MHz, DMSO-d$_6$): δ 6.79 (d, J=8.0 Hz, 1H), 6.39 (s, 1H), 6.35 (dd, J=7.6, 2.0 Hz, 1H), 4.74 (s, 2H), 4.51 (t, J=4.8 Hz, 1H), 4.39 (t, J=4.8 Hz, 1H), 3.46-3.41 (m, 1H), 2.93-2.84 (m, 3H), 2.78 (t, J=4.2 Hz, 1H), 2.49-2.43 (m, 2H).

Example 257B 6-(2-chloro-6-fluorophenyl)-2-({2-[(2-fluoroethyl)amino]-2,3-dihydro-1H-inden-5-yl}amino)imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 257A, respectively. An aqueous workup was done before the HPLC purification. $^1$H NMR (500 MHz, CD$_3$OD) δ 3.27-3.09 (m, 2H), 3.57-3.41 (m, 4H), 4.26-4.17 (m, 1H), 4.73 (t, J=4.5 Hz, 1H), 4.84-4.82 (m, 1H), 7.08 (d, J=1.8 Hz, 1H), 7.44-7.26 (m, 2H), 7.69-7.46 (m, 3H), 7.91-7.78 (m, 2H), 9.15 (s, 1H). MS (ESI$^+$) m/z 508.2 (M+H)$^+$.

Example 258

6-(2-chloro-6-fluorophenyl)-2-{[2-(propylamino)-2,3-dihydro-1H-inden-5-yl]amino}imidazo[1,2-a]pyrimido[5,4-e]pyrimidin-5(6H)-one

Example 258A

N$^2$-propyl-2,3-dihydro-1H-indene-2,5-diamine

The title compound was prepared as described in Example 226A, Example 226B, and Example 226C, substituting diethylamine with propan-1-amine. MS m/z: 191 (M+H)$^+$. $^1$H NMR (400 MHz, DMSO-d$_6$): δ 6.78 (d, J=8.0 Hz, 1H), 6.38 (s, 1H), 6.33-6.30 (m, 1H), 4.72 (s, 2H), 3.39 (dt, J=13.6, 7.2 Hz, 1H), 2.87 (dt, J=14.8, 7.2 Hz, 2H), 2.45-2.42 (m, 4H), 1.45-1.36 (m, 2H), 0.87 (t, J=7.2 Hz, 3H).

Example 258B 6-(2-chloro-6-fluorophenyl)-2-{[2-(propylamino)-2,3-dihydro-1H-inden-5-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 258A, respectively. An aqueous workup was done before the HPLC purification. $^1$H NMR (500 MHz, CD$_3$OD) δ 1.06 (t, J=7.4 Hz, 3H), 1.81-1.69 (m, 2H), 3.24-3.01 (m, 4H), 3.56-3.38 (m, 2H), 4.18-4.08 (m, 1H), 7.07 (s, 1H), 7.47-7.26 (m, 2H), 7.70-7.45 (m, 3H), 7.92-7.74 (m, 2H), 9.13 (s, 1H). MS (ESI$^+$) m/z 504.2 (M+H)$^+$.

Example 259

6-(2-chloro-6-fluorophenyl)-2-{[2-(pyrrolidin-1-yl)-2,3-dihydro-1H-inden-5-yl]amino}imidazo[1,2-a]pyrimido[5,4-e]pyrimidin-5(6H)-one

Example 259A 2-(pyrrolidin-1-yl)-2,3-dihydro-1H-inden-5-amine

The title compound was prepared as described in Example 226A, Example 226B, and Example 226C, substituting diethylamine with pyrrolidine. MS m/z: 203 (M+H)$^+$. $^1$H NMR (400 MHz, CDCl$_3$): δ 6.95 (d, J=8.0 Hz, 1H), 6.54 (s, 1H), 6.48 (dd, J=8.0, 2.0 Hz, 1H), 3.53 (s, 2H), 3.03-2.97 (m, 3H), 2.96-2.92 (m, 2H), 2.61-2.57 (m, 4H), 1.86-1.80 (m, 4H).

Example 259B 6-(2-chloro-6-fluorophenyl)-2-{[2-(pyrrolidin-1-yl)-2,3-dihydro-1H-inden-5-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 259A, respectively. An aqueous workup was done before the HPLC purification. $^1$H NMR (500 MHz, CD$_3$OD) δ 2.12-2.02 (m, 2H), 2.24-2.10 (m, 2H), 3.25-3.15 (m, 4H), 3.56-3.38 (m, 2H), 3.72 (bs, 2H), 4.21-4.11 (m, 1H), 7.09-7.04 (m, 1H), 7.35-7.28 (m, 1H), 7.39 (t, J=8.8 Hz, 1H), 7.68-7.45 (m, 3H), 7.91-7.74 (m, 2H), 9.11 (s, 1H). MS (ESI$^+$) m/z 516.2 (M+H)$^+$.

Example 260

6-(2-chlorophenyl)-2-[(4-{4-[2-(dimethylamino)ethyl]piperazin-1-yl}phenyl)amino]imidazo[1,2-a]pyrimido[5,4-e]pyrimidin-5(6H)-one Example 260A N,N-dimethyl-2-(4-(4-nitrophenyl)piperazin-1-yl)ethanamine The title compound was prepared as described in Example 183A substituting N,N-dimethyl-2-(piperazin-1-yl)ethanamine for bis(2-methoxyethyl)amine. MS (ESI$^+$) m/e 279.2 (M+H)$^+$.

Example 260B 4-(4-(2-(dimethylamino)ethyl)piperazin-1-yl)aniline

The title compound was prepared as described in Example 183B substituting Example 260A for Example 183A.

Example 260C 6-(2-chlorophenyl)-2-[(4-{4-[2-(dimethylamino)ethyl]piperazin-1-yl}phenyl)amino]imidazo[1,2-a]pyrimido[5,4-e]pyrimidin-5(6H)-one The title compound was prepared as described in Example 183C substituting Example 260B for Example 183B. $^1$H NMR (400 MHz, DMSO-d$_6$) δ 10.67 (br s, 1H), 9.08 (s, 1H), 7.64 (m, 7H), 7.07 (m, 3H), 3.61 (m, 8H), 3.41 (m, 4H), 2.85 (s, 6H). MS (ESI$^+$) m/e 544.2 (M+H)$^+$.

Example 261

6-(2-chlorophenyl)-2-[(4-{[3-(dimethylamino)propyl](methyl)amino}phenyl)amino]imidazo[1,2-a]pyrimido[5,4-e]pyrimidin-5(6H)-one Example 261A N$^1$,N$^1$,N$^3$-trimethyl-N$^3$-(4-nitrophenyl)propane-1,3-diamine The title compound was prepared as described in Example 183A substituting N$^1$,N$^1$,N$^3$-trimethylpropane-1,3-diamine for bis(2-methoxyethyl)amine. MS (ESI$^+$) m/e 238.1 (M+H)$^+$.

Example 261B

N$^1$-(3-(dimethylamino)propyl)-N$^1$-methylbenzene-1,4-diamine

The title compound was prepared as described in Example 183B substituting Example 261A for Example 183A.

Example 261C 6-(2-chlorophenyl)-2-[(4-{[3-(dimethylamino)propyl](methyl)amino}phenyl)amino]imidazo[1,2-a]pyrimido[5,4-e]pyrimidin-5(6H)-one The title compound was prepared as described in Example 183C substituting Example 261B for Example 183B. $^1$H NMR (400 MHz, DMSO-d$_6$) δ 10.59 (br s, 1H), 9.05 (s, 1H), 7.65 (m, 7H), 7.07 (s, 1H), 6.83 (m, 2H), 3.38 (m, 2H), 3.10 (m, 2H), 2.91 (s, 3H), 2.78 (s, 6H), 1.88 (m, 2H). MS (ESI$^+$) m/e 503.2 (M+H)$^+$.

Example 262

6-(2-chlorophenyl)-2-[(4-{[2-(dimethylamino)ethyl](ethyl)amino}phenyl)amino]imidazo[1,2-a]pyrimido[5,4-e]pyrimidin-5(6H)-one Example 262A N$^1$-ethyl-N$^2$,N$^2$-dimethyl-N$^1$-(4-nitrophenyl)ethane-1,2-diamine The title compound was prepared as described in Example 183A substituting N$^1$-ethyl-N$^2$,N$^2$-dimethylethane-1,2-diamine for bis(2-methoxyethyl)amine. MS (ESI$^+$) m/e 238.2 (M+H)$^+$.

Example 262B

N$^1$-(2-(dimethylamino)ethyl)-N$^1$-ethylbenzene-1,4-diamine

The title compound was prepared as described in Example 183B substituting Example 262A for Example 183A.

Example 262C 6-(2-chlorophenyl)-2-[(4-{[2-(dimethylamino)ethyl](ethyl)amino}phenyl)amino]imidazo[1,2-a]pyrimido[5,4-e]pyrimidin-5(6H)-one The title compound was prepared as described in Example 183C substituting Example 262B for Example 183B. $^1$H NMR (400 MHz, DMSO-d$_6$) δ 10.61 (br, 1H), 9.06 (s, 1H), 7.72 (m, 3H), 7.57 (m, 4H), 7.07 (s, 1H), 6.86 (m, 2H), 3.59 (m, 2H), 3.39 (m, 2H), 3.24 (m, 2H), 2.87 (s, 6H), 1.08 (m, 3H). MS (ESI$^+$) m/e 503.1 (M+H)$^+$.

Example 263

6-(2-chlorophenyl)-2-[(4-{[2-(dimethylamino)ethyl](methyl)amino}phenyl)amino]imidazo[1,2-a]pyrimido[5,4-e]pyrimidin-5(6H)-one

Example 263A $N^1,N^1,N^2$-trimethyl-$N^2$-(4-nitrophenyl)ethane-1,2-diamine The title compound was prepared as described in Example 183A substituting $N^1,N^1,N^2$-trimethylethane-1,2-diamine for bis(2-methoxyethyl)amine. MS (ESI$^+$) m/e 224.1 (M+H)$^+$.

Example 263B $N^1$-(2-(dimethylamino)ethyl)-$N^1$-methylbenzene-1,4-diamine

The title compound was prepared as described in Example 183B substituting Example 263A for Example 183A.

Example 263C 6-(2-chlorophenyl)-2-[(4-{[2-(dimethylamino)ethyl](methyl)amino}phenyl)amino]imidazo[1,2-a]pyrimido[5,4-e]pyrimidin-5(6H)-one The title compound was prepared as described in Example 183C substituting Example 263B for Example 183B. $^1$H NMR (400 MHz, DMSO-d$_6$) δ 10.62 (br s, 1H), 9.06 (s, 1H), 7.73 (m, 3H), 7.58 (m, 4H), 7.07 (s, 1H), 6.89 (m, 2H), 3.65 (m, 2H), 3.26 (m, 2H), 2.93 (s, 3H), 2.86 (s, 6H). MS (ESI$^+$) m/e 489.1 (M+H)$^+$.

Example 264

6-(2-chlorophenyl)-2-({4-[(2S)-2-(methoxymethyl)pyrrolidin-1-yl]phenyl}amino)imidazo[1,2-a]pyrimido[5,4-e]pyrimidin-5(6H)-one

Example 264A (S)-2-(methoxymethyl)pyrrolidine

The title compound was prepared as described in Example 183A substituting (S)-2-(methoxymethyl)pyrrolidine for bis(2-methoxyethyl)amine. MS (ESI$^+$) m/e 237.1 (M+H)$^+$.

Example 264B (S)-4-(2-(methoxymethyl)pyrrolidin-1-yl)aniline

The title compound was prepared as described in Example 183B substituting Example 264A for Example 183A.

Example 264C 6-(2-chlorophenyl)-2-({4-[(2S)-2-(methoxymethyl)pyrrolidin-1-yl]phenyl}amino)imidazo[1,2-a]pyrimido[5,4-e]pyrimidin-5(6H)-one The title compound was prepared as described in Example 183C substituting Example 264B for Example 183B. $^1$H NMR (400 MHz, DMSO-d$_6$, 90° C.) δ 10.12 (br s, 1H), 9.01 (s, 1H), 7.71 (s, 1H), 7.67 (m, 1H), 7.54 (m, 5H), 7.02 (s, 1H), 6.68 (m, 2H), 3.87 (m, 1H), 3.44 (m, 2H), 3.30 (s, 3H), 3.13 (m, 2H), 1.98 (m, 4H). MS (ESI$^+$) m/e 502.3 (M+H)$^+$.

Example 265

6-(2-chloro-6-fluorophenyl)-2-{[2'-(2-methylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 241, substituting acetic acid with isobutyric acid. $^1$H NMR (400 MHz, DMSO-d$_6$) δ 1.06-0.91 (m, 10H), 3.12-2.92 (m, 1H), 3.67-3.54 (m, 2H), 4.90-4.74 (m, 2H), 6.92-6.85 (m, 1H), 7.12 (d, J=1.8 Hz, 1H), 7.76-7.47 (m, 5H), 7.83-7.77 (m, 1H), 9.14 (s, 1H), 10.79 (bs, 1H). MS (ESI$^+$) m/z 558.2 (M+H)$^+$.

Example 266

6-(2-chloro-6-fluorophenyl)-2-{[2'-(2,2-dimethylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 241, substituting acetic acid with pivalic acid. $^1$H NMR (400 MHz, DMSO-d$_6$) δ 1.12-0.90 (m, 4H), 1.24 (s, 9H), 3.64 (bs, 2H), 4.87 (bs, 2H), 6.90-6.83 (m, 1H), 7.12 (d, J=1.8 Hz, 1H), 7.75-7.48 (m, 5H), 7.77 (d, J=1.8 Hz, 1H), 9.14 (s, 1H), 10.75 (bs, 1H). MS (ESI$^+$) m/z 572.2 (M+H)$^+$.

Example 267

6-(2-chloro-6-fluorophenyl)-2-{[2'-(cyclopentylcarbonyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound was prepared as described in Example 241, substituting acetic acid with cyclopentanecarboxylic acid. $^1$H NMR (400 MHz, DMSO-d$_6$) δ 1.04-0.94 (m, 4H), 1.81-1.52 (m, 8H), 3.20-3.02 (m, 1H), 3.64-3.57 (m, 2H), 4.87-4.77 (m, 2H), 6.90-6.88 (m, 1H), 7.12 (s, 1H), 7.75-7.47 (m, 5H), 7.86-7.72 (m, 1H), 9.14 (s, 1H), 10.80 (bs, 1H). MS (ESI$^+$) m/z 584.2 (M+H)$^+$.

Example 268

6-(2-chlorophenyl)-2-[(4-{[2-(1H-imidazol-4-yl)
ethyl]amino}phenyl)amino]imidazo[1,2-a]pyrimido
[5,4-e]pyrimidin-5(6H)-one

Example 268A

N-(2-(1H-imidazol-4-yl)ethyl)-4-nitroaniline

The title compound was prepared as described in Example 183A substituting 2-(1H-imidazol-4-yl)ethanamine for bis(2-methoxyethyl)amine. MS (ESI$^+$) m/e 233.2 (M+H)$^+$.

Example 268B

N$^1$-(2-(1H-imidazol-4-yl)ethyl)benzene-1,4-diamine

The title compound was prepared as described in Example 183B substituting Example 268A for Example 183A.

Example 268C 6-(2-chlorophenyl)-2-[(4-{[2-(1H-imidazol-4-yl)
ethyl]amino}phenyl)amino]imidazo[1,2-a]pyrimido
[5,4-e]pyrimidin-5(6H)-one The title compound was prepared as described in Example 183C substituting Example 268B for Example 183B. $^1$H NMR (400 MHz, DMSO-d$_6$, 90° C.) δ 10.10 (br s, 1H), 9.01 (s, 1H), 8.88 (s, 1H), 7.66 (m, 2H), 7.53 (m, 5H), 7.42 (s, 1H), 7.02 9s, 1H), 6.67 (d, 2H), 3.39 (t, 2H), 2.95 (t, 2H). MS (ESI$^+$) m/e 498.2 (M+H)$^+$.

Example 269

6-(2-chlorophenyl)-2-[(4-{[3-(1H-imidazol-1-yl)
propyl]amino}phenyl)amino]imidazo[1,2-a]py-
rimido[5,4-e]pyrimidin-5(6H)-one

Example 269A

N-(3-(1H-imidazol-1-yl)propyl)-4-nitroaniline

The title compound was prepared as described in Example 183A substituting 3-(1H-imidazol-1-yl)propan-1-amine for bis(2-methoxyethyl)amine. MS (ESI$^+$) m/e 247.1 (M+H)$^+$.

Example 269B

The title compound was prepared as described in Example 183B substituting Example 269A for Example 183A.

Example 269C 6-(2-chlorophenyl)-2-[(4-{[3-(1H-imidazol-1-yl)
propyl]amino}phenyl)amino]imidazo[1,2-a]py-
rimido[5,4-e]pyrimidin-5(6H)-one The title compound was prepared as described in Example 183C substituting Example 269B for Example 183B. $^1$H NMR (400 MHz, DMSO-d$_6$, 90° C.) δ 10.10 (br s, 1H), 9.00 (s, 1H), 7.67 (m, 3H), 7.56 (m, 7H), 7.02 (s, 1H), 6.63 (m, 2H), 4.33 (t, 2H), 3.10 (m, 2H), 2.14 (t, 2H). MS (ESI$^+$) m/e 512.2 (M+H)$^+$.

Example 270

6-(2-chlorophenyl)-2-{[4-(thiomorpholin-4-yl)phe-
nyl]amino}imidazo[1,2-a]pyrimido[5,4-e]pyrimidin-
5(6H)-one

Example 270A 4-(4-nitrophenyl)thiomorpholine

The title compound was prepared as described in Example 183A substituting thiomorpholine for bis(2-methoxyethyl)amine. MS (ESI$^+$) m/e 225.1 (M+H)$^+$.

Example 270B 4-thiomorpholinoaniline

The title compound was prepared as described in Example 183B substituting Example 270A for Example 183A.

Example 270C 6-(2-chlorophenyl)-2-{[4-(thiomorpholin-4-yl)phe-
nyl]amino}imidazo[1,2-a]pyrimido[5,4-e]pyrimidin-
5(6H)-one The title compound was prepared as described in Example 183C substituting Example 270B for Example 183B. $^1$H NMR (400 MHz, DMSO-d$_6$) δ 10.67 (br s, 1H), 9.08 (s, 1H), 7.64 (m, 7H), 7.07 (m, 3H), 3.54 (m, 4H), 2.74 (m, 4H). MS (ESI$^+$) m/e 490.2 (M+H)$^+$.

Example 271

6-(2-chlorophenyl)-2-[(4-{propan-2-yl[2-(propan-2-
ylamino)ethyl]amino}phenyl)amino]imidazo[1,2-a]
pyrimido[5,4-e]pyrimidin-5(6H)-one

Example 271A

N$^1$,N$^2$-diisopropyl-N$^1$-(4-nitrophenyl)ethane-1,2-
diamine

The title compound was prepared as described in Example 183A substituting N$^1$,N$^2$-diisopropylethane-1,2-diamine for bis(2-methoxyethyl)amine. MS (ESI$^+$) m/e 266.2 (M+H)$^+$.

Example 271B

N$^1$-isopropyl-N$^1$-(2-(isopropylamino)ethyl)benzene-
1,4-diamine

The title compound was prepared as described in Example 183B substituting Example 271A for Example 183A.

Example 271C 6-(2-chlorophenyl)-2-[(4-{propan-2-yl[2-(propan-2-
ylamino)ethyl]amino}phenyl)amino]imidazo[1,2-a]
pyrimido[5,4-e]pyrimidin-5(6H)-one The title compound was prepared as described in Example 183C substituting Example 271B for Example 183B. $^1$H NMR (500 MHz, DMSO-d$_6$) δ 10.55 (br s, 1H), 9.05 (s, 1H), 7.65 (m, 7H), 7.06 (s, 1H), 6.69 (m, 2H), 3.44 (m, 4H), 3.23 (m, 2H). MS (ESI$^+$) m/e 531.2 (M+H)$^+$.

Example 272

1-(4-{[6-(2-chlorophenyl)-5-oxo-5,6-dihydroimidazo[1,2-a]pyrimido[5,4-e]pyrimidin-2-yl]amino}phenyl)piperidine-3-carboxamide

Example 272A 1-(4-nitrophenyl)piperidine-3-carboxamide

The title compound was prepared as described in Example 183A substituting piperidine-3-carboxamide for bis(2-methoxyethyl)amine. MS (ESI$^+$) m/e 250.2 (M+H)$^+$.

Example 272B 1-(4-aminophenyl)piperidine-3-carboxamide

The title compound was prepared as described in Example 183B substituting Example 272A for Example 183A.

Example 272C 1-(4-{[6-(2-chlorophenyl)-5-oxo-5,6-dihydroimidazo[1,2-a]pyrimido[5,4-e]pyrimidin-2-yl]amino}phenyl)piperidine-3-carboxamide The title compound was prepared as described in Example 183C substituting Example 272B for Example 183B. $^1$H NMR (400 MHz, DMSO-d$_6$, 90° C.) δ 10.29 9 (br s, 1H), 9.05 (s, 1H), 7.68 (m, 4H), 7.54 (m, 3H), 7.09 (m, 2H), 7.03 (s, 1H), 3.65 (m, 2H), 2.90 (m, 2H), 2.54 (m, 1H), 1.71 (m, 4H). MS (ESI$^+$) m/e 515.2 (M+H)$^+$.

Example 273

6-(2,6-dichlorophenyl)-2-[(4-{[2-(1-methylpyrrolidin-2-yl)ethyl]amino}phenyl)amino]imidazo[1,2-a]pyrimido[5,4-e]pyrimidin-5(6H)-one The title compound (0.07 g) was prepared as described in Example 150, substituting 1,1,2-trimethyl-1,2,3,4-tetrahydroisoquinolin-6-amine with N$^1$-(2-(1-methylpyrrolidin-2-yl)ethyl)benzene-1,4-diamine. Chromatography was performed with an Analogix 280 with an SF 12-24 column, 5% methanol/dichloromethane with a small amount of ammonium hydroxide over 30 minutes. $^1$H NMR (500 MHz, DMSO-d$_6$) δ 1.40-1.56 (m, 2H) 1.55-1.74 (m, 2H) 1.82-1.97 (m, 2H) 2.00-2.17 (m, 2H) 2.17-2.27 (m, 3H) 2.83-3.14 (m, 3H) 5.38-5.68 (m, 1H) 6.47-6.72 (m, 2H) 7.09 (s, 1H) 7.37 (d, J=8.24 Hz, 1H) 7.50-7.68 (m, 3H) 7.69-7.84 (m, 3H) 9.05 (s, 1H) 10.57 (s, 1H). MS (ESI$^+$) m/z 549.2 (M+H)$^+$.

Example 274

6-(2,6-dichlorophenyl)-2-{[2'-(2-methylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound (0.075 g) was prepared as described in Example 207, substituting acetic anhydride with isobutyryl chloride. The crude material was triturated with ethyl acetate to provide the title compound. $^1$H NMR (500 MHz, DMSO-d$_6$) δ 0.77-1.14 (m, 10H) 2.91-3.17 (m, 1H) 3.49-3.75 (m, 2H) 4.61-4.99 (m, 2H) 6.89 (s, 1H) 7.13 (s, 1H) 7.40-8.06 (m, 6H) 9.16 (s, 1H) 10.84 (s, 1H). MS (ESI$^+$) m/z 574.2 (M+H)$^+$.

Example 275

2-{[2'-(cyclopropylcarbonyl)-2',3'-dihydro-1'H-spiro[cyclopropane-1,4'-isoquinolin]-7'-yl]amino}-6-(2,6-dichlorophenyl)imidazo[1,2-a]pyrimido[5,4-e]pyrimidin-5(6H)-one The title compound (0.065 g) was prepared as described in Example 207, substituting acetic anhydride with cyclopropanecarbonyl chloride. The crude material was triturated with ethyl acetate to provide the title compound. $^1$H NMR (500 MHz, DMSO-d$_6$) δ 0.74 (d, 4H) 1.00 (d, 4H) 2.13 (d, 1H) 3.46-3.92 (m, 2H) 4.51-5.20 (m, 2H) 6.90 (d, J=1.22 Hz, 1H) 7.12 (s, 1H) 7.42-8.08 (m, 6H) 9.16 (s, 1H) 10.84 (s, 1H). MS (ESI$^+$) m/z 572.2 (M+H)$^+$.

Example 276

6-(2,6-dichlorophenyl)-2-{[2'-(2,2-dimethylpropanoyl)-2',3'-dihydro-1'H-spiro[cyclopropane-1,4'-isoquinolin]-7'-yl]amino}imidazo[1,2-a]pyrimido[5,4-e]pyrimidin-5(6H)-one The title compound (0.055 g) was prepared as described in Example 207, substituting acetic anhydride with pivaloyl chloride. Chromatography was performed with an Analogix 280 with an SF 12-24 column, 50% to 100% ethyl acetate/hexane gradient over 30 minutes to provide the title compound. $^1$H NMR (500 MHz, DMSO-d$_6$) δ 0.87-1.09 (m, 4H) 1.15-1.33 (m, 9H) 3.62 (d, 2H) 4.86 (d, 2H) 6.87 (d, J=6.71 Hz, 1H) 7.13 (s, 1H) 7.48-7.72 (m, 3H) 7.70-7.86 (m, 3H) 9.15 (s, 1H) 10.61-10.98 (m, J=10.99 Hz, 1H). MS (ESI$^+$) m/z 588.3 (M+H)$^+$.

Example 277

6-(2-chloro-6-fluorophenyl)-2-(5,6,7,8-tetrahydro-1,6-naphthyridin-3-ylamino)imidazo[1,2-a]pyrimido[5,4-e]pyrimidin-5(6H)-one

Example 277A

3-[4-(2-Chloro-6-fluoro-phenyl)-5-oxo-4,5-dihydro-3,4,7,9,9b-pentaaza-cyclopenta[a]naphthalen-8-ylamino]-7,8-dihydro-5H-[1,6]naphthyridine-6-carboxylic acid tert-butyl ester A mixture of Example 95C (70.0 mg, 0.193 mmol) and m-chloroperoxybenzoic acid (52.0 mg, 0.232 mmol) in CH$_2$Cl$_2$ (2 ml) was stirred for 20 minutes. tert-Butyl 3-amino-7,8-dihydro-1,6-naphthyridine-6(5H)-carboxylate (57.9 mg, 0.232 mmol) was added to the reaction mixture. After 5 hours, the reaction mixture was diluted with ethyl acetate, washed with saturated aqueous NaHCO$_3$, and brine. The organic layer was dried over MgSO$_4$, filtered, concentrated, and purified on a 12 g column using the ISCO Companion flash system eluting with ethyl acetate to provide the title compound.

Example 277B 6-(2-chloro-6-fluorophenyl)-2-(5,6,7,8-tetrahydro-1,6-naphthyridin-3-ylamino)imidazo[1,2-a]pyrimido[5,4-e]pyrimidin-5(6H)-one A mixture of Example 277A (54.6 mg, 0.097 mmol) and trifluoroacetic acid (0.075 mL, 0.970 mmol) in $CH_2Cl_2$ (3 mL) was stirred overnight. The solids were filtered, rinsed with $CH_2Cl_2$, and dried to provide the title compound as a trifluoroacetic acid salt. $^1H$ NMR (400 MHz, $CD_3OD$) δ 3.29-3.26 (m, 2H), 3.68 (t, J=6.4 Hz, 2H), 4.55 (s, 2H), 7.11 (d, J=1.9 Hz, 1H), 7.44-7.35 (m, 1H), 7.56-7.53 (m, 1H), 7.66-7.60 (m, 1H), 7.91 (d, J=1.9 Hz, 1H), 8.38 (bs, 1H), 8.93 (bs, 1H), 9.26 (s, 1H). MS ($ESI^+$) m/z 463.2 $(M+H)^+$.

Example 278

6-(2-chloro-3-hydroxyphenyl)-2-(2',3'-dihydro-1'H-spiro[cyclopropane-1,4'-isoquinolin]-7'-ylamino)imidazo[1,2-a]pyrimido[5,4-e]pyrimidin-5(6H)-one

Example 278A 1-(allyloxy)-2-chloro-3-nitrobenzene

To a solution of 2-chloro-3-nitrophenol (1.5 g, 8.64 mmol) in acetone was added potassium carbonate (1.194 g, 8.64 mmol). After 5 minutes, allyl bromide (0.823 ml, 9.51 mmol) was added and the solution was heated to reflux overnight. The reaction mixture was cooled, filtered, and concentrated. Chromatography was performed with an Analogix 280 with an SF 40-80 column, 0% to 10% ethyl acetate/hexane gradient over 30 minutes to provide the title compound. MS ($DCI^+$) m/z 231.1 $(M+NH_4)^+$.

Example 278B 3-(allyloxy)-2-chloroaniline

To a solution of Example 278A (2 g, 10.35 mmol) in ethyl acetate (60 ml) added tin(II) chloride dihydrate (8.18 g, 36.2 mmol), and the mixture was heated at 65° C. overnight. The reaction mixture was cooled to room temperature, diluted with 100 mL ethyl acetate, and 1M aqueous $Na_2CO_3$ was added until precipitation stopped. The solid was filtered through a pad of diatomaceous earth. The filter pad was suspended in ethyl acetate, stirred for a few minutes, and rinsed with ethyl acetate. The filtrate was washed with saturated aqueous $Na_2CO_3$, water, and brine, dried over $MgSO_4$, filtered, and concentrated. Chromatography was performed with an Analogix 280 with an SF 40-80 column, 0% to 5% methanol/dichloromethane gradient over 30 minutes to provide the title compound. MS ($DCI^+$) m/z 164.1 $(M+H)^+$.

Example 278C 1-(allyloxy)-2-chloro-3-isocyanatobenzene

To a solution of triphosegene (0.593 g, 1.999 mmol) in 40 mL toluene was slowly added a solution triethylamine (1.290 ml, 9.26 mmol) and 3-(allyloxy)-2-chloroaniline (1 g, 5.45 mmol) dissolved in 10 mL toluene. The mixture was heated to 70° C. overnight, filtered, and concentrated. The residue was diluted with 100 ml ethyl acetate, and the organics were washed with saturated aqueous $NaHCO_3$, water, and brine, dried over $MgSO_4$, filtered, and concentrated. The title compound was used quickly in the next step without further purification.

Example 278D 3-(3-(allyloxy)-2-chlorophenyl)-7-(methylthio)pyrimido[4,5-d]pyrimidine-2,4(1H,3H)-dione The title compound (1.36 g) was prepared as described in Example 1A, substituting 1-chloro-2-isocyanatobenzene with Example 278C. Chromatography was performed with an Analogix 280 with an SF 40-80 column, 20% to 60% ethyl acetate/hexane gradient over 30 minutes to provide the title compound. MS ($ESI^+$) m/z 377.0 $(M+H)^+$.

Example 278E 3-(3-(allyloxy)-2-chlorophenyl)-2-chloro-7-(methylthio)pyrimido[4,5-d]pyrimidin-4(3H)-one The title compound (1.7 g) was prepared as described in Example 1B, substituting Example 1A with Example 278D. MS ($ESI^+$) m/z 361.19 $(M+H)^+$.

Example 278F 3-(3-(allyloxy)-2-chlorophenyl)-2-(2,2-dimethoxyethylamino)-7-(methylthio)pyrimido[4,5-d]pyrimidin-4(3H)-one The title compound (1.3 g) was prepared as described in Example 1C, substituting Example 1B with Example 278E. MS ($ESI^+$) m/z 464.4 $(M+H)^+$.

Example 278G

6-[2-chloro-3-(prop-2-en-1-yloxy)phenyl]-2-(methylsulfanyl)imidazo[1,2-a]pyrimido[5,4-e]pyrimidin-5(6H)-one The title compound (1 g) was prepared as described in Example 1D, substituting Example 1C with Example 278F. Chromatography was performed with an Analogix 280 with an SF 40-120 column, 40% to 100% ethyl acetate/hexane gradient over 30 minutes to provide the title compound. MS ($ESI^+$) m/z 400.22 $(M+H)^+$.

Example 278H tert-butyl 7'-({6-[2-chloro-3-(prop-2-en-1-yloxy)phenyl]-5-oxo-5,6-dihydroimidazo[1,2-c]pyrimido[5,4-e]pyrimidin-2-yl}amino)-1'H-spiro[cyclopropane-1,4'-isoquinoline]-2'(3'H)-carboxylate The title compound (0.2 g) was prepared as described in Example 109A, substituting Example 55D with Example 278G. The crude material was taken onto the next step without purification. MS ($ESI^+$) m/z 625.85 $(M+H)^+$.

Example 278I

6-[2-chloro-3-(prop-2-en-1-yloxy)phenyl]-2-(2',3'-dihydro-1'H-spiro[cyclopropane-1,4'-isoquinolin]-7'-ylamino)imidazo[1,2-a]pyrimido[5,4-e]pyrimidin-5(6H)-one The title compound (0.2 g) was prepared as described in Example 109B, substituting Example 109A with Example 278H, except the reaction was diluted with ethyl acetate and the organics were washed with saturated aqueous NaHCO$_3$, water, and brine, dried over MgSO$_4$, filtered, and concentrated to provide the title compound as a free base. MS (ESI$^+$) m/z 526.2 (M+H)$^+$.

Example 278J 6-(2-chloro-3-hydroxyphenyl)-2-(2',3'-dihydro-1'H-spiro[cyclopropane-1,4'-isoquinolin]-7'-ylamino) imidazo[1,2-a]pyrimido[5,4-e]pyrimidin-5(6H)-one The title compound (0.025 g) was prepared as described in Example 54G, substituting Example 54F with Example 278I. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. MS (ESI+) m/z 378.2 (M+H)+. $^1$H NMR (300 MHz, DMSO-d$_6$) δ 1.11 (d, J=2.37 Hz, 4H) 3.28 (s, 2H) 4.46 (s, 2H) 6.86-7.20 (m, 4H) 7.32 (t, J=8.14 Hz, 1H) 7.75 (d, J=32.21 Hz, 3H) 9.12 (s, 1H) 9.38 (s, 2H) 10.55 (s, 1H) 10.78 (s, 1H). MS (ESI$^+$) m/z 457.1 (M+H)$^+$.

Example 279

2-(2',3'-dihydro-1'H-spiro[cyclopropane-1,4'-isoquinolin]-7'-ylamino)-6-(4-hydroxy-2-methylphenyl) imidazo[1,2-a]pyrimido[5,4-e]pyrimidin-5(6H)-one Example 279A 4-(allyloxy)-1-isocyanato-2-methylbenzene The title compound (0.075 g) was prepared as described in Example 278C, substituting Example 278B with 4-(allyloxy)-2-methylaniline, and used in the next step without purification.

Example 279B 3-(4-(allyloxy)-2-methylphenyl)-7-(methylthio)pyrimido[4,5-d]pyrimidine-2,4(1H,3H)-dione The title compound (1.7 g) was prepared as described in Example 1A, substituting 1-chloro-2-isocyanatobenzene with Example 279A. The compound was used in the next step without purification. MS (ESI$^+$) m/z 357.19 (M+H)$^+$.

Example 279C 3-(4-(allyloxy)-2-methylphenyl)-2-chloro-7-(methylthio)pyrimido[4,5-d]pyrimidin-4(3H)-one The title compound (1.7 g) was prepared as described in Example 1B, substituting Example 1A with Example 279B. The compound was used in the next step without purification. MS (ESI$^+$) m/z 375.11 (M+H)$^+$.

Example 279D 3-(4-(allyloxy)-2-methylphenyl)-2-(2,2-dimethoxyethylamino)-7-(methylthio)pyrimido[4,5-d]pyrimidin-4(3H)-one The title compound (1.5 g) was prepared as described in Example 1C, substituting Example 1B with Example 279C. MS (ESI$^+$) m/z 444.4 (M+H)$^+$.

Example 279E

6-[2-methyl-4-(prop-2-en-1-yloxy)phenyl]-2-(methylsulfanyl)imidazo[1,2-a]pyrimido[5,4-e]pyrimidin-5(6H)-one The title compound (1.3 g) was prepared as described in Example 1D, substituting Example 1C with Example 279D. Chromatography was performed with an Analogix 280 with an SF 40-120 column, 40% to 100% ethyl acetate/hexane gradient over 30 minutes to provide the title compound. MS (ESI$^+$) m/z 380.33 (M+H)$^+$.

Example 279F tert-butyl 7'-({6-[2-methyl-4-(prop-2-en-1-yloxy) phenyl]-5-oxo-5,6-dihydroimidazo[1,2-c]pyrimido [5,4-e]pyrimidin-2-yl}amino)-1'H-spiro[cyclopropane-1,4'-isoquinoline]-2'(3'H)-carboxylate The title compound (0.085 g) was prepared as described in Example 109A, substituting Example 55D with Example 279E. The crude material was taken onto the next step without purification. MS (ESI$^+$) m/z 625.85 (M+H)$^+$.

Example 279G 2-(2',3'-dihydro-1'H-spiro[cyclopropane-1,4'-isoquinolin]-7'-ylamino)-6-(4-hydroxy-2-methylphenyl) imidazo[1,2-a]pyrimido[5,4-e]pyrimidin-5(6H)-one The title compound (0.076 g) was prepared as described in Example 54G, substituting Example 54F with Example 279F. Purification was performed using preparative HPLC on a Phenomenex Luna C8(2) 5 um 100 Å AXIA column (30 mm×75 mm). A gradient of acetonitrile (A) and 0.1% trifluoroacetic acid in water (B) was used, at a flow rate of 50 mL/min (0-0.5 min 10% A, 0.5-7.0 min linear gradient 10-95% A, 7.0-10.0 min 95% A, 10.0-12.0 min linear gradient 95-10% A). The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 0.97-1.27 (m, 4H) 1.82-2.07 (m, 3H) 3.13-3.40 (m, 2H) 4.33-4.58 (m, 2H) 6.66-6.82 (m, 2H) 6.86-6.96 (m, 1H) 7.04-7.13 (m, 2H) 7.51-7.91 (m, 3H) 9.10 (s, 1H) 9.54 (s, 2H) 10.73 (s, 2H). MS (ESI$^+$) m/z 466.19 (M+H)$^+$.

Example 280

6-(2-chloro-6-fluorophenyl)-2-{[2-(2,2-difluoroethyl)-4,4-dimethyl-1,2,3,4-tetrahydroisoquinolin-7-yl]amino}imidazo[1,2-a]pyrimido[5,4-e]pyrimidin-5(6H)-one

Example 280A 2-(2,2-difluoroethyl)-4,4-dimethyl-1,2,3,4-tetrahydroisoquinolin-7-amine The title compound was prepared as described in Example 224B, substituting Example 224A with 4,4-dimethyl-1,2,3,4-tetrahydroisoquinolin-7-amine, and using 2.5 equivalents of $K_2CO_3$.

Example 280B 6-(2-chloro-6-fluorophenyl)-2-{[2-(2,2-difluoroethyl)-4,4-dimethyl-1,2,3,4-tetrahydroisoquinolin-7-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 280A, respectively. Aqueous workup was done before the HPLC purification (see HPLC protocol in Example 241). $^1$H NMR (400 MHz, CD$_3$OD) δ 1.48 (s, 6H), 3.43 (s, 2H), 3.75 (td, J=14.7, 3.8 Hz, 2H), 4.49 (s, 2H), 6.48 (tt, J=54.0, 3.9 Hz, 1H), 7.09 (d, J=1.8 Hz, 1H), 7.39 (td, J=9.1, 1.2 Hz, 1H), 7.56-7.52 (m, 2H), 7.66-7.60 (m, 1H), 7.81-7.67 (m, 2H), 7.87 (s, 1H), 9.18 (s, 1H). MS (ESI$^+$) m/z 554.2 (M+H)$^+$.

Example 281

6-(2-chloro-6-fluorophenyl)-2-{[2-(2-fluoro ethyl)-4,4-dimethyl-1,2,3,4-tetrahydroisoquinolin-7-yl]amino}imidazo[1,2-a]pyrimido[5,4-e]pyrimidin-5(6H)-one

Example 281A 2-(2-fluoroethyl)-4,4-dimethyl-1,2,3,4-tetrahydroisoquinolin-7-amine The title compound was prepared as described in Example 224B, substituting Example 224A and 1,1-difluoro-2-iodoethane with 4,4-dimethyl-1,2,3,4-tetrahydroisoquinolin-7-amine and 1-bromo-2-fluoroethane, respectively, and using 2.5 equivalent of $K_2CO_3$.

Example 281B 6-(2-chloro-6-fluorophenyl)-2-{[2-(2-fluoro ethyl)-4,4-dimethyl-1,2,3,4-tetrahydroisoquinolin-7-yl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and Example 281A, respectively. An aqueous workup was done before the HPLC purification (see HPLC protocol in Example 241). $^1$H NMR (400 MHz, CD$_3$OD) δ 1.50 (s, 6H), 3.56 (bs, 2H), 3.88-3.67 (m, 2H), 4.62 (bs, 2H), 5.06-4.93 (m, 2H), 7.08 (d, J=1.8 Hz, 1H), 7.43-7.33 (m, 1H), 7.68-7.47 (m, 3H), 7.85-7.71 (m, 2H), 7.88 (s, 1H), 9.18 (s, 1H). MS (ESI$^+$) m/z 536.2 (M+H)$^+$.

Example 282

2-{[4-(1,4'-bipiperidin-1'-yl)phenyl]amino}-6-(2,6-dichlorophenyl)imidazo[1,2-a]pyrimido[5,4-e]pyrimidin-5(6H)-one The title compound (0.075 g) was prepared as described in Example 150, substituting 1,1,2-trimethyl-1,2,3,4-tetrahydroisoquinolin-6-amine with 4-(1,4'-bipiperidin-1'-yl)aniline. The crude material was triturated with ethyl acetate to provide the title compound. $^1$H NMR (300 MHz, DMSO-d$_6$) δ 1.49 (d, 9H) 1.81 (d, 2H) 2.32 (d, 1H) 2.56-2.75 (m, 3H) 3.70 (d, 2H) 7.00 (d, J=8.14 Hz, 2H) 7.10 (d, J=1.70 Hz, 1H) 7.47-7.87 (m, 6H) 9.09 (s, 1H) 10.69 (s, 1H). MS (ESI$^+$) m/z 589.2 (M+H)$^+$.

Example 283

6-(2,6-dichlorophenyl)-2-({4-[(3R)-3-(dimethylamino)pyrrolidin-1-yl]phenyl}amino)imidazo[1,2-a]pyrimido[5,4-e]pyrimidin-5(6H)-one The title compound (0.08 g) was prepared as described in Example 150, substituting 1,1,2-trimethyl-1,2,3,4-tetrahydroisoquinolin-6-amine with (R)-1-(4-aminophenyl)-N,N-dimethylpyrrolidin-3-amine. Chromatography was performed with an Analogix 280 with an SF 12-24 column, 4% methanol/dichloromethane with a small amount of ammonium hydroxide over 30 minutes. The purified material was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 2.33 (d, 2H) 2.83 (d, 6H) 3.27 (d, 1H) 3.59 (d, 4H) 6.72 (d, J=8.82 Hz, 2H) 7.10 (d, J=1.70 Hz, 1H) 7.44-7.96 (m, 6H) 9.08 (s, 1H) 10.66 (s, 1H) 10.90 (s, 1H). MS (ESI$^+$) m/z 535.2 (M+H)$^+$.

Example 284

6-(2,6-dichlorophenyl)-2-[(4-{[2-(dimethylamino)ethyl]amino}phenyl)amino]imidazo[1,2-a]pyrimido[5,4-e]pyrimidin-5(6H)-one The title compound (0.05 g) was prepared as described in Example 150, substituting 1,1,2-trimethyl-1,2,3,4-tetrahydroisoquinolin-6-amine with 3-chloro-4-(4-methylpiperazin-1-yl)aniline. Chromatography was performed with an Analogix 280 with an SF 12-24 column, 4% methanol/dichloromethane with a small amount of ammonium hydroxide over 30 minutes. The purified material was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 2.80 (d, 6H) 3.23 (d, 2H) 3.45 (d, 2H) 6.75 (d, J=8.82 Hz, 2H) 7.10 (d, J=1.70 Hz, 1H) 7.46 (s, 1H) 7.53-7.72 (m, 3H) 7.69-7.84 (m, 3H) 9.08 (s, 1H) 10.63 (s, 1H). MS (ESI$^+$) m/z 509.2 (M+H)$^+$.

Example 285

2-{[2'-(cyclopropylsulfonyl)-2',3'-dihydro-1'H-spiro[cyclopropane-1,4'-isoquinolin]-7'-yl]amino}-6-(2,6-dichlorophenyl)imidazo[1,2-a]pyrimido[5,4-e]pyrimidin-5(6H)-one The title compound (0.048 g) was prepared as described in Example 206, substituting mesyl chloride with cyclopropanesulfonyl chloride. Chromatography was performed with an Analogix 280 with an SF 12-24 column, 40% to 100% ethyl acetate/hexane gradient over 30 minutes. $^1$H NMR (300 MHz, DMSO-$d_6$) δ 0.95 (d, 8H) 2.61 (d, 1H) 3.39 (d, 2H) 4.58 (d, 2H) 6.88 (d, J=8.33 Hz, 1H) 7.13 (d, J=1.98 Hz, 1H) 7.46-7.99 (m, 6H) 9.16 (s, 1H) 10.83 (s, 1H). MS (ESI$^+$) m/z 608.2 (M+H)$^+$.

Example 286

6-(2,6-dichlorophenyl)-2-{[2'-(propan-2-ylsulfonyl)-2',3'-dihydro-1'H-spiro[cyclopropan-1,4'-isoquinolin]-7'-yl]amino}imidazo[1,2-a]pyrimido[5,4-e]pyrimidin-5(6H)-one The title compound (0.04 g) was prepared as described in Example 206, substituting methanesulfonyl chloride with propane-2-sulfonyl chloride. Chromatography was performed with an Analogix 280 with an SF 12-24 column, 40% to 100% ethyl acetate/hexane gradient over 30 minutes. $^1$H NMR (300 MHz, DMSO-$d_6$) δ 1.00 (d, 4H) 1.25 (d, 6H) 3.43 (d, 2H) 4.57 (d, 2H) 6.88 (d, J=9.12 Hz, 1H) 7.13 (d, J=1.98 Hz, 1H) 7.41-7.96 (m, 6H) 9.15 (s, 1H) 10.83 (s, 1H). MS (ESI$^+$) m/z 610.2 (M+H)$^+$.

Example 287

6-(2,6-dichlorophenyl)-2-{[4-(1-methylpiperidin-4-yl)phenyl]amino}imidazo[1,2-a]pyrimido[5,4-e]pyrimidin-5(6H)-one The title compound (0.07 g) was prepared as described in Example 150, substituting 1,1,2-trimethyl-1,2,3,4-tetrahydroisoquinolin-6-amine with 4-(1-methylpiperidin-4-yl) aniline. Chromatography was performed with an Analogix 280 with an SF 12-24 column, 5% methanol/dichloromethane with a small amount of ammonium hydroxide over 30 minutes. The purified material was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 1.94 (d, 4H) 2.78 (d, 4H) 2.97-3.17 (m, 2H) 7.12 (d, J=1.98 Hz, 1H) 7.21-7.40 (m, 2H) 7.51-8.09 (m, 6H) 9.16 (s, 1H) 10.10 (s, 1H) 10.87 (s, 1H). MS (ESI$^+$) m/z 520.3 (M+H)$^+$.

Example 288

2-{[4-(2,7-diazaspiro[3.5]non-7-yl)phenyl]amino}-6-(2,6-dichlorophenyl)imidazo[1,2-a]pyrimido[5,4-e]pyrimidin-5(6H)-one

Example 288A tert-butyl 7-(4-nitrophenyl)-2,7-diazaspiro[3.5] nonane-2-carboxylate To a solution of 1-fluoro-4-nitrobenzene (0.155 ml, 1.458 mmol) in DMSO was added N,N-diisopropylethylamine (0.926 ml, 5.30 mmol) followed by tert-butyl 2,7-diazaspiro[3.5]nonane-2-carboxylate (300 mg, 1.326 mmol). The reaction mixture was heated to 100° C. overnight, and cooled to room temperature. The reaction mixture was quenched with 75 mL water, filtered, washed with water and dried over high-vac to provide the title compound. MS (ESI$^+$) m/z 348.1 (M+H)$^+$.

Example 288B tert-butyl 7-(4-aminophenyl)-2,7-diazaspiro[3.5] nonane-2-carboxylate Example 288A (350 mg, 1.007 mmol) and 49 mg 10% Pd/C were charged into a 100 mL flask followed by 5 mL methanol. The flask was then charged with hydrogen by vacuum cycle from a balloon. The reaction was stirred overnight, diluted with dichloromethane, filtered through diatomaceous earth, and concentrated to provide the title compound. MS (ESI$^+$) m/z 318.4 (M+H)$^+$.

Example 288C tert-butyl 7-(4-{[6-(2,6-dichlorophenyl)-5-oxo-5,6-dihydroimidazo[1,2-a]pyrimido[5,4-e]pyrimidin-2-yl]amino}phenyl)-2,7-diazaspiro[3.5]nonane-2-carboxylate The title compound (0.12 g) was prepared as described in Example 109A, substituting tert-butyl 7'-amino-1'H-spiro[cyclopropane-1,4'-isoquinoline]-2'(3'H)-carboxylate with Example 288B. Chromatography was performed with an Analogix 280 with an SF 12-24 column, 40% to 100% ethyl acetate/hexane gradient over 30 minutes. MS (ESI$^+$) m/z 647.35 (M+H)$^+$.

Example 288D

2-{[4-(2,7-diazaspiro[3.5]non-7-yl)phenyl]amino}-6-(2,6-dichlorophenyl)imidazo[1,2-a]pyrimido[5,4-e]pyrimidin-5(6H)-one The title compound (0.11 g) was prepared as described in Example 109B, substituting Example 109A with Example 135A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-$d_6$) δ 2.01 (d, 4H) 3.25 (d, 4H) 3.80 (d, 4H) 7.12 (d, J=1.70 Hz, 1H) 7.26 (s, 2H) 7.51-8.01 (m, 6H) 8.90 (s, 2H) 9.14 (s, 1H) 10.80 (s, 1H). MS (ESI$^+$) m/z 547.2 (M+H)$^+$.

Example 289

6-(2-chlorophenyl)-2-({4-[2-(trifluoromethyl)pyrrolidin-1-yl]phenyl}amino)imidazo[1,2-a]pyrimido[5,4-e]pyrimidin-5(6H)-one

Example 289A 1-(4-nitrophenyl)-2-(trifluoromethyl)pyrrolidine

The title compound was prepared as described in Example 183A substituting 2-(trifluoromethyl)pyrrolidine for bis(2-methoxyethyl)amine. MS (ESI$^+$) m/e 261.1 (M+H)$^+$.

Example 289B 4-(2-(trifluoromethyl)pyrrolidin-1-yl)aniline

The title compound was prepared as described in Example 183B substituting Example 289A for Example 183A.

Example 289C 6-(2-chlorophenyl)-2-({4-[2-(trifluoromethyl)pyrrolidin-1-yl]phenyl}amino)imidazo[1,2-a]pyrimido[5,4-e]pyrimidin-5(6H)-one The title compound was prepared as described in Example 183C substituting Example 289B for Example 183B. $^1$H NMR (400 MHz, DMSO-$d_6$, 90° C.) δ 10.19 (br s, 1H), 9.02 (s, 1H), 7.59 (m, 7H), 7.02 (s, 1H), 6.85 (d, 2H), 4.54 (m, 1H), 3.61 (M, 1H), 3.23 (q, 1H), 2.11 (m, 4H). MS (ESI$^+$) m/e 526.3 (M+H)$^+$.

Example 290

6-(2-chlorophenyl)-2-{[4-(piperidin-4-yloxy)phenyl]amino}imidazo[1,2-a]pyrimido[5,4-e]pyrimidin-5(6H)-one The title compound was prepared as described in Example 203C substituting tert-butyl 4-(4-aminophenoxy)piperidine-1-carboxylate for Example 203B. $^1$H NMR (500 MHz, DMSO-$d_6$, 90° C.) δ 10.33 (s, 1H), 9.06 (s, 1H), 7.67 (m, 4H), 7.55 (m, 3H), 7.04 (m, 3H), 4.51 (m, 1H), 3.29 (m, 2H), 3.13 (m, 2H), 2.13 (m, 2H), 1.90 (m, 2H). MS (ESI$^+$) m/e 488.2 (M+H)$^+$.

Example 291

6-(2-chlorophenyl)-2-{[4-(piperidin-4-ylmethyl)phenyl]amino}imidazo[1,2-a]pyrimido[5,4-e]pyrimidin-5(6H)-one The title compound was prepared as described in Example 203C substituting tert-butyl 4-(4-aminobenzyl)piperidine-1-carboxylate for Example 203B. $^1$H NMR (400 MHz, DMSO-$d_6$, 90° C.) δ 10.39 (s, 1H), 9.09 (s, 1H), 7.70 (m, 4H), 7.58 (m, 3H), 7.22 (d, 2H), 7.04 (s, 1H), 3.27 (m, 2H), 2.86 (m, 2H), 2.58 (d, 2H), 1.83 (m, 3H), 1.39 (m, 2H). MS (ESI$^+$) m/e 486.3 (M+H)$^+$.

Example 292

6-(2-chlorophenyl)-2-{[4-(hexahydropyrrolo[3,4-c]pyrrol-2(1H)-yl)phenyl]amino}imidazo[1,2-a]pyrimido[5,4-e]pyrimidin-5(6H)-one

Example 292A tert-butyl 5-(4-nitrophenyl)hexahydropyrrolo[3,4-c]pyrrole-2(1H)-carboxylate The title compound was prepared as described in Example 183A substituting tert-butyl hexahydropyrrolo[3,4-c]pyrrole-2(1H)-carboxylate for bis(2-methoxyethyl)amine.

Example 292B tert-butyl 5-(4-aminophenyl)hexahydropyrrolo[3,4-c]pyrrole-2(1H)-carboxylate The title compound was prepared as described in Example 183B substituting Example 292A for Example 183B.

Example 292C 6-(2-chlorophenyl)-2-{[4-(hexahydropyrrolo[3,4-c]pyrrol-2(1H)-yl)phenyl]amino}imidazo[1,2-a]pyrimido[5,4-e]pyrimidin-5(6H)-one The title compound was prepared as described in Example 203C substituting Example 292B for Example 203B. $^1$H NMR (400 MHz, DMSO-$d_6$, 90° C.) δ 10.18 (br s, 1H), 9.02 (s, 1H), 7.60 (m, 7H), 7.02 (s, 1H), 6.72 (d, 2H), 3.51 (m, 2H), 3.34 (m, 4H), 3.10 (m, 4H). MS (ESI$^+$) m/e 499.3 (M+H)$^+$.

Example 293

1-(4-{[6-(2-chlorophenyl)-5-oxo-5,6-dihydroimidazo[1,2-a]pyrimido[5,4-e]pyrimidin-2-yl]amino}phenyl)-N-methylmethanesulfonamide The title compound was prepared as described in Example 183C substituting N-(4-aminobenzyl)methanesulfonamide hydrochloride for Example 183B. $^1$H NMR (400 MHz, DMSO-$d_6$) δ 10.84 (br s, 1H), 9.15 (s, 1H), 7.86 (m, 2H), 7.72 (m, 1H), 7.60 (m, 3H), 7.42 (br d, 2H), 7.08 (s, 1H), 6.93 (m, 1H), 4.32 (s, 2H), 2.59 (d, 3H). MS (ESI$^+$) m/e 496.1 (M+H)$^+$.

Example 294

4-{[6-(2-chlorophenyl)-5-oxo-5,6-dihydroimidazo[1,2-a]pyrimido[5,4-e]pyrimidin-2-yl]amino}-N,N-diethylbenzenesulfonamide The title compound was prepared as described in Example 183C substituting 4-amino-N,N-diethylbenzenesulfonamide for Example 183B. $^1$H NMR (400 MHz, DMSO-$d_6$) δ 11.16 (s, 1H), 9.21 (s, 1H), 8.12 (d, 2H), 8.01 (br s, 1H), 7.85 (d, 2H), 7.73 (m, 1H), 7.61 (m, 3H), 7.11 (s, 1H), 3.18 (q, 4H), 1.05 (t, 6H). MS (ESI$^+$) m/e 524.2 (M+H)$^+$.

Example 295

2-{[2-(cyclopropylamino)-2,3-dihydro-1H-inden-5-yl]amino}-6-(2,6-dichlorophenyl)imidazo[1,2-a]pyrimido[5,4-e]pyrimidin-5(6H)-one The title compound (0.07 g) was prepared as described in Example 150, substituting 1,1,2-trimethyl-1,2,3,4-tetrahydroisoquinolin-6-amine with Example 227A. Chromatography was performed with an Analogix 280 with an SF 12-24 column, 4% methanol/dichloromethane with a small amount of ammonium hydroxide over 30 minutes. $^1$H NMR (300 MHz, DMSO-$d_6$) δ 0.15-0.50 (m, 4H) 2.04-2.20 (m, 1H) 2.58-2.87 (m, 2H) 2.92-3.22 (m, 2H) 3.52-3.72 (m, 1H) 7.05-7.17 (m, 1H) 7.14-7.31 (m, 1H) 7.49-7.71 (m, 3H) 7.70-7.88 (m, 3H) 9.13 (s, 1H) 10.63-10.80 (m, 1H). MS (ESI$^+$) m/z 518.2 (M+H)$^+$.

Example 296

6-(2,6-dichlorophenyl)-2-({2-[(2-fluoroethyl)amino]-2,3-dihydro-1H-inden-5-yl}amino)imidazo[1,2-a]pyrimido[5,4-e]pyrimidin-5(6H)-one The title compound (0.075 g) was prepared as described in Example 150, substituting 1,1,2-trimethyl-1,2,3,4-tetrahydroisoquinolin-6-amine with Example 257A. Chromatography was performed with an Analogix 280 with an SF 12-24 column, 4% methanol/dichloromethane with a small amount

Example 297

6-(2,6-dichlorophenyl)-2-{[2-(propylamino)-2,3-dihydro-1H-inden-5-yl]amino}imidazo[1,2-a]pyrimido[5,4-e]pyrimidin-5(6H)-one The title compound (0.075 g) was prepared as described in Example 150, substituting 1,1,2-trimethyl-1,2,3,4-tetrahydroisoquinolin-6-amine with Example 258A. Chromatography was performed with an Analogix 280 with an SF 12-24 column, 4% methanol/dichloromethane with a small amount of ammonium hydroxide over 30 minutes. $^1$H NMR (300 MHz, DMSO-$d_6$) δ 0.73-1.01 (m, 3H) 1.29-1.56 (m, 2H) 2.52-2.62 (m, 2H) 2.58-2.79 (m, 2H) 2.87-3.21 (m, 2H) 3.42-3.63 (m, 1H) 6.97-7.29 (m, 2H) 7.37-7.85 (m, 7H) 9.14 (s, 1H) 10.48-10.94 (m, 1H). MS (ESI$^+$) m/z 520.2 (M+H)$^+$.

Example 298

2-{[4-(2-acetyl-2,7-diazaspiro[3.5]non-7-yl)phenyl]amino}-6-(2,6-dichlorophenyl)imidazo[1,2-a]pyrimido[5,4-e]pyrimidin-5(6H)-one The title compound (0.05 g) was prepared as described in Example 207 substituting Example 109B with Example 288D. The crude material was triturated with ethyl acetate to provide the title compound. $^1$H NMR (300 MHz, DMSO-$d_6$) δ 1.66-1.94 (m, 7H) 3.02-3.22 (m, 4H) 3.47-3.63 (m, 2H) 3.77-3.90 (m, 2H) 6.81-7.26 (m, 3H) 7.40-8.01 (m, 6H) 9.10 (s, 1H) 10.70 (s, 1H). MS (ESI$^+$) m/z 589.3 (M+H)$^+$.

Example 299

6-(2,6-dichlorophenyl)-2-({4-[2-(methylsulfonyl)-2,7-diazaspiro[3.5]non-7-yl]phenyl}amino)imidazo[1,2-a]pyrimido[5,4-e]pyrimidin-5(6H)-one The title compound (0.025 g) was prepared as described in Example 206 substituting Example 109B with Example 288D. The crude material was triturated with ethyl acetate to provide the title compound. $^1$H NMR (300 MHz, DMSO-$d_6$) δ 1.67-1.94 (m, 4H) 2.95-3.09 (m, 3H) 3.07-3.18 (m, 4H) 3.58-3.74 (m, 4H) 6.74-7.27 (m, 3H) 7.37-8.01 (m, 6H) 9.10 (s, 1H) 10.73 (s, 1H). MS (ESI$^+$) m/z 625.2 (M+H)$^+$.

Example 300

7'-{[6-(2-chloro-6-fluorophenyl)-5-oxo-5,6-dihydroimidazo[1,2-a]pyrimido[5,4-e]pyrimidin-2-yl]amino}-N-methyl-1'H-spiro[cyclopropane-1,4'-isoquinoline]-2'(3'H)-carboxamide A solution of Example 228 (0.075 g, 0.134 mmol), 2,5-dioxopyrrolidin-1-yl methylcarbamate (0.035 g, 0.201 mmol), and triethylamine (0.093 ml, 0.669 mmol) in N,N-dimethylformamide (2.5 ml) was stirred at room temperature overnight. Water was added to the reaction mixture slowly. The resulting solids were filtered, washed with water and purified by HPLC (see protocol in Example 241) to provide the title compound as a trifluoroacetic acid salt. $^1$H NMR (400 MHz, CD$_3$OD) δ 1.07-0.95 (m, 4H), 2.77 (s, 3H), 3.46 (s, 2H), 4.71 (s, 2H), 6.93-6.85 (m, 1H), 7.08 (d, J=1.9 Hz, 1H), 7.38 (td, J=8.7, 1.3 Hz, 1H), 7.70-7.47 (m, 4H), 7.86 (s, 1H), 9.14 (s, 1H). MS (ESI$^+$) m/z 545.2 (M+H)$^+$.

Example 301

7'-{[6-(2-chloro-6-fluorophenyl)-5-oxo-5,6-dihydroimidazo[1,2-a]pyrimido[5,4-e]pyrimidin-2-yl]amino}-N-(propan-2-yl)-1'H-spiro[cyclopropane-1,4'-isoquinoline]-2'(3'H)-carboxamide The title compound was prepared as described in Example 300, substituting 2,5-dioxopyrrolidin-1-yl methylcarbamate with 2-isocyanatopropane. $^1$H NMR (400 MHz, CD$_3$OD) δ 1.01 (s, 4H), 1.17 (d, J=6.6 Hz, 6H), 3.48 (s, 2H), 3.99-3.91 (m, 1H), 4.71 (s, 2H), 6.92-6.84 (m, 1H), 7.07 (d, J=1.9 Hz, 1H), 7.42-7.34 (m, 1H), 7.67-7.46 (m, 4H), 7.84 (bs, 1H), 9.13 (s, 1H). MS (ESI$^+$) m/z 573.2 (M+H)$^+$.

Example 302

6-(2,6-dichlorophenyl)-2-{[2-(2-fluoroethyl)-4,4-dimethyl-1,2,3,4-tetrahydroisoquinolin-7-yl]amino}imidazo[1,2-a]pyrimido[5,4-e]pyrimidin-5(6H)-one The title compound (0.015 g) was prepared as described in Example 150, substituting 1,1,2-trimethyl-1,2,3,4-tetrahydroisoquinolin-6-amine with Example 281A. Chromatography was performed with an Analogix 280 with an SF 12-24 column, 40% to 100% ethyl acetate/hexane gradient over 30 minutes to provide the title compound. $^1$H NMR (300 MHz, DMSO-$d_6$) δ 1.25 (d, 6H) 2.79 (d, 2H) 3.67 (d, 2H) 4.59 (d, 2H) 7.12 (d, J=1.70 Hz, 1H) 7.27-7.55 (m, 2H) 7.53-7.87 (m, 5H) 9.14 (s, 1H) 10.75 (s, 1H). MS (ESI$^+$) m/z 552.2 (M+H)$^+$.

Example 303

6-(2,6-dichlorophenyl)-2-({4-[6-(methylsulfonyl)-2,6-diazaspiro[3.3]hept-2-yl]phenyl}amino)imidazo[1,2-a]pyrimido[5,4-e]pyrimidin-5(6H)-one The title compound (0.07 g) was prepared as described in Example 206 substituting Example 109B with Example 304D. The crude material was triturated with dichloromethane to provide the title compound. $^1$H NMR (300 MHz, DMSO-$d_6$) δ 2.99 (d, 3H) 3.96 (d, 4H) 4.09 (d, 4H) 6.53 (d, J=8.14 Hz, 2H) 7.09 (d, J=1.70 Hz, 1H) 7.42-7.98 (m, 6H) 9.08 (s, 1H) 10.66 (s, 1H). MS (ESI$^+$) m/z 597.2 (M+H)$^+$.

Example 304

2-{[4-(2,6-diazaspiro[3.3]hept-2-yl)phenyl]amino}-6-(2,6-dichlorophenyl)imidazo[1,2-a]pyrimido[5,4-e]pyrimidin-5(6H)-one

Example 304A tert-butyl 6-(4-nitrophenyl)-2,6-diazaspiro[3.3]heptane-2-carboxylate The title compound (0.4 g) was prepared as described in Example 288A, substituting tert-butyl 2,7-diazaspiro[3.5]nonane-2-carboxylate with tert-butyl 2,6-diazaspiro[3.3]heptane-2-carboxylate, mono oxalate salt. MS (ESI$^+$) m/z 320.1 (M+H)$^+$.

Example 304B tert-butyl 6-(4-aminophenyl)-2,6-diazaspiro[3.3]
heptane-2-carboxylate The title compound (0.35 g) was prepared as described in Example 288B, substituting Example 288A with Example 304A. MS (ESI⁺) m/z 290.1 (M+H)⁺.

Example 304C tert-butyl 6-(4-{[6-(2,6-dichlorophenyl)-5-oxo-5,6-dihydroimidazo[1,2-a]pyrimido[5,4-e]pyrimidin-2-yl]amino}phenyl)-2,6-diazaspiro[3.3]heptane-2-carboxylate The title compound (0.08 g) was prepared as described in Example 109A, substituting tert-butyl 7'-amino-1'H-spiro[cyclopropane-1,4'-isoquinoline]-2'(3'H)-carboxylate with Example 304B. Chromatography was performed with an Analogix 280 with an SF 12-24 column, 10% to 70% ethyl acetate/hexane gradient over 30 minutes. MS (ESI⁺) m/z 619.3 (M+H)⁺.

Example 304D

2-{[4-(2,6-diazaspiro[3.3]hept-2-yl)phenyl]amino}-6-(2,6-dichlorophenyl)imidazo[1,2-a]pyrimido[5,4-e]pyrimidin-5(6H)-one The title compound (0.07 g) was prepared as described in Example 109B, substituting Example 109A with Example 304C, except the reaction mixture was diluted with 100 mL ethyl acetate and the organics were washed with saturated aqueous NaHCO₃ solution, water, and brine, dried over MgSO₄, filtered, and concentrated to provide the title compound. ¹H NMR (300 MHz, DMSO-d) δ 3.85-4.04 (m, 4H) 4.04-4.24 (m, 4H) 6.54 (d, J=8.33 Hz, 2H) 7.10 (d, J=1.98 Hz, 1H) 7.38-7.92 (m, 7H) 9.08 (s, 1H) 10.67 (s, 1H). MS (ESI⁺) m/z 519.2 (M+H)⁺.

Example 305

6-(2,6-dichlorophenyl)-2-{[2-(pyrrolidin-1-yl)-2,3-dihydro-1H-inden-5-yl]amino}imidazo[1,2-a]pyrimido[5,4-e]pyrimidin-5(6H)-one The title compound (0.085 g) was prepared as described in Example 150, substituting 1,1,2-trimethyl-1,2,3,4-tetrahydroisoquinolin-6-amine with Example 259A. Chromatography was performed with an Analogix 280 with an SF 12-24 column, 4% methanol/dichloromethane with a small amount of ammonium hydroxide over 30 minutes. The compound was dissolved in methanol, treated with excess 2M HCl in diethyl ether and stirred until a solid began to form. The mixture was diluted with ether, stirred for 10 minutes, and filtered to provide the title compound. ¹H NMR (500 MHz, DMSO-d₆) δ 1.99 (d, 4H) 3.10 (d, 2H) 3.33 (d, 5H) 4.10 (d, 1H) 7.13 (d, J=1.53 Hz, 1H) 7.31 (s, 1H) 7.45-8.04 (m, 6H) 9.16 (s, 1H) 10.89 (s, 1H) 11.50 (s, 1H). MS (ESI⁺) m/z 532.2 (M+H)⁺.

Example 306

6-(2,6-dichlorophenyl)-2-({2-[(3S)-3-fluoropyrrolidin-1-yl]-2,3-dihydro-1H-inden-5-yl}amino)imidazo[1,2-a]pyrimido[5,4-e]pyrimidin-5(6H)-one The title compound (0.085 g) was prepared as described in Example 150, substituting 1,1,2-trimethyl-1,2,3,4-tetrahydroisoquinolin-6-amine with Example 256A. Chromatography was performed with an Analogix 280 with an SF 12-24 column, 4% methanol/dichloromethane with a small amount of ammonium hydroxide over 30 minutes. The compound was dissolved in methanol, treated with excess 2M HCl in diethyl ether and stirred until a solid began to form. The mixture was diluted with ether, stirred for 10 minutes, and filtered to provide the title compound. ¹H NMR (500 MHz, DMSO-d₆) δ 1.99-2.44 (m, 2H) 3.19-3.64 (m, 6H) 3.63-3.80 (m, 2H) 4.05-4.35 (m, 1H) 5.34-5.69 (m, 1H) 7.13 (s, 1H) 7.31 (s, 1H) 7.51-7.99 (m, 6H) 9.16 (s, 1H) 10.89 (s, 1H). MS (ESI⁺) m/z 550.2 (M+H)⁺.

Example 307

6-(2,6-dichlorophenyl)-2-[(4,4-dimethyl-1,2,3,4-tetrahydroisoquinolin-7-yl)amino]imidazo[1,2-a]pyrimido[5,4-e]pyrimidin-5(6H)-one

Example 307A tert-butyl 7-{[6-(2,6-dichlorophenyl)-5-oxo-5,6-dihydroimidazo[1,2-a]pyrimido[5,4-e]pyrimidin-2-yl]amino}-4,4-dimethyl-3,4-dihydroisoquinoline-2(1H)-carboxylate The title compound (0.42 g) was prepared as described in Example 109A, substituting tert-butyl 7'-amino-1'H-spiro[cyclopropane-1,4'-isoquinoline]-2'(3'H)-carboxylate with tert-butyl 7-amino-4,4-dimethyl-3,4-dihydroisoquinoline-2(1H)-carboxylate. The final compound was triturated from the crude reaction mixture with dichloromethane/ethyl acetate. MS (ESI⁺) m/z 606.01 (M+H)⁺.

Example 307B 6-(2,6-dichlorophenyl)-2-[(4,4-dimethyl-1,2,3,4-tetrahydroisoquinolin-7-yl)amino]imidazo[1,2-a]pyrimido[5,4-e]pyrimidin-5(6H)-one The title compound (0.4 g) was prepared as described in Example 109B, substituting Example 109A with Example 307A. The TFA salt was dissolved in methanol, treated with excess 2M HCl in diethyl ether and stirred until a solid began to form. The mixture was diluted with ether, stirred for 10 minutes, and filtered to provide the title compound. ¹H NMR (500 MHz, DMSO-d₆) δ 1.37 (d, 6H) 3.22 (d, 2H) 4.28 (d, 2H) 7.14 (d, J=1.53 Hz, 1H) 7.42-8.02 (m, 7H) 9.17 (s, 1H) 9.48-9.70 (m, 2H) 10.93 (s, 1H). MS (ESI⁺) m/z 506.2 (M+H)⁺.

Example 308

6-(2,6-dichlorophenyl)-2-{[4-(piperidin-4-ylamino)phenyl]amino}imidazo[1,2-a]pyrimido[5,4-e]pyrimidin-5(6H)-one

Example 308A tert-butyl 4-[(4-{[6-(2,6-dichlorophenyl)-5-oxo-5,6-dihydroimidazo[1,2-a]pyrimido[5,4-e]pyrimidin-2-yl]amino}phenyl)amino]piperidine-1-carboxylate The title compound (0.15 g) was prepared as described in Example 109A, substituting tert-butyl 7'-amino-1'H-spiro[cyclopropane-1,4'-isoquinoline]-2'(3'H)-carboxylate with tert-butyl 4-(4-aminophenylamino)piperidine-1-carboxylate. The final compound was triturated from the crude reaction mixture with dichloromethane/ethyl acetate. MS (ESI$^+$) m/z 620.95 (M+H)$^+$.

Example 308B 6-(2,6-dichlorophenyl)-2-{[4-(piperidin-4-ylamino) phenyl]amino}imidazo[1,2-a]pyrimido[5,4-e]pyrimidin-5(6H)-one The title compound (0.14 g) was prepared as described in Example 109B, substituting Example 109A with Example 308A. The TFA salt was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 1.46-1.75 (m, 2H) 1.96-2.17 (m, 2H) 2.84-3.14 (m, 2H) 3.21-3.38 (m, 2H) 6.92 (s, 2H) 7.11 (d, J=1.59 Hz, 1H) 7.41-7.91 (m, 6H) 8.69 (d, J=38.48 Hz, 2H) 9.10 (s, 1H) 10.71 (s, 1H). MS (ESI$^+$) m/z 521.3 (M+H)$^+$.

Example 309

6-(2-chloro-6-fluorophenyl)-2-{[4-(1-methylpiperidin-4-yl)phenyl]amino}imidazo[1,2-a]pyrimido[5,4-e]pyrimidin-5(6H)-one The title compound was prepared as described in Example 123B, substituting Example 123A and 4-(4-methylpiperazin-1-yl)aniline with Example 95C and 4-(1-methylpiperidin-4-yl)aniline, respectively. An aqueous workup was done before the HPLC purification. $^1$H NMR (400 MHz, CD$_3$OD) δ 2.12-1.89 (m, 2H), 2.21-2.12 (m, 2H), 2.97-2.86 (m, 4H), 3.23-3.09 (m, 2H), 3.67-3.60 (m, 2H), 7.08 (d, J=1.9 Hz, 1H), 7.46-7.22 (m, 3H), 7.65-7.52 (m, 2H), 7.90-7.71 (m, 3H), 9.14 (bs, 1H). MS (ESI$^+$) m/z 504.3 (M+H)$^+$.

Example 310

2-[(2-acetyl-4,4-dimethyl-1,2,3,4-tetrahydroisoquinolin-7-yl)amino]-6-(2-chloro-6-fluorophenyl) imidazo[1,2-a]pyrimido[5,4-e]pyrimidin-5(6H)-one

Example 310A 6-(2-chloro-6-fluorophenyl)-2-[(4,4-dimethyl-1,2,3,4-tetrahydroisoquinolin-7-yl)amino]imidazo[1,2-a]pyrimido[5,4-e]pyrimidin-5(6H)-one The title compound was prepared as described in Example 160A and Example 160B, substituting Example 123A and tert-butyl 7'-amino-1'H-spiro[cyclopropane-1,4'-isoquinoline]-2'(3'H)-carboxylate with Example 95C and tert-butyl 7-amino-4,4-dimethyl-3,4-dihydroisoquinoline-2(1H)-carboxylate, respectively, in Example 160A.

Example 310B

2-[(2-acetyl-4,4-dimethyl-1,2,3,4-tetrahydroisoquinolin-7-yl)amino]-6-(2-chloro-6-fluorophenyl) imidazo[1,2-a]pyrimido[5,4-e]pyrimidin-5(6H)-one The title compound was prepared as described in Example 241, substituting Example 228 with Example 310A. $^1$H NMR (400 MHz, CD$_3$OD) δ 1.29 (s, 3H), 1.34 (s, 3H), 2.26-2.19 (m, 3H), 3.63-3.54 (m, 2H), 4.80-4.78 (m, 2H), 7.07 (s, 1H), 7.49-7.33 (m, 2H), 7.55-7.49 (m, 1H), 7.71-7.54 (m, 3H), 7.85 (bs, 1H), 9.14 (s, 1H). MS (ESI$^+$) m/z 532.3 (M+H)$^+$.

Example 311

6-(2-chloro-6-fluorophenyl)-2-{[2-(cyclopropylcarbonyl)-4,4-dimethyl-1,2,3,4-tetrahydroisoquinolin-7-yl]amino}imidazo[1,2-a]pyrimido[5,4-e]pyrimidin-5(6H)-one The title compound was prepared as described in Example 241, substituting Example 228 and acetic acid with Example 310A and cyclopropanecarboxylic acid, respectively. $^1$H NMR (400 MHz, DMSO-d$_6$) δ 0.85-0.70 (m, 4H), 1.32-1.18 (m, 6H), 2.20-2.05 (m, 1H), 3.54 (s, 0.7H), 3.74 (s, 1.3H), 4.71 (s, 1.3H), 4.99 (s, 0.7H), 7.12 (d, J=1.8 Hz, 1H), 7.91-7.15 (m, 7H), 9.15 (s, 1H), 10.80 (bs, 1H). MS (ESI$^+$) m/z 558.3 (M+H)$^+$.

Example 312

6-(2-chloro-6-fluorophenyl)-2-{[4,4-dimethyl-2-(methylsulfonyl)-1,2,3,4-tetrahydroisoquinolin-7-yl] amino}imidazo[1,2-a]pyrimido[5,4-e]pyrimidin-5(6H)-one The title compound was prepared as described in Example 172, substituting Example 160B with Example 310A. $^1$H NMR (400 MHz, DMSO-d$_6$) δ 1.30 (s, 6H), 3.01 (s, 3H), 3.17 (s, 2H), 4.39 (s, 2H), 7.13 (d, J=1.8 Hz, 1H), 7.88-7.22 (m, 7H), 9.15 (s, 1H), 10.83 (bs, 1H). MS (ESI$^+$) m/z 568.2 (M+H)$^+$.

Example 313

2-{[4-(2,6-diazaspiro[3.4]oct-2-yl)phenyl]amino}-6-(2,6-dichlorophenyl)imidazo[1,2-a]pyrimido[5,4-e] pyrimidin-5(6H)-one

Example 313A tert-butyl 2-(4-nitrophenyl)-2,6-diazaspiro[3.4]octane-6-carboxylate The title compound (0.48 g) was prepared as described in Example 288A, substituting tert-butyl 2,7-diazaspiro[3.5] nonane-2-carboxylate with tert-butyl 2,6-diazaspiro[3.4]octane-6-carboxylate. MS (ESI$^+$) m/z 334.1 (M+H)$^+$.

Example 313B tert-butyl 2-(4-aminophenyl)-2,6-diazaspiro[3.4] octane-6-carboxylate The title compound (0.4 g) was prepared as described in Example 288B, substituting Example 288A with Example 313A. MS (ESI$^+$) m/z 304.1 (M+H)$^+$.

Example 313C tert-butyl 2-(4-{[6-(2,6-dichlorophenyl)-5-oxo-5,6-dihydroimidazo[1,2-a]pyrimido[5,4-e]pyrimidin-2-yl]amino}phenyl)-2,6-diazaspiro[3.4]octane-6-carboxylate The title compound (0.12 g) was prepared as described in Example 109A, substituting tert-butyl 7'-amino-1'H-spiro

[cyclopropane-1,4'-isoquinoline]-2'(3'H)-carboxylate with Example 313B. Chromatography was performed with an Analogix 280 with an SF 25-40 column, 40% to 100% ethyl acetate/hexane gradient over 30 minutes to provide the title compound. MS (ESI$^+$) m/z 635.4 (M+H)$^+$.

Example 313D

2-{[4-(2,6-diazaspiro[3.4]oct-2-yl)phenyl]amino}-6-(2,6-dichlorophenyl)imidazo[1,2-a]pyrimido[5,4-e]pyrimidin-5(6H)-one The title compound (0.1 g) was prepared as described in Example 109B, substituting Example 109A with Example 313C and the reaction mixture was diluted with 100 mL ethyl acetate. The organics were washed with saturated aqueous NaHCO$_3$ solution, water, and brine, dried over MgSO$_4$, filtered, and concentrated to provide the title compound as the free base. $^1$H NMR (300 MHz, DMSO-d$_6$) δ 2.18 (d, 2H) 3.16 (d, 4H) 3.79 (d, 4H) 6.54 (d, J=8.14 Hz, 2H) 7.10 (d, J=1.70 Hz, 1H) 7.38-7.92 (m, 7H) 8.98-9.16 (m, 1H) 10.66 (s, 1H). MS (ESI$^+$) m/z 533.3 (M+H)$^+$.

Example 314

2-{[4-(2,7-diazaspiro[3.5]non-2-yl)phenyl]amino}-6-(2,6-dichlorophenyl)imidazo[1,2-a]pyrimido[5,4-e]pyrimidin-5(6H)-one

Example 314A tert-butyl 2-(4-nitrophenyl)-2,7-diazaspiro[3.5]nonane-7-carboxylate The title compound (0.5 g) was prepared as described in Example 288A, substituting tert-butyl 2,7-diazaspiro[3.5]nonane-2-carboxylate with tert-butyl 2,7-diazaspiro[3.5]nonane-7-carboxylate. MS (ESI$^+$) m/z 348.1 (M+H)$^+$.

Example 314B tert-butyl 2-(4-aminophenyl)-2,7-diazaspiro[3.5]nonane-7-carboxylate The title compound (0.4 g) was prepared as described in Example 288B, substituting Example 288A with Example 314A. MS (ESI$^+$) m/z 317.9 (M+H)$^+$.

Example 314C tert-butyl 2-(4-{[6-(2,6-dichlorophenyl)-5-oxo-5,6-dihydroimidazo[1,2-a]pyrimido[5,4-e]pyrimidin-2-yl]amino}phenyl)-2,7-diazaspiro[3.5]nonane-7-carboxylate The title compound (0.12 g) was prepared as described in Example 109A, substituting tert-butyl 7'-amino-1'H-spiro[cyclopropane-1,4'-isoquinoline]-2'(3'H)-carboxylate with Example 314B. Chromatography was performed with an Analogix 280 with an SF 12-24 column, 40% to 100% ethyl acetate/hexane gradient over 30 minutes. MS (ESI$^+$) m/z 647.26 (M+H)$^+$.

Example 314D

2-{[4-(2,7-diazaspiro[3.5]non-2-yl)phenyl]amino}-6-(2,6-dichlorophenyl)imidazo[1,2-a]pyrimido[5,4-e]pyrimidin-5(6H)-one The title compound (0.12 g) was prepared as described in Example 109B, substituting Example 109A with Example 314C, except the reaction mixture was diluted with ethyl acetate and the organics were washed with saturated aqueous NaHCO$_3$ solution. The resulting emulsion was filtered and the solid was set aside. The organics were washed with brine, dried over MgSO$_4$, filtered, and concentrated. The solid from the filter step was added to this and the material was dried over high-vacuum to provide the title compound. $^1$H NMR (300 MHz, DMSO-d$_6$) δ 1.93 (d, 4H) 3.02 (d, 4H) 3.61 (d, 4H) 6.51 (d, J=8.48 Hz, 2H) 7.09 (d, J=2.03 Hz, 1H) 7.36-8.01 (m, 6H) 8.48 (s, 2H) 9.08 (s, 1H) 10.65 (s, 1H). MS (ESI$^+$) m/z 547.3 (M+H)$^+$.

Example 315

6-(2,6-dichlorophenyl)-2-({4-[(3S)-3-(dimethylamino)pyrrolidin-1-yl]phenyl}amino)imidazo[1,2-a]pyrimido[5,4-e]pyrimidin-5(6H)-one The title compound (0.08 g) was prepared as described in Example 150, substituting 1,1,2-trimethyl-1,2,3,4-tetrahydroisoquinolin-6-amine with (S)-1-(4-aminophenyl)-N,N-dimethylpyrrolidin-3-amine. Chromatography was performed with an Analogix 280 with an SF 12-24 column, 4% methanol/dichloromethane with a small amount of ammonium hydroxide over 30 minutes. The purified compound was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 2.30 (d, 2H) 2.82 (d, 6H) 3.26 (d, 1H) 3.65 (d, 2H) 3.99 (d, 1H) 6.72 (d, J=8.33 Hz, 2H) 7.10 (d, J=1.59 Hz, 1H) 7.43-7.91 (m, 6H) 9.08 (s, 1H) 10.52-10.80 (m, 2H). MS (ESI$^+$) m/z 535.3 (M+H)$^+$.

Example 316

6-(2-chloro-6-fluorophenyl)-2-{[2-(hydroxyacetyl)-4,4-dimethyl-1,2,3,4-tetrahydroisoquinolin-7-yl]amino}imidazo[1,2-a]pyrimido[5,4-e]pyrimidin-5(6H)-one The title compound was prepared as described in Example 241, substituting Example 228 and acetic acid with Example 310A and 2-hydroxyacetic acid, respectively.

Example 317

7-{[6-(2-chloro-6-fluorophenyl)-5-oxo-5,6-dihydroimidazo[1,2-a]pyrimido[5,4-e]pyrimidin-2-yl]amino}-4,4-dimethyl-3,4-dihydroisoquinoline-2(1H)-sulfonamide To a suspension of Example 310A (0.070 g, 0.124 mmol) in CH$_2$Cl$_2$ (6 mL) was added triethylamine (0.069 mL, 0.497 mmol) and (tert-butoxycarbonyl){[4-(dimethyliminio)pyridin-[(4H)-yl]sulfonyl}azanide (US2007/0149512, 0.037 g, 0.124 mmol). The reaction mixture was stirred overnight and treated with trifluoroacetic acid (0.5 mL, 6.49 mmol). After 4 hours, the reaction mixture was concentrated and purified by HPLC (see protocol in Example 1F) to provide the title compound as a trifluoroacetic acid salt.

Example 318

2-[(2-acetyl-4,4-dimethyl-1,2,3,4-tetrahydroisoquinolin-7-yl)amino]-6-(2,6-dichlorophenyl)imidazo[1,2-a]pyrimido[5,4-e]pyrimidin-5(6H)-one The title compound (0.075 g) was prepared as described in Example 207 substituting Example 109B with Example 307B. Chromatography was performed with an Analogix 280 with an SF 25-40 column, 0% to 6% methanol/dichloromethane gradient over 30 minutes. $^1$H NMR (300 MHz, DMSO-d$_6$) δ 1.16-1.36 (m, 6H) 2.04-2.22 (m, 3H) 3.39-3.59 (m, 2H) 4.51-4.92 (m, 2H) 7.01-7.20 (m, 1H) 7.30-8.06 (m, 7H) 9.05-9.32 (m, 1H) 10.51-11.00 (m, 1H). MS (ESI$^+$) m/z 548.3 (M+H)$^+$.

Example 319

6-(2,6-dichlorophenyl)-2-{[4,4-dimethyl-2-(methylsulfonyl)-1,2,3,4-tetrahydroisoquinolin-7-yl]amino}imidazo[1,2-a]pyrimido[5,4-e]pyrimidin-5(6H)-one The title compound (0.07 g) was prepared as described in Example 206 substituting Example 109B with Example 307B. Chromatography was performed with an Analogix 280 with an SF 12-24 column, 40% to 100% ethyl acetate/hexane gradient over 30 minutes. $^1$H NMR (300 MHz, DMSO-d$_6$) δ 1.30 (d, 6H) 3.00 (d, 3H) 3.16 (d, 2H) 4.38 (d, 2H) 7.13 (d, J=1.70 Hz, 1H) 7.35-7.95 (m, 7H) 9.16 (s, 1H) 10.82 (s, 1H). MS (ESI$^+$) m/z 584.2 (M+H)$^+$.

Example 320

6-(2,6-dichlorophenyl)-2-{[2-(ethylsulfonyl)-4,4-dimethyl-1,2,3,4-tetrahydroisoquinolin-7-yl]amino}imidazo[1,2-a]pyrimido[5,4-e]pyrimidin-5(6H)-one The title compound (0.07 g) was prepared as described in Example 206 substituting Example 109B with Example 307B and methanesulfonyl chloride with ethanesulfonyl chloride. Chromatography was performed with an Analogix 280 with an SF 12-24 column, 40% to 70% ethyl acetate/hexane gradient over 30 minutes. $^1$H NMR (300 MHz, DMSO-d$_6$) δ 1.12-1.46 (m, 9H) 3.16 (d, 4H) 4.44 (d, 2H) 7.13 (d, J=1.70 Hz, 1H) 7.28-8.05 (m, 7H) 9.16 (s, 1H) 10.82 (s, 1H). MS (ESI$^+$) m/z 598.2 (M+H)$^+$.

Example 321

2-({4-[(1-acetylpiperidin-4-yl)amino]phenyl}amino)-6-(2,6-dichlorophenyl)imidazo[1,2-a]pyrimido[5,4-e]pyrimidin-5(6H)-one The title compound (0.025 g) was prepared as described in Example 207 substituting Example 109B with Example 308B. Chromatography was performed with an Analogix 280 with an SF 25-40 column, 0% to 6% methanol/dichloromethane gradient over 30 minutes. $^1$H NMR (300 MHz, DMSO-d$_6$) δ 1.27 (d, 2H) 1.95 (d, 4H) 2.78 (d, 1H) 3.16 (d, 1H) 3.49 (d, 1H) 3.81 (d, 1H) 4.23 (d, 1H) 5.52 (d, J=8.14 Hz, 1H) 6.68 (d, J=8.82 Hz, 2H) 7.09 (d, J=1.70 Hz, 1H) 7.39 (s, 1H) 7.48-7.68 (m, 3H) 7.71-7.82 (m, 3H) 9.05 (s, 1H) 10.56 (s, 1H). MS (ESI$^+$) m/z 563.4 (M+H)$^+$.

Example 322

6-(2,6-dichlorophenyl)-2-[(4-{[1-(methylsulfonyl)piperidin-4-yl]amino}phenyl)amino]imidazo[1,2-a]pyrimido[5,4-e]pyrimidin-5(6H)-one The title compound (0.02 g) was prepared as described in Example 206 substituting Example 109B with Example 308B. Chromatography was performed with an Analogix 280 with an SF 12-24 column, 40% to 100% ethyl acetate/hexane gradient over 30 minutes. $^1$H NMR (300 MHz, DMSO-d$_6$) δ 1.30-1.64 (m, 2H) 1.74-2.19 (m, 2H) 2.81-3.01 (m, 5H) 3.35-3.51 (m, 1H) 3.44-3.65 (m, 2H) 5.56 (s, 1H) 6.68 (d, J=8.33 Hz, 2H) 7.09 (d, J=1.59 Hz, 1H) 7.37 (s, 1H) 7.50-7.69 (m, 2H) 7.69-7.83 (m, 3H) 9.06 (s, 1H) 10.58 (s, 1H). MS (ESI$^+$) m/z 599.2 (M+H)$^+$.

Example 323

6-(2,6-dichlorophenyl)-2-{[4-(9-methyl-3,9-diazaspiro[5.5]undec-3-yl)phenyl]amino}imidazo[1,2-a]pyrimido[5,4-e]pyrimidin-5(6H)-one The title compound (0.11 g) was prepared as described in Example 150, substituting 1,1,2-trimethyl-1,2,3,4-tetrahydroisoquinolin-6-amine with 4-(9-methyl-3,9-diazaspiro[5.5]undecan-3-yl)aniline. Chromatography was performed with an Analogix 280 with an SF 25-40 column, 4% methanol/dichloromethane with a small amount of ammonium hydroxide over 30 minutes. The purified material was dissolved in methanol, treated with excess 2M HCl in diethyl ether and stirred until a solid began to form. The mixture was diluted with ether, stirred for 10 minutes, and filtered to provide the title compound. $^1$H NMR (300 MHz, DMSO-d$_6$) δ 1.80 (d, 10H) 2.74 (d, 3H) 3.06 (d, 2H) 3.27 (d, 2H) 7.13 (d, J=1.59 Hz, 1H) 7.40-8.11 (m, 9H) 9.17 (s, 1H) 9.93 (s, 1H) 10.91 (s, 1H). MS (ESI$^+$) m/z 589.4 (M+H)$^+$.

Example 324

6-(2,6-dichlorophenyl)-2-({4-[6-(methylsulfonyl)-2,6-diazaspiro[3.4]oct-2-yl]phenyl}amino)imidazo[1,2-a]pyrimido[5,4-e]pyrimidin-5(6H)-one The title compound (0.045 g) was prepared as described in Example 206 substituting Example 109B with Example 313D. The crude material was triturated with dichloromethane to provide the title compound. $^1$H NMR (300 MHz, DMSO-d$_6$) δ 2.17 (d, 2H) 2.94 (d, 3H) 3.46 (d, 2H) 3.79 (d, 4H) 6.54 (d, J=8.73 Hz, 2H) 7.09 (d, J=1.98 Hz, 1H) 7.36-7.89 (m, 6H) 9.08 (s, 1H) 10.66 (s, 1H). MS (ESI$^+$) m/z 611.3 (M+H)$^+$.

Example 325

6-(2-chlorophenyl)-2-({4-[(8aS)-hexahydropyrrolo[1,2-a]pyrazin-2(1H)-yl]phenyl}amino)imidazo[1,2-a]pyrimido[5,4-e]pyrimidin-5(6H)-one

Example 325A (S)-2-(4-nitrophenyl)octahydropyrrolo[1,2-a]pyrazine

The title compound was prepared as described in Example 183A substituting (5)-octahydropyrrolo[1,2-a]pyrazine for bis(2-methoxyethyl)amine. MS (ESI$^+$) m/e 248.2 (M+H)$^+$.

Example 325B (S)-4-(hexahydropyrrolo[1,2-a]pyrazin-2(1H)-yl)aniline

The title compound was prepared as described in Example 183B substituting Example 325A for Example 183B. MS (ESI$^+$) m/e 218.2 (M+H)$^+$.

Example 325C 6-(2-chlorophenyl)-2-({4-[(8aS)-hexahydropyrrolo[1,2-a]pyrazin-2(1H)-yl]phenyl}amino)imidazo[1,2-a]pyrimido[5,4-e]pyrimidin-5(6H)-one The title compound was prepared as described in Example 183C substituting Example 325B for Example 183B. $^1$H NMR (400 MHz, DMSO-d$_6$, 90°) δ 10.28 (s, 1H), 9.05 (s, 1H), 7.68 (m, 4H), 7.53 (m, 3H), 3.51 (m, 9H), 2.14 (m, 4H). MS (ESI$^+$) m/e 513.3 (M+H)$^+$.

Example 326

6-(2,6-dichlorophenyl)-2-({4-[(3aR,6aR)-5-methyl-hexahydropyrrolo[3,4-b]pyrrol-1(2H)-yl]phenyl}amino)imidazo[1,2-a]pyrimido[5,4-e]pyrimidin-5(6H)-one The title compound (0.025 g) was prepared as described in Example 150, substituting 1,1,2-trimethyl-1,2,3,4-tetrahydroisoquinolin-6-amine with 4-((3aR,6aR)-5-methylhexahydropyrrolo[3,4-b]pyrrol-1(2H)-yl)aniline, bis HCl salt. Chromatography was performed with an Analogix 280 with an SF 12-24 column, 4% methanol/dichloromethane with a small amount of ammonium hydroxide over 30 minutes. The compound was dissolved in methanol, treated with 2M HCl in diethyl ether for 20 minutes, and filtered to provide the title compound. $^1$H NMR (300 MHz, DMSO-d$_6$) δ 1.85-2.36 (m, 3H) 2.71-2.90 (m, 3H) 3.03-3.21 (m, 1H) 3.21-3.40 (m, 2H) 3.98-4.48 (m, 3H) 6.48-6.87 (m, 2H) 7.11 (s, 1H) 7.43-7.93 (m, 7H) 9.09 (d, J=1.59 Hz, 1H) 10.05 (s, 1H) 10.71 (s, 1H). MS (ESI$^+$) m/z 547.3 (M+H)$^+$.

Example 327

6-(2,6-dichlorophenyl)-2-[(4-{[2-(dimethylamino)ethyl](ethyl)amino}phenyl)amino]imidazo[1,2-a]pyrimido[5,4-e]pyrimidin-5(6H)-one The title compound (0.025 g) was prepared as described in Example 150, substituting 1,1,2-trimethyl-1,2,3,4-tetrahydroisoquinolin-6-amine with N$^1$-(2-(dimethylamino)ethyl)-N$^1$-ethylbenzene-1,4-diamine. The crude material was purified using an Analogix280 SF 15-12 column (0% to 4% methanol/dichloromethane gradient over 30). The solid was dissolved in methanol, treated with 2M HCl in diethyl ether for 20 minutes, and filtered. $^1$H NMR (300 MHz, DMSO-d$_6$) δ 1.08 (d, 3H) 2.86 (d, 6H) 3.20 (d, 2H) 3.37 (d, 2H) 3.64 (d, 2H) 6.89 (d, J=8.14 Hz, 2H) 7.11 (s, 1H) 7.38-8.03 (m, 6H) 9.09 (s, 1H) 10.06 (s, 1H) 10.43-10.81 (m, 1H). MS (ESI$^+$) m/z 537.2 (M+H)$^+$.

Example 328

6-(2,6-dichlorophenyl)-2-[(4-{propan-2-yl[2-(propan-2-ylamino)ethyl]amino}phenyl)amino]imidazo[1,2-a]pyrimido[5,4-e]pyrimidin-5(6H)-one The title compound (0.025 g) was prepared as described in Example 150, substituting 1,1,2-trimethyl-1,2,3,4-tetrahydroisoquinolin-6-amine with N$^1$-isopropyl-N$^1$-(2-(isopropylamino)ethyl)benzene-1,4-diamine. The crude material was purified using an Analogix280 SF 15-12 column (0% to 4% methanol/dichloromethane gradient over 30). The purified compound was dissolved in methanol, treated with 2M HCl in diethyl ether for 20 minutes, and filtered to provide the title compound. $^1$H NMR (300 MHz, DMSO-d$_6$) δ 1.12-1.42 (m, 12H) 3.11-3.31 (m, 2H) 3.39-3.57 (m, 4H) 6.72 (s, 2H) 7.10 (d, J=1.98 Hz, 1H) 7.48 (s, 1H) 7.55-7.72 (m, 3H) 7.70-7.85 (m, 3H) 9.08 (s, 1H) 10.65 (s, 1H). MS (ESI$^+$) m/z 565.3 (M+H)$^+$.

Example 329

2-[(2-acetyl-1,2,3,4-tetrahydroisoquinolin-7-yl)amino]-6-(2,6-dichlorophenyl)imidazo[1,2-a]pyrimido[5,4-e]pyrimidin-5(6H)-one The title compound (0.085 g) was prepared as described in Example 207 substituting Example 109B with Example 111B. Chromatography was performed with an Analogix 280 with an SF 25-40 column, using a 0% to 7% methanol/dichloromethane gradient over 30 minutes. $^1$H NMR (300 MHz, DMSO-d$_6$) δ 2.04-2.16 (m, 3H) 2.66-2.96 (m, 2H) 3.55-3.78 (m, 2H) 4.51-4.79 (m, 2H) 7.12 (s, 1H) 7.23 (d, J=8.33 Hz, 1H) 7.52-7.92 (m, 6H) 9.16 (s, 1H) 10.82 (s, 1H). MS (ESI$^+$) m/z 520.3 (M+H)$^+$.

Example 330

6-(2,6-dichlorophenyl)-2-{[2-(methylsulfonyl)-1,2,3,4-tetrahydroisoquinolin-6-yl]amino}imidazo[1,2-a]pyrimido[5,4-e]pyrimidin-5(6H)-one The title compound (0.09 g) was prepared as described in Example 206 substituting Example 109B with Example 122. Trituration of crude material with ethyl acetate provided the title compound. $^1$H NMR (300 MHz, DMSO-d$_6$) δ 2.86-3.08 (m, 5H) 3.46 (t, J=5.95 Hz, 2H) 4.37 (s, 2H) 7.12 (d, J=1.98 Hz, 1H) 7.24 (d, J=8.73 Hz, 1H) 7.54-7.91 (m, 6H) 9.17 (s, 1H) 10.84 (s, 1H). MS (ESI$^+$) m/z 556.2 (M+H)$^+$.

Example 331

2-[(2-acetyl-1,2,3,4-tetrahydroisoquinolin-6-yl)amino]-6-(2,6-dichlorophenyl)imidazo[1,2-a]pyrimido[5,4-e]pyrimidin-5(6H)-one The title compound (0.085 g) was prepared as described in Example 207 substituting Example 109B with Example 122. Solid material was filtered from the workup to provide the title compound. $^1$H NMR (300 MHz, DMSO-$d_6$) δ 2.10 (s, 3H) 2.65-3.04 (m, 2H) 3.68 (t, J=5.93 Hz, 2H) 4.61 (d, J=15.60 Hz, 2H) 7.10 (d, J=1.70 Hz, 1H) 7.22 (d, J=8.14 Hz, 1H) 7.51-7.70 (m, 3H) 7.71-7.84 (m, 3H) 9.12 (s, 1H) 10.81 (s, 1H). MS (ESI$^+$) m/z 520.3 (M+H)$^+$.

Example 332

6-(2-chlorophenyl)-2-{[4-(4-methylpiperazin-1-yl) phenyl]amino}imidazo[1,2-a]pyrimido[5,4-e]pyrimidine-5(6H)-thione Example 332A 4-(2-Chloro-phenyl)-8-methylsulfanyl-4H-3,4,7,9, 9b-pentaaza-cyclopenta[a]naphthalene-5-thione A solution of Example 1D (0.730 g, 2.123 mmol) and Lawesson's reagent (0.515 g, 1.274 mmol) in toluene (40 mL) was heated to reflux for 4 hours. The reaction mixture was concentrated and purified on a 40 g column using the ISCO Companion flash system eluting with hexane/ethyl acetate (1:1 to 4:6) to provide the title compound.

Example 332B 6-(2-chlorophenyl)-2-{[4-(4-methylpiperazin-1-yl) phenyl]amino}imidazo[1,2-a]pyrimido[5,4-e]pyrimidine-5(6H)-thione A mixture of Example 332A (100.0 mg, 0.278 mmol), 4-(4-methylpiperazin-1-yl)aniline (106 mg, 0.556 mmol) and 1 drop of N,N-dimethylformamide in acetonitrile (4 mL) was heated at 180° C. for 180 minutes in a Biotage microwave reactor. The reaction mixture was concentrated and purified by HPLC (see protocol in Example 1F) to provide the title compound as a trifluoroacetic acid salt. $^1$H NMR (400 MHz, CD$_3$OD) δ 2.99 (s, 3H), 3.19-3.00 (m, 2H), 3.35-3.27 (m, 2H), 3.67-3.59 (m, 2H), 3.90-3.81 (m, 2H), 7.14-7.04 (m, 3H), 7.60-7.45 (m, 3H), 7.79-7.62 (m, 3H), 7.98-7.83 (m, 1H), 9.51 (s, 1H). MS (ESI$^+$) m/z 503.1 (M+H)$^+$.

Example 333

6-(2-chlorophenyl)-5-imino-N-[4-(4-methylpiperazin-1-yl)phenyl]-5,6-dihydroimidazo[1,2-a]pyrimido[5,4-e]pyrimidin-2-amine 7M NH$_3$ in methanol (10 mL) was added to Example 332B (4.98 mg, 6.81 μmol) in a 25 mL stainless steel reactor. The mixture was stirred at 120° C. for 1 hour. The reaction mixture was concentrated and purified by HPLC (see protocol in Example 1F) to provide the title compound as a trifluoroacetic acid salt. $^1$H NMR (400 MHz, CD$_3$OD) δ 2.99 (s, 3H), 3.13-3.03 (m, 2H), 3.38-3.24 (m, 2H), 3.72-3.56 (m, 2H), 3.95-3.80 (m, 2H), 7.22-7.07 (m, 3H), 7.80-7.64 (m, 5H), 7.86-7.83 (m, 1H), 8.05-7.98 (m, 1H), 9.46-9.43 (m, 1H). MS (ESI$^+$) m/z 486.3 (M+H)$^+$.

Example 334

6-(2-chlorophenyl)-2-[(2,4,4-trimethyl-1,2,3,4-tetrahydroisoquinolin-7-yl)amino]imidazo[1,2-a]pyrimido[5,4-e]pyrimidine-5(6H)-thione A mixture of Example 332A (126 mg, 0.35 mmol) and 2,4,4-trimethyl-1,2,3,4-tetrahydroisoquinolin-7-amine (133 mg, 0.70 mmol) was heated neat at 140° C. for 4.5 hours. The reaction mixture was treated with ethyl acetate and washed with saturated NaHCO$_3$. The organic layer was dried over MgSO$_4$, filtered, concentrated, and purified on a 12 g column using the ISCO Companion flash system eluting with methanol/ethyl acetate (5:95 to 10:90) followed by HPLC (see protocol in Example 1F) to provide the title compound as a trifluoroacetic acid salt. $^1$H NMR (400 MHz, CD$_3$OD) δ 1.49 (s, 6H), 3.12 (s, 3H), 3.40-3.23 (m, 1H), 3.63-3.48 (m, 1H), 4.62-4.41 (m, 2H), 7.13 (d, J=1.8 Hz, 1H), 7.61-7.46 (m, 4H), 7.70-7.64 (m, 1H), 7.83-7.72 (m, 2H), 7.93 (d, J=1.8 Hz, 1H), 9.59 (s, 1H). MS (ESI$^+$) m/z 502.1 (M+H)$^+$.

Example 335

6-(2-chlorophenyl)-5-imino-N-(2,4,4-trimethyl-1,2,3,4-tetrahydroisoquinolin-7-yl)-5,6-dihydroimidazo [1,2-a]pyrimido[5,4-e]pyrimidin-2-amine 7M NH$_3$ in methanol (12 mL) was added to Example 334 (10.5 mg) in a 25 mL stainless steel reactor. The mixture was stirred for 8 hours at 75° C. The reaction mixture was concentrated and purified by HPLC (see protocol in Example 1F) to provide the title compound as a trifluoroacetic acid salt. $^1$H NMR (400 MHz, CD$_3$OD) δ 1.43 (s, 6H), 3.13 (s, 3H), 3.64-3.27 (m, 2H), 4.68-4.40 (m, 2H), 7.22 (bs, 1H), 7.82-7.57 (m, 5H), 7.87-7.84 (m, 2H), 8.06 (s, 1H), 9.55-9.48 (m, 1H). MS (ESI$^+$) m/z 485.2 (M+H)$^+$.

The following compounds were prepared using methods similar to those described in Examples 1-335.

Example 336

6-(3-fluorophenyl)-2-{[4-(4-methylpiperazin-1-yl) phenyl]amino}imidazo[1,2-a]pyrimido[5,4-e]pyrimidin-5(6H)-one Example 337

6-(3-chlorophenyl)-2-{[4-(4-methylpiperazin-1-yl) phenyl]amino}imidazo[1,2-a]pyrimido[5,4-e]pyrimidin-5(6H)-one Example 338

6-(2,4-dimethoxyphenyl)-2-{[4-(4-methylpiperazin-1-yl)phenyl]amino}imidazo[1,2-a]pyrimido[5,4-e] pyrimidin-5(6H)-one Example 339

6-(2-chlorophenyl)-2-{[5-(4-ethylpiperazin-1-yl) pyridin-2-yl]amino}imidazo[1,2-a]pyrimido[5,4-e] pyrimidin-5(6H)-one Example 340

6-[2-chloro-4-(trifluoromethyl)phenyl]-2-{[4-(4-methylpiperazin-1-yl)phenyl]amino}imidazo[1,2-a] pyrimido[5,4-e]pyrimidin-5(6H)-one Example 341

2-{[4-(4-methylpiperazin-1-yl)phenyl]amino}-6-[2-(trifluoromethoxy)phenyl]imidazo[1,2-a]pyrimido[5, 4-e]pyrimidin-5(6H)-one

Example 342

4-{[6-(2-chlorophenyl)-5-oxo-5,6-dihydroimidazo[1,2-a]pyrimido[5,4-e]pyrimidin-2-yl]amino}benzoic acid

Example 343

2-[(4-bromophenyl)amino]-6-(2-chlorophenyl)imidazo[1,2-a]pyrimido[5,4-e]pyrimidin-5(6H)-one

Example 344

6-(3-methoxy-2-methylphenyl)-2-(phenylamino)imidazo[1,2-a]pyrimido[5,4-e]pyrimidin-5(6H)-one

Example 345

2-{[4-(1,4-diazepan-1-yl)-3-methylphenyl]amino}-6-(2,6-dichlorophenyl)imidazo[1,2-a]pyrimido[5,4-e]pyrimidin-5(6H)-one

Example 346

2-{[4-(4-methylpiperazin-1-yl)phenyl]amino}-6-(propan-2-yl)imidazo[1,2-a]pyrimido[5,4-e]pyrimidin-5(6H)-one

Example 347

6-(2-chlorophenyl)-2-{[3,5-difluoro-4-(4-methylpiperazin-1-yl)phenyl]amino}imidazo[1,2-a]pyrimido[5,4-e]pyrimidin-5(6H)-one

Example 348

6-(2-chlorophenyl)-2-{[4-(trifluoromethyl)phenyl]amino}imidazo[1,2-a]pyrimido[5,4-e]pyrimidin-5(6H)-one

Example 349

6-(2-chlorophenyl)-2-{[4-(1,3-thiazol-4-yl)phenyl]amino}imidazo[1,2-a]pyrimido[5,4-e]pyrimidin-5(6H)-one

Example 350

6-(2-chlorophenyl)-2-{[4-(1,3-thiazol-2-yl)phenyl]amino}imidazo[1,2-a]pyrimido[5,4-e]pyrimidin-5(6H)-one

Example 351

6-(2-chlorophenyl)-2-{[4-(1,8-naphthyridin-2-yl)phenyl]amino}imidazo[1,2-a]pyrimido[5,4-e]pyrimidin-5(6H)-one

Example 352

6-(2-chlorophenyl)-2-({4-[(2S)-2-(trifluoromethyl)pyrrolidin-1-yl]phenyl}amino)imidazo[1,2-a]pyrimido[5,4-e]pyrimidin-5(6H)-one

Example 353

2-{[3-chloro-4-(4-methylpiperazin-1-yl)-5-(trifluoromethyl)phenyl]amino}-6-(2-chlorophenyl)imidazo[1,2-a]pyrimido[5,4-e]pyrimidin-5(6H)-one

Example 354

6-(2-chlorophenyl)-2-{[3-chloro-4-(piperazin-1-yl)-5-(trifluoromethyl)phenyl]amino}imidazo[1,2-a]pyrimido[5,4-e]pyrimidin-5(6H)-one

Example 355

6-(2-chlorophenyl)-2-[(2'-methyl-2',3'-dihydro-1'H-spiro[cyclopropane-1,4'-isoquinolin]-7'-yl)amino]imidazo[1,2-a]pyrimido[5,4-e]pyrimidine-5(6H)-thione

Example 356

2-{[7-{[6-(2-chlorophenyl)-5-oxo-5,6-dihydroimidazo[1,2-a]pyrimido[5,4-e]pyrimidin-2-yl]amino}-4,4-dimethyl-3,4-dihydroisoquinolin-2(1H)-yl]methyl}benzonitrile

Example 357

6-(2-chlorophenyl)-2-{[4,4-dimethyl-2-(4-propoxybenzyl)-1,2,3,4-tetrahydroisoquinolin-7-yl]amino}imidazo[1,2-a]pyrimido[5,4-e]pyrimidin-5(6H)-one

Example 358

6-(2-chlorophenyl)-2-({2-[3-fluoro-5-(trifluoromethyl)benzyl]-4,4-dimethyl-1,2,3,4-tetrahydroisoquinolin-7-yl}amino)imidazo[1,2-a]pyrimido[5,4-e]pyrimidin-5(6H)-one

Example 359

6-(2-chlorophenyl)-2-[(4-{2-[(2R)-2-methylpyrrolidin-1-yl]ethyl}phenyl)amino]imidazo[1,2-a]pyrimido[5,4-e]pyrimidin-5(6H)-one

Example 360

6-(2-chlorophenyl)-2-({4-[2-(morpholin-4-yl)-1,3-thiazol-4-yl]phenyl}amino)imidazo[1,2-a]pyrimido[5,4-e]pyrimidin-5(6H)-one

Example 361

6-(2-chlorophenyl)-2-({4-[2-(6-methylquinolin-2-yl)ethyl]phenyl}amino)imidazo[1,2-a]pyrimido[5,4-e]pyrimidin-5(6H)-one

Example 362

Wee1 Assay

Wee1 kinase was assayed using a time-resolved fluorescence equilibrium binding assay monitoring displacement of a rapidly reversible Oregon Green-labeled ATP-competitive kinase probe (N-(2-(2-(2-(4-(4-(5-chloro-4-(2-(1-hydroxycyclobutyl)thiazol-5-yl)-1H-pyrrolo[2,3-b]pyridin-2-yl) phenyl)piperazin-1-yl)ethoxy)ethoxy)ethyl)-2',7'-difluoro-3',6'-dihydroxy-3-oxo-3H-spiro[isobenzofuran-1,9'-xanthene]-5-carboxamide) by competitive Wee1 inhibitors. GST-tagged-Wee1 kinase (Carnabio #05-177, 2 nM final concentration), was mixed with fluorescent probe (300 nM final concentration, $K_d$=137 nM) and terbium-labeled anti-GST antibody (1 nM final concentration, Invitrogen #PV3551) and then inhibitor (0.003 to 10 micromolar) in final volume of 18 µl kinase buffer (20 mM HEPES, pH 7.5, 10 mM MgCl$_2$, 100 µM Na$_3$VO$_4$, 0.0075% Triton X-100, 1 mM DTT, 2% DMSO), incubated (1 hour) to allow attainment of equilibrium and time-resolved fluorescence measured using an Envision plate reader (Perkin Elmer; ex=337 nM, em=495/520 nM).

Table 1 depicts enzyme inhibition data ($K_i$) for exemplary compounds. In Table 1, "A" represents a $K_i$ of less than 10 nM, "B" represents a $K_i$ of between 10 nM and 100 nM, and "C" represents a $K_i$ of greater than 100 nM.

| Example | Wee-1 inhibition |
|---|---|
| 1 | A |
| 2 | B |
| 3 | C |
| 4 | A |
| 5 | B |
| 6 | A |
| 7 | B |
| 8 | A |
| 9 | A |
| 10 | A |
| 11 | B |
| 12 | A |
| 13 | A |
| 14 | A |
| 15 | B |
| 16 | B |
| 17 | C |
| 18 | B |
| 19 | B |
| 20 | B |
| 21 | A |
| 22 | A |
| 23 | C |
| 24 | C |
| 25 | A |
| 26 | B |
| 27 | B |
| 28 | B |
| 29 | A |
| 30 | A |
| 31 | B |
| 32 | A |
| 33 | A |
| 34 | A |
| 35 | A |
| 36 | B |
| 37 | A |
| 38 | A |
| 39 | B |
| 40 | A |
| 41 | B |
| 42 | B |
| 43 | B |
| 44 | A |
| 45 | B |
| 46 | B |
| 47 | B |
| 48 | B |
| 49 | B |
| 50 | A |
| 51 | A |
| 52 | A |
| 53 | A |
| 54 | B |
| 55 | A |
| 56 | B |
| 57 | B |
| 58 | B |
| 59 | B |
| 60 | A |
| 61 | A |
| 62 | A |
| 63 | B |
| 64 | A |
| 65 | A |
| 66 | A |
| 67 | A |
| 68 | B |
| 69 | B |
| 70 | A |
| 71 | A |
| 72 | A |
| 73 | A |
| 74 | A |
| 75 | A |
| 76 | A |
| 77 | C |
| 78 | A |
| 79 | A |
| 80 | B |
| 81 | A |
| 82 | B |
| 83 | B |
| 84 | A |
| 85 | A |
| 86 | A |
| 87 | B |
| 88 | A |
| 89 | B |
| 90 | A |
| 91 | A |
| 92 | A |
| 93 | A |
| 94 | A |
| 95 | A |
| 96 | A |
| 97 | A |
| 98 | B |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | B |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |

| Example | Wee-1 inhibition |
|---------|------------------|
| 132 | A |
| 133 | A |
| 134 | A |
| 135 | A |
| 136 | A |
| 137 | A |
| 138 | A |
| 139 | A |
| 140 | A |
| 141 | A |
| 142 | B |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | B |
| 160 | A |
| 161 | A |
| 162 | B |
| 163 | A |
| 164 | A |
| 165 | A |
| 166 | A |
| 167 | B |
| 168 | A |
| 169 | A |
| 170 | B |
| 171 | A |
| 172 | A |
| 173 | A |
| 174 | A |
| 175 | A |
| 176 | A |
| 177 | A |
| 178 | A |
| 179 | A |
| 180 | A |
| 181 | B |
| 182 | A |
| 183 | B |
| 184 | A |
| 185 | A |
| 186 | A |
| 187 | A |
| 188 | A |
| 189 | B |
| 190 | A |
| 191 | A |
| 192 | B |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | B |
| 212 | A |
| 213 | A |
| 214 | A |
| 215 | A |
| 216 | A |
| 217 | B |
| 218 | B |
| 219 | A |
| 220 | B |
| 221 | B |
| 222 | B |
| 223 | A |
| 224 | A |
| 225 | A |
| 226 | A |
| 227 | A |
| 228 | A |
| 229 | A |
| 230 | A |
| 231 | B |
| 232 | B |
| 233 | B |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | A |
| 253 | A |
| 254 | B |
| 255 | A |
| 256 | A |
| 257 | A |
| 258 | A |
| 259 | A |
| 260 | A |
| 261 | A |
| 262 | A |
| 263 | A |
| 264 | B |
| 265 | A |
| 266 | A |
| 267 | A |
| 268 | A |
| 269 | A |
| 270 | A |
| 271 | A |
| 272 | B |
| 273 | A |
| 274 | A |
| 275 | A |
| 276 | A |
| 277 | B |
| 278 | A |
| 279 | A |
| 280 | B |
| 281 | A |
| 282 | A |
| 283 | A |
| 284 | A |
| 285 | A |
| 286 | A |
| 287 | A |

-continued

| Example | Wee-1 inhibition |
|---|---|
| 288 | A |
| 289 | B |
| 290 | A |
| 291 | A |
| 292 | A |
| 293 | B |
| 294 | B |
| 295 | A |
| 296 | A |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | A |
| 311 | A |
| 312 | A |
| 313 | A |
| 314 | A |
| 315 | A |
| 316 | A |
| 317 | A |
| 318 | A |
| 319 | A |
| 320 | A |
| 321 | A |
| 322 | A |
| 323 | A |
| 324 | A |
| 325 | A |
| 326 | A |
| 327 | A |
| 328 | A |
| 329 | A |
| 330 | A |
| 331 | A |
| 332 | A |
| 333 | A |
| 334 | A |
| 335 | A |
| 336 | B |
| 337 | C |
| 338 | C |
| 339 | C |
| 340 | C |
| 341 | C |
| 342 | C |
| 343 | B |
| 344 | C |
| 345 | B |
| 346 | B |
| 347 | C |
| 348 | C |
| 349 | B |
| 350 | B |
| 351 | B |
| 352 | B |
| 353 | C |
| 354 | C |
| 355 | A |
| 356 | B |
| 357 | B |
| 358 | B |
| 359 | B |
| 360 | B |
| 361 | B |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound of formula (I):

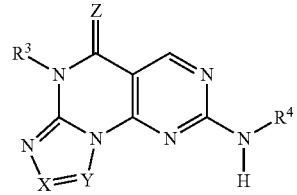

formula (I)

wherein
X is N;
Y is $CR^2$;
Z is O;
$R^2$ is H or $C_{1-6}$-alkyl;
$R^3$ is aryl, wherein the aryl is optionally substituted with one or more substituents selected from the group consisting of $C_{1-6}$-alkyl, $C_{1-6}$-haloalkyl, $C_{2-6}$-alkenyl, heterocycloalkyl, aryl, heteroaryl, halogen, oxo, cyano, nitro, —$OR^d$, —$C(O)R^d$, —$C(O)OR^d$, —$OC(O)R^d$, —$SR^d$, —$S(O)R^d$, —$SO_2R^d$, —$NR^eR^f$, —$NHC(O)R^e$, —$NHC(O)NHR^e$, —$NHC(O)OR^e$, —$NHSO_2R^d$, —$C(O)NHR^e$, and —$SO_2NHNR^e$;
$R^4$ is
phenyl, which is optionally substituted with one or more $R^5$; or
$R^5$, at each occurrence, is independently CN, $NO_2$, halo, $C_{1-6}$-alkyl, $OR^g$, $SR^g$, $C(O)R^g$, $C(O)NR^hR^i$, $C(O)OR^g$, $NR^hR^i$, $NR^hC(O)R^g$, $S(O)_2R^g$, $NR^hS(O)_2R^g$, $S(O)_2NR^hR^i$, aryl, cycloalkyl, heteroaryl, heterocycloalkyl, or heterocycloalkenyl, wherein the $C_{1-6}$-alkyl is optionally substituted with one or more substituents selected from the group consisting of CN, halo, hydroxy, $S(O)_2NH(C_{1-6}$-alkyl), $C_{1-6}$-alkoxy, heterocycloalkyl, cycloalkyl, heteroaryl, aryl, —$NH_2$, —$NHC_{1-6}$-alkyl, and —$N(C_{1-6}$-alkyl$)_2$; wherein the aryl, cycloalkyl, heteroaryl, or heterocycloalkyl, alone or as part of another moiety, is optionally substituted with one or more $R^7$;
$R^7$, at each occurrence, is independently CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR^nR^o$, $C(O)OR^m$, $OC(O)R^m$, $OC(O)NR^nR^o$, $NR^nR^o$, $NR^nC(O)R^m$, $S(O)R^m$, $S(O)NR^nR^o$, $S(O)_2R^m$, $NR^nS(O)_2R^m$, or $S(O)_2NR^nR^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl$)_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl;
$R^d$, at each occurrence, is independently selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^g$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)$_2C_{1-6}$-alkyl, —$NH_2$, —$NH(C_{1-6}$-alkyl), —$N(C_{1-6}$-alkyl$)_2$, and —$N(C_{1-6}$-alkyl)($C_{3-8}$-cycloalkyl);

$R^h$ and $R^i$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of CN, halo, hydroxy, $C_{1-6}$-alkoxy, heterocycloalkyl, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl, alone or as part of another moiety, is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —C(O)$C_{1-6}$-alkyl, —S(O)$_2C_{1-6}$-alkyl, —$NH_2$, —$NH(C_{1-6}$-alkyl), $N(C_{1-6}$-alkyl$)_2$, and —$N(C_{1-6}$-alkyl)($C_{3-8}$-cycloalkyl);

$R^m$, at each occurrence, is independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl)$_2$;

$R^n$ and $R^o$, at each occurrence, are independently selected from the group consisting of H, $C_{1-6}$ alkyl, aryl, $C_{3-8}$ cycloalkyl, heteroaryl, and heterocycloalkyl; wherein the $C_{1-6}$-alkyl is optionally substituted with one or more substituents selected from the group consisting of halo, hydroxy, $C_{1-6}$-alkoxy, —$NH_2$, —$NHC_{1-6}$-alkyl, and —$N(C_{1-6}$-alkyl$)_2$, and wherein the aryl, $C_{3-8}$ cycloalkyl, heteroaryl, or heterocycloalkyl is optionally substituted with one or more substituents selected from the group consisting of halo, $C_{1-6}$-alkyl, $C_{1-6}$-haloalkyl, $C_{1-6}$-hydroxyalkyl, hydroxy, oxo, $C_{1-6}$-alkoxy, $C_{1-6}$-haloalkoxy, —$NH_2$, —$NH(C_{1-6}$-alkyl), and $N(C_{1-6}$-alkyl)$_2$;

or a pharmaceutically acceptable salt or solvate thereof.

2. The compound of claim 1, wherein $R^3$ is phenyl, wherein the phenyl is optionally substituted with one or two substituents selected from the group consisting of halogen, $C_{1-6}$ alkyl, $C_{1-6}$ haloalkyl, —$OC_{1-6}$ alkyl, and —$OC_{1-6}$ haloalkyl.

3. The compound of claim 1, wherein $R^4$ is phenyl, wherein the phenyl is substituted with heterocycloalkyl and optionally one or two $R^5$, wherein $R^5$ is halo, $C_{1-6}$-alkyl, $C_{1-6}$ haloalkyl, or $OR^g$, wherein the heterocycloalkyl is optionally substituted with one, two, or three $R^7$; wherein $R^7$ is CN, $NO_2$, halo, oxo, $C_{1-6}$ alkyl, aryl, $C_{3-8}$ cycloalkyl, heteroaryl, heterocycloalkyl, $OR^m$, $SR^m$, $C(O)R^m$, $C(O)NR''R^o$, $C(O)OR^m$, $OC(O)R^m$, $OC(O)NR''R^o$, $NR''R^o$, $NR''C(O)R^m$, $S(O)R^m$, $S(O)NR''R^o$, $S(O)_2R^m$, $NR''S(O)_2R^m$, or $S(O)_2NR''R^o$, wherein the $C_{1-6}$-alkyl is optionally substituted with one or more substituents selected from the group consisting of CN, halo, hydroxy, $C_{1-6}$-alkoxy, heterocycloalkyl, cycloalkyl, aryl, heteroaryl, —$NH_2$, —$NHC_{1-6}$-alkyl, and —$N(C_{1-6}$-alkyl$)_2$, wherein the aryl, $C_{3-8}$ cycloalkyl, heteroaryl, and heterocycloalkyl, alone or as part of another moiety, are optionally substituted with one, two or three substituents independently selected from CN, halo, and $C_{1-6}$ alkyl.

4. A pharmaceutical composition comprising a compound or pharmaceutically acceptable salt of claim 1 and pharmaceutically acceptable excipient.

5. The compound of claim 1 selected from the group consisting of 6-(2-chlorophenyl)-2-{[4-(4-methylpiperazin-1-yl)phenyl]amino}pyrimido[5,4-e][1,2,4]triazolo[4,3-a]pyrimidin-5(6H)-one; and 6-(2-chlorophenyl)-9-methyl-2-{[4-(4-methylpiperazin-1-yl)phenyl]amino}pyrimido[5,4-e][1,2,4]triazolo[4,3-a]pyrimidin-5(6H)-one.

* * * * *